US009559305B2

(12) United States Patent
Blouin et al.

(10) Patent No.: US 9,559,305 B2
(45) Date of Patent: Jan. 31, 2017

(54) CONJUGATED POLYMERS

(71) Applicant: MERCK PATENT GMBH, Darmstadt (DE)

(72) Inventors: Nicolas Blouin, Southampton (GB); Amy Phillips, Southampton (GB); Lana Nanson, Southampton (GB); Steven Tierney, Southampton (GB); Toby Cull, Romsey (GB); Priti Tiwana, Winchester (GB); Stephane Berny, Southampton (GB); Miguel Carrasco-Orozco, Winchester (GB); Frank Egon Meyer, Winchester (GB)

(73) Assignee: MERCK PATENT GMBH, Darmstadt (DE)

( * ) Notice: Subject to any disclaimer, the term of this patent is extended or adjusted under 35 U.S.C. 154(b) by 33 days.

(21) Appl. No.: 14/385,609

(22) PCT Filed: Feb. 15, 2013

(86) PCT No.: PCT/EP2013/000447
§ 371 (c)(1),
(2) Date: Sep. 16, 2014

(87) PCT Pub. No.: WO2013/135339
PCT Pub. Date: Sep. 19, 2013

(65) Prior Publication Data
US 2015/0076418 A1    Mar. 19, 2015

(30) Foreign Application Priority Data
Mar. 16, 2012 (EP) .................... 12001815

(51) Int. Cl.
| H01L 51/00 | (2006.01) |
|---|---|
| C08K 3/04 | (2006.01) |
| C08G 61/12 | (2006.01) |
| C07D 495/04 | (2006.01) |
| C07D 271/12 | (2006.01) |
| C07D 285/14 | (2006.01) |
| C07D 513/04 | (2006.01) |
| C07F 5/04 | (2006.01) |
| C07F 7/22 | (2006.01) |
| C08G 75/00 | (2006.01) |
| C08G 75/32 | (2006.01) |
| H01L 51/42 | (2006.01) |

(52) U.S. Cl.
CPC ......... *H01L 51/0036* (2013.01); *C07D 271/12* (2013.01); *C07D 285/14* (2013.01); *C07D 495/04* (2013.01); *C07D 513/04* (2013.01); *C07F 5/04* (2013.01); *C07F 7/2212* (2013.01); *C08G 61/122* (2013.01); *C08G 61/123* (2013.01); *C08G 61/126* (2013.01); *C08G 75/00* (2013.01); *C08G 75/32* (2013.01); *C08K 3/04* (2013.01); *H01L 51/0043* (2013.01); *C08G 2261/124* (2013.01); *C08G 2261/1412* (2013.01); *C08G 2261/18* (2013.01); *C08G 2261/3221* (2013.01); *C08G 2261/3223* (2013.01); *C08G 2261/3243* (2013.01); *C08G 2261/3245* (2013.01); *C08G 2261/3246* (2013.01); *C08G 2261/414* (2013.01); *C08G 2261/51* (2013.01); *C08G 2261/91* (2013.01); *C08G 2261/92* (2013.01); *C08G 2261/95* (2013.01); *H01L 51/0053* (2013.01); *H01L 51/42* (2013.01); *H01L 51/4253* (2013.01); *Y02E 10/549* (2013.01); *Y02P 70/521* (2015.11)

(58) Field of Classification Search
CPC ..... C08G 61/126; C08G 61/12; C08G 61/122; C08G 61/123; H01B 1/10; H01B 1/12; C08K 3/04; C08K 3/06
USPC ........ 252/500, 501.1, 511; 526/257; 549/50; 136/263
See application file for complete search history.

(56) References Cited

U.S. PATENT DOCUMENTS

| 7,524,922 B2 | 4/2009 | Heeney et al. |
|---|---|---|
| 8,304,512 B2 | 11/2012 | Wigglesworth et al. |
| 8,367,798 B2 | 2/2013 | Yang et al. |
| 8,436,134 B2 | 5/2013 | Yu et al. |
| 8,535,974 B2 | 9/2013 | Brown et al. |

(Continued)

FOREIGN PATENT DOCUMENTS

| EP | 2399947 A1 | 12/2011 |
|---|---|---|
| JP | 2007246579 A | 9/2007 |

(Continued)

OTHER PUBLICATIONS

International Search Report for PCT/EP2013/000447 dated Apr. 10, 2014.

(Continued)

*Primary Examiner* — Douglas McGinty
(74) *Attorney, Agent, or Firm* — Millen White Zelano and Branigan, PC; Csaba Henter; Anthony Zelano

(57) ABSTRACT

The invention relates to novel conjugated polymers comprising in their backbone one or more divalent donor units, like for example benzo[1,2-b:4,5-b']dithiophene-2,6-diyl (BDT), that are linked on both sides to an acceptor unit, to methods of preparing the polymers and educts or intermediates used in such preparation, to polymer blends, mixtures and formulations containing the polymers, to the use of the polymers, polymer blends, mixtures and formulations as semiconductors organic electronic (OE) devices, especially in organic photovoltaic (OPV) devices and organic photodetectors (OPD), and to OE, OPV and OPD devices comprising these polymers, polymer blends, mixtures or formulations.

44 Claims, 3 Drawing Sheets

(56) References Cited

U.S. PATENT DOCUMENTS

| | | |
|---|---|---|
| 8,598,449 B2 | 12/2013 | Pan et al. |
| 8,653,228 B2 | 2/2014 | Yu et al. |
| 8,748,739 B2 | 6/2014 | Zhu et al. |
| 8,815,639 B2 | 8/2014 | Brown et al. |
| 8,816,035 B2 | 8/2014 | Leclerc et al. |
| 9,337,358 B2 * | 5/2016 | Byrne .................. C08G 61/123 |
| 9,365,679 B2 * | 6/2016 | Zhou ...................... C09K 11/06 |
| 9,376,529 B2 * | 6/2016 | Brown .................. C07D 285/14 |
| 2005/0082525 A1 | 4/2005 | Heeney et al. |
| 2010/0078074 A1 | 4/2010 | Yang et al. |
| 2010/0307594 A1 * | 12/2010 | Zhu ........................ B82Y 10/00 136/263 |
| 2011/0006287 A1 | 1/2011 | You et al. |
| 2011/0062426 A1 | 3/2011 | Kirner et al. |
| 2011/0095283 A1 | 4/2011 | Buchholz et al. |
| 2011/0124822 A1 | 5/2011 | Yu et al. |
| 2011/0156018 A1 | 6/2011 | Moriwaki et al. |
| 2011/0178255 A1 | 7/2011 | Wigglesworth et al. |
| 2011/0315225 A1 | 12/2011 | Choi et al. |
| 2012/0001127 A1 | 1/2012 | Brown et al. |
| 2012/0003790 A1 | 1/2012 | Brown et al. |
| 2012/0187385 A1 | 7/2012 | Pan et al. |
| 2012/0305853 A1 | 12/2012 | Mitchell et al. |
| 2013/0043434 A1 | 2/2013 | Tierney et al. |
| 2013/0048075 A1 | 2/2013 | Leclerc et al. |
| 2013/0092912 A1 | 4/2013 | You |
| 2013/0098448 A1 | 4/2013 | Zhu et al. |
| 2013/0344648 A1 | 12/2013 | Brown et al. |
| 2014/0005347 A1 | 1/2014 | Yu et al. |
| 2014/0084220 A1 * | 3/2014 | Inagaki ............... H01L 51/0036 252/511 |
| 2014/0124035 A1 | 5/2014 | Byrne et al. |
| 2014/0235817 A1 | 8/2014 | Yu et al. |
| 2016/0194439 A1 * | 7/2016 | Qin ...................... C08G 61/126 252/501.1 |

FOREIGN PATENT DOCUMENTS

| | | |
|---|---|---|
| JP | 2011124422 A | 6/2011 |
| WO | 2010008672 A1 | 1/2010 |
| WO | 2010135701 A1 | 11/2010 |
| WO | 2011063534 A1 | 6/2011 |
| WO | 2011085004 A4 | 7/2011 |
| WO | 2011098113 A2 | 8/2011 |
| WO | 2011131280 A1 | 10/2011 |
| WO | 2011156478 A2 | 12/2011 |
| WO | 2012003485 A2 | 1/2012 |

OTHER PUBLICATIONS

Griffini, G. et al., "Long-term thermal stability of high-efficiency polymer solar cells based on photocrosslinkable donor-acceptor conjugated polymers," Advanced Materials, 2011, vol. 23, pp. 1660-1664.

Henson, Z. B. et al., "Pyridalthiadiazole-based narrow band gap chromophores," Journal of the American Chemical Soceity, 2012, vol. 134, pp. 3766-3779.

Khlyabich, P. P. et al., "Compositional dependence of the open-circuit voltage in ternary blend bulk heterojunction solar cells based on two donor polymers," Journal of the American Chemical Society, 2012, vol. 134, pp. 9074-9077.

Burkhard, B. et al., "Influence of the acceptor composition on physical properties and solar cell performance in semi-random two-acceptor copolymers," ACS Macro Lett., 2012, vol. 1, pp. 660-666.

Burkhard, B. et al., "'Semi-random' Multichromophoric rr-P3HT Analogues for Solar Photon Harvesting," Macromolecules, 2011, vol. 44, pp. 1242-1246.

English Abstract of JP-2011-124422, Publication Date: Jun. 23, 2011.

English Abstract of JP-2007-246579, Publication Date: Sep. 27, 2007.

Khlyabich, P. P. et al., "Efficient solar cells from semi-random P3HT Analogues Incorporating Diketopyrrolopyrrole," Macromolecules, 2011.

Office Action and Search Report for related Taiwanese Patent Application No. 102105438 dated Jun. 13, 2016.

* cited by examiner

CONJUGATED POLYMERS

TECHNICAL FIELD

The invention relates to novel conjugated polymers comprising in their backbone one or more divalent donor units, like for example benzo[1,2-b:4,5-b']dithiophene-2,6-diyl (BDT), that are linked on both sides to an acceptor unit, to methods of preparing the polymers and educts or intermediates used in such preparation, to polymer blends, mixtures and formulations containing the polymers, to the use of the polymers, polymer blends, mixtures and formulations as semiconductors organic electronic (OE) devices, especially in organic photovoltaic (OPV) devices and organic photodetectors (OPD), and to OE, OPV and OPD devices comprising these polymers, polymer blends, mixtures or formulations.

BACKGROUND

Organic semiconducting (OSC) materials are receiving growing interest mostly due to their rapid development in the recent years and the lucrative commercial prospects of organic electronics.

One particular area of importance is that of organic photovoltaics (OPV). Conjugated polymers have found use in OPV as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based OPV devices are reported to achieve a power conversion efficiency (PCE) above 8%.

Benzo[1,2-b:4,5-b']dithiophene (BDT) polymers have been suggested in prior art for use in OPV devices, and have been reported to show high power conversion efficiency. BDT polymers have been reported for example in U.S. Pat. No. 7,524,922 (Merck), WO 2010/008672 A1 (Univ. Chicago), US 2010/0078074 A1 (Univ. Cal. L.A.), WO 2010/135701 A1 (Polyera), US 2011/0006287 A1 (Univ. N.C.), WO 2011/063534 A1 (Univ. Laval), WO 2011/085004 A2 (Konarka), US 2011/0178255 A1 (Xerox), WO 2011/131280 A1 (Merck), and WO 2011/156478 A2 (Univ. N.C.).

The polymers disclosed in prior art, like for example in the above-mentioned documents, can be categorised into different types of generic backbone structures.

In a first type, the polymer backbone is formed by two electron donating units D (hereinafter also referred to as "electron donor units" or simply "donor units"), like for example BDT, which are separated by an electron accepting unit A (hereinafter also referred to as "electron acceptor unit" or simply "acceptor unit"), and an optional monomer unit M, which is consisting of one or more aromatic units, as shown in formula a) below.

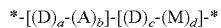

In a second type the polymer backbone is formed by two segments, each consisting of an electron donor unit D, a first spacer unit Sp, an electron acceptor unit A, and a second spacer unit Sp, wherein the spacer units Sp are consisting of one or more aromatic units, such as thiophene, which are not acting as electron acceptors, as shown in formula b) below.

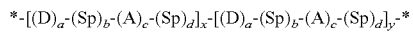

In a third type the polymer backbone is formed by an electron donor unit D, such as BDT, a first spacer unit Sp, an electron acceptor unit A, and a second spacer unit Sp, wherein the spacer units Sp are consisting of one or more aromatic units, such as thiophene, which are not acting as electron acceptors. A polymer of this third type is exemplarily shown in structure 1 below

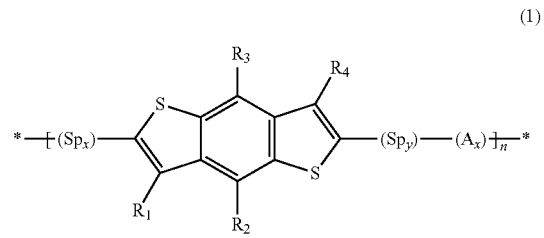

(1)

where $R^{1-4}$ are substituents like for example alkyl or alkoxy groups.

Thus, in the above-mentioned types of polymers the electron donor unit (like BDT) is not directly connected to an electron acceptor unit in the polymer backbone, but is instead flanked by at least two spacer units. Polymers of these types are disclosed for example in WO 2010/135701 A1, US 2011/0006287 A1, WO 2011/085004 A2, WO 2011/131280 A1 and WO 2011/156478 A2.

In a fourth type the polymer backbone is formed by an electron donor unit, such as BDT, that is directly linked to an electron acceptor unit A. A polymer of this fourth type is exemplarily shown in structure 2 below

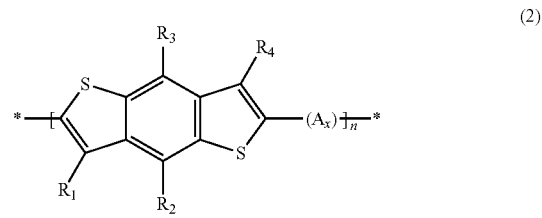

(2)

wherein $R^{1-4}$ are as defined above. Thus, in this fourth type of polymers the electron donor unit (BDT) is directly connected to one electron acceptor unit, and the number of donor units in the polymer backbone is at least equal to the number of acceptor units. Polymers of this second type are disclosed for example in WO 2010/008672 A1, US 2010/0078074 A1, WO 2011/063534 A1 and US 2011/0178255 A1.

However, the polymers disclosed in prior art still leave room for further improvements, like a lower bandgap, better processability especially from solution, higher OPV cell efficiency, and higher stability.

Thus there is still a need for organic semiconducting (OSC) polymers which are easy to synthesize, especially by methods suitable for mass production, show good structural organization and film-forming properties, exhibit good electronic properties, especially a high charge carrier mobility, a good processibility, especially a high solubility in organic solvents, and high stability in air. Especially for use in OPV cells, there is a need for OSC materials having a low bandgap, which enable improved light harvesting by the photoactive layer and can lead to higher cell efficiencies, compared to the polymers from prior art.

It was an aim of the present invention to provide compounds for use as organic semiconducting materials that are easy to synthesize, especially by methods suitable for mass production, and do especially show good processibility, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that one or more of the above aims can be achieved by providing conjugated polymers, which are based on a generic co-polymer design that comprises a core structure of a donor unit D, like for example BDT, which is flanked on each side by an electron acceptor unit A, like for example benzothiadiazole, to form a triad A-D-A, and wherein one or more of these triads are optionally separated in the polymer backbone by further spacer units, like for example thiophene.

The inventors of the present invention found that the incorporation of this structural motif into a polymer backbone extends the electron delocalisation, thus leading to a lower band-gap material while maintaining good structural organisation and charge transport properties which are essential for high power conversion efficiency solar cell.

Such a generic co-polymer design concept has not been suggested in prior art so far. JP 2011-124422 A discloses a copolymer of a formula 4 which comprises a 4,8-dihexyl BDT unit and 1-hexyl-1,2-dihydro-pyrazol-3-one units attached to each side of the BDT unit and being separated by 2,2'-bithiophene units, as shown in structure 3 below.

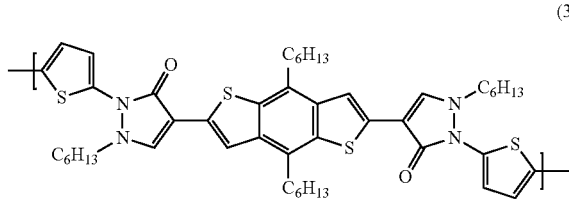

(3)

However, the OPV device disclosed in JP 2011-124422 A which comprises this polymer only has a moderate power conversion efficiency of 3.3%. Apart of this specific polymer JP 2011-124422 A does not propose a systematic approach to a generic polymer design where the polymer backbone is composed from "acceptor-BDT-acceptor" triads.

US 2011/0156018 A1 (corresponding to WO 2010/026972 A1) discloses a polymer for the emitting layer of a polymer LED, wherein the polymer backbone is composed of repeating units of structure 4 or 5 below,

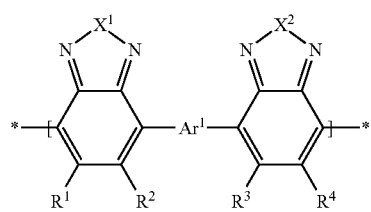

(4)

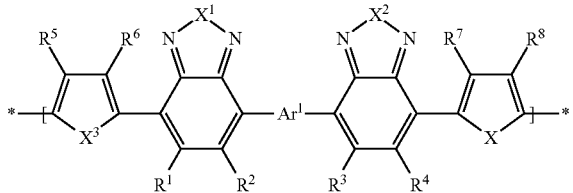

(5)

wherein $Ar^1$ is a divalent heterocyclic group, $X^1$ and $X^2$ are O, S, NR or CR=CR, $X^3$ and $X^4$ are O, S or NR, and $R^{1-8}$ are H alkyl, aryl, and the like. In these repeating units two acceptor units, such as benzothiadiazole or benzooxadiazole, are flanking a central unit $Ar^1$, wherein said central unit $Ar^1$ is selected from a broad variety of possible aromatic units, including both donor and acceptor units.

However, US 2011/0156018 A1 does not disclose or suggest polymers that can be used as donor material in OPV cells. Also, it does not describe the generic concept of a polymer containing only triads A-D-A. Besides, it does not contain any specific examples of substituted acceptor units with solubilising groups in $R^1$ to $R^4$ positions are prepared. Also, the examples are limited to thiophene based polymers only.

Furthermore, the above cited prior art documents do not describe any polymer backbones composed of random or statistical block copolymers including A-D-A sequences, segments or blocks.

Also, in prior art hitherto no generic co-polymer design has been disclosed that comprises repeating units containing donor and acceptor units, wherein all donor units are flanked on both sides by an acceptor unit to form a triad A-D-A, and wherein these triads are linked in the polymer backbone by spacer units such as a thiophene.

SUMMARY

The invention relates to a conjugated polymer that comprises in its backbone one or more electron donor units $D^i$ and one or more electron acceptor units $A^i$, and optionally one or two terminal units T, wherein each donor unit $D^i$ in the polymer backbone is flanked by two acceptor units $A^i$ to form a triad $A^i$-$D^i$-$A^i$, except for $D^i$ units adjacent to a terminal or endcap group T, and wherein these triads $A^i$-$D^i$-$A^i$ are optionally, and preferably, linked by one or more spacer units $Sp^i$, excluding polymers comprising repeating units [A-D-A], wherein A is optionally substituted pyrazolone and D is optionally substituted benzo[1,2-b:4,5-b'] dithiophene.

In a preferred embodiment the polymer comprises in its backbone one or more spacer units $Sp^i$, which are linking the triads $A^i$-$D^i$-$A^i$. The polymers of this preferred embodiment are understood to exclude any polymers or copolymers that are consisting only of repeating units, sequences, segments or blocks selected from the formulae -[$A^1$-$D^1$]-, -[$A^1$-$D^1$-$A^2$-$D^1$]-, -[$A^1$-$D^1$]$_x$-[$A^2$-$D^1$]$_y$- and -[$A^1$-$D^1$-$A^1$]-, wherein $A^1$ and $A^2$ denote independently of each other an acceptor unit and $D^1$ independently of each other denote a donor unit. The spacer units $Sp^i$ are preferably selected such that they do not act as electron acceptor towards the donor unit $D^i$.

Further preferably, the polymer according to this preferred embodiment comprises in its backbone one or more repeating units, sequences, segments or blocks selected from the formulae -[$A^1$-$D^1$]$_x$-[$A^2$-$Sp^1$]$_y$- and -[$A^1$-$D^1$-$A^2$-$Sp^1$]- wherein $A^1$ and $A^2$ denote independently of each other an acceptor unit, $D^1$ denotes a donor unit, and $Sp^1$ denotes a spacer unit which is not acting as electron acceptor towards $D^1$ and is different from $D^1$, and wherein preferably $0<x<1$, $0<y<1$, $x+y=1$, wherein x is the molar ratio of the segments $A^1$-$D^1$ and y is the molar ratio of the segments $A^2$-$Sp^1$. Preferably, in an alternated copolymer -[$A^1$-$D^1$-$A^2$-$Sp^1$]-, the $Sp^1$ unit is consisting only of one ring or condensed ring system, but does not comprise two or more covalently linked rings or ring systems, like for example 5- or 6-members rings such as thiophene or benzene.

In another preferred embodiment the conjugated polymer comprises in its backbone one or more donor units $D^i$ and one or more acceptor units $A^i$, wherein each of said units $D^i$, provided it is not in terminal position in the backbone adjacent to a terminal group or endcap group, is flanked by two units $A^i$ to form a triad $A^i$-$D^i$-$A^i$, and wherein these polymers fulfil the condition f≤s/2+2, wherein f is the total number of said units $D^i$ in the polymer backbone, s is the total number of said units $A^i$ in the polymer backbone and is at least 2, and excluding polymers comprising both optionally substituted pyrazolone units and optionally substituted benzo[1,2-b:4,5-b']dithiophene units.

Preferably the aforementioned donor units $D^1$ and acceptor units $A^1$, and more preferably also the spacer units $Sp^1$, are selected from arylene or heteroarylene units, which are monocyclic or polycyclic and are unsubstituted or substituted.

Preferably the aforementioned donor units $D^i$ are selected from benzo[1,2-b:4,5-b']dithiophene-2,6-diyl that is optionally substituted in one or more of the 3-, 4-, 7- and 8-positions, preferably in 3- and 7-position and/or in 4- and 8-position, 7H-3,4-dithia-7-sila-cyclopenta[a]pentalene-di-2,5-diyl, that is optionally substituted in one or more of the 1-, 6-, 7-, 7'-positions, preferably in 7,7'-positions and 4H-cyclopenta[2,1-b;3,4-b']dithiophene-2,6-diyl, that is optionally substituted in one or more of the 3-, 4-, 4'-, 5-positions preferably in 4,4'-positions.

The invention further relates to a formulation comprising one or more conjugated polymers as described above and below and one or more solvents, preferably selected from organic solvents.

The invention further relates to the use of the conjugated polymers as described above and below as electron donor or p-type semiconductor.

The invention further relates to the use of the conjugated polymers as described above and below as electron donor component in a semiconducting or photoactive material, formulation, polymer blend, device or component of a device.

The invention further relates to a semiconducting material, formulation, polymer blend, device or component of a device comprising a conjugated polymer as described above and below as electron donor component, and preferably further comprising one or more compounds or polymers having electron acceptor properties.

The invention further relates to a mixture or polymer blend comprising one or more conjugated polymers as described above and below and one or more additional compounds which are preferably selected from compounds having one or more of semiconducting, charge transport, hole or electron transport, hole or electron blocking, electrically conducting, photoconducting or light emitting properties.

The invention further relates to a mixture or polymer blend as described above and below, which comprises one or more conjugated polymers as described above and below, and one or more n-type organic semiconductor compounds, preferably selected from fullerenes or substituted fullerenes.

The invention further relates to a formulation comprising a mixture or polymer blend as described above and below and one or more solvents, preferably selected from organic solvents.

The invention further relates to the use of a conjugated polymer, formulation, mixture or polymer blend as described above and below as charge transport, semiconducting, electrically conducting, photoconducting or light emitting material, or in an optical, electrooptical, electronic, electroluminescent or photoluminescent device, or in a component of such a device or in an assembly comprising such a device or component.

The invention further relates to a charge transport, semiconducting, electrically conducting, photoconducting or light emitting material comprising a conjugated polymer, formulation, mixture or polymer blend as described above and below.

The invention further relates to an optical, electrooptical, electronic, electroluminescent or photoluminescent device, or a component thereof, or an assembly comprising it, which comprises a conjugated polymer, formulation, mixture or polymer blend, or comprises a charge transport, semiconducting, electrically conducting, photoconducting or light emitting material, as described above and below.

The optical, electrooptical, electronic, electroluminescent and photoluminescent devices include, without limitation, organic field effect transistors (OFET), organic thin film transistors (OTFT), organic light emitting diodes (OLED), organic light emitting transistors (OLET), organic photovoltaic devices (OPV), organic photodetectors (OPD), organic solar cells, laser diodes, Schottky diodes and organic photoconductors.

The components of the above devices include, without limitation, charge injection layers, charge transport layers, interlayers, planarising layers, antistatic films, polymer electrolyte membranes (PEM), conducting substrates and conducting patterns.

The assemblies comprising such devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

In addition the compounds, polymers, formulations, mixtures or polymer blends of the present invention can be used as electrode materials in batteries and in components or devices for detecting and discriminating DNA sequences.

DETAILED DESCRIPTION

Figure 1:
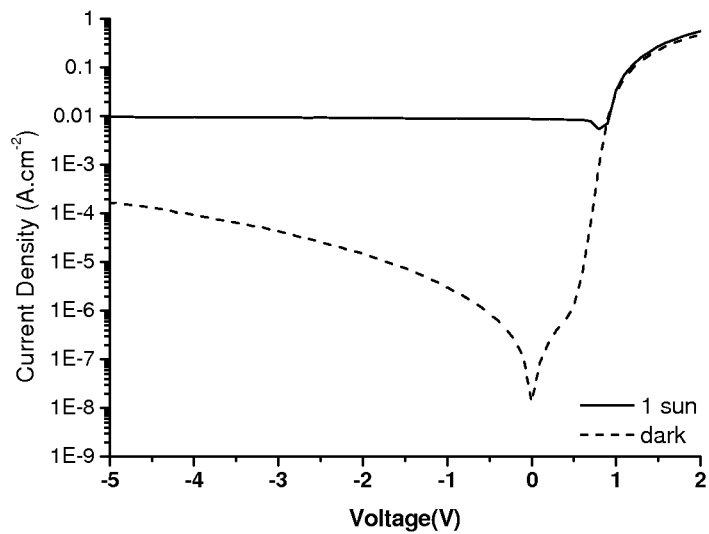
FIG. 1 shows the J-V curve for a blend of polymer 10 and $PC_{60}BM$ (1.0:2.0 ratio) in an OPD device according to the Examples.

As used herein, the term "polymer" will be understood to mean a molecule of high relative molecular mass, the structure of which essentially comprises the multiple repetition of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5 repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, like for example a unit or polymer of formula I, III, IV or their subformulae, an asterisk (*) will be understood to mean a chemical linkage to an adjacent unit or group in the polymer backbone.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit. For example a donor unit D and an acceptor unit A can each represent a repeating unit on its own, or can together form a sequence such as -(A-D-A)- which is a constitutional repeating unit in a polymer of formula -(A-D-A)$_n$-, wherein n is an integer >1.

As used herein, the expression "each donor unit is flanked by two acceptor units" will be understood as being inclusive of repeat units or sequences like -(A-D-A)- or -(A-D-A-A)-, while being exclusive of repeat units like -(A-D-D)-.

As used herein, the feature "f≤s/2+2", wherein f is the total number of donor units, and s is the total number of acceptor units in the polymer backbone and is at least 2, will be understood as being inclusive for example of polymers of the formula -(A-D-A)$_n$- or -(A-D-A-A)$_n$-, while being exclusive of polymers of the formula -(A-D)$_n$-, wherein n is an integer 1. It will further be understood that this feature is also inclusive of polymers with units D that are attached on one side to a terminal group T and on the other side to a unit A, like in the formula T-D-(A-D-A)$_n$-D-T.

As used herein, a "terminal group" (T) will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of R$^5$ or R$^6$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. (see also U.S. Environmental Protection Agency, 2009, Glossary of technical terms, http://www.epa.gov/oust/cat/TUMGLOSS.HTM.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with Sp$^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, which may lead to interruption of the conjugation, is still regarded as a conjugated compound.

As used herein, unless stated otherwise the molecular weight is given as the number average molecular weight $M_n$ or weight average molecular weight $M_W$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" will be understood to mean a carbyl group that does additionally contain one or more H atoms and optionally contains one or more hetero atoms like for example N, O, S, P, Si, Se, As, Te or Ge.

As used herein, the term "hetero atom" will be understood to mean an atom in an organic compound that is not a H- or C-atom, and preferably will be understood to mean N, O, S, P, Si, Se, As, Te or Ge.

A carbyl or hydrocarbyl group comprising a chain of 3 or more C atoms may be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

The terms "aryl" and "heteroaryl" as used herein preferably mean a mono-, bi- or tricyclic aromatic or heteroaromatic group with 4 to 30 ring C atoms that may also comprise condensed rings and is optionally substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, or carbyl or hydrocarbyl with 1 to 40 C atoms that is optionally substituted and optionally comprises one or more hetero atoms, and is preferably alkyl, alkoxy, thioalkyl, alkylcarbonyl, alkoxycarbonyl or alkoxycarbonyloxy with 1 to 20 C atoms that is optionally fluorinated, R$^0$ and R$^{00}$ are independently of each other H or optionally substituted $C_{1-40}$ carbyl or hydrocarbyl, and preferably denote H or alkyl with 1 to 12 C-atoms, and X$^0$ is halogen.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene preferably 2-thiophene, selenophene, preferably 2-selenophene, thieno[3,2-b]thiophene, indole, isoindole, benzofuran, benzothiophene, benzodithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, all of which can be unsubstituted, mono- or polysubstituted with L as defined above. Further examples of heteroaryl groups are those selected from the following formulae.

An alkyl or alkoxy radical, i.e. where the terminal CH$_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more CH$_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $Sp^2$ hybridised vinyl carbon atom is replaced.

A fluoroalkyl group is preferably perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, in particular 1,1-difluoroalkyl, all of which are straight-chain or branched.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-meth-oxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment of the present invention, $R^{1-4}$ are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

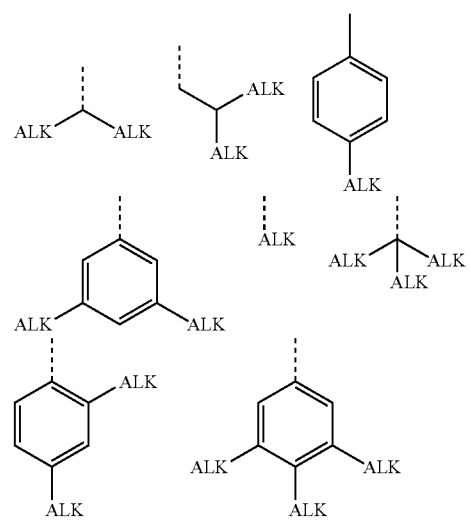

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

—CY¹=CY¹— is preferably —CH=CH—, —CF=CF— or —CH=C(CN)—.

As used herein, "halogen" includes F, Cl, Br or I, preferably F, Cl or Br.

A used herein, —CO—, —C(=O)— and —C(O)— will be understood to mean a carbonyl group, i.e. a group having the structure

The polymers of the present invention are easy to synthesize and exhibit advantageous properties. They show good processability for the device manufacture process, high solubility in organic solvents, and are especially suitable for large scale production using solution processing methods. At the same time, the co-polymers derived from monomers of the present invention and electron donor monomers show low bandgaps, high charge carrier mobilities, high external quantum efficiencies in BHJ solar cells, good morphology when used in p/n-type blends e.g. with fullerenes, high oxidative stability, and a long lifetime in electronic devices, and are promising materials for organic electronic OE devices, especially for OPV devices with high power conversion efficiency.

The polymers of the present invention are especially suitable as p-type semiconducting polymers, in particular for the preparation of blends of p-type and n-type semiconductors which are suitable for use in BHJ photovoltaic devices.

Besides, the polymers of the present invention show the following advantageous properties:
i) The increase in electron acceptor unit content in the polymer leads to a reduced band-gap and therefore the potential for improved light absorption.
ii) The electron acceptor units (A, A¹, A²) flanking both sides of the donor unit, especially of the 3,7- and/or 4,8-substituted benzo[1,2-b:4,5-b']dithiophene donor unit, provide a deeper LUMO energy level, thus reducing the energy loss in the electron transfer process between the polymer and an n-type material (i.e. fullerene, graphene, metal oxide) when used for example in the active layer of a BHJ OPV device.
iii) The addition of unsaturated spacer unit(s) provides additional disorder, flexibility and freedom of rotation in the polymer backbone, leading to improved entropy of solution, especially in non-halogenated solvents, while maintaining sufficient structural order in the polymer backbone, resulting in improved polymer solubility.
iv) The flanking electron acceptor units, which can each possess more than one solubilising group, enable higher polymer solubility in non-halogenated solvents due this increased number of solubilising groups per repeat unit.
v) Additional fine-tuning of the electronic energies (HOMO/LUMO levels) can be done by careful selection of electron acceptor units on each side of the benzo[1,2-b:4,5-b']dithiophene core.
vi) Additional fine-tuning of the electronic energies (Bandgap and HOMO/LUMO levels) by careful selection of the molar ratio for each segment of the polymer.
vii) Additional fine-tuning by careful selection of the molar ratio for each segment of the polymer induces additional disorder in the polymer backbone by increasing the flexibility, the freedom of rotation and/or the disorder in the monomer sequence in the polymer backbone, thus improving the entropy of dissolution while maintaining sufficient structural order in the polymer backbone resulting in improved polymer solubility.

Preferably the donor units $D^i$ are selected from formulae Ia to Ig:

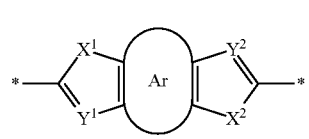

Ia

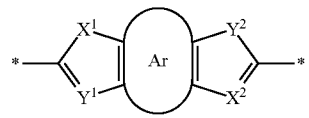

Ib

Ic

Id

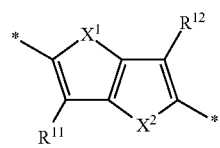

Ie

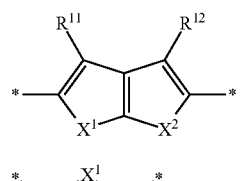

If

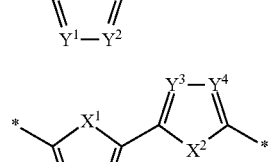

Ig

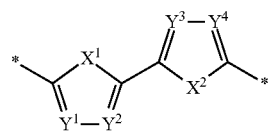

wherein
Ar denotes a carbocyclic, heterocyclic, aromatic or heteroaromatic group, which comprises one or more saturated or unsaturated rings that are covalently linked or fused, which is fused to the terminal five-membered rings in formula Ia and Ib to form a conjugated system, and which is unsubstituted or substituted, preferably by one or more groups $R^1$,
$Ar^1$ denotes a carbocyclic, heterocyclic, aromatic or heteroaromatic group, which comprises one or more saturated or unsaturated rings that are covalently linked or fused, which is fused to the divalent five-membered ring in formula Ig, and which is unsubstituted or substituted, preferably by one or more groups $R^1$,
$X^1$ and $X^2$ denote independently of each other O, S, Se, Si or $NR^1$,
$Y^{1-4}$ denote independently of each other $CR^1$ or N,
$R^1$ denotes H, halogen, or an optionally substituted carbyl or hydrocarbyl group wherein one or more C atoms are optionally replaced by a hetero atom and $R^{11}$ and $R^{12}$ independently of each other denote H or have one of the meanings of $R^1$.

Preferred groups Ar and $Ar^1$ are selected from benzene, pyrazine, 2H-pyran, 1,4-dioxane, naphthalene, anthracene, cyclopentadiene, thiophene, pyrrole, furan, 1H-silole, thieno[3,2-b]thiophene, thieno[2,3-b]thiophene, 1,5-dihydro-s-indacene, 1,7-dihydro-s-indacene, 1,5-disila-s-indacene, 1,7-disila-s-indacene, pyrrolo[3,2-f]indole, pyrrolo[2,3-f]indole, all of which are unsubstituted or substituted by one or more groups $R^1$.

Very preferably donor units $D^i$ are selected from the following formulae or their mirror images:

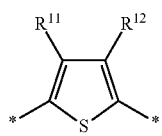 (D1)

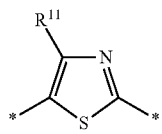 (D2)

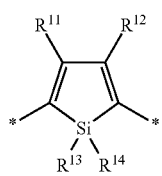 (D3)

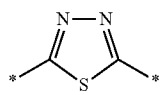 (D4)

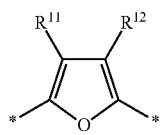 (D5)

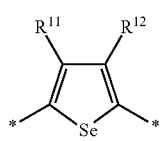 (D6)

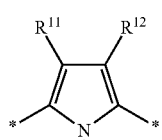 (D7)

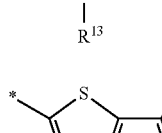 (D8)

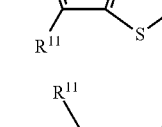 (D9)

-continued

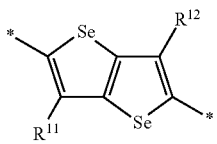 (D10)

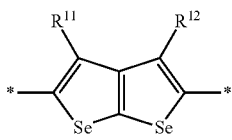 (D11)

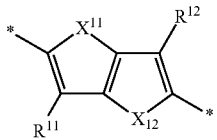 (D12)

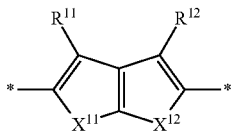 (D13)

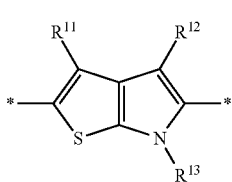 (D14)

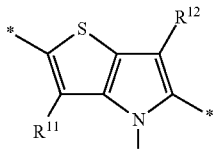 (D15)

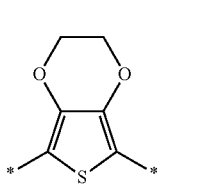 (D16)

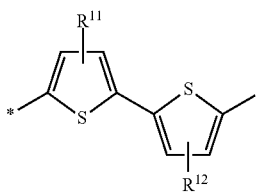 (D17)

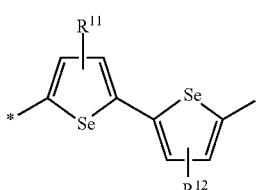 (D18)

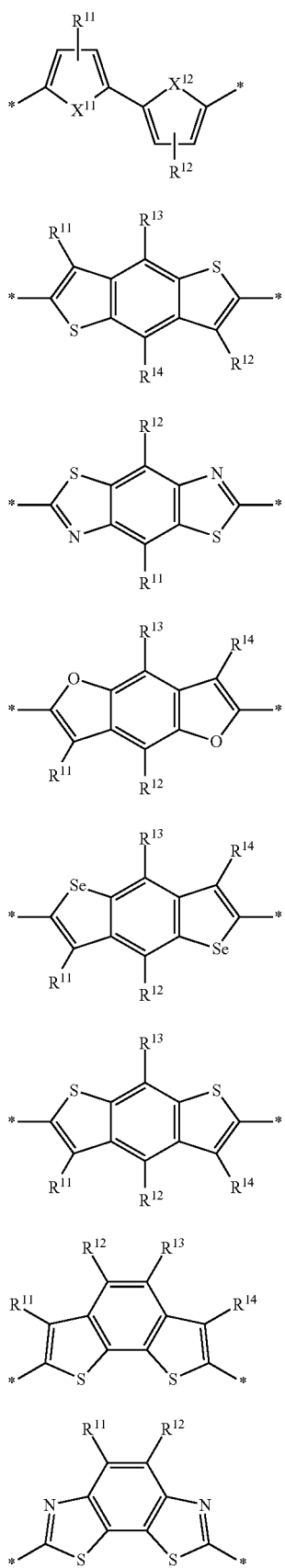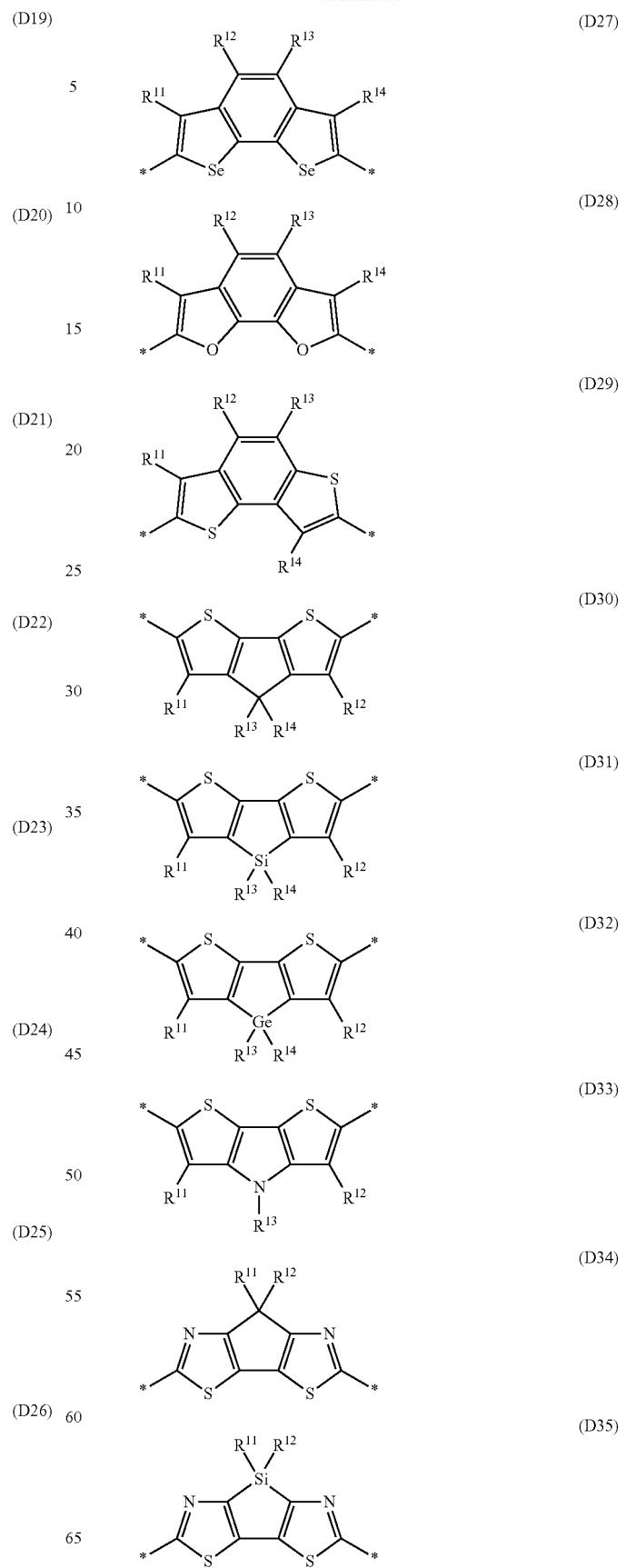

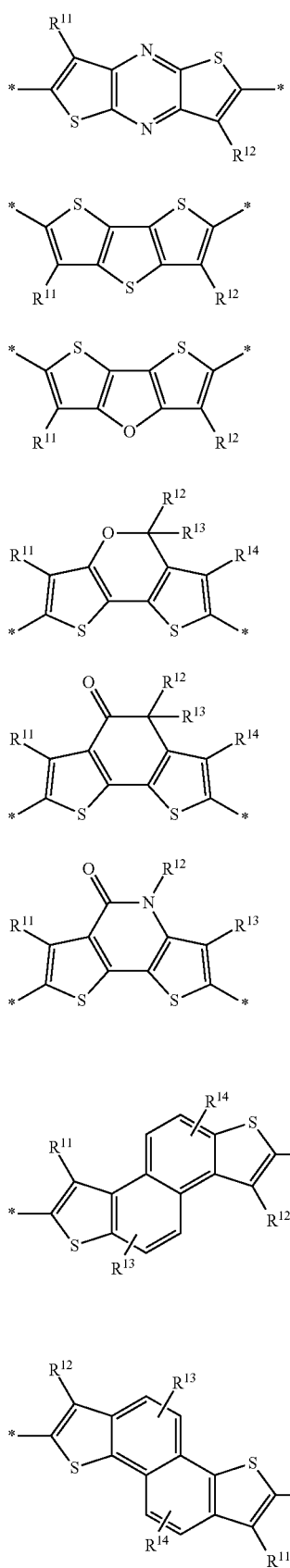
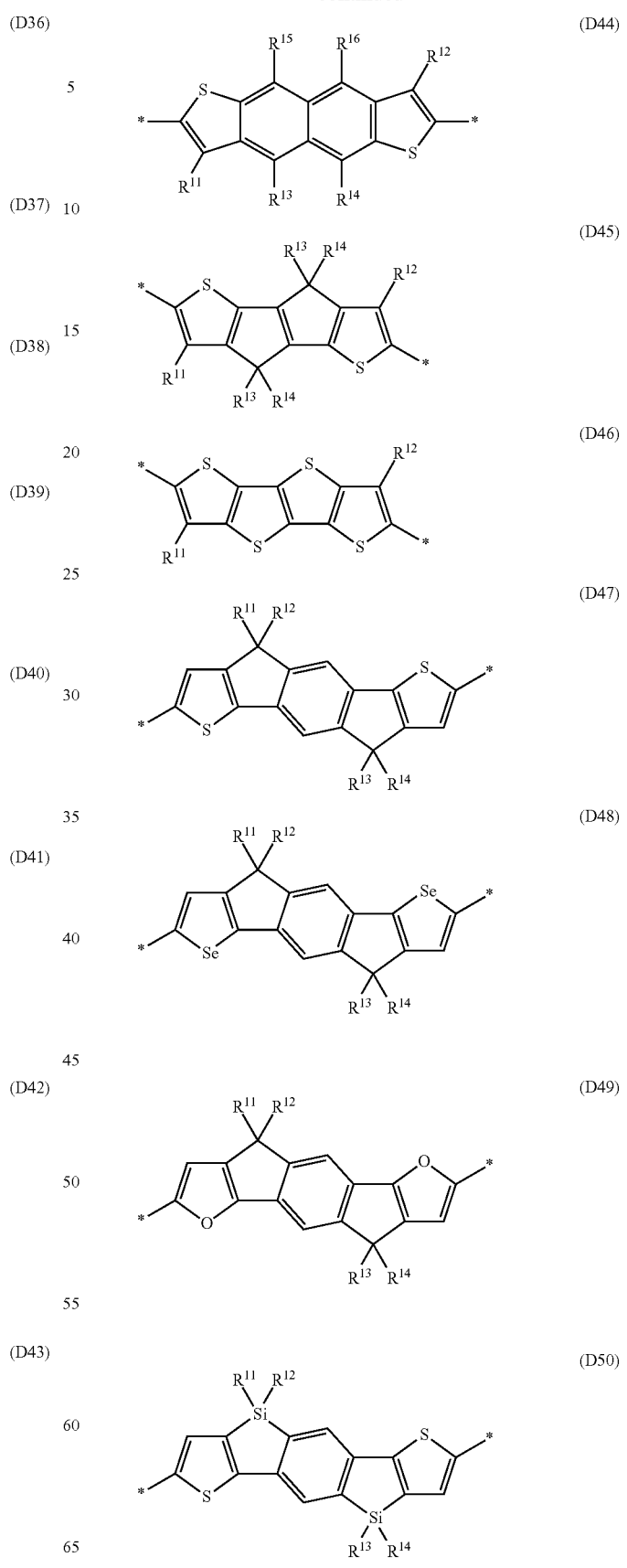

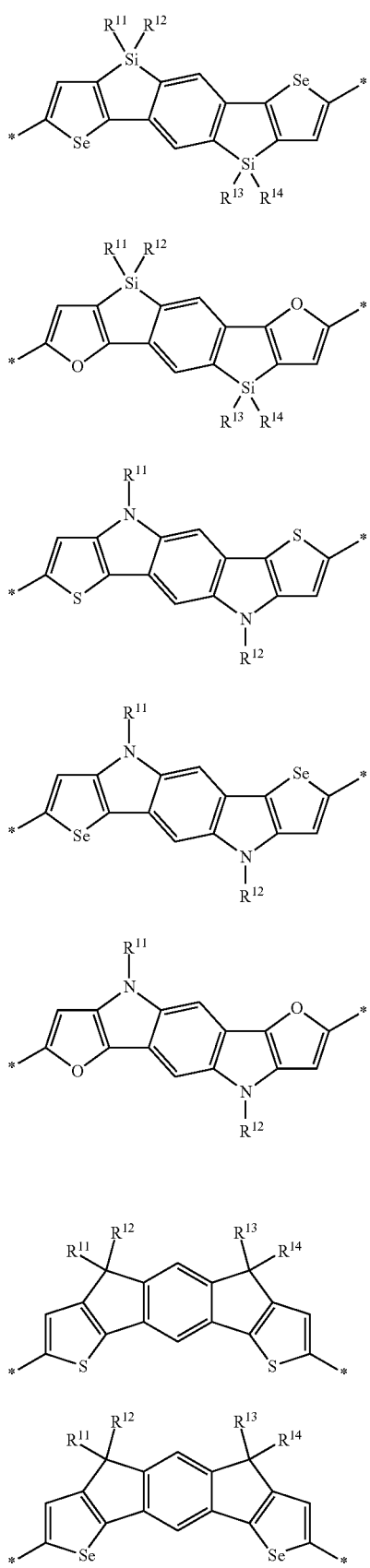
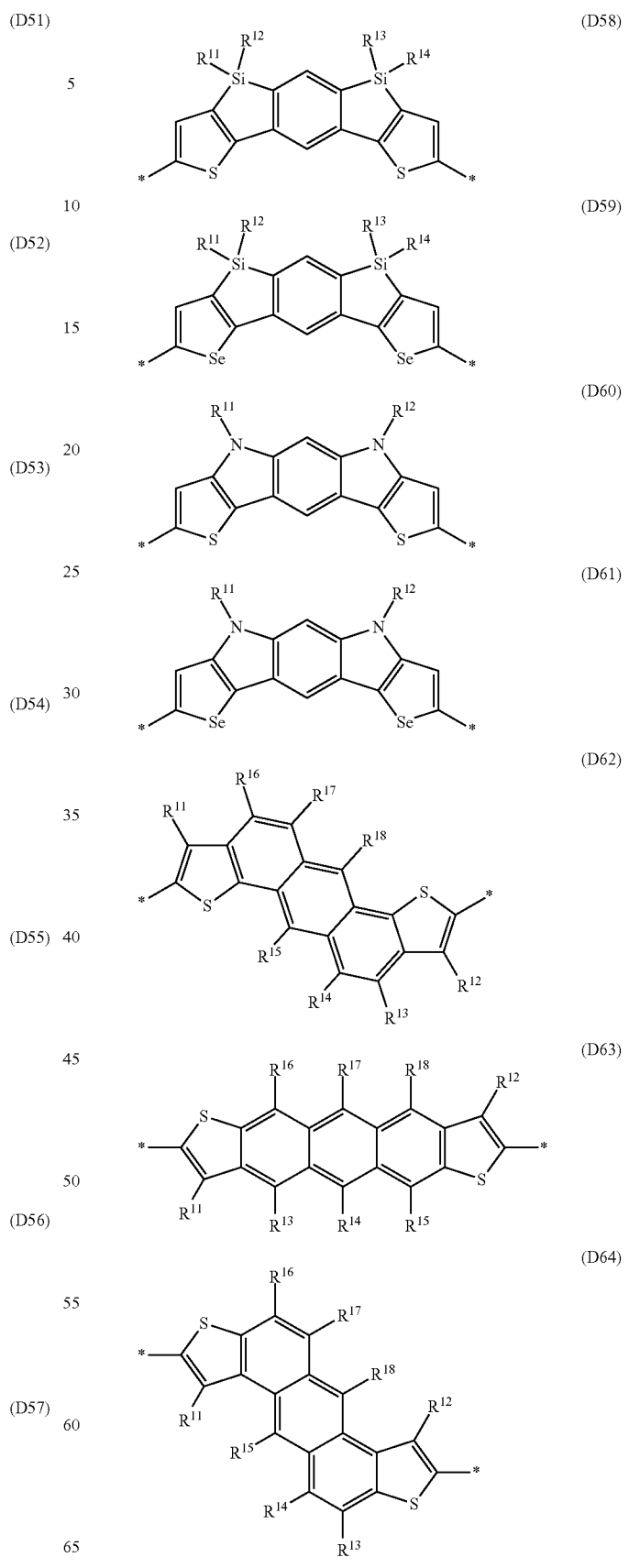

-continued (D65)
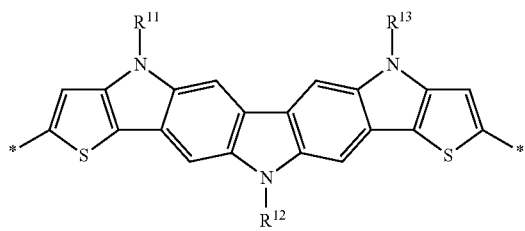

(D66)
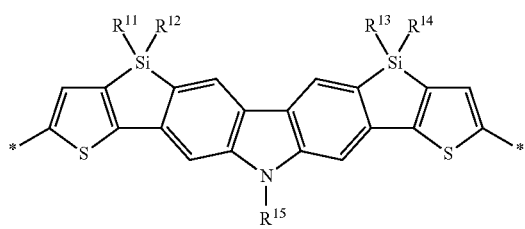

(D67)
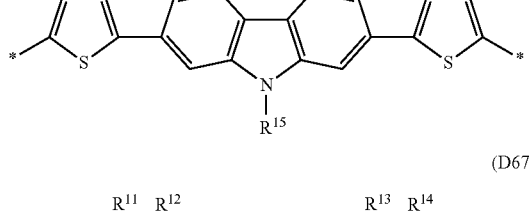

(D68)
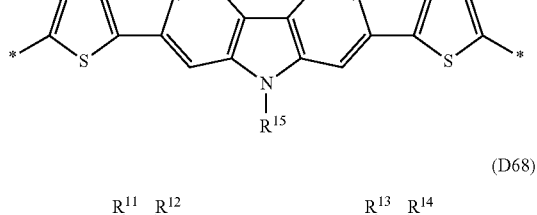

(D69)
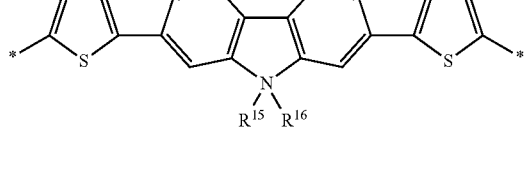

(D70)
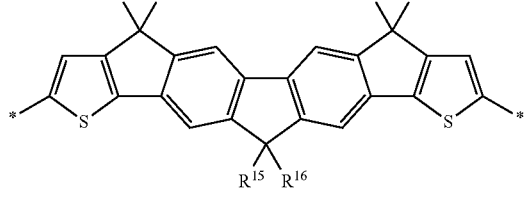

-continued (D71)
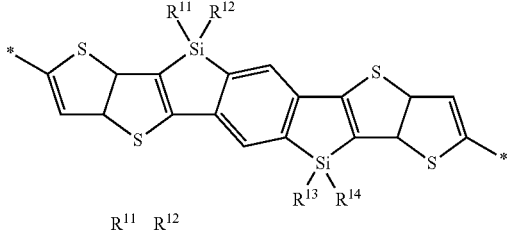

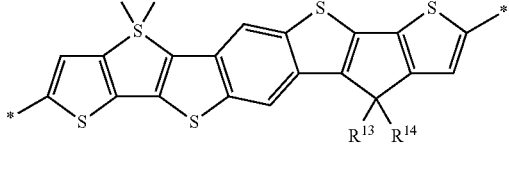

wherein one of $X^{11}$ and $X^{12}$ is S and the other is Se, and $R^{11}$, $R^{12}$, $R^{13}$, $R^{14}$, $R^{15}$, $R^{16}$, $R^{16}$, $R^{17}$ and $R^{18}$ independently of each other denote H or have one of the meanings of $R^1$ as defined above and below.

Very preferably the donor units $D^i$ are selected from the following formulae

Ia1
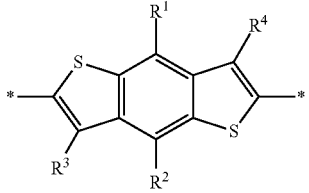

Ia2
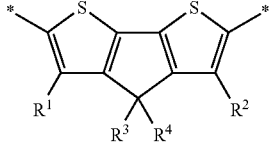

Ia3
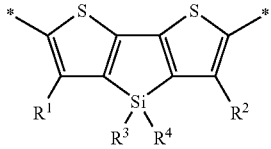

wherein $R^{1-4}$ independently of each other denote H, halogen, or an optionally substituted carbyl or hydrocarbyl group wherein one or more C atoms are optionally replaced by a hetero atom.

Preferably in the units of formula Ia1 $R^1$ and $R^2$ are different from H and/or $R^3$ and $R^4$ are different from H, and in the unit of formula Ia2 and Ia3 $R^3$ and $R^4$ are different from H or halogen.

Preferably $R^{1-4}$, when being different from H, are selected from straight-chain, branched or cyclic alkyl with 1 to 30 C atoms, in which one or more non-adjacent CH$_2$ groups are optionally replaced by —O—, —S—, —C(O)—, —C(O)—O—, —O—C(O)—, —O—C(O)—O—, —SO$_2$—, —SO$_3$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, wherein R$^0$ and R$^{00}$ are independently of each other H or optionally substituted $C_{1-40}$ carbyl or hydrocarbyl, and preferably denote H or alkyl with 1 to 12 C-atoms, and $Y^1$ and $Y^2$ denote H, F or CN.

Very preferably $R^{1-4}$, when being different from H, are selected from straight-chain or branched alkyl, alkoxy, sulfanylalkyl, sulfonylalkyl, alkylcarbonyl, alkoxycarbonyl and alkylcarbonyloxy with 1 to 30 C atoms which is unsubstituted or substituted by one or more F atoms.

Further preferably $R^{1-4}$, when being different from H, are selected from from aryl or heteroaryl that is optionally substituted and has 4 to 30 ring atoms.

If one or more of $R^{1-4}$ is substituted aryl or heteroaryl, it is preferably substituted by one or more groups L, wherein L is selected from P-Sp-, F, Cl, Br, I, —OH, —ON, —NO$_2$, —NCO, —NCS, —OCN, —SON, —C(=O)NR$^0$R$^{00}$, —C(=O)X$^0$, —C(=O)R$^0$, —NR$^0$R$^{00}$, C(=O)OH, optionally substituted aryl or heteroaryl having 4 to 20 ring atoms, or straight chain, branched or cyclic alkyl with 1 to 20, preferably 1 to 12 C atoms wherein one or more non-adjacent CH$_2$ groups are optionally replaced, in each case independently from one another, by —O—, —S—, —NR$^0$—, —SiR$^0$R$^{00}$—, —C(=O)—, —C(=O)O—, —CY$^1$=CY$^2$— or —C≡C— in such a manner that O and/or S atoms are not linked directly to one another and which is unsubstituted or substituted with one or more F or Cl atoms or OH groups, X$^0$ is halogen, preferably F, Cl or Br, and $Y^1$, $Y^2$, R$^0$ and R$^{00}$ have the meanings given above and below.

Further preferred groups $R^{1-4}$ are selected from —C(O)-aryl, —C(O)-heteroaryl, —C(O)—O-aryl, —C(O)—O-heteroaryl, —O—C(O)-aryl and —O—C(O)-heteroaryl, —SO$_2$-aryl, —SO$_2$-heteroaryl, —SO$_3$-aryl, —SO$_3$-heteroaryl, wherein "aryl" and "heteroaryl" have the meanings given above and below.

Preferably the acceptor units $A^i$ are selected from the following formulae or their mirror images:

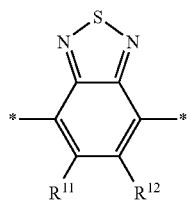

(A1)

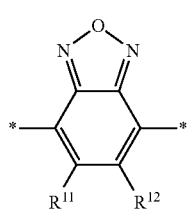

(A2)

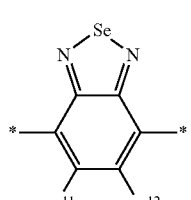

(A3)

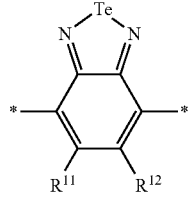

(A4)

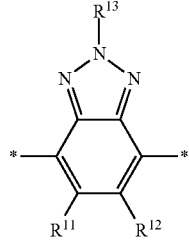

(A5)

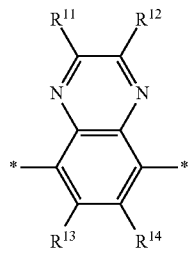

(A6)

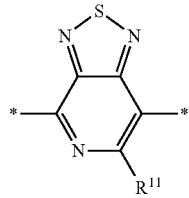

(A7)

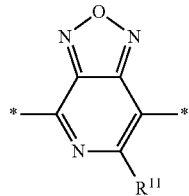

(A8)

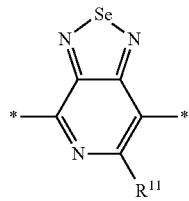

(A9)

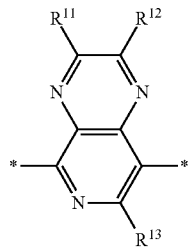

(A10)

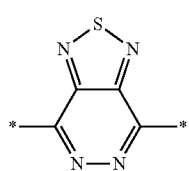 (A11)
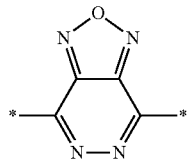 (A12)
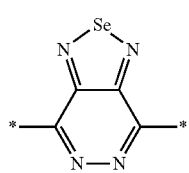 (A13)
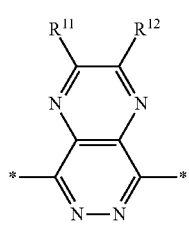 (A14)
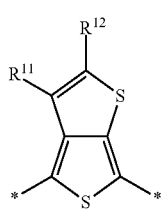 (A15)
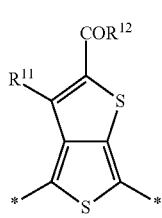 (A16)
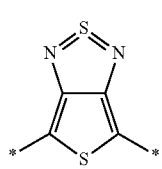 (A17)
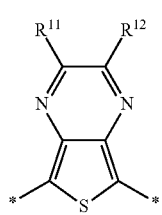 (A18)
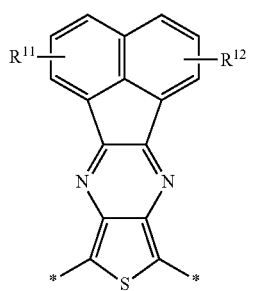 (A19)
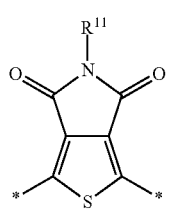 (A20)
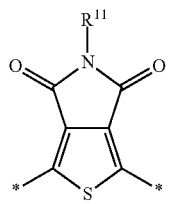 (A21)
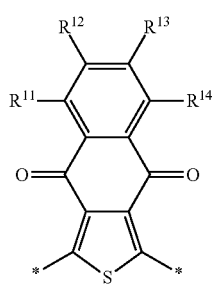 (A22)
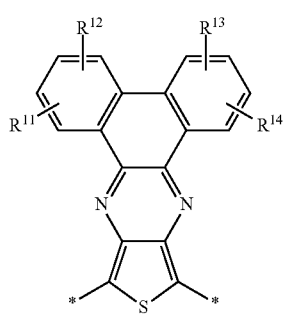 (A23)

-continued
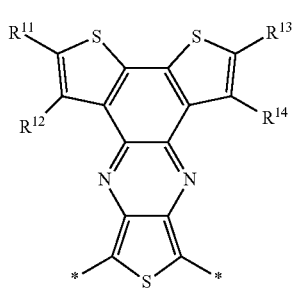
(A24)
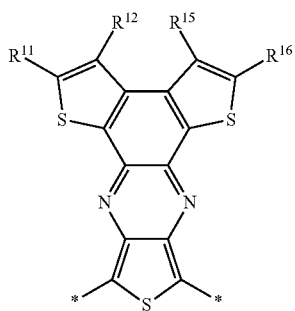
(A25)
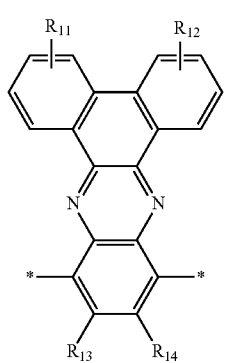
(A26)
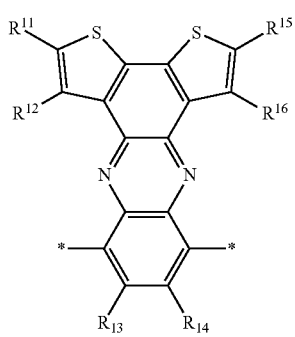
(A27)
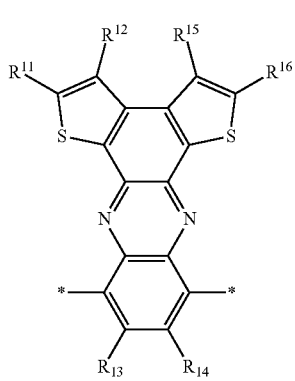
(A28)
-continued
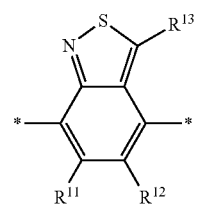
(A29)
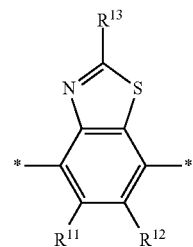
(A30)
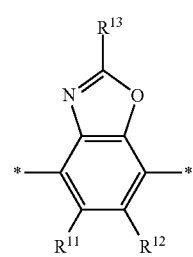
(A31)
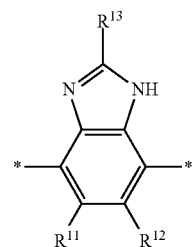
(A32)
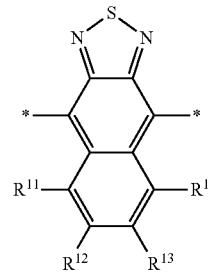
(A33)
(A34)

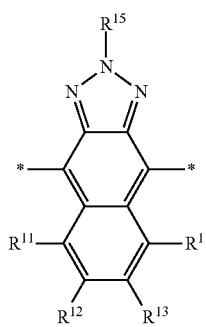 (A35)
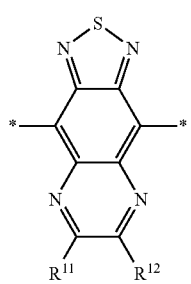 (A36)
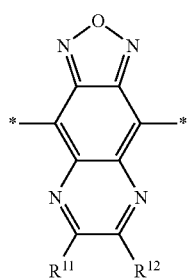 (A37)
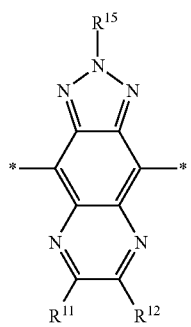 (A38)
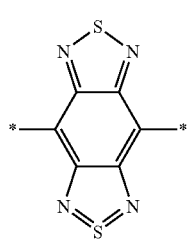 (A39)
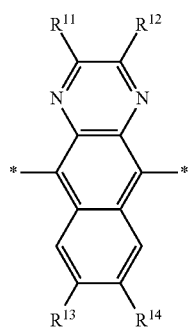 (A40)
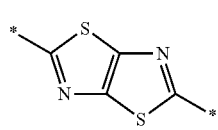 (A41)
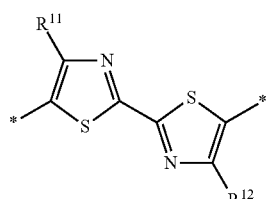 (A42)
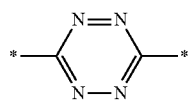 (A43)
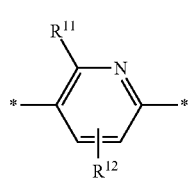 (A44)
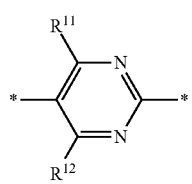 (A45)
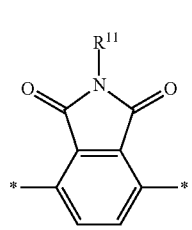 (A46)
(A47)

(A48)
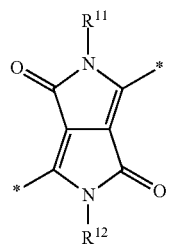
(A49)
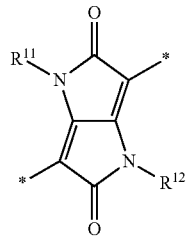
(A50)
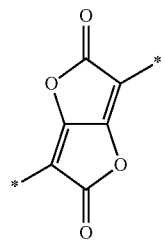
(A51)
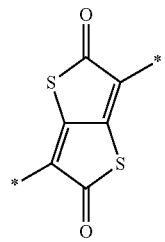
(A52)
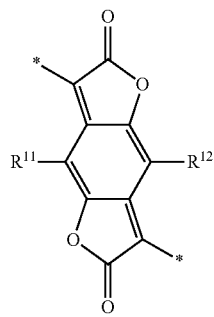
(A53)
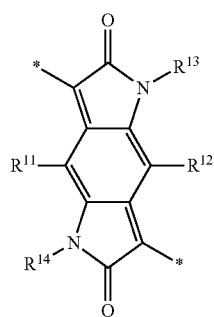
(A54)
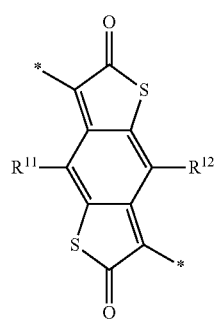
(A55)
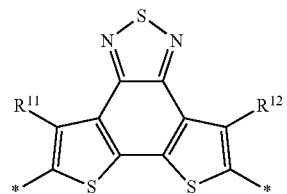
(A56)
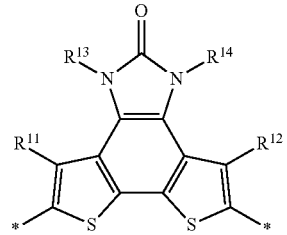
(A57)
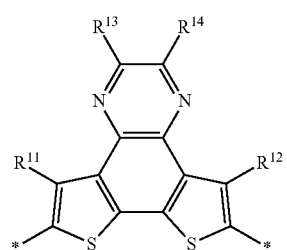
(A58)
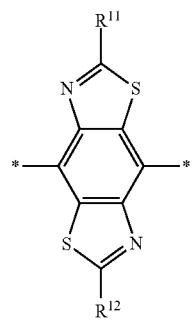

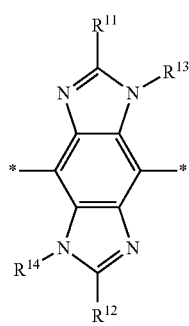 (A59)
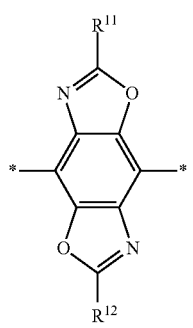 (A60)
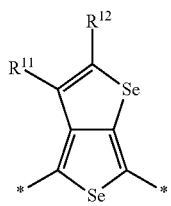 (A61)
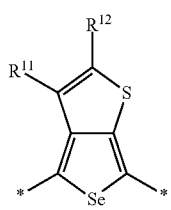 (A62)
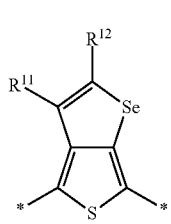 (A63)
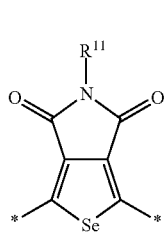 (A64)
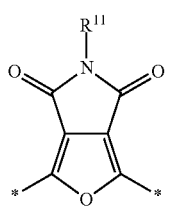 (A65)
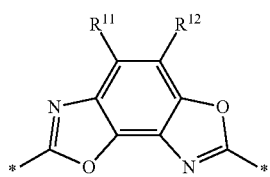 (A66)
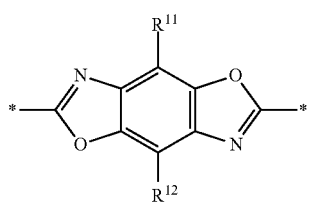 (A67)
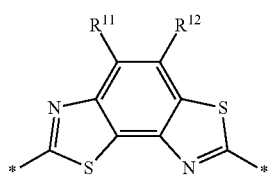 (A68)
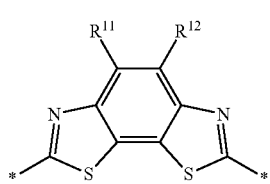 (A69)
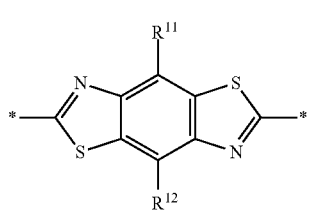 (A70)
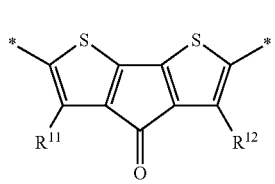 (A71)
(A72)

-continued
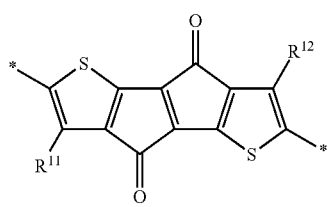 (A73)
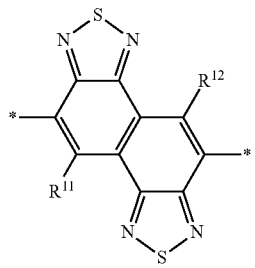 (A74)
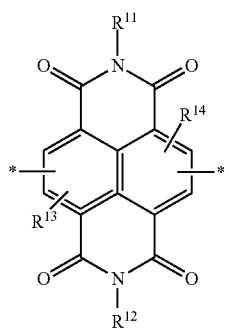 (A75)
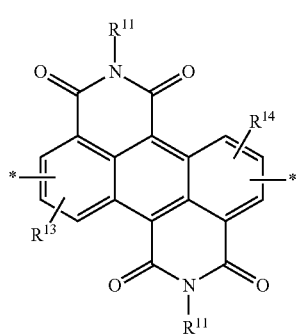 (A76)
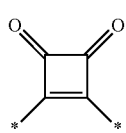 (A77)
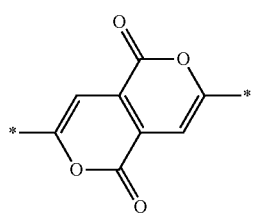 (A78)
-continued
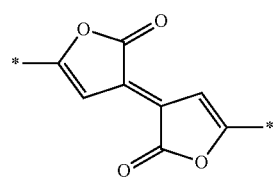 (A79)
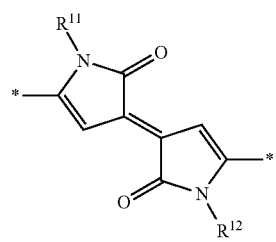 (A80)
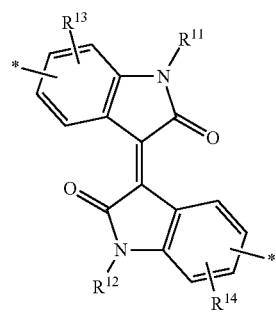 (A81)
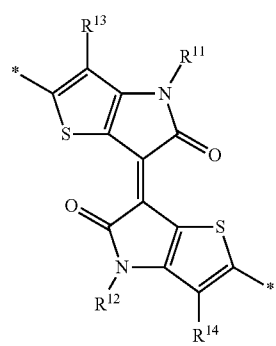 (A82)
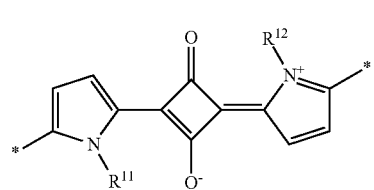 (A83)

(A84) 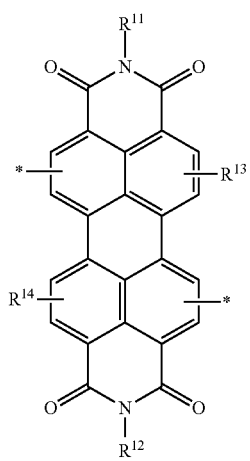
(A85) 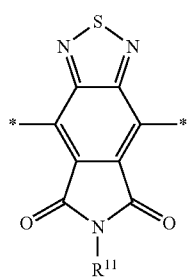
(A86) 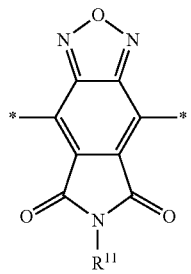
(A87) 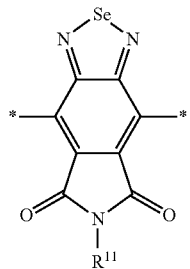
(A88) 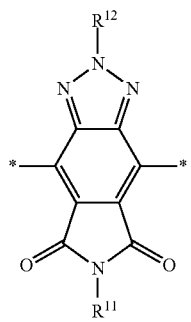
(A89) 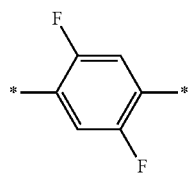
(A90) 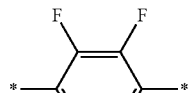
(A91) 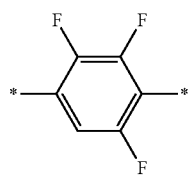
(A92) 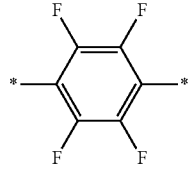
(A93) 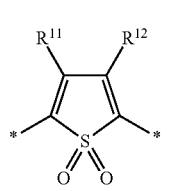
(A94) 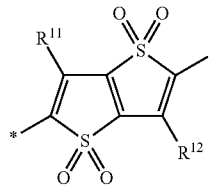
(A95) 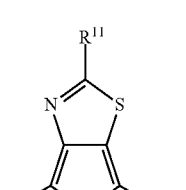
(A96) 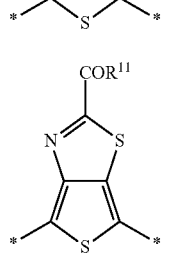
wherein $R^{11}$, $R^{12}$, $R^{13}$ and $R^{14}$ independently of each other denote H or have one of the meanings of $R^1$ as defined above and below.
Very preferably the polymer according to the present invention comprises in its backbone one or more acceptor units $A^i$ selected from the formulae A1, A2, A3, A7, A15, A16, A20, A21, A36, A39, A40, A74 and A85 or their mirror images.

In another preferred embodiment of the present invention the conjugated polymers comprise, in addition to the donor and acceptor units $D^i$ and $A^i$, one or more third units $Sp^i$, hereinafter also referred to as "spacer units", that are different from the donor and acceptor units $D^i$ and $A^i$ and are selected from divalent, mono- or polycyclic, and optionally substituted, arylene and heteroarylene, or from —$CY^1$=$CY^2$— or —C≡C—, wherein $Y^1$ and $Y^2$ independently of each other denote H, F, Cl or CN.

Preferably the spacer units $Sp^i$ are linked to the acceptor units A', but are not linked to the donor units $D^i$, thus acting as spacers between the acceptor units. Further preferably the spacer units $Sp^i$ are not acting as electron acceptor towards the donor units.

Preferably the spacer units $Sp^i$ are selected from formulae D1 to D72 above or their mirror images. If the donor units $D^i$ are selected from formulae Ia1 to Ia3 then the spacer units $Sp^i$ are preferably selected from formulae D1-D19, D21 to D29 and D32 to D72 or their mirror images.

Very preferably the polymer according to the present invention comprises in its backbone one or more spacer units $Sp^i$ selected from the following formulae:

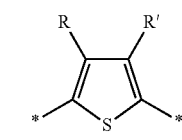
Sp1

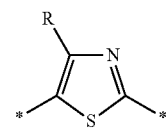
Sp2

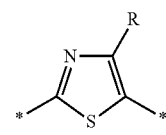
Sp3

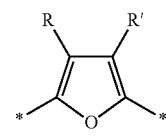
Sp4

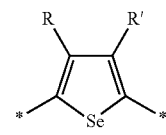
Sp5

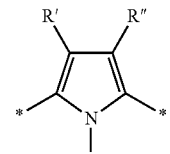
Sp6

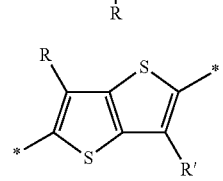
Sp7

-continued

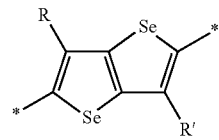
Sp8

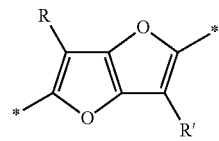
Sp9

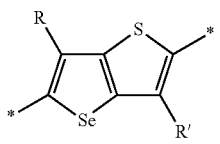
Sp10

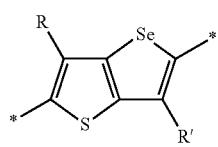
Sp11

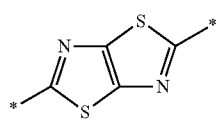
Sp12

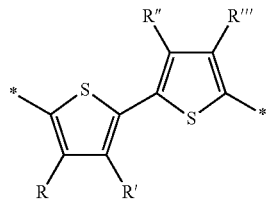
Sp13

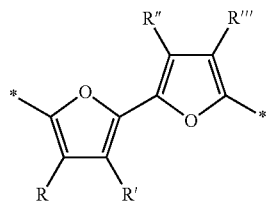
Sp14

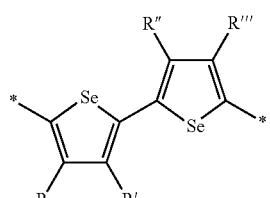
Sp15

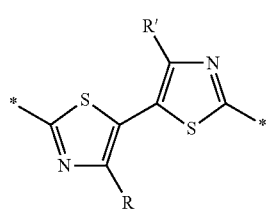
Sp16

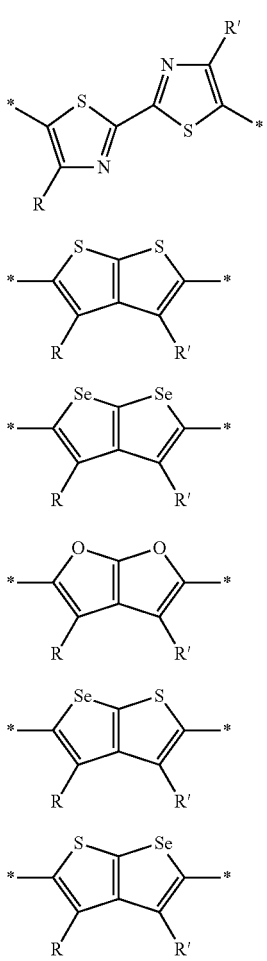

wherein R, R', R" and R'" have one of the meanings of $R^1$ in formula Ia-g or its preferred meanings as given above and below.

Preferred conjugated polymers according to the present invention comprise in their backbone one or more repeat units of formula II:

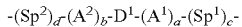   II wherein
$D^1$ is a donor unit selected of formulae Ia to Ig or Ia1, Ia2 or Ia3,
$A^1$ and $A^2$ independently of each other denote an acceptor unit that is different from $D^1$, $Sp^1$ and $Sp^2$, and is preferably selected from arylene or heteroarylene that are mono- or polycyclic and are optionally substituted, very preferably of formulae A1-A96,
$Sp^1$ and $Sp^2$ independently of each other denote a spacer unit, which is different from $D^1$, $A^1$ and $A^2$, and is selected from arylene or heteroarylene that are mono- or polycyclic and are optionally substituted, very preferably of formulae D1 to D72 or Sp1 to Sp22, or denote —$CY^1$=$CY^2$— or —C≡C—,
$Y^1$ and $Y^2$ independently of each other denote H, F, Cl or CN,
a, b independently of each other denote 1, 2, 3 or 4,
c, d independently of each other denote 0, 1, 2, 3 or 4, and preferably c+d≥1.

Further preferred conjugated polymers comprise in their backbone one or more repeat units of formula II1

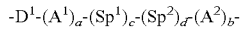   II1 wherein $D^1$, $A^1$, $A^2$, $Sp^1$, $Sp^2$, a, b, c and d are as defined in formula II.

Further preferred conjugated polymers according to the present invention comprise in their backbone one or more repeat units selected of formulae III1, III2, III3 and III4, and optionally one or more repeat units of formula III5 or III6, or their respective mirror images:

   III1

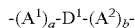   III2

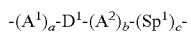   III3

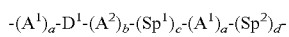   III4

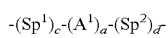   III5

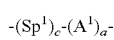   III6 wherein $D^1$, $A^1$, $Sp^1$, a and c are as defined in formula II, and wherein a unit $D^1$ is not linked to a unit $Sp^1$.

Preferred conjugated polymers according to the present invention are selected from the following formulae:

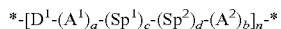   IV1

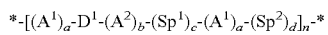   IV2 wherein $D^1$, $A^1$, $A^2$, $Sp^1$, $Sp^2$, a, b, c and d are as defined in formula II, and n is an integer >1.

The polymers of formula IV1 can also be represented by formula IV1*

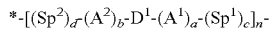   IV1* wherein $D^1$, $A^1$, $A^2$, $Sp^1$, $Sp^2$, a, b, c, d and n are as defined in formula IV1.

Further preferred polymers according to the present invention are selected from the following formula

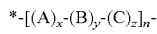   V wherein
A is a unit of formula III1, III2, III3 or III4, or its mirror image,
B and C are independently of each other a unit of formula III5 or III6, or its mirror image,
x is >0 and <1,
y is >0 and <1,
z is ≥0 and >1,
y≥x,
x+y+z is 1,
n is an integer >1.

Preferred polymers of formula V are selected from the following formulae:

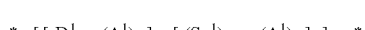   V1

   V2

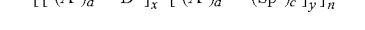   V3

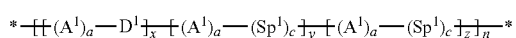   V4

-continued

V5

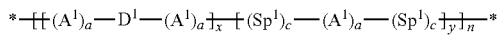

wherein $D^1$, $A^1$, $Sp^1$, a, c, x, y and n are as defined in formula V.

In the polymers according to the present invention, the total number of repeat units n is preferably from 2 to 10,000. Preferably the total number of repeat units n is ≥5, very preferably ≥10, most preferably ≥50, further preferably ≤500, very preferably ≤1,000, most preferably ≤2,000, including any combination of the aforementioned lower and upper limits of n.

The polymers of the present invention include homopolymers and copolymers, like statistical or random copolymers, alternating copolymers and block copolymers, as well as combinations thereof.

In the polymers represented by formula V, x denotes the mole fraction of units A, y denotes the mole fraction of units B, z denotes the mole fraction of units C, and n denotes the degree of polymerisation or total number of units A, B and C. These formulae includes block copolymers, random or statistical copolymers and alternating copolymers of A, B and C. Preferred polymers of formula IV1, IV2 and V are selected of the following subformulae.

IV1a

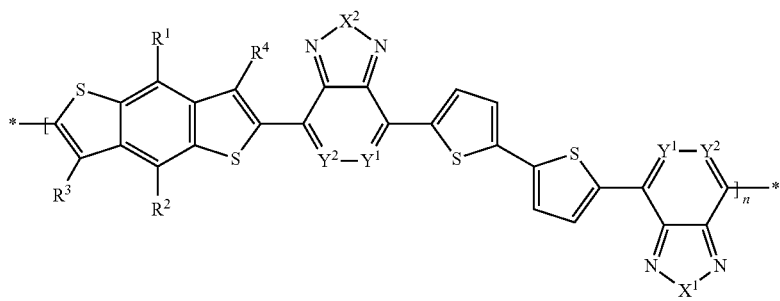

IV1b

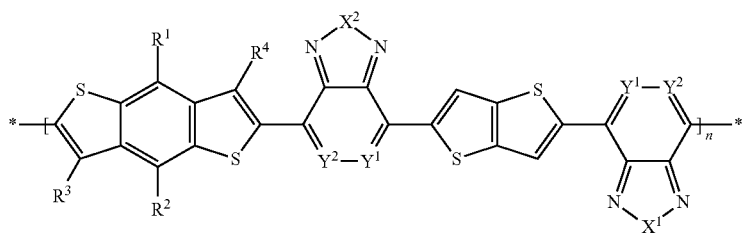

IV1c

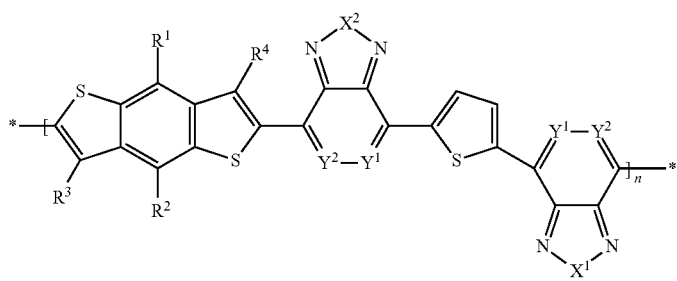

IV1d

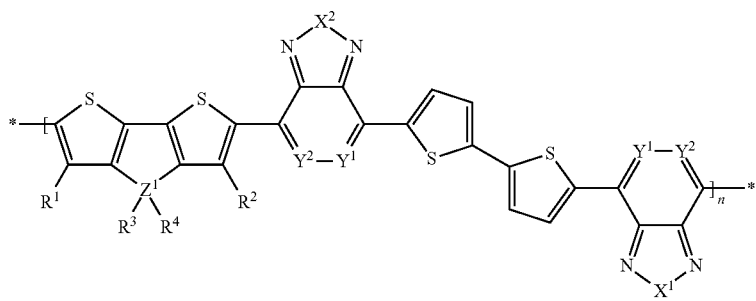

-continued
IV1e
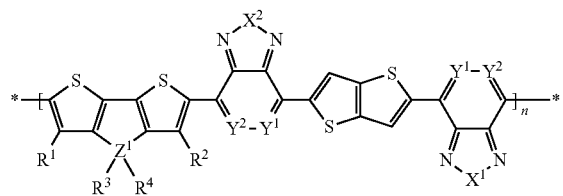
IV1f
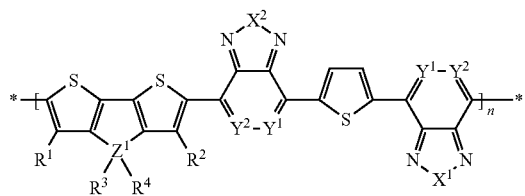
IV1g
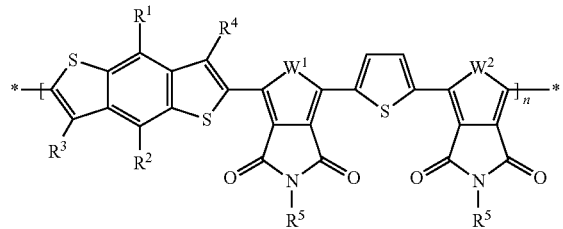
IV1h
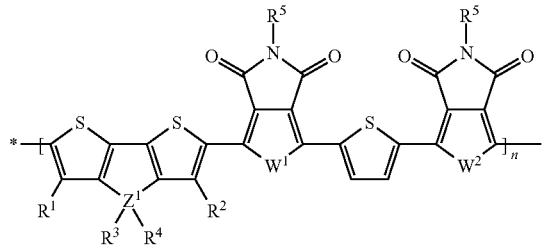
IV2a
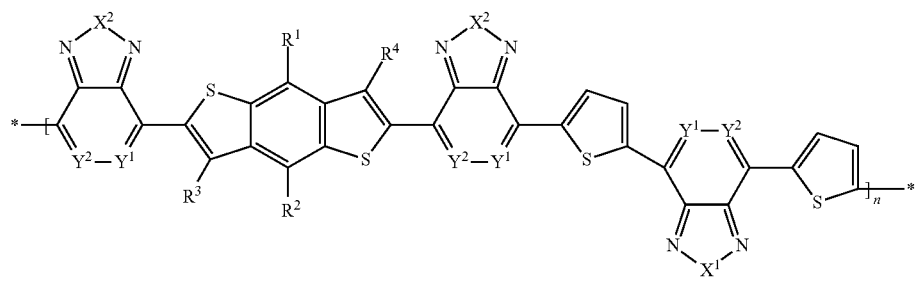
V1a
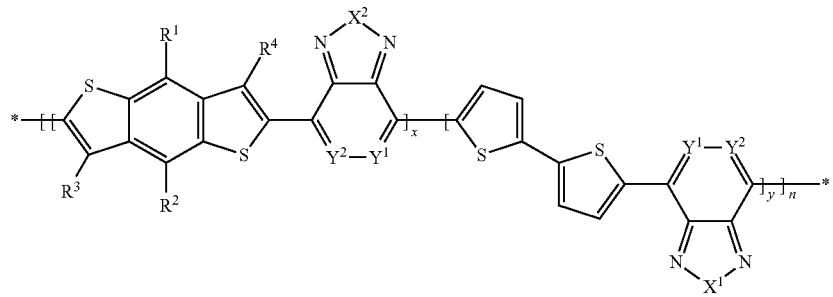
V1b
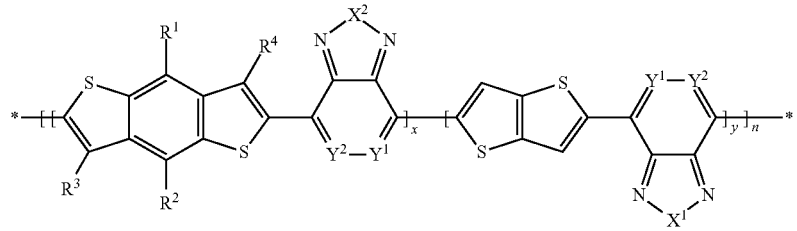
V1c
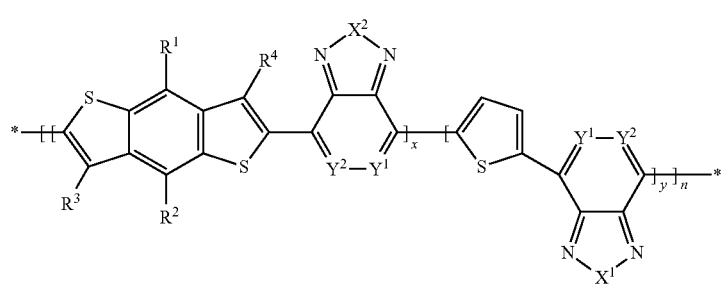

-continued
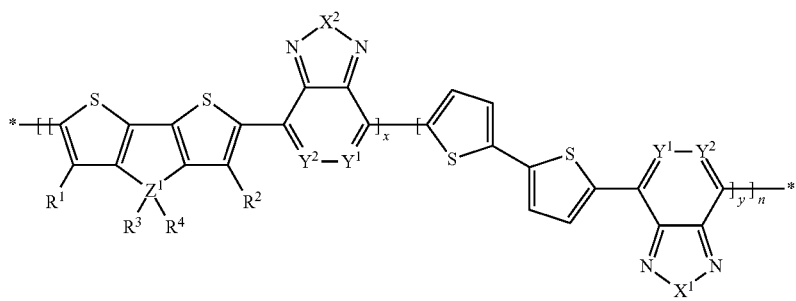
V1d
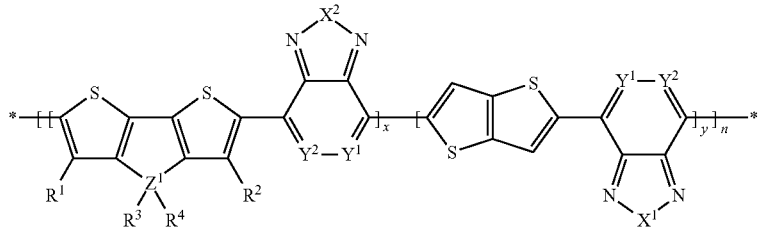
V1e
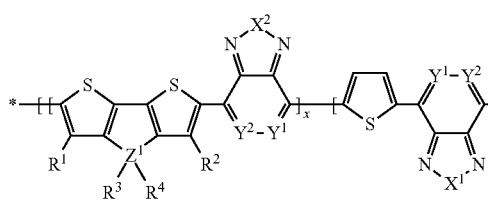
V1f
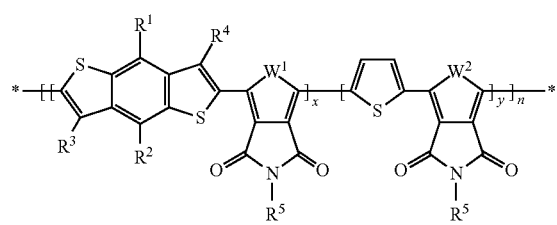
V1g
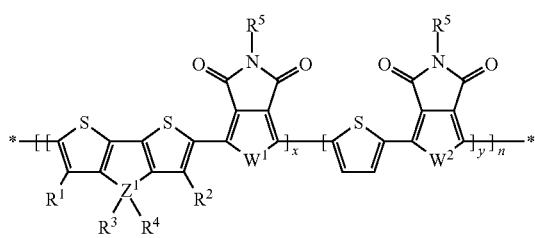
V1h
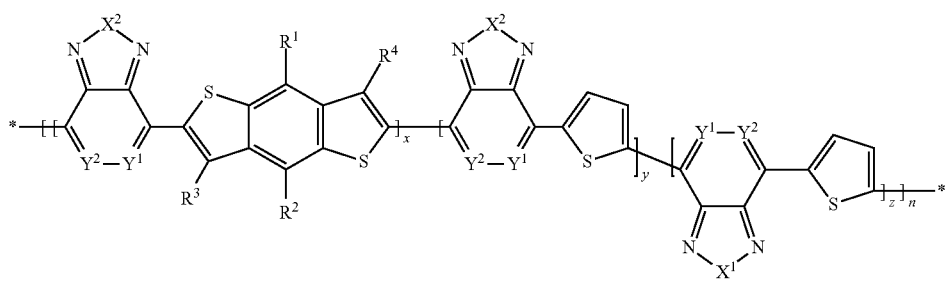
V2a
V3a
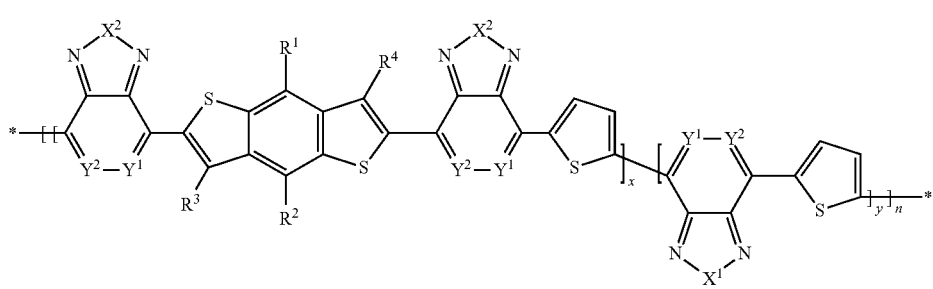
V4a -continued

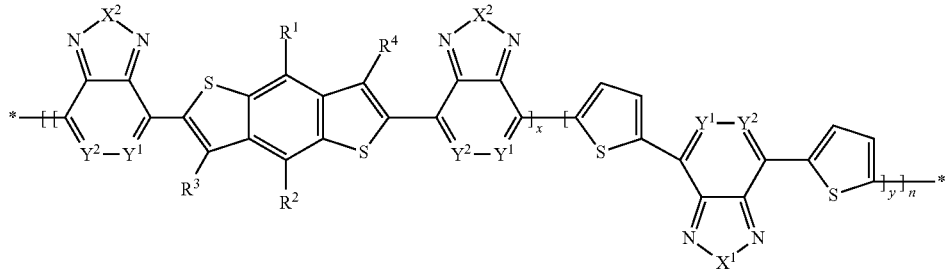
V5a wherein $X^1$ and $X^2$ are independently of each other NR, O, S or Se, $Y^1$ and $Y^2$ are independently of each other N, CH or CR, $Z^1$ is independently of each other C, Si or Ge, $W^1$ and $W^2$ are independently of each other O, S or Se, $R^{1-4}$ have the meanings given above and below, R has one of the meanings of $R^1$ as given above and below, and x, y and n are as defined in formula V.

Very preferred polymers of formula IV1, IV2 and V are selected of the following subformulae.

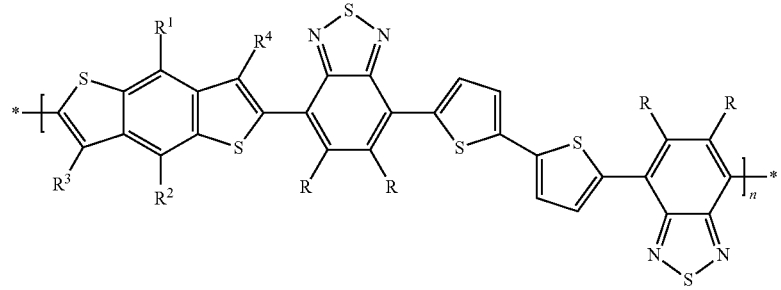
IV1a1

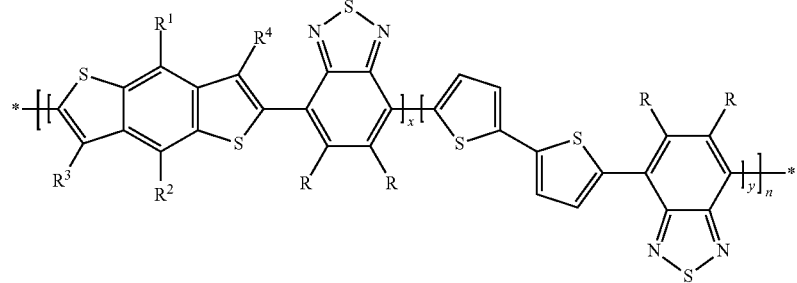
V1a1

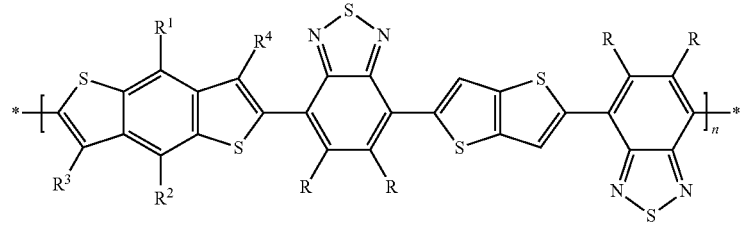
IV1b1

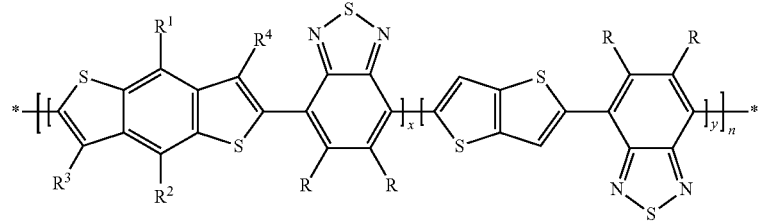
V1b1

-continued
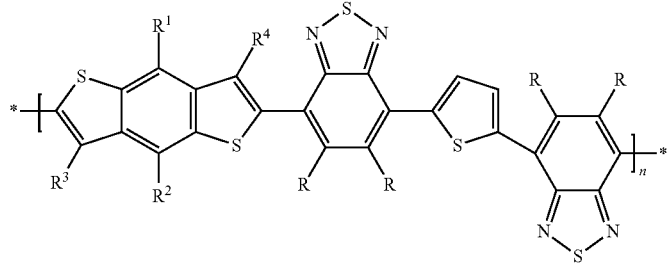
IV1c1
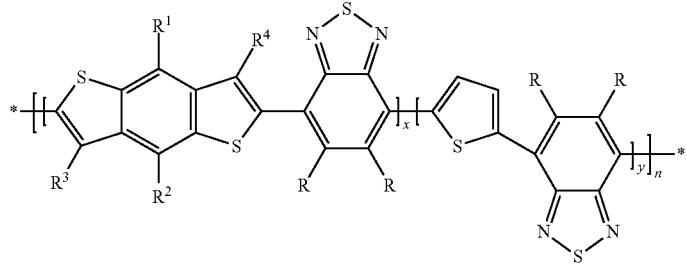
V1c1
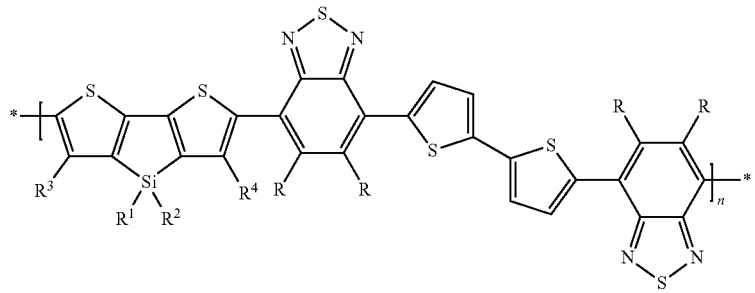
IV1d1
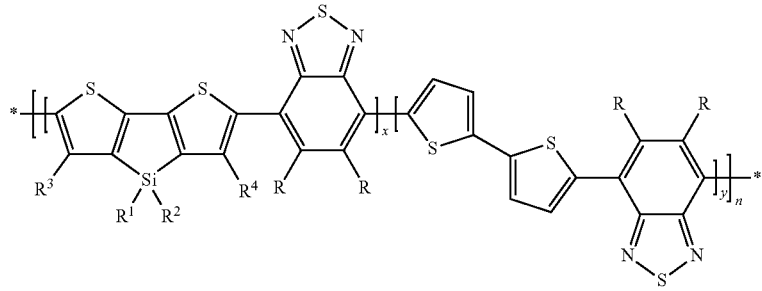
V1d1
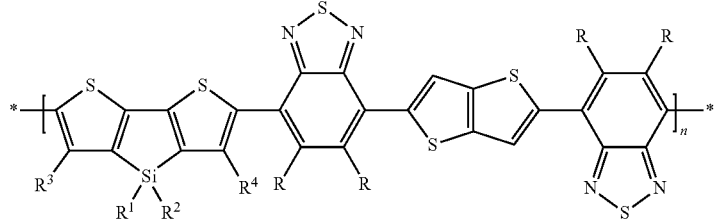
IV1e1
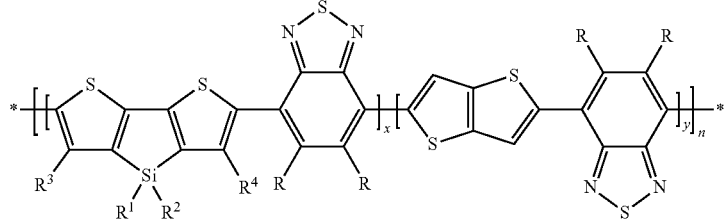
V1e1

-continued
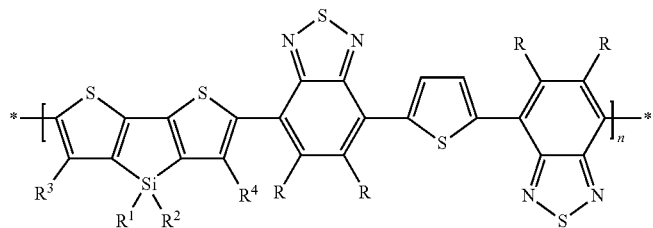
IV1f1
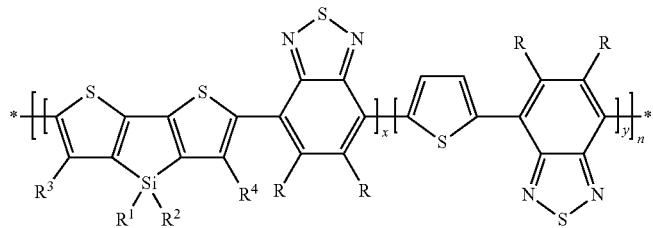
V1f1
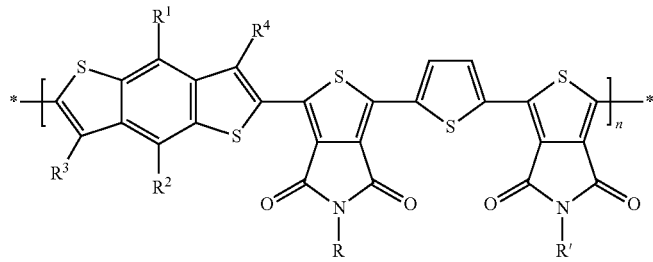
IV1g1
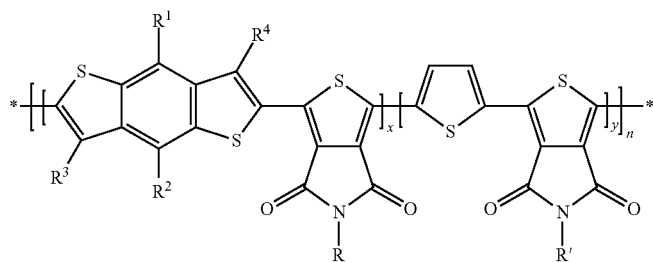
V1g1
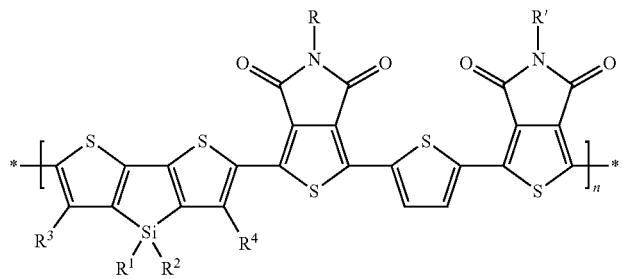
IV1h1
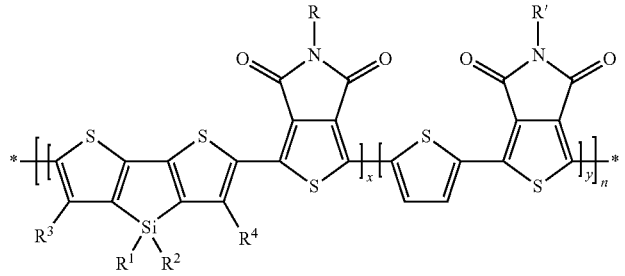
V1h1

-continued
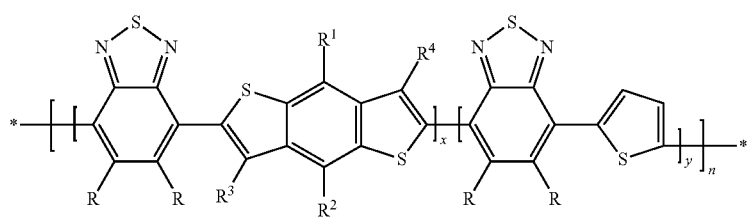
V2a1
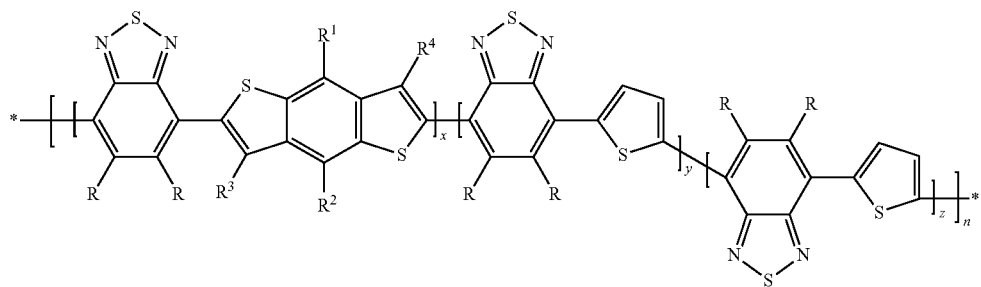
V3a1
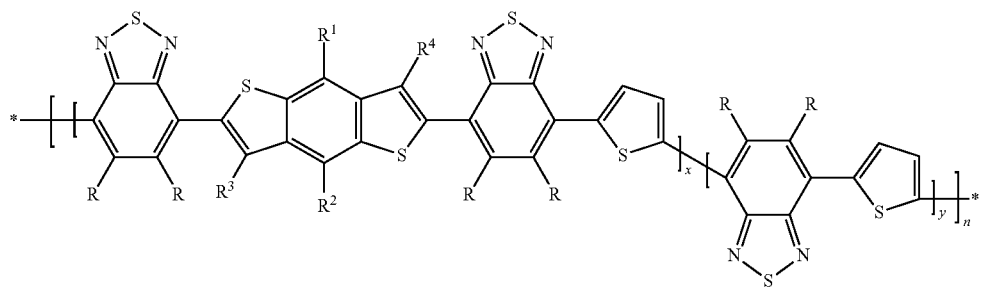
V4a1
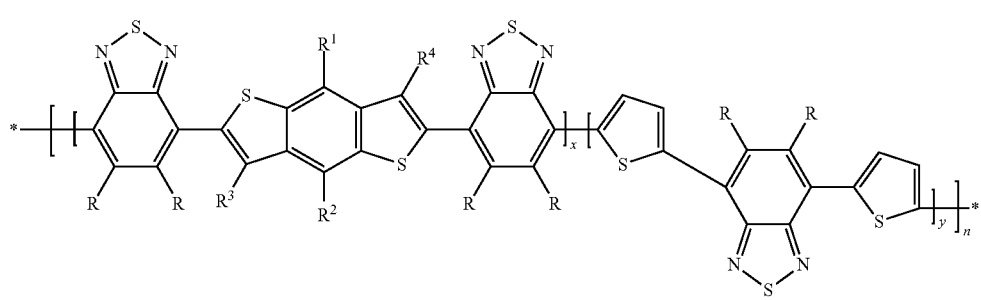
V5a1
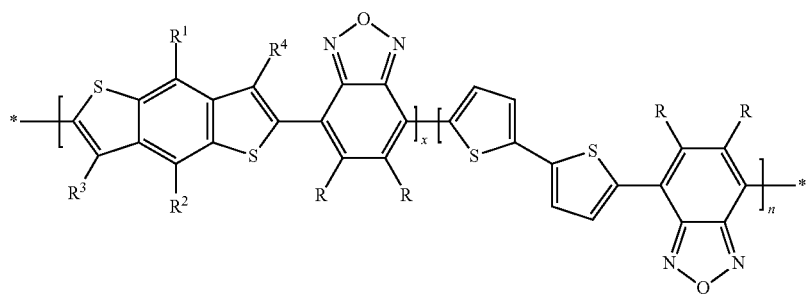
IV1a2

-continued
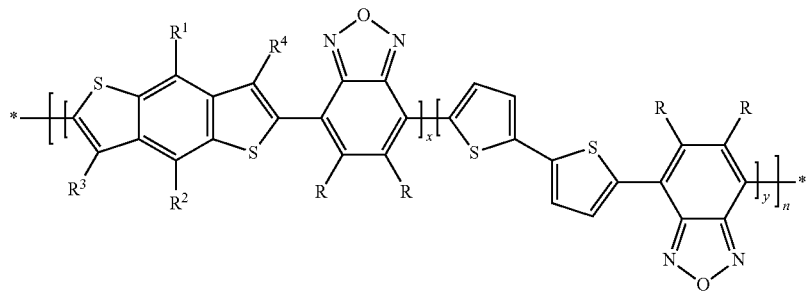
V1a2
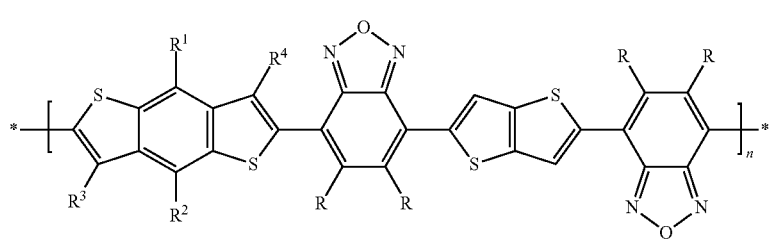
IV1b2
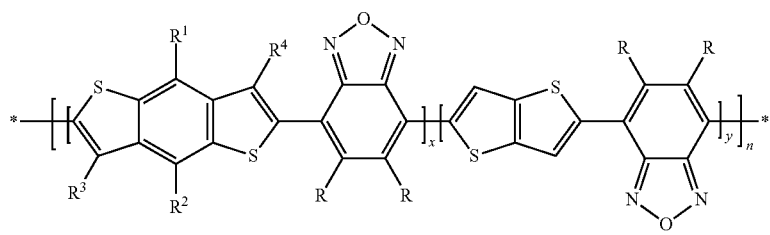
V1b2
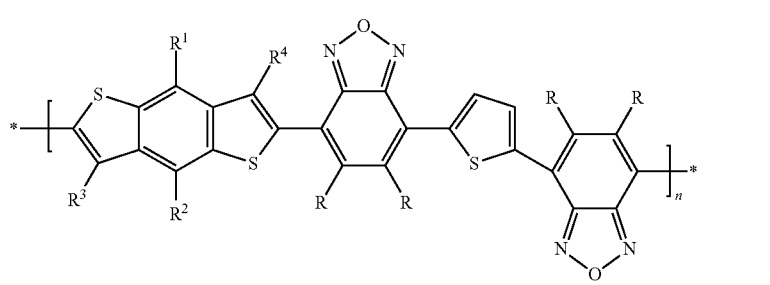
IV1c2
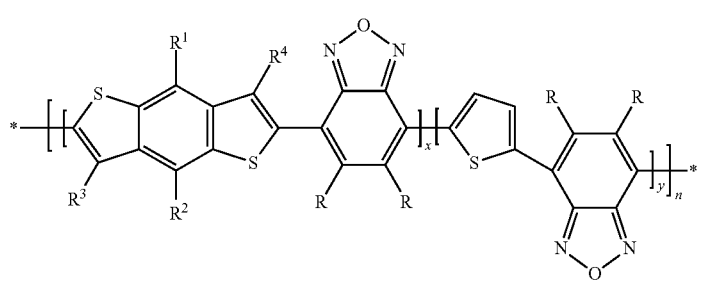
V1c2
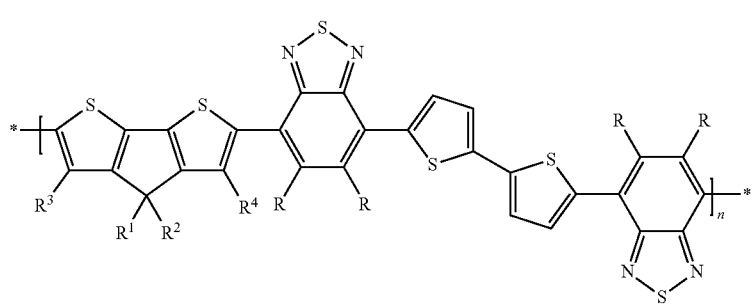
IV1d2

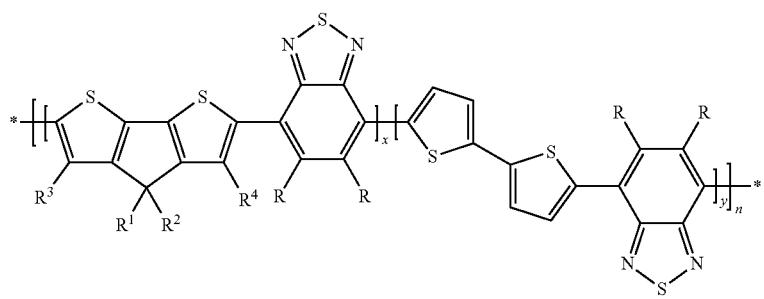
V1d2
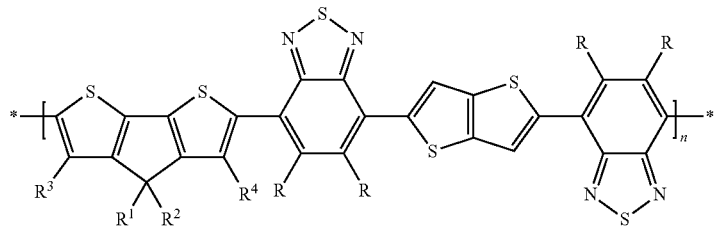
IV1e2
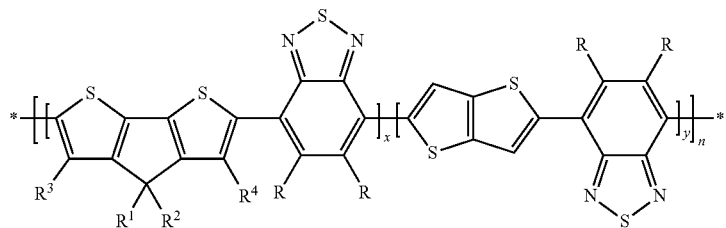
V1e2
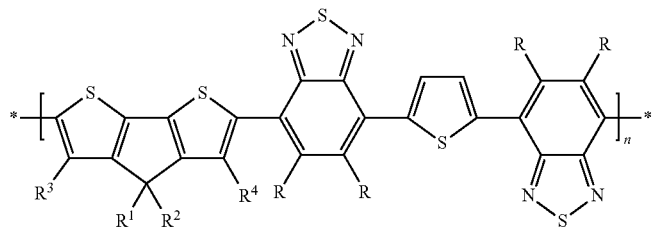
IV1f2
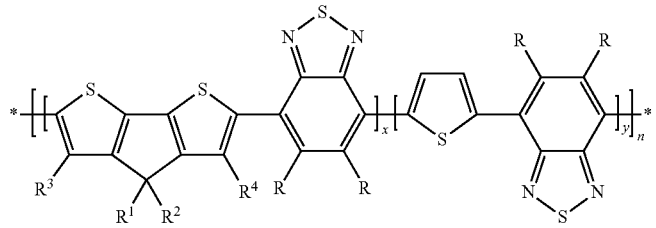
V1f2
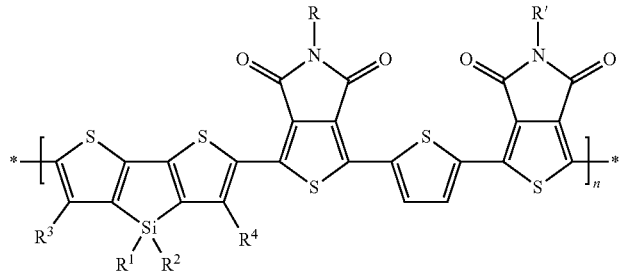
IV1h2

-continued
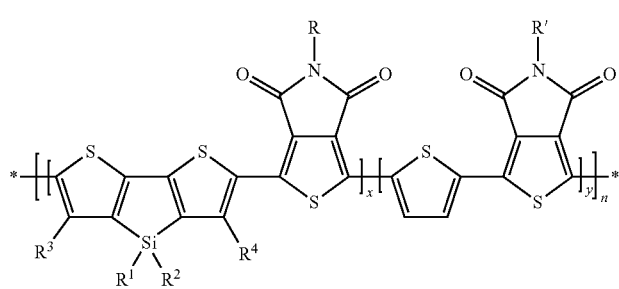
V1h2
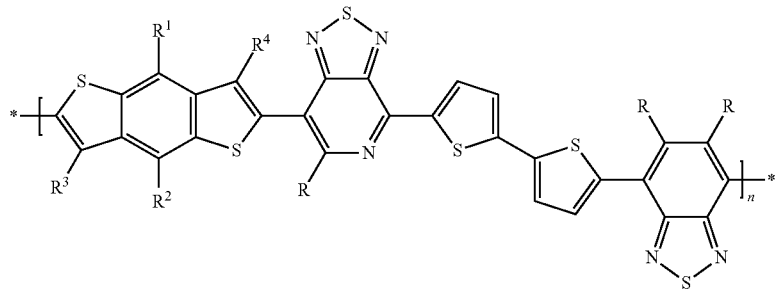
IV1a3
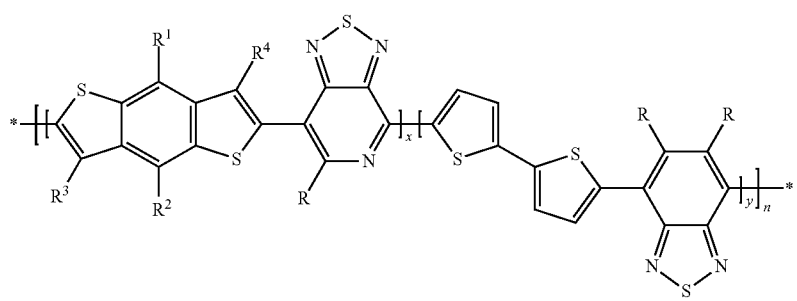
V1a3
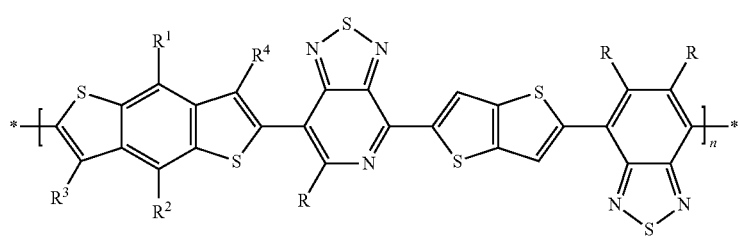
IV1b3
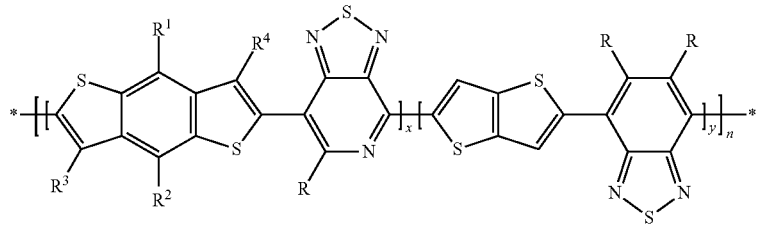
V1b3
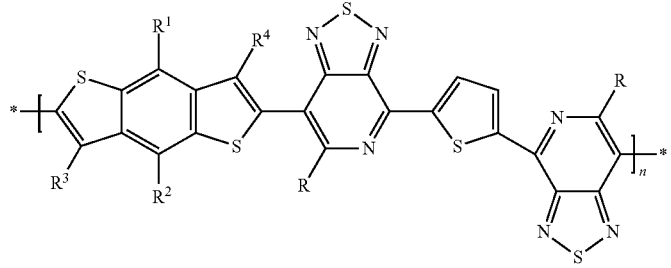
IV1c3

-continued
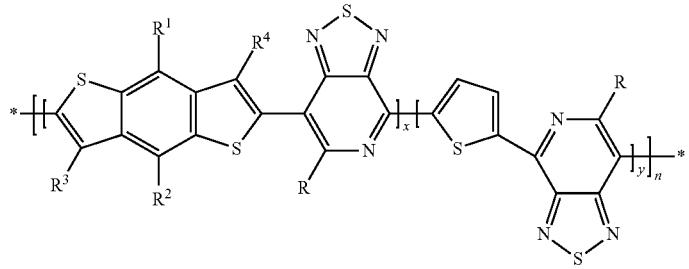
V1c3
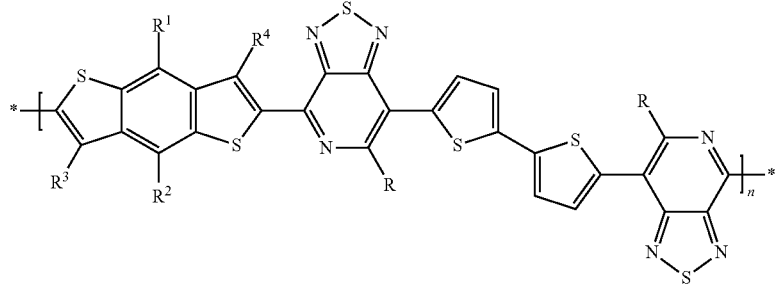
IV1a4
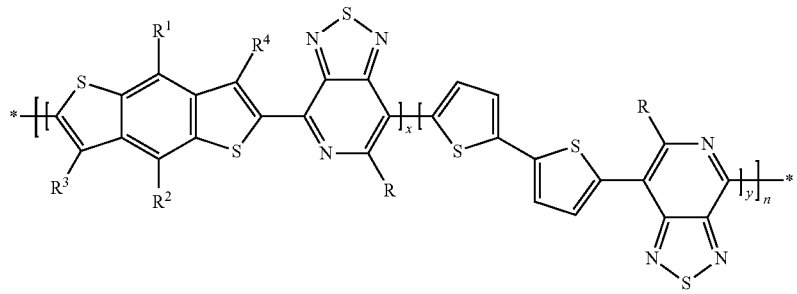
V1a4
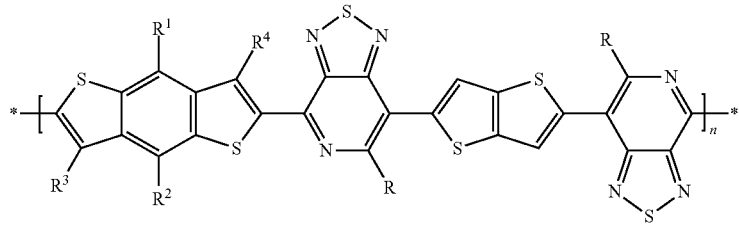
IV1b4
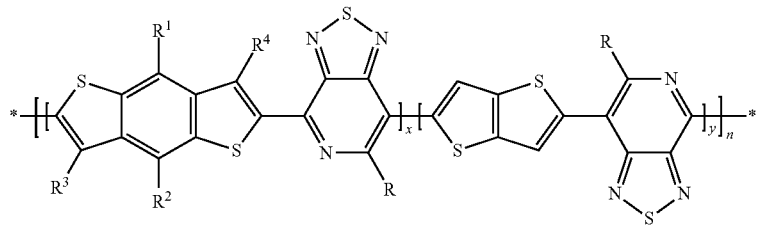
V1b4
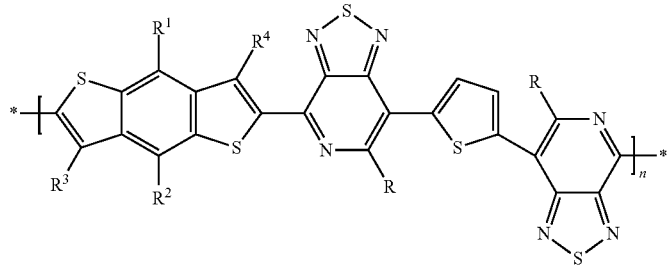
IV1c4

-continued

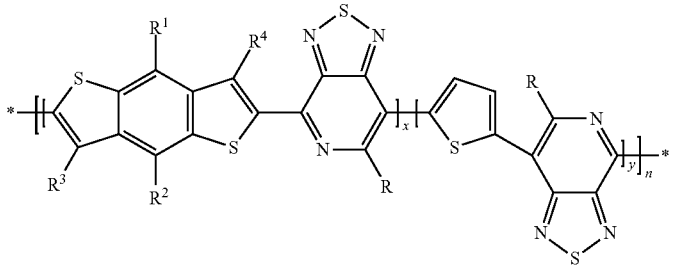

VIc4 wherein $R^{1-4}$, R, x, y and n are as defined in formula IV1a. Preferably $R^1$ and $R^2$ are different from H and $R^3$ and $R^4$ are H. Further preferably $R^1$, $R^2$ and R and R' are selected from alkyl, alkoxy, alkylcarbonyl, alkoxycarbonyl and alkylcarbonyloxy, all of which are straight-chain or branched, are optionally fluorinated, and have from 1 to 30, very preferably from 1 to 20 C atoms.

Further preferred polymers of formula IV1, IV2 and V and their subformulae are selected of formula VI $$R^5\text{-chain-}R^6 \qquad \text{VI}$$

wherein "chain" denotes a polymer chain selected of formulae IV1, IV2, V or their subformulae V1-V5, IV1a-V5a, and IV1a1-V1c4, and $R^5$ and $R^6$ have independently of each other one of the meanings of $R^1$ as defined above, or denote, independently of each other, H, F, Br, Cl, I, —$CH_2Cl$, —CHO, —$CR^a$=$CR^b{}_2$, —$SiR^aR^bR^c$, —$SiR^aX^aX^b$, —$SiR^aR^bX^a$, —$SiR^aR^bR^c$, —$BR^aR^b$, —$B(OR^a)(OR^c)$, —$B(OH)_2$, —O—$SO_2$—$R^a$, —C≡CH, —$MgX^a$, —$ZnX^a$, or a terminal or endcap group T, wherein $X^a$ and $X^b$ denote halogen, $R^a$, $R^b$ and $R^c$ independently of each other denote H or alkyl with 1 to 20 C atoms, and two of $R^a$, $R^b$ and $R^c$ may also form an aliphatic ring together with the hetero atom to which they are attached.

Preferred terminal or endcap groups T are H, $C_{1-20}$ alkyl, optionally substituted $C_{6-12}$ aryl or optionally substituted $C_{2-10}$ heteroaryl, very preferably H, phenyl or thiophene.

Further preferred are statistical block copolymers selected from the following formulae:

T-{$[A^1$-$D^1]_x$-$[A^1$-$Sp^1]_y$-$[A^2$-$D^1]_w$-$[A^2$-$Sp^1]_z$-$[A^3$-$D^1]_\alpha$-$[A^3$-$Sp^1]_\beta$}$_n$-T    VI1 where 0<x<1, 0<y<1, 0≤w<1, 0≤z<1, 0≤α<1, 0≤β<1, x+y+x+w+α+β=1, $A^1$≠$A^2$≠$A^3$=1, and $D^1$≠$Sp^1$, T-{$[A^1$-$D^1]_x$-$[A^1$-$Sp^1]_y$-$[A^2$-$D^1]_w$-$[A^2$-$Sp^1]_z$-$[A^3$-$D^1]_\alpha$-$[A^3$-$Sp^1]_\beta$}$_n$-T    VI2 where 0<x<1, 0<y<1, 0≤w<1, 0≤z<1, 0<α<1, 0<β<1, x+y+x+w+α+β=1, $A^1$≠$A^2$ and $D^1$≠$Sp^1$, T-{-$[A^1$-$D^1]_x$-$[A^1$-$Sp^1]_y$-$[A^2$-$D^1]_w$-$[A^2$-$Sp^1]_z$-$[M^1$-$A^3$-$M^2$-$A^1]_\alpha$-$[M^1$-$A^3$-$M^2$-$A^2]_\beta$}$_n$-T    VI3 where 0<x<1, 0<y<1, 0≤w<1, 0≤z<1, 0<α<1, 0<β<1, x+y+x+w+α+β=1, $A^1$≠$A^2$ and $D^1$≠$Sp^1$, T-{$[A^1$-$D^1]_x$-$[A^1$-$Sp^1]_y$-$[A^1$-$D^1]_w$-$[A^2$-$Sp^1]_z$-$[A^2$-$Sp^1]_\alpha$-$[A^2$-$D^2]_\beta$}$_n$-T    VI4 where 0<x<1, 0<y<1, 0<w<1, 0≤z<1, 0α<1, 0≤β<1, x+y+x+w+α+β=1, $A^1$≠$A^2$ and $D^1$≠$D^2$≠$Sp^1$, T-{$[A^1$-$D^1]_x$-$[A^1$-$Sp^1]_y$-$[A^1$-$Sp^2]_w$-$[A^2$-$D^1]_z$-$[A^2$-$Sp^1]_\alpha$-$[A^2$-$Sp^2]_\beta$}$_n$-T    VI5 where 0<x<1, 0<y<1, 0<w<1, 0≤z<1, 0≤α<1, 0≤β<1, x+y+x+w+α+β=1, $A^1$≠$A^2$ and $D^1$≠$Sp^1$≠$Sp^2$, T-{$[A^1$-$D^1$-$A^1$-$Sp^1]_x$-$[A^2$-$D^2$-$A^2$-$Sp^1]_y$-$[A^3$-$D^3$-$A^3$-$Sp^1]_z$}$_n$-T    VI6 where 0<x<1, 0<y<1, 0≤z<1, x+y+x=1, $Sp^1$≠$D^1$ and $A^1$-$D^1$-$A^1$≠$A^2$-$D^2$-$A^2$≠$A^3$-$D^3$-$A^3$, T-{$[A^1$-$D^1$-$A^1$-$Sp^1]_x$-$[A^1$-$D^1$-$A^1$-$Sp^2]_y$-$[A^1$-$D^1$-$A^1$-$Sp^3]_z$}$_n$-T    VI7 where 0<x<1, 0<y<1, 0≤z<1, x+y+x=1 and $D^1$≠$Sp^1$≠$Sp^2$≠$Sp^3$,

T-{$[A^1$-$D^1$-$A^1$-$Sp^1]_x$-$[A^2$-$Sp^1]_y$-$[A^2$-$D^2]_w$-$[A^1$-$D^1$-$A^1$-$D^2]_z$}$_n$-T    VI8 where 0<x<1, 0<y<1, 0≤w<1, 0≤z<1, w+x+y+x=1, $D^1$≠$Sp^1$ and $D^2$≠$Sp^1$ or

T-{$[A^1$-$D^1$-$A^1$-$Sp^1]_x$-$[M^1$-$A^2$-$M^2$-$Sp^1]_y$}$_n$-T    VI9 where 0<x<1, 0<y<1, x+y=1 and $D^1$≠$Sp^1$.

In the above formulae VI1 to VI9, w, x, y, z, α and β are the molar fractions of the individual polymer segments, w+x+y+z+α+β=1, $D^1$ and $D^2$ are donor units as defined above, $A^1$, $A^2$ and $A^3$ are acceptor units as defined above, $Sp^1$ and $Sp^2$ are spacer units as defined above, $M^1$ and $M^2$ are consisting of one or more aromatic units, such as thiophene, and T is a terminal or endcap unit as defined above, preferably consisting of one or more aromatic units, such as benzene or thiophene.

Further preferred are alternating copolymers selected from the following formulae:

T-{$A^1$-$D^1$-$A^1$-$Sp^1$}$_n$-T    VI10 where $D^1$≠$Sp^1$,

T-{$A^1$-$D^1$-$A^1$-$Sp^1$-$A^2$-$D^2$-$A^2$-$Sp^2$}$_n$-T    VI11 where $D^1$≠$Sp^1$≠$D^2$≠$Sp^2$.

In the above formulae VI10 and VI11, $D^1$ and $D^2$ are donor units as defined above, $A^1$, $A^2$ and $A^3$ are acceptor units as defined above, $Sp^1$ and $Sp^2$ are spacer units as defined above, and T is a terminal or endcap unit as defined above, preferably consisting of one or more aromatic units, such as benzene or thiophene.

The invention further relates to monomers of formula VII $$R^7\text{-}(Sp^2)_d\text{-}(A^2)_b\text{-}D^1\text{-}(A^1)_a\text{-}(Sp^1)_c\text{-}R^8 \qquad \text{VII}$$

wherein $D^1$, $A^1$, $A^2$, $Sp^1$, $Sp^2$, a, b, c and d have the meanings of formula II or the preferred meanings given above, and $R^7$ and $R^8$ are, preferably independently of each other, selected from the group consisting of H, Cl, Br, I, O-tosylate, O-triflate, O-mesylate, O-nonaflate, —$SiMe_2F$, —$SiMeF_2$, —O—$SO_2Z^1$, —$B(OZ^2)_2$, —$CZ^3$=$C(Z^3)_2$, —C≡CH, —C≡$CSi(Z^1)_3$, —$MgX^a$, —$ZnX^a$ and —$Sn(Z^4)_3$, wherein $X^a$ is halogen, preferably Cl, Br or I, $Z^{1-4}$ are selected from the group consisting of alkyl and aryl, each being optionally substituted, and two groups $Z^2$ may also together form a cyclic group.

Preferred monomers of formula VII are selected from the following subformulae $$R^7\text{-}A^2\text{-}D^1\text{-}A^1\text{-}R^8 \qquad \text{VII1}$$

$$R^7\text{-}Sp^2\text{-}A^2\text{-}D^1\text{-}R^8 \qquad \text{VII2}$$

$$R^7\text{-}D^1\text{-}A^1\text{-}Sp^1\text{-}R^8 \qquad \text{VII3}$$

$$R^7\text{-}Sp^2\text{-}A^2\text{-}D^1\text{-}A^1\text{-}R^8 \qquad \text{VII4}$$

$$R^7\text{-}A^2\text{-}D^1\text{-}A^1\text{-}Sp^1\text{-}R^8 \qquad \text{VII5}$$

$$R^7\text{-}Sp^2\text{-}A^2\text{-}D^1\text{-}A^1\text{-}Sp^1\text{-}R^8 \qquad \text{VII6}$$

wherein $D^1$, $A^1$, $A^2$, $Sp^1$, $Sp^2$, $R^7$, $R^8$, a, b, c, d are as defined in formula VII.

Further preferred are repeat units, monomers and polymers of formulae I-VII and their subformulae selected from the following list of preferred embodiments:

- a=b=c=d=1, preferably in all repeat units,
- a=b=1, c=1 and d=0,
- a=b=1, c=d=0,
- $A^1$ and $A^2$ have the same meaning,
- $Sp^1$ and $Sp^2$ have the same meaning,
- n is at least 5, preferably at least 10, very preferably at least 50, and up to 2,000, preferably up to 500.
- $M_w$ is at least 5,000, preferably at least 8,000, very preferably at least 10,000, and preferably up to 300,000, very preferably up to 100,000,
- $R^1$ and/or $R^2$ are independently of each other selected from the group consisting of primary alkyl with 1 to 30 C atoms, secondary alkyl with 3 to 30 C atoms, and tertiary alkyl with 4 to 30 C atoms, wherein in all these groups one or more H atoms are optionally replaced by F,
- $R^1$ and/or $R^2$ are independently of each other selected from the group consisting of aryl and heteroaryl, each of which is optionally fluorinated, alkylated or alkoxylated and has 4 to 30 ring atoms,
- $R^1$ and/or $R^2$ are independently of each other selected from the group consisting of primary alkoxy or sulfanylalkyl with 1 to 30 C atoms, secondary alkoxy or sulfanylalkyl with 3 to 30 C atoms, and tertiary alkoxy or sulfanylalkyl with 4 to 30 C atoms, wherein in all these groups one or more H atoms are optionally replaced by F,
- $R^1$ and/or $R^2$ are independently of each other selected from the group consisting of aryloxy and heteroaryloxy, each of which is optionally alkylated or alkoxylated and has 4 to 30 ring atoms,
- $R^1$ and/or $R^2$ are independently of each other selected from the group consisting of alkylcarbonyl, alkoxycarbonyl and alkylcarbonyloxy, all of which are straight-chain or branched, are optionally fluorinated, and have from 1 to 30 C atoms,
- $R^1$ and/or $R^2$ denote independently of each other F, Cl, Br, I, CN, $R^9$, —C(O)—$R^9$, —C(O)—O—$R^9$, or —O—C(O)—$R^9$, —SO$_2$—$R^9$, —SO$_3$—$R^9$, wherein $R^9$ is straight-chain, branched or cyclic alkyl with 1 to 30 C atoms, in which one or more non-adjacent C atoms are optionally replaced by —O—, —S—, —C(O)—, —C(O)—O—, —O—C(O)—, —O—C(O)—O—, —SO$_2$—, —SO$_3$—, —CR$^0$=CR$^{00}$— or —C≡C— and in which one or more H atoms are optionally replaced by F, Cl, Br, I or CN, or $R^9$ is aryl or heteroaryl having 4 to 30 ring atoms which is unsubstituted or which is substituted by one or more halogen atoms or by one or more groups $R^1$ as defined above,
- $R^3$ and $R^4$ are H,
- $R^3$ and $R^4$ are H, and $R^1$ and $R^2$ are different from H,
- $R^1$ and $R^2$ are H, and $R^3$ and $R^4$ are different from H,
- $R^3$ and/or $R^4$ are independently of each other selected from the group consisting of primary alkyl with 1 to 30 C atoms, secondary alkyl with 3 to 30 C atoms, and tertiary alkyl with 4 to 30 C atoms, wherein in all these groups one or more H atoms are optionally replaced by F,
- $R^3$ and/or $R^4$ are independently of each other selected from the group consisting of aryl and heteroaryl, each of which is optionally fluorinated, alkylated or alkoxylated and has 4 to 30 ring atoms,
- $R^3$ and/or $R^4$ are independently of each other selected from the group consisting of primary alkoxy or sulfanylalkyl with 1 to 30 C atoms, secondary alkoxy or sulfanylalkyl with 3 to 30 C atoms, and tertiary alkoxy or sulfanylalkyl with 4 to 30 C atoms, wherein in all these groups one or more H atoms are optionally replaced by F,
- $R^3$ and/or $R^4$ are independently of each other selected from the group consisting of aryloxy and heteroaryloxy, each of which is optionally alkylated or alkoxylated and has 4 to 30 ring atoms,
- $R^3$ and/or $R^4$ are independently of each other selected from the group consisting of alkylcarbonyl, alkoxycarbonyl and alkylcarbonyloxy, all of which are straight-chain or branched, are optionally fluorinated, and have from 1 to 30 C atoms,
- $R^3$ and/or $R^4$ denote independently of each other F, Cl, Br, I, CN, $R^9$, —C(O)—$R^9$, —C(O)—O—$R^9$, or —O—C(O)—$R^9$, —SO$_2$—$R^9$, —SO$_3$—$R^9$, wherein $R^9$ is straight-chain, branched or cyclic alkyl with 1 to 30 C atoms, in which one or more non-adjacent C atoms are optionally replaced by —O—, —S—, —C(O)—, —C(O)—O—, —O—C(O)—, —O—C(O)—O—, —SO$_2$—, —SO$_3$—, —CR$^0$=CR$^{00}$— or —C≡C— and in which one or more H atoms are optionally replaced by F, Cl, Br, I or CN, or $R^9$ is aryl or heteroaryl having 4 to 30 ring atoms which is unsubstituted or which is substituted by one or more halogen atoms or by one or more groups $R^1$ as defined above,
- $R^0$ and $R^{00}$ are selected from H or $C_1$-$C_{10}$-alkyl,
- $R^5$ and $R^6$ are selected from H, halogen, —CH$_2$Cl, —CHO, —CH=CH$_2$—SiR$^a$R$^b$R$^c$, —SnR$^a$R$^b$R$^c$, —BR$^a$R$^b$, —B(OR$^a$)(OR$^c$), —B(OH)$_2$, P-Sp, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl, preferably phenyl,
- $R^7$ and $R^8$ are, preferably independently of each other, selected from the group consisting of H, Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^4$)$_2$, —C≡CH, C≡CSi(Z$^1$)$_3$, —MgX$^a$, —ZnX$^a$ and —Sn(Z$^4$)$_3$, wherein X$^a$ is halogen, Z$^{1-4}$ are selected from the group consisting of alkyl and aryl, preferably $C_{1-10}$ alkyl, each being optionally substituted, and two groups Z$^2$ may also form a cyclic group.

The monomers and polymers of the present invention can be synthesized according to or in analogy to methods that are known to the skilled person and are described in the literature. Other methods of preparation can be taken from the examples.

For example, the polymers can be suitably prepared by aryl-aryl coupling reactions, such as Yamamoto coupling, Suzuki coupling, Stille coupling, Sonogashira coupling, Heck coupling or Buchwald coupling. Suzuki coupling and Yamamoto coupling are especially preferred. The monomers which are polymerised to form the repeat units of the polymers can be prepared according to methods which are known to the person skilled in the art.

Another aspect of the invention is a process for preparing a polymer by coupling one or more identical or different monomeric units of formula II, II1, II2, III1-III6, or monomers of formula VII or VII1-VII6, with each other and/or with one or more comonomers in a polymerisation reaction, preferably in an aryl-aryl coupling reaction.

Very preferred is a process for preparing a polymer by coupling one or more monomers selected from formula VII or its subformulae VIII1-VII6 with each other and/or with one or more comonomers in an aryl-aryl coupling reaction, wherein preferably $R^7$ and $R^8$ are selected from Cl, Br, I, —B(OZ$^2$)$_2$ and —Sn(Z$^4$)$_3$.

Suitable co-monomers for the above process are for example selected from the following formulae $R^7$-A$^1$-R$^8$     VIII1

$R^7$-Sp$^1$-R$^8$     VIII2

$R^7$-Sp$^2$-R$^8$     VIII3

$R^7$-Sp$^1$-Sp$^2$-R$^8$     VIII4

$R^7$-Sp$^2$-Sp$^1$-R$^8$     VIII5

$R^7$-A$^1$-Sp$^1$-Sp$^2$-A$^2$-R$^8$     VIII6 wherein A$^1$, A$^2$, Sp$^1$, Sp$^2$, R$^7$, R$^8$ are as defined in formula VII. The novel co-monomers of formulae VIII1 to VIII6 are another aspect of the invention.

Preferred methods for polymerisation are those leading to C—C-coupling, like Suzuki polymerisation, as described for example in WO 00/53656, Yamamoto polymerisation, as described in for example in T. Yamamoto et al., *Progress in Polymer Science*, 1993, 17, 1153-1205 or in WO 2004/022626 A1, and Stille coupling, as described for example in Z. Bao et al., *J. Am. Chem. Soc.*, 1995, 117, 12426-12435 and C—H activation polymerisation, as described for example in M. Leclerc et al, *Angew. Chem. Int. Ed.* 2012, 51, 2068-2071. For example, when synthesizing a linear polymer by Yamamoto polymerisation, monomers as described above having two reactive halide groups R$^7$ and R$^8$ is preferably used. When synthesizing a linear polymer by Suzuki polymerisation, preferably a monomer as described above is used wherein at least one reactive group R$^7$ or R$^8$ is a boronic acid or boronic acid derivative group. When synthesizing a linear polymer by Stille polymerisation, preferably a monomer as described above is used wherein at least one reactive group R$^7$ or R$^8$ is a alkylstannane derivative group. When synthesizing a linear polymer by C—H activation polymerisation, preferably a monomer as described above is used wherein at least one reactive group R$^7$ or R$^8$ is a activated hydrogen bond.

Suzuki, Stille and C—H activation polymerisation may be used to prepare homopolymers as well as statistical, alternating and block random copolymers. Statistical or block copolymers can be prepared for example from the above monomers of formula VI or its subformulae, wherein one of the reactive groups R$^7$ and R$^8$ is halogen and the other reactive group is a boronic acid, boronic acid derivative group, C—H activated bond or alkylstannane. The synthesis of statistical, alternating and block copolymers is described in detail for example in WO 03/048225 A2 or WO 2005/014688 A2.

Suzuki, Stille and C—H activation polymerisation employs a Pd(0) complex or a Pd(II) salt. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$ or trans-di(µ-acetato)-bis[o-(di-o-tolylphosphino)benzyl]dipalladium(II). Alternatively the Pd(0) complex can be prepared by mixing a Pd(0) dibenzylideneacetone complex e.g. tris (dibenzylideneacetone)dipalladium(0) bis(dibenzylideneacetone)palladium(0), or Pd(II) salts e.g. palladium acetate, with a phosphine ligand e.g. triphenylphosphine, tris(orthotolyl)phosphine, tris(o-methoxyphenyl)phosphine or tri(tert-butyl)phosphine. Suzuki polymerisation is performed in the presence of a base, for example sodium carbonate, potassium carbonate, cesium carbonated, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl) nickel(0).

As alternatives to halogens as described above, leaving groups of formula —O—SO$_2$Z$^1$ can be used wherein Z$^1$ is as described above. Particular examples of such leaving groups are tosylate, mesylate and triflate.

Suitable and preferred synthesis methods of the repeat units, monomers and polymers of formulae I-VIII and their subformulae are shown below.

Statistical block co-polymers containing at least one or more the sequence such as -[A$^1$-D$^1$]$_x$-[A$^1$-Sp$^1$]$_y$- can be prepared from x and y molar ratio of segment A$^1$-D$^1$ and A$^1$-Sp$^1$. The polymer is prepared in such a way that a A$^1$-D$^1$-A$^1$ triad, where D$^1$ is covalently linked on both sides to A$^1$, must be formed in the polymerization reaction or before the polymerization reaction. Typically, at least three generic monomers are used to form the polymer backbone, R$^7$-A$^1$-R$^7$, R$^8$-D$^1$-R$^8$ and R$^8$-Sp$^1$-R$^8$.

The R$^7$ and R$^8$ group are complementary to each other in a polycondensation reaction such as Suzuki coupling, Stille coupling, Sonogashira coupling, Heck coupling or Buchwald coupling, Negishi coupling or C—H activation coupling. The reactive groups are preferably selected from of a first set of reactive groups composed of —Cl, —Br, —I, O-tosylate, O-triflate, O-mesylate and O-nonaflate and a second set of reactive groups composed of —H, —SiR$^a$R$^b$F, —SiR$^a$F$_2$, —B(OR$^a$)(OR$^b$), —CR$^a$=CHR$^b$, —C≡CH, —ZnX$^a$, —MgX$^a$ and —SnR$^a$R$^b$R$^c$.

If a Yamamoto coupling reaction is used to prepare the polymer, two generic monomers, R$^7$-A$^1$-D$^1$-A$^1$-R$^8$ and R$^7$-Sp$^1$-R$^8$, are used to form the polymer backbone. In this case, the reactive monomer ends R$^7$ and R$^8$ of the monomers are both composed independently of —Cl, —Br, —I, O-tosylate, O-triflate, O-mesylate and O-nonaflate. Additional T-R$^7$ and T-R$^8$ units composed of one or more aromatic units T, such as benzene or thiophene, can also be used as a terminating unit of the polymer backbone.

For example, a polymer containing one or more sequence [A-D]$_x$-[A-Sp]$_y$- is prepared as follows:

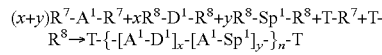

where x and y is the molar ratio of the segments A$^1$-D$^1$ and A$^1$-Sp$^1$. Alternatively an additional monomer R$^7$-M-A$^2$-M-R$^7$ can also be used to prepare a polymer containing one or more sequence -[A$^1$-D$^1$]$_x$-[A$^1$-Sp$^1$]$_y$- as followed

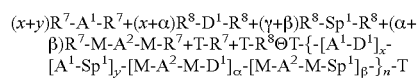

or

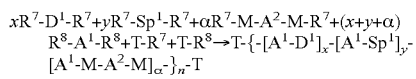

where x, y, α and β are the molar ratio of the segments $A^1$-$D^1$, M-$A^2$-$D^1$, M-$A^2$-$A^1$ and M-$A^2$-$Sp^1$. In the above examples, $D^1$ is consisting of one or more donor unit only, $A^1$ is consisting of one or more acceptor unit only, $Sp^1$ is consisting of one or more aromatic units, such as thiophene, which are not acting as electron acceptor and different to $D^1$, M is composed of one or more aromatic units, such as thiophene. Additional T-$R^7$ and T-$R^8$ units composed of one or more aromatic units, such as benzene or thiophene, can also be used as terminating unit of the polymer backbone.

Alternated block co-polymers containing at least one or more the sequence such as -[$A^1$-$D^1$-$A^1$-$Sp^1$]- are prepared in such a way that a $A^1$-$D^1$-$A^1$ triad, where $D^1$ is covalently linked on both sides to $A^1$, must be formed in the polymerization reaction or before the polymerization reaction. Typically, at least one generic monomers is used to form the polymer backbone, $R^7$-$A^1$-$D^1$-$A^1$-$Sp^1$-$R^8$, but preferably at least two monomers are used such as the following combination $R^7$-$A^1$-$D^1$-$A^1$-$R^7$ and $R^8$-$Sp^1$-$R^8$ or $R^1$-$D^1$-$R^7$ and $R^8$-$A^1$-$Sp^1$-$A^1$-$R^8$.

The $R^7$ and $R^8$ group are complementary to each other in a polycondensation reaction such as Suzuki coupling, Stille coupling, Sonogashira coupling, Heck coupling or Buchwald coupling, Negishi coupling or C—H activation coupling. The reactive groups are preferably selected from of a first set of reactive groups composed of —Cl, —Br, —I, O-tosylate, O-triflate, O-mesylate and O-nonaflate and a second set of reactive groups composed of —H, —SiR$^a$R$^b$F, —SiR$^a$F$_2$, —B(OR$^a$)(OR$^b$), —CR$^a$=CHR$^b$, —C≡CH, —ZnX$^a$, —MgX$^a$ and —SnR$^a$R$^b$R$^c$.

If a Yamamoto coupling reaction is used to prepare the polymer, the reactive ends $R^7$ and $R^8$ of the monomer $R^7$-$A^1$-$D^1$-$A^1$-$Sp^1$-$R^8$ are both composed independently of —Cl, —Br, —I, O-tosylate, O-triflate, O-mesylate and O-nonaflate. Additional T-$R^7$ and T-R units composed of one or more aromatic units, such as benzene or thiophene, can also be used as a terminating unit of the polymer backbone.

The synthesis of the polymers of the present invention is exemplarily described hereinafter for benzo[1,2-b:4,5-b']dithiophene co-polymers. Polymers with other donor groups instead of benzo[1,2-b:4,5-b']dithiophene can be synthesized in an analogous manner. The synthesis of the benzo[1,2-b:4,5-b']dithiophene core is disclosed for example in WO 2011/085004 A2, WO 2011/131280 A1 or U.S. Pat. No. 7,524,922 B2.

The generic synthesis scheme for the benzo[1,2-b:4,5-b'] dithiophene based alternating co-polymers is shown in Schemes 1 to 3, wherein $A^{1,2}$, $Sp^{1,2}$, $R^{1,8}$, a-d, x, y and n are as defined above, and R, R' have one of the meanings of $Z^1$ in formula VII. Alternating co-polymers can be obtained by co-polymerisation as shown in Schemes 1 and 2.

Scheme 1

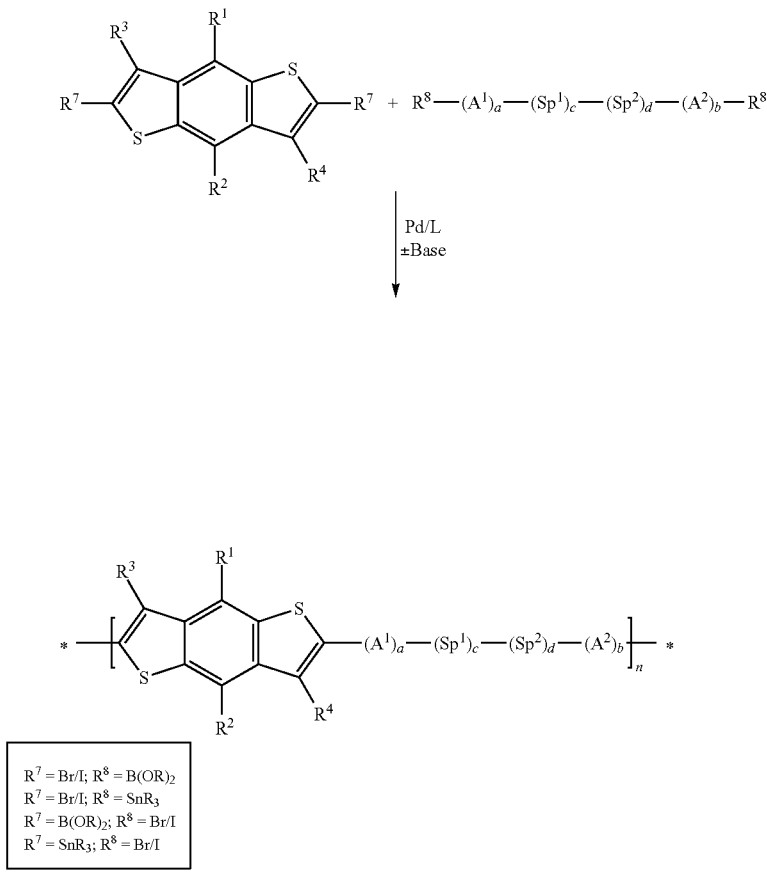

Scheme 2

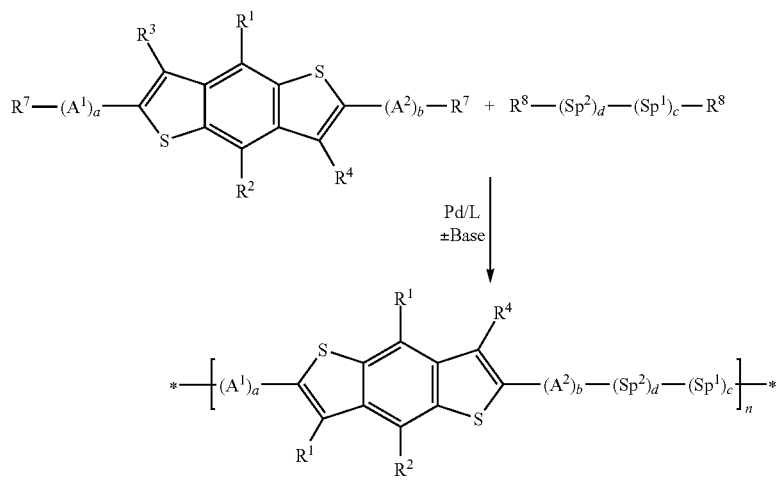

R[7] = Br/I; R[8] = B(OR)$_2$
R[7] = Br/I; R[8] = SnR$_3$
R[7] = B(OR)$_2$; R[8] = Br/I
R[7] = SnR$_3$; R[8] = Br/I

Alternating co-polymers can also be obtained by homo-polymerisation as shown in Scheme 3.

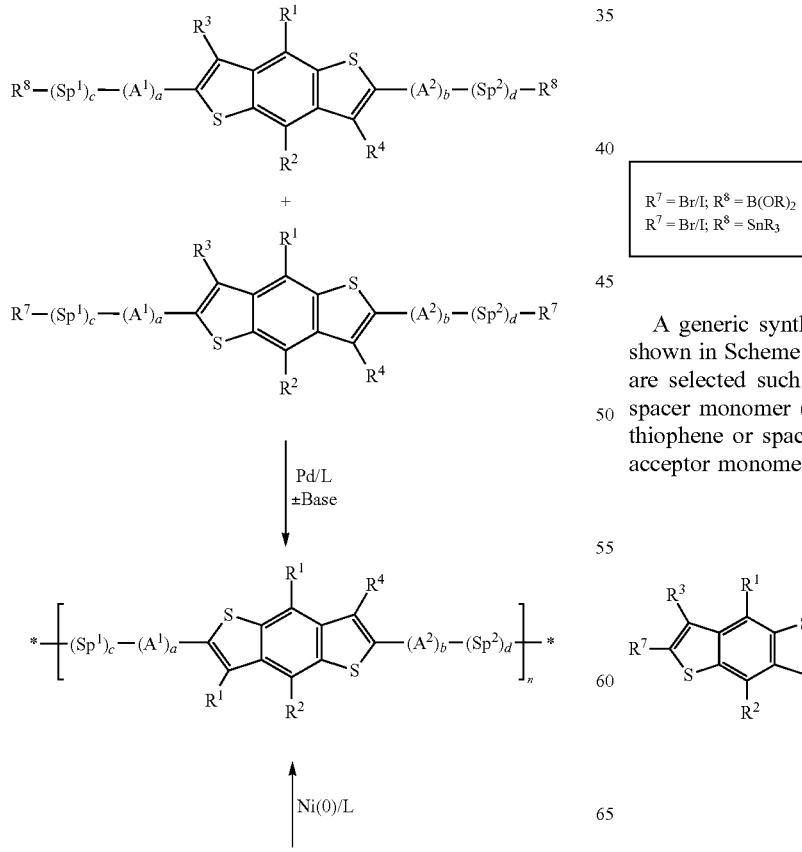

Scheme 3

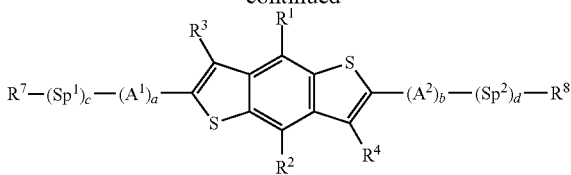

R[7] = Br/I; R[8] = B(OR)$_2$
R[7] = Br/I; R[8] = SnR$_3$

A generic synthesis for statistical block co-polymers is shown in Scheme 4. Therein the reactive groups R[7] and R[8] are selected such that a benzodithiophene monomer or a spacer monomer (Sp$^1$) cannot react with another benzodithiophene or spacer monomer, but can only react with an acceptor monomer (A$^1$).

Scheme 4

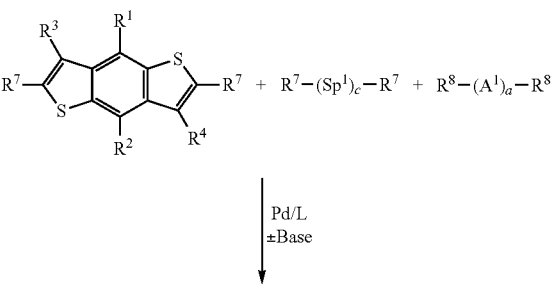

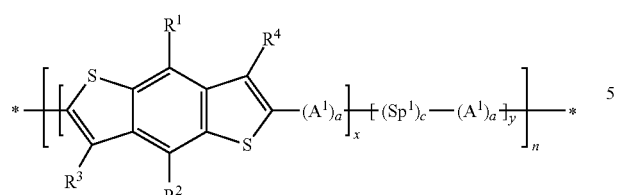
R[7] = Br/I; R[8] = B(OR)$_2$
R[7] = Br/I; R[8] = SnR$_3$
R[7] = B(OR)$_2$; R[8] = Br/I
R[7] = SnR$_3$; R[8] = Br/I
The monomers used in the polymerisation reactions can be prepared according to the following generic schemes for an electron acceptor-benzo[1,2-b:4,5-b']dithiophene-electron acceptor core (Scheme 5) and an electron acceptor-spacer-electron acceptor core (Scheme 6).
Scheme 5
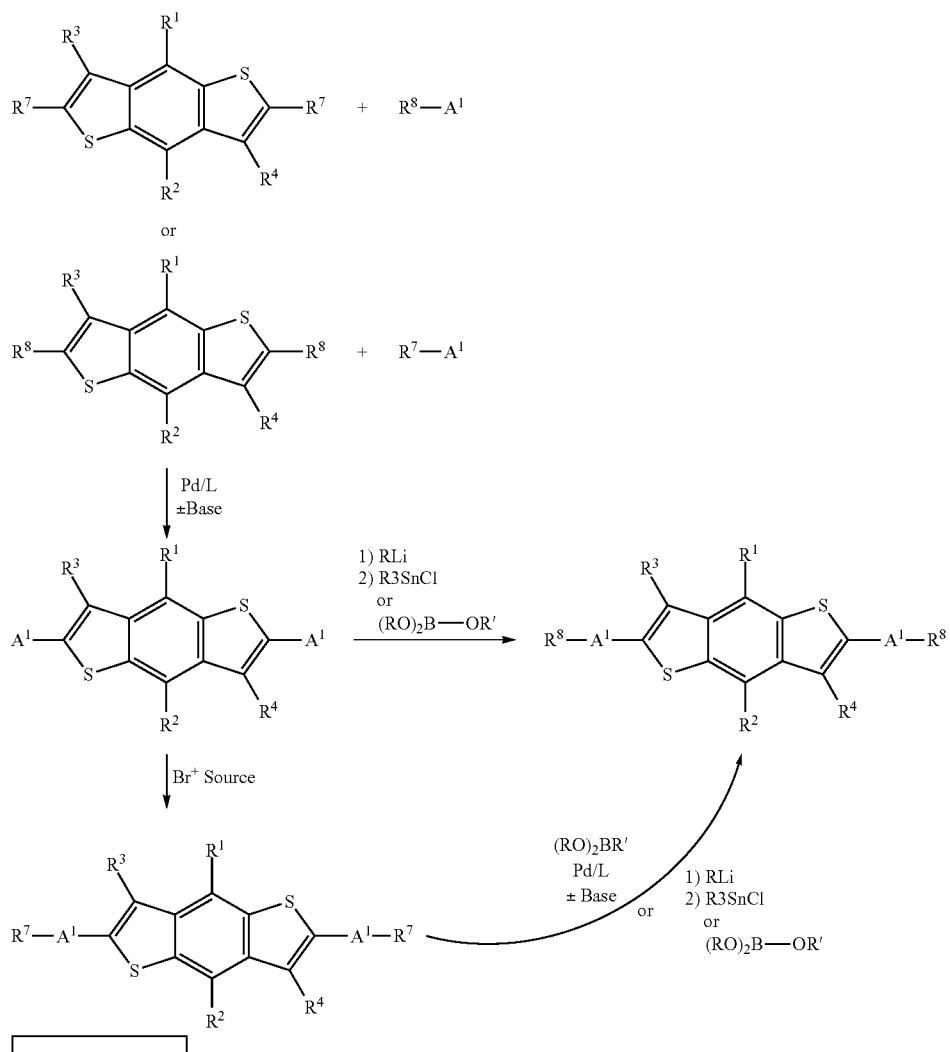
R[7] = Br; R[8] = B(OR)$_2$
R[7] = Br; R[8] = SnR$_3$ Scheme 6

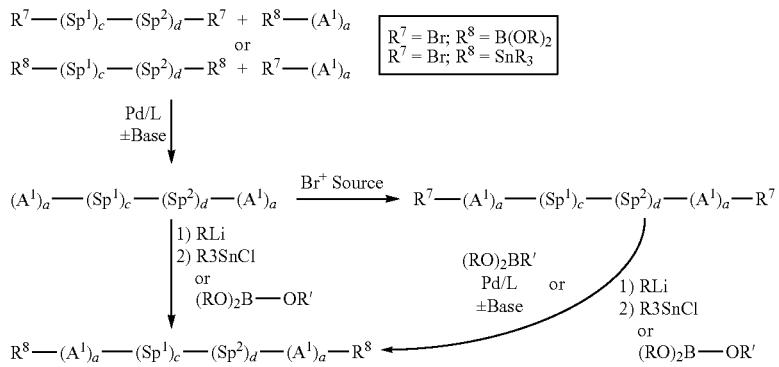

The novel methods of preparing monomers and polymers as described above and below are another aspect of the invention.

The compounds and polymers according to the present invention can also be used in mixtures or polymer blends, for example together with monomeric compounds or together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more small molecules, polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluoro-toluene, 1-chloro-2,4-difluorobenzene, 2-fluoropyridine, 3-chlorofluorobenzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, tetraline, decaline, indane, methyl benzoate, ethyl benzoate, mesitylene and/or mixtures thereof.

Additional solvents include solvents or co-solvents of the following formula

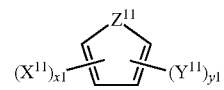

where $Z^{11}$ is O, S or CH=CH, $X^{11}$ is halogen, $Y^{11}$ is methyl, x1 is 0 or 1, and y1 is 1 or 2.

The concentration of the compounds or polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology,* 1966, 38 (496), 296". Solvent blends may also be used and can be identified as described in "Solvents, W.H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The compounds and polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound or polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited area and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymer blends and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, nanoparticles, colourants, dyes or pigments, furthermore, especially in case crosslinkable binders are used, catalysts, sensitizers, stabilizers, inhibitors, chain-transfer agents or co-reacting monomers.

The compounds and polymers to the present invention are useful as charge transport, semiconducting, electrically conducting, photoconducting or light emitting materials in optical, electrooptical, electronic, electroluminescent or photoluminescent components or devices. In these devices, the polymers of the present invention are typically applied as thin layers or films.

Thus, the present invention also provides the use of the semiconducting compound, polymer, polymers blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a compound, polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a compound, polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs and OPV devices, in particular bulk heterojunction (BHJ) OPV devices and OPD devices. In an OFET, for example, the active semiconductor channel between the drain and source may comprise the layer of the invention. As another example, in an OLED device, the charge (hole or electron) injection or transport layer may comprise the layer of the invention.

For use in OPV or OPD devices the polymer according to the present invention is preferably used in a formulation that comprises or contains, more preferably consists essentially of, very preferably exclusively of, a p-type (electron donor) semiconductor and an n-type (electron acceptor) semiconductor. The p-type semiconductor is constituted by a polymer according to the present invention. The n-type semiconductor can be an inorganic material such as zinc oxide (ZnO$_x$), zinc tin oxide (ZTO), titan oxide (TiO$_x$), molybdenum oxide (MoO$_x$), nickel oxide (NiO$_x$), or cadmium selenide (CdSe), or an organic material such as graphene or a fullerene or substituted fullerene, for example an indene-C$_{60}$-fullerene bisaduct like ICBA, or a (6,6)-phenyl-butyric acid methyl ester derivatized methano C$_{60}$ fullerene, also known as "PCBM-C$_{60}$" or "C$_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a C$_{61}$ fullerene group, a C$_{70}$ fullerene group, or a C$_{71}$ fullerene group, or an organic polymer (see for example Coakley, K. M. and McGehee, M. D. Chem. Mater. 2004, 16, 4533).

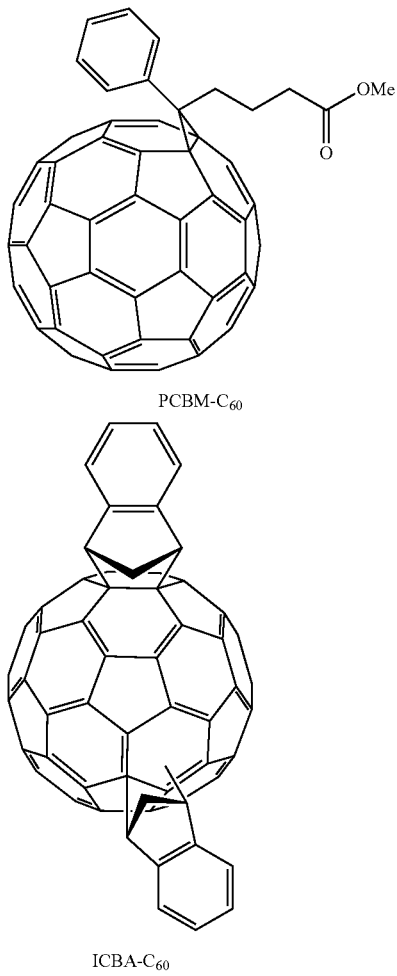

PCBM-C$_{60}$

ICBA-C$_{60}$

Preferably the polymer according to the present invention is blended with an n-type semiconductor such as a fullerene or substituted fullerene, like for example PCBM-C$_{60}$, PCBM-C$_{70}$, bis-PCBM-C$_{60}$, bis-PCBM-C$_{70}$, ICMA-C$_{60}$ (1',4'-dihydro-naphtho[2',3'1,2][5,6]fullerene-C$_{60}$), ICBA, oQDM-C$_{60}$ (1',4'-dihydro-naphtho[2',3':1,9][5,6]fullerene-C60-Ih), bis-oQDM-C$_{60}$, graphene, or a metal oxide, like for example, ZnO$_x$, TiO$_x$, ZTO, MoO$_x$, NiO$_x$, or quantum dots, like for example, CdSe or CdS, to form the active layer in an OPV or OPD device. The device preferably further comprises a first transparent or semi-transparent electrode on a transparent or semi-transparent substrate on one side of the active layer, and a second metallic or semi-transparent electrode on the other side of the active layer.

Further preferably the OPV or OPD device comprises, between the active layer and the first or second electrode, one or more additional buffer layers acting as hole transporting layer and/or electron blocking layer, which comprise a material such as metal oxide, like for example, ZTO, MoO$_x$, NiO$_x$, a conjugated polymer electrolyte, like for example PEDOT:PSS, a conjugated polymer, like for example polytriarylamine (PTAA), an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, ZnO$_x$, TiO$_x$, a salt, like for example LiF, NaF, CsF, a conjugated polymer electrolyte, like for example poly[3-(6-trimethylammoniumhexyl)thiophene], poly(9,9-bis(2-ethylhexyl)-fluorene]-b-poly[3-(6-trimethylammonium-hexyl)thiophene], or poly[(9,9-bis(3'-(N,N-dimethylamino)propyl)-2,7-fluorene)-alt-2,7-(9,9-dioctylfluorene)] or an organic compound, like for example tris(8-quinolinolato)-aluminium(III) (Alq$_3$), 4,7-diphenyl-1,10-phenanthroline.

In a blend or mixture of a polymer according to the present invention with a fullerene or modified fullerene, the ratio polymer:fullerene is preferably from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, dip coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the blend or mixture of a polymer according to the present invention with a C$_{60}$ or C$_{70}$ fullerene or modified fullerene like PCBM must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, morpholine, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
  optionally a substrate,
  a high work function electrode, preferably comprising a metal oxide, like for example ITO, serving as anode,
  an optional conducting polymer layer or hole transport layer, preferably comprising an organic poymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
  a layer, also referred to as "active layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties, for example comprising LiF,
  a low work function electrode, preferably comprising a metal like for example aluminum, serving as cathode,
  wherein at least one of the electrodes, preferably the anode, is transparent to visible light, and
  wherein the p-type semiconductor is a polymer according to the present invention.

A second preferred OPV device according to the invention is an inverted OPV device and comprises the following layers (in the sequence from bottom to top):
  optionally a substrate,
  a high work function metal or metal oxide electrode, comprising for example ITO, serving as cathode,
  a layer having hole blocking properties, preferably comprising a metal oxide like $TiO_x$ or $Zn_x$,
  an active layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
  an optional conducting polymer layer or hole transport layer, preferably comprising an organic poymer or polymer blend, for example of PEDOT:PSS or TBD or NBD,
  an electrode comprising a high work function metal like for example silver, serving as anode,
  wherein at least one of the electrodes, preferably the cathode, is transparent to visible light, and
  wherein the p-type semiconductor is a polymer according to the present invention.

In the OPV devices of the present invention the p-type and n-type semiconductor materials are preferably selected from the materials, like the polymer/fullerene systems, as described above.

When the active layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater*, 2004, 14(10), 1005. An optional annealing step may be then necessary to optimize blend morpohology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. *J. Am. Chem. Soc.*, 2010, 132, 7595-7597.

The compounds, polymers, formulations and layers of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound, polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processability of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers,
  optionally a substrate.
wherein the semiconductor layer preferably comprises a compound, polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377).

Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals*, 2000, 111-112, 31-34, Alcala, *J. Appl. Phys.*, 2000, 88, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., *Science*, 1998, 279, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantation of the dopant into the semiconductor material.

When electrons are used as carriers, suitable dopants are for example halogens (e.g., $I_2$, $Cl_2$, $Br_2$, $ICl$, $ICl_3$, $IBr$ and $IF$), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid, anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention may also be suitable for use in organic plasmon-emitting diodes (OPEDs), as described for example in Koller et al., *Nat. Photonics*, 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913 A1.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius. The values of the dielectric constant c ("permittivity") refer to values taken at 20° C. and 1,000 Hz.

in some instances a second bis-brominated monomer 5, tri-o-tolyl-phosphine and $Pd_2(dba)_3$. The vessel is evacuated and nitrogen purged three times and degassed chlorobenzene is added before the reaction mixture is degassed further for 5 minutes. The reaction mixture is heated for the specified amount of time. Immediately after completion of the polymerisation reaction, the reaction mixture is allowed to cool to 65° C. and tributyl-phenyl-stannane is added, and the reaction mixture heated back for a specified amount of time. Immediately after completion of the first end-capping reaction, the reaction mixture is allowed to cool to 65° C. and bromo-benzene is added and the reaction mixture heated back a specified amount of time. Immediately after completion of the second end-capping reaction, the reaction mixture is allowed to cool to 65° C. and precipitated into stirred methanol (100 cm$^3$). The polymer is collected by filtration and washed with methanol (2×100 cm$^3$) to give a solid. The polymer is subjected to sequential Soxhlet extraction with acetone, petroleum ether (40-60° C.), cyclohexane, chloroform and chlorobenzene. The relevant fraction is precipitated into stirred methanol or 2-isopropanol and collected by filtration to give a solid.

Example 1

Polymer 1

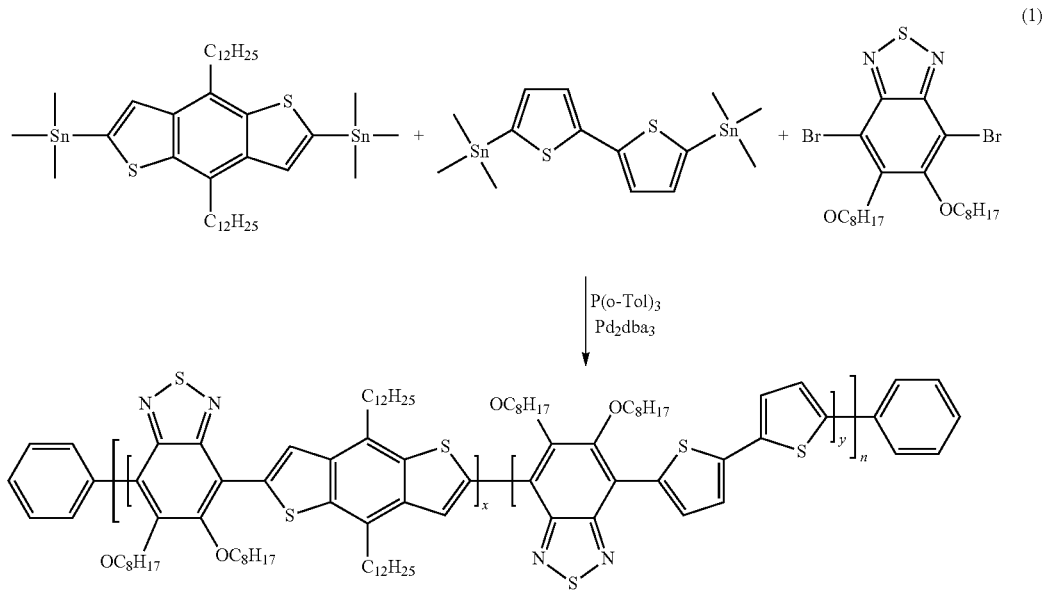

The invention will now be described in more detail by reference to the following examples, which are illustrative only and do not limit the scope of the invention.

EXAMPLES

A) Polymer Examples

General Polymerization Procedure

To a dry flask is added a first bis-stannyle monomer 1, a second bis-stannyle monomer 2, in some instances a third bis-stannyle monomer 3, a first bis-brominated monomer 4, Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 5,5'-bis-trimethylstannanyl-[2,2']bithiophenyl (196.8 mg; 0.4000 mmol; 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.0 cm$^3$) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 175° C. for 600 seconds each time. After the reaction completion, the polymer is precipitated collected, subjected to Soxhlet extraction. Isopropyl alcohol (200 cm³) is added dropwise to the cyclohexane fraction (150 cm³) and the resulting precipitate collected by filtration and dried in vacuo to give a black solid (575 mg, Yield: 98%). GPC (140° C., 1,2,4-trichlorobenzene): $M_n$=25.7 kg·mol⁻¹; $M_w$=55.8 kg·mol⁻¹; PDI=2.17.

Example 2

Polymer 2 and chlorobenzene (5.0 cm³) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm³; 0.80 mmol; 2.0 eq.) and bromobenzene (0.13 cm³; 1.2 mmol; 3.0 eq.) at 175° C. for 600 seconds each time. After the reaction completion, the polymer is precipitated, collected by filtration and subjected to Soxhlet extraction. Methanol (200 cm³) is added dropwise to the chloroform fraction (150 cm³) and the resulting precipitate is collected by filtration and dried in vacuo to give a black solid (426 mg,

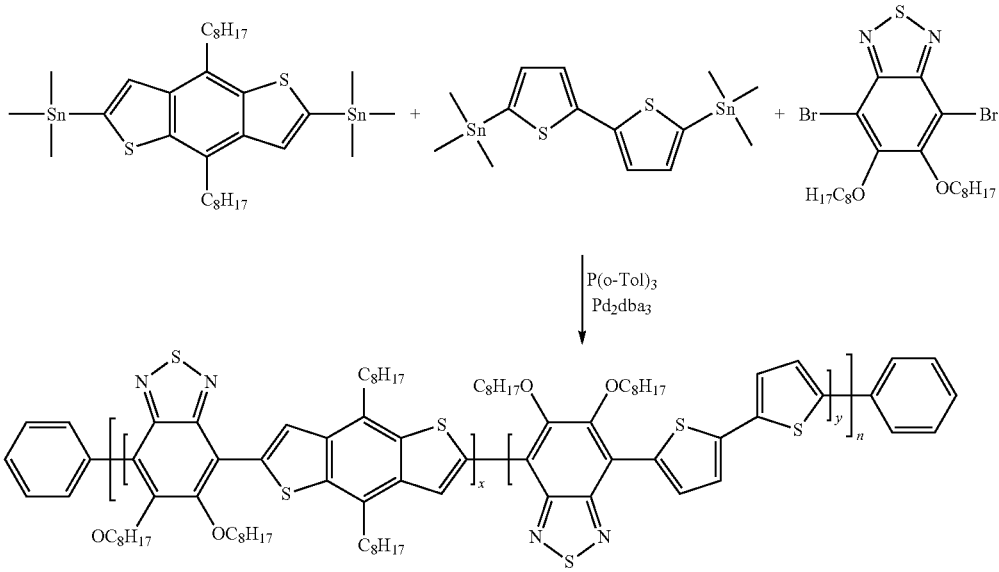

(2)

Following the general polymerisation reaction, 4,8-dioctyl-2,6-bis-trimethylstannanyl-benzo[1,2-b;4,5-b']dithiophene (296.1 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 5,5'-bis-trimethylstannanyl-[2,2']bithiophenyl (196.8 mg; 0.4000 mmol; 1.000 eq.), tri-o-tolylphosphine (19.5 mg; 64.0 µmol; 0.160 eq.), tris(dibenzylideneacetone)dipalladium(0) (14.7 mg; 16.0 µmol; 0.0400 eq.)

Yield: 78%). GPC (140° C., 1,2,4-trichlorobenzene): $M_n$=38.9 kg·mol⁻¹; $M_w$=68.4 kg·mol⁻¹; PDI=1.76.

Example 3

Polymer 3

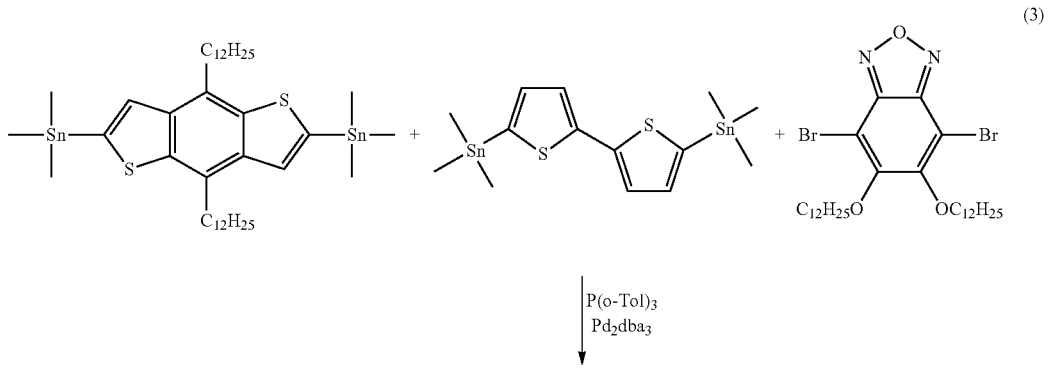

(3)

-continued

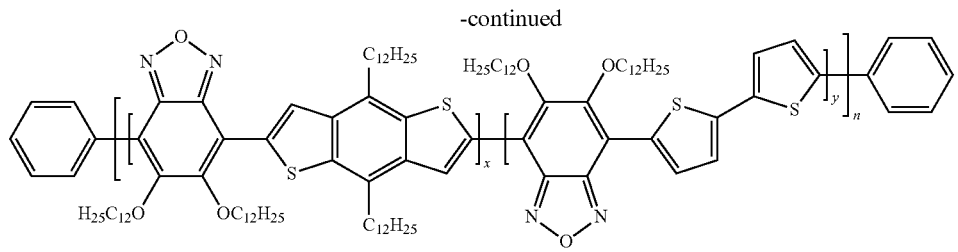

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-dodecyloxy-benzo[1,2,5]oxadiazole (517.2 mg; 0.8000 mmol; 2.000 eq.), 5,5'-bis-trimethylstannanyl-[2,2'] bithiophenyl (196.8 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm$^3$) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 175° C. for 600 seconds each time. After the reaction completion, the polymer is precipitated collected, subjected to Soxhlet extraction. Isopropyl alcohol (200 cm$^3$) is added dropwise to the cyclohexane fraction (150 cm$^3$) and the resulting precipitate collected by filtration and dried in vacuo to give a black solid (628 mg, Yield: 94%). GPC (140° C., 1,2,4-trichlorobenzene): $M_n$=30.4 kg·mol$^{-1}$; $M_w$=660 kg·mol$^{-1}$; PDI=2.17.

Example 4

Polymer 4

Following the general polymerisation reaction, 4,8-dioctyl-2,6-bis-trimethylstannanyl-benzo[1,2-b;4,5-b']dithiophene (296.1 mg; 0.4000 mmol; 1.000 eq.), 4,7-dibromo-5,6-bis-dodecyloxy-benzo[1,2,5]oxadiazole (517.2 mg; 0.8000 mmol; 2.000 eq.), 5,5'-bis-trimethylstannanyl-[2,2'] bithiophenyl (196.8 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm$^3$) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 175° C. for 600 seconds each time. After the reaction completion, the polymer is precipitated, collected by filtration and subjected to Soxhlet extraction. Methanol (200 cm$^3$) is added dropwise to the chloroform fraction (150 cm$^3$) and the resulting precipitate is collected by filtration and dried in vacuo to give a black solid (536 mg, Yield: 86%). GPC (140° C., 1,2,4-trichlorobenzene): $M_n$=29.3 kg·mol$^{-1}$; $M_w$=57.3 kg·mol$^{-1}$; PDI=2.32.

(4)

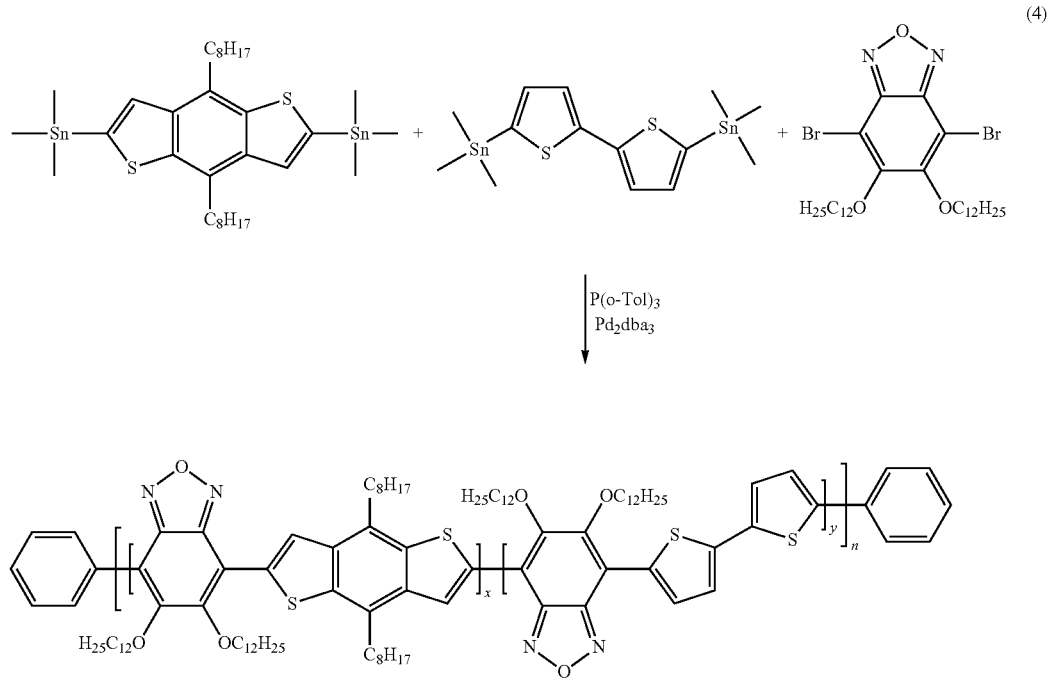

Example 5

Polymer 5

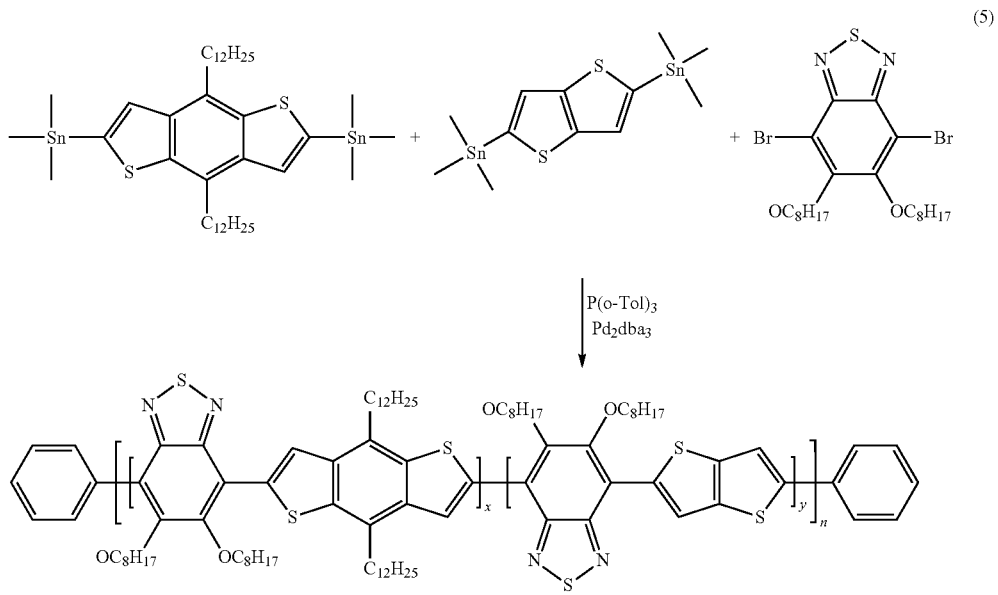

(5)

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 2,5-bis-trimethylstannanyl-thieno[3,2-b]thiophene (186.3 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.000 cm$^3$) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 175° C. for 600 seconds each time. After the reaction completion, the polymer is precipitated, collected and subjected to Soxhlet extraction. Isopropyl alcohol (200 cm$^3$) is added dropwise to the cyclohexane fraction (150 cm$^3$) and the resulting precipitate is collected by filtration and dried in vacuo to give a black solid (546 mg, Yield: 95%). GPC (140° C., 1,2,4-trichlorobenzene): $M_n$=23.6 kg·mol$^{-1}$; $M_w$=54.9 kg·mol$^{-1}$; PDI=2.33.

Example 6

Polymer 6

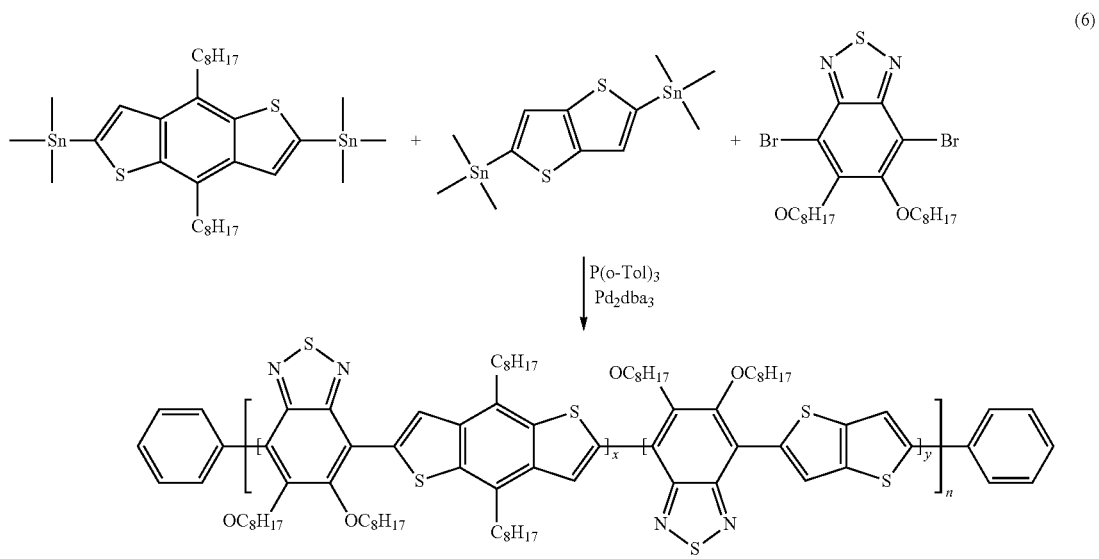

(6)

Following the general polymerisation reaction, 4,8-dioctyl-2,6-bis-trimethylstannanyl-benzo[1,2-b;4,5-b']dithiophene (296.1 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 2,5-bis-trimethylstannanyl-thieno[3,2-b]thiophene (186.3 mg; 0.4000 mmol; 1.000 eq.), tri-o-tolyl-phosphine (19.5 mg; 64.0 μmol; 0.160 eq.) tris(dibenzylideneacetone)dipalladium(0) (14.7 mg; 16.0 μmol; 0.0400 eq.) and chlorobenzene (5.0 cm$^3$) are heated sequentially at 140° C. (60 seconds), 160° C. (60 seconds) and 175° C. (1800 seconds) in a microwave reactor (Biotage Initiator). This reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 175° C. for 600 seconds each time. After the reaction completion, the polymer is precipitated, collected and Soxhlet extraction. Methanol (200 cm$^3$) is added dropwise to the chloroform fraction (150 cm$^3$) and the resulting precipitate is collected by filtration and dried in vacuo to give a black solid (348 mg, Yield: 65%). GPC (140° C., 1,2,4-trichlorobenzene): $M_n$=22.4 kg·mol$^{-1}$; $M_w$=54.6 kg·mol$^{-1}$; PDI=2.43.

Example 7

Polymer 7

Following the general polymerisation reaction, 4,8-dioctyl-2,6-bis-trimethylstannanyl-benzo[1,2-b;4,5-b']dithiophene (296.1 mg; 0.4000 mmol; 1.000 eq.), 4,7-dibromo-5,6-bis-octyloxy-benzo[1,2,5]oxadiazole (427.7 mg; 0.8000 mmol; 2.000 eq.), 2,5-bis-trimethylstannanyl-thieno[3,2-b]thiophene (186.3 mg; 0.4000 mmol; 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.0 cm$^3$) are heated sequentially at 140° C. (60 seconds), 160° C. (60 seconds) and 175° C. (1800 seconds) in a microwave reactor (Biotage Initiator). This reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 175° C. for 600 seconds each time. After the reaction completion, the polymer is precipitated, collected and Soxhlet extraction. Methanol (200 cm$^3$) is added dropwise to the chloroform fraction (150 cm$^3$) and the resulting precipitate is collected by filtration and dried in vacuo to give a black solid (350 mg, Yield: 67%). GPC (140° C., 1,2,4-trichlorobenzene): $M_n$=12.8 kg·mol$^{-1}$; $M_w$=38.1 kg·mol$^{-1}$; PDI=2.98.

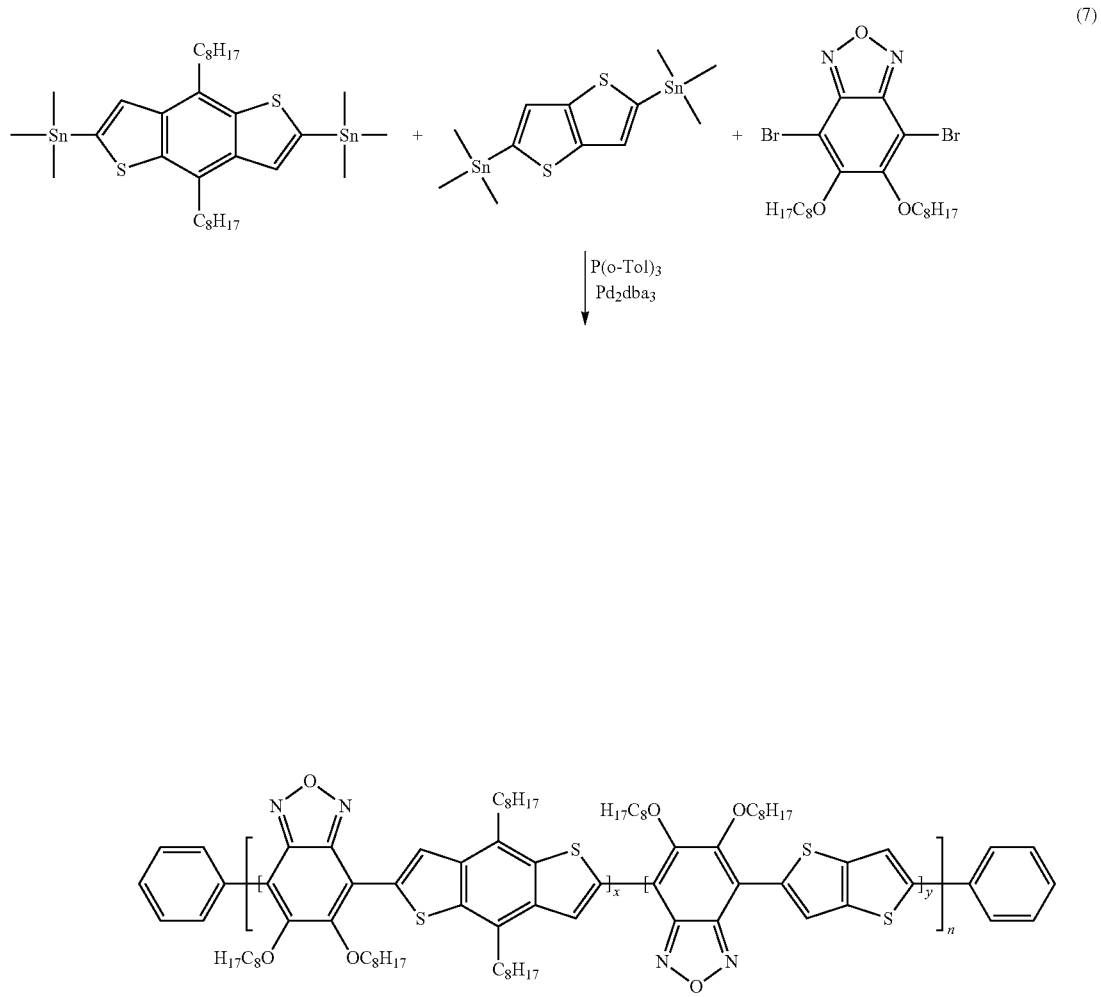

(7)

Example 8

Polymer 8

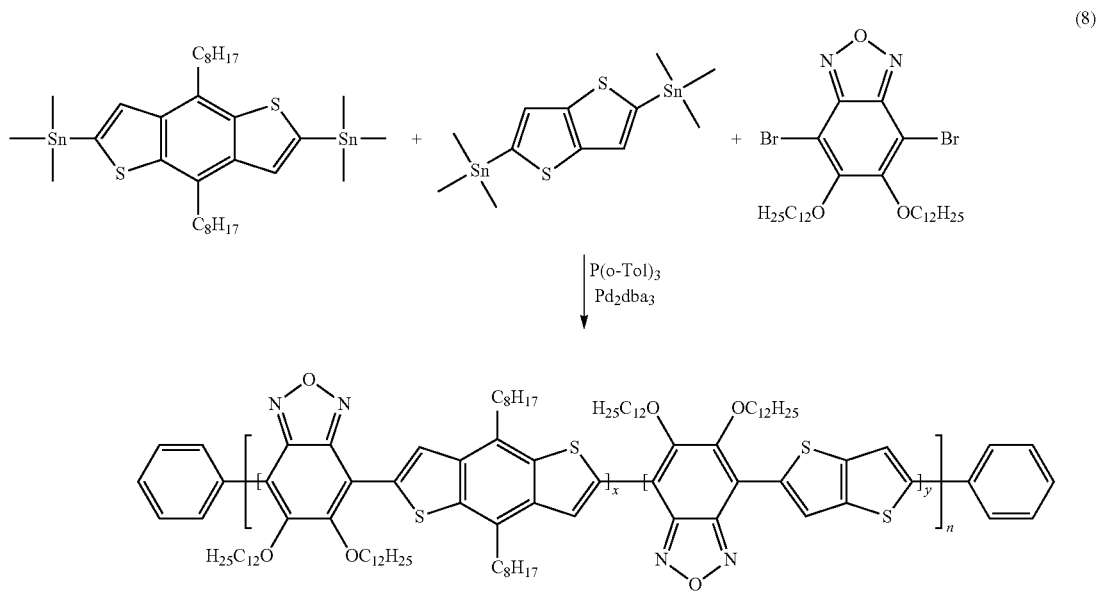

(8)

Following the general polymerisation reaction, 4,8-dioctyl-2,6-bis-trimethylstannanyl-benzo[1,2-b;4,5-b']dithiophene (296.1 mg; 0.4000 mmol; 1.000 eq.), 4,7-dibromo-5,6-bis-dodecyloxy-benzo[1,2,5]oxadiazole (517.2 mg; 0.8000 mmol; 2.000 eq.), 2,5-bis-trimethylstannanyl-thieno[3,2-b]thiophene (186.3 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm³) are heated sequentially at 140° C. (60 seconds), 160° C. (60 seconds) and 175° C. (1800 seconds) in a microwave reactor (Biotage Initiator). This reaction is end-capped with tributyl-phenyl-stannane (0.26 cm³; 0.80 mmol; 2.0 eq.) and bromobenzene (0.13 cm³; 1.2 mmol; 3.0 eq.) at 175° C. for 600 seconds each time. After the reaction completion, the polymer is precipitated, collected and Soxhlet extraction. Methanol (200 cm³) is added dropwise to the chloroform fraction (150 cm³) and the resulting precipitate is collected by filtration and dried in vacuo to give a black solid (450 mg, Yield: 74%). GPC (140° C., 1,2,4-trichlorobenzene): $M_n$=28.1 kg·mol⁻¹; $M_w$=68.4 kg·mol⁻¹; PDI=2.44.

Example 9

Polymer 9

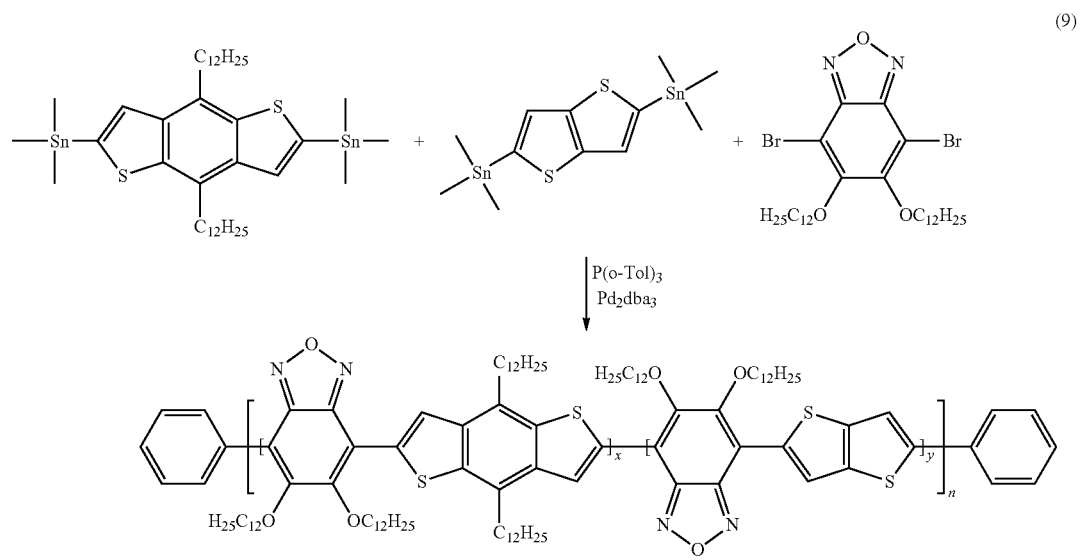

(9)

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-dodecyloxy-benzo[1,2,5]oxadiazole (517.2 mg; 0.8000 mmol; 2.000 eq.), 2,5-bis-trimethylstannanyl-thieno[3,2-b]thiophene (186.3 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.000 cm³) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm³; 0.80 mmol; 2.0 eq.) and bromobenzene (0.13 cm³; 1.2 mmol; 3.0 eq.) at 175° C. for 600 seconds each time. After the reaction completion, the polymer is precipitated, collected and subjected to Soxhlet extraction. Isopropyl alcohol (200 cm³) is added dropwise to the cyclohexane fraction (150 cm³) and the resulting precipitate is collected by filtration and dried in vacuo to give a black solid (620 mg, Yield: 95%). GPC (140° C., 1,2,4-trichlorobenzene): $M_n$=26.3 kg·mol$^{-1}$; $M_w$=60.3 kg·mol$^{-1}$; PDI=2.29.

Example 10

Polymer 10

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 2,5-bis-trimethylstannanyl-thiophene (163.9 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm³) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm³; 0.80 mmol; 2.0 eq.) and bromobenzene (0.13 cm³; 1.2 mmol; 3.0 eq.) at 175° C. for 600 seconds each time. After the reaction completion, the polymer is precipitated, collected and subjected to Soxhlet extraction. Isopropyl alcohol (200 cm³) is added dropwise to the cyclohexane fraction (150 cm³) and the resulting precipitate collected by filtration and dried in vacuo to give a black solid (465 mg, Yield: 84%). GPC (140° C., 1,2,4-trichlorobenzene): $M_n$=27.2 kg·mol$^{-1}$; $M_w$=52.6 kg·mol$^{-1}$; PDI=1.93.

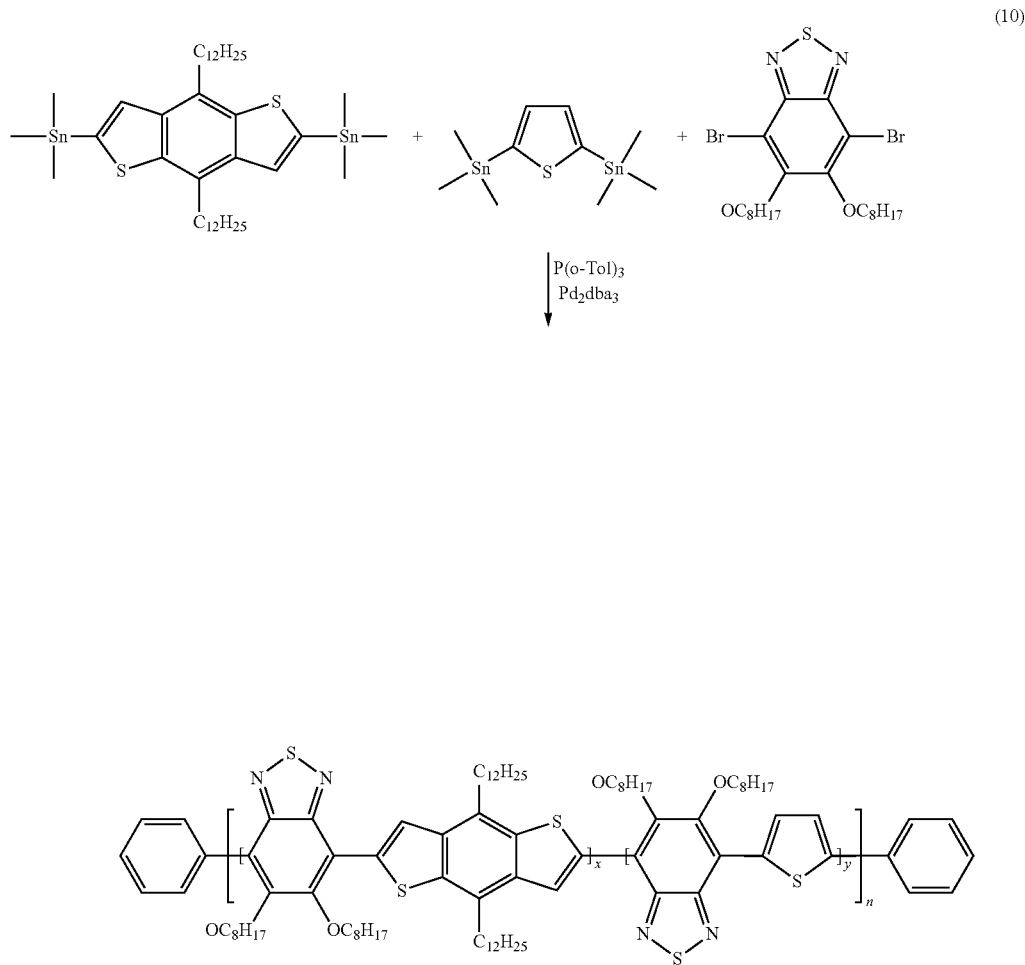

(10)

Example 11

Polymer 11

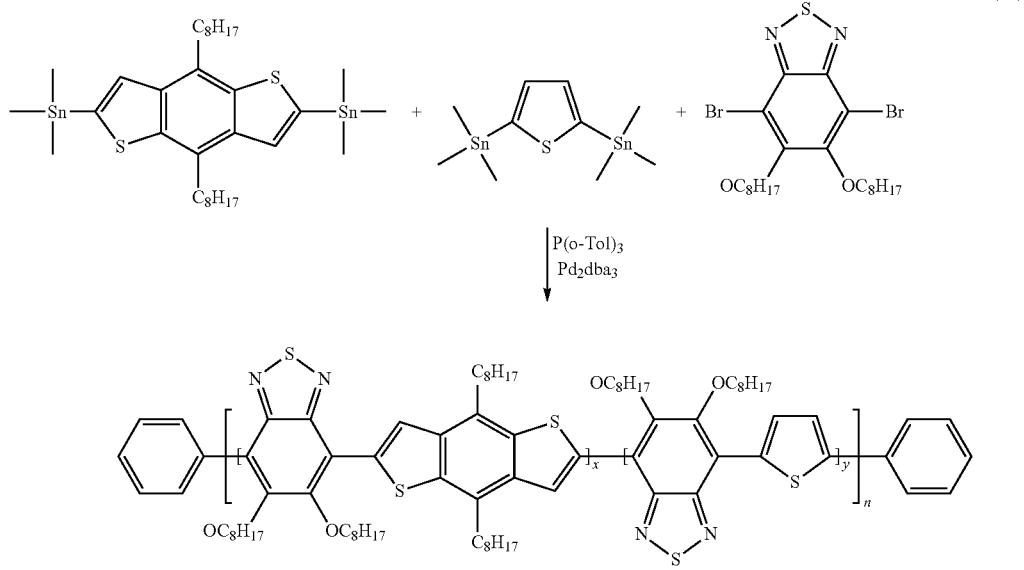

(11)

Following the general polymerisation reaction, 4,8-dioctyl-2,6-bis-trimethylstannanyl-benzo[1,2-b;4,5-b']dithiophene (296.1 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 2,5-bis-trimethylstannanyl-thiophene (163.9 mg; 0.4000 mmol; 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.0 cm$^3$) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 175° C. for 600 seconds each time. After the reaction completion, the polymer is precipitated into, collected and subjected to Soxhlet extraction. Isopropyl alcohol (200 cm$^3$) is added dropwise to the cyclohexane fraction (150 cm$^3$) and the resulting precipitate collected by filtration and dried in vacuo to give a black solid (430 mg, Yield: 84%). GPC (140° C., 1,2,4-trichlorobenzene): $M_n$=22.3 kg·mol$^{-1}$; $M_w$=43.8 kg·mol$^{-1}$; PDI=1.97.

Example 12

Polymer 12

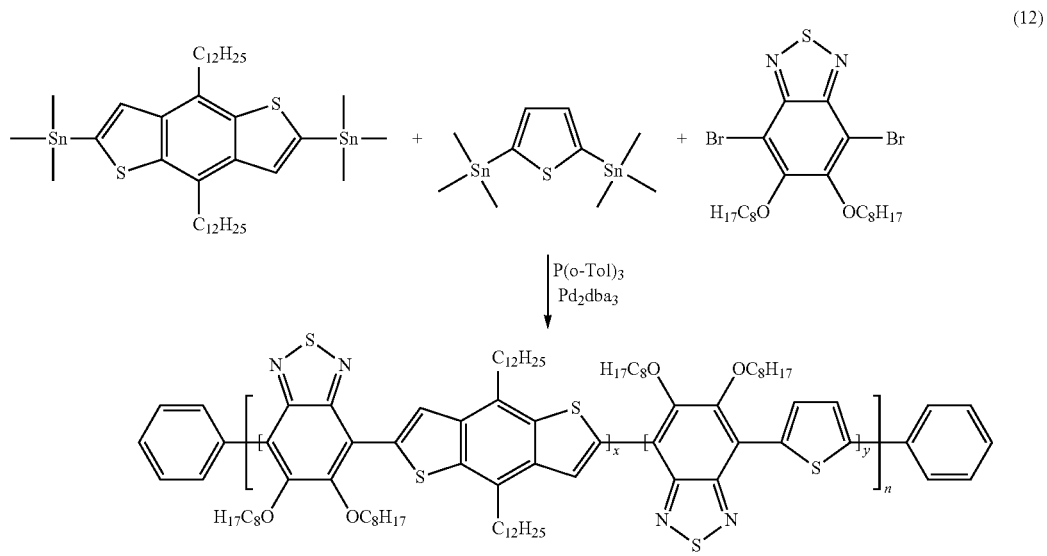

(12)

Following the general polymerisation reaction, 4,8-didodecyl-2,6-bis-trimethylstannanyl-benzo[1,2-b;4,5-b']dithiophene (272.8 mg, 0.3200 mmol, 0.8000 eq.), 4,7-dibromo-5,6-bis-octyloxy-benzo[1,2,5]thiadiazole (440.3 mg, 0.8000 mmol, 2.000 eq.), 2,5-bis-trimethylstannanyl-thiophene (196.7 mg, 0.4800 mmol, 1.200 eq.), tri-o-tolyl-phosphine (19.5 mg, 64.0 µmol, 0.160 eq.), tris(dibenzylideneacetone)dipalladium(0) (14.7 mg; 16.0 µmol; 0.0400 eq.) and chlorobenzene (5.0 cm³) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm³; 0.80 mmol; 2.0 eq.) and bromobenzene (0.13 cm³; 1.2 mmol; 3.0 eq.) at 175° C. for 600 seconds each time. After the reaction completion, the polymer is precipitated into, collected and subjected to Soxhlet extraction. Isopropyl alcohol (200 cm³) is added dropwise to the cyclohexane fraction (150 cm³) and the resulting precipitate collected by filtration and dried in vacuo to give a black solid (430 mg, Yield: 83%). GPC (140° C., 1,2,4-trichlorobenzene): $M_n$=28.1 kg·mol⁻¹; $M_w$=55.6 kg·mol⁻¹; PDI=1.98.

Example 13

Polymer 13

Following the general polymerisation reaction, 2,6-bis-trimethylstannanyl-benzo[1,2-b;4,5-b']dithiophene (206.4 mg; 0.4000 mmol; 1.000 eq.), 4,7-dibromo-5,6-bis-dodecyloxy-benzo[1,2,5]thiadiazole (530.1 mg; 0.8000 mmol; 2.000 eq.), 2,5-bis-trimethylstannanyl-thiophene (163.9 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm³) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm³; 0.80 mmol; 2.0 eq.) and bromobenzene (0.13 cm³; 1.2 mmol; 3.0 eq.) at 175° C. for 600 seconds each time. After the reaction completion, the polymer is precipitated, collected and subjected to Soxhlet extraction. Isopropyl alcohol (200 cm³) is added dropwise to the cyclohexane fraction (150 cm³) and the resulting precipitate collected by filtration and dried in vacuo to give a black solid (495 mg, Yield: 97%). GPC (140° C., 1,2,4-trichlorobenzene): $M_n$=23.3 kg·mol⁻¹; $M_w$=50.4 kg·mol⁻¹; PDI=2.16.

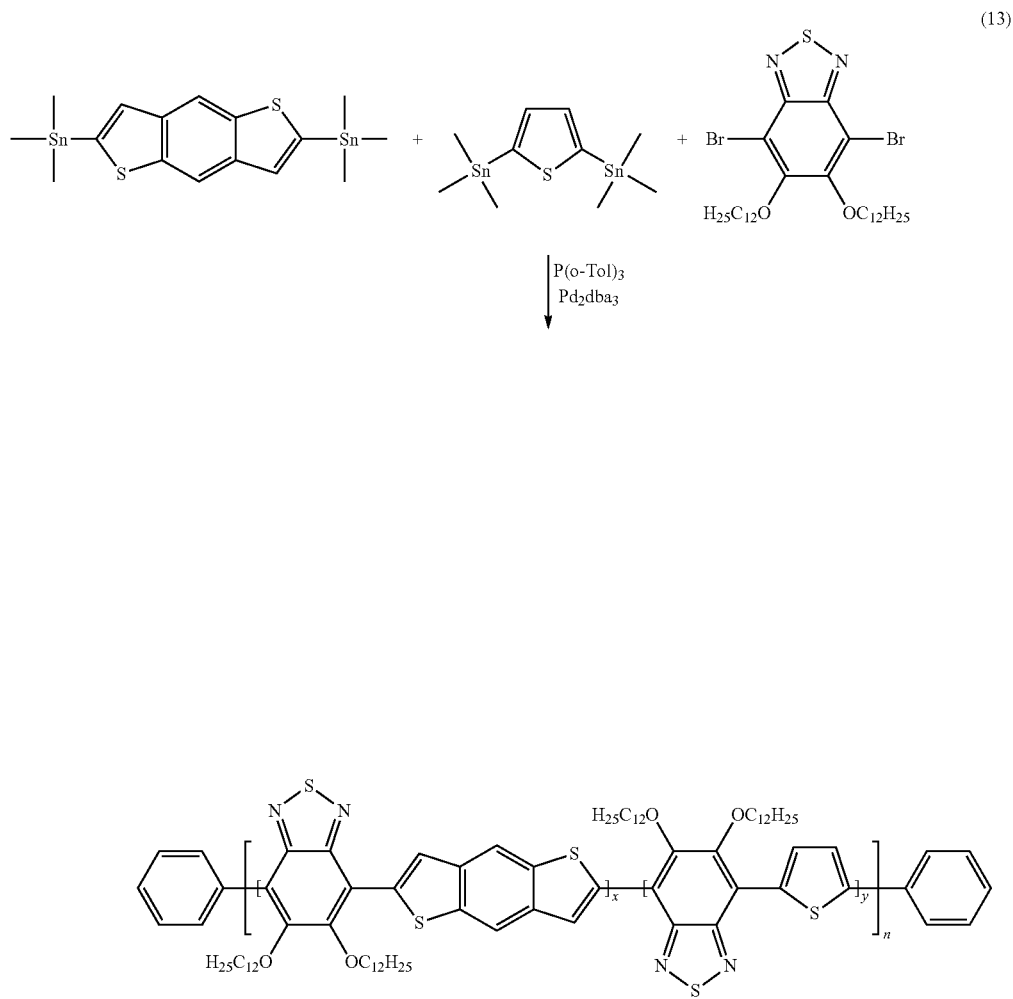

(13)

Example 14

Polymer 14

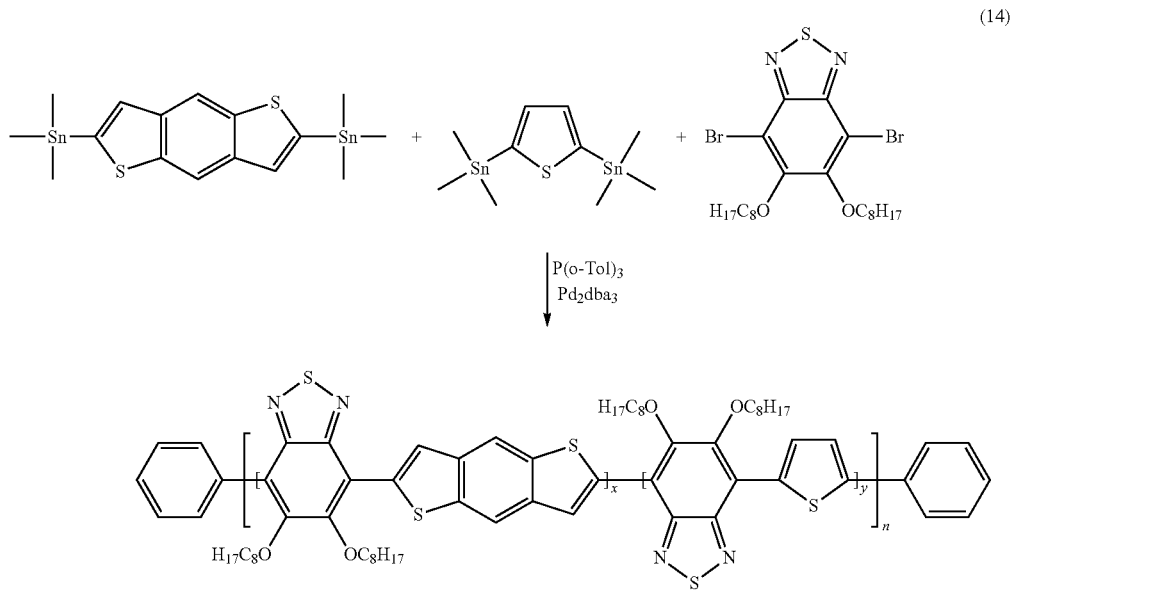

Following the general polymerisation reaction, 2,6-bis-trimethylstannanyl-benzo[1,2-b;4,5-b']dithiophene (206.4 mg; 0.4000 mmol; 1.000 eq.), 4,7-dibromo-5,6-bis-octyloxy-benzo[1,2,5]thiadiazole (440.3 mg, 0.8000 mmol, 2.000 eq.), 2,5-bis-trimethylstannanyl-thiophene (163.9 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm$^3$) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 175° C. for 600 seconds each time. After the reaction completion, the polymer is precipitated, collected and subjected to Soxhlet extraction. Methanol (200 cm$^3$) is added dropwise to the chloroform fraction (150 cm$^3$) and the resulting precipitate collected by filtration and dried in vacuo to give a black solid (394 mg, Yield: 94%). GPC (140° C., 1,2,4-trichlorobenzene): $M_n$=24.4 kg·mol$^{-1}$; $M_w$=59.6 kg·mol$^{-1}$; PDI=2.44.

Example 15

Polymer 15

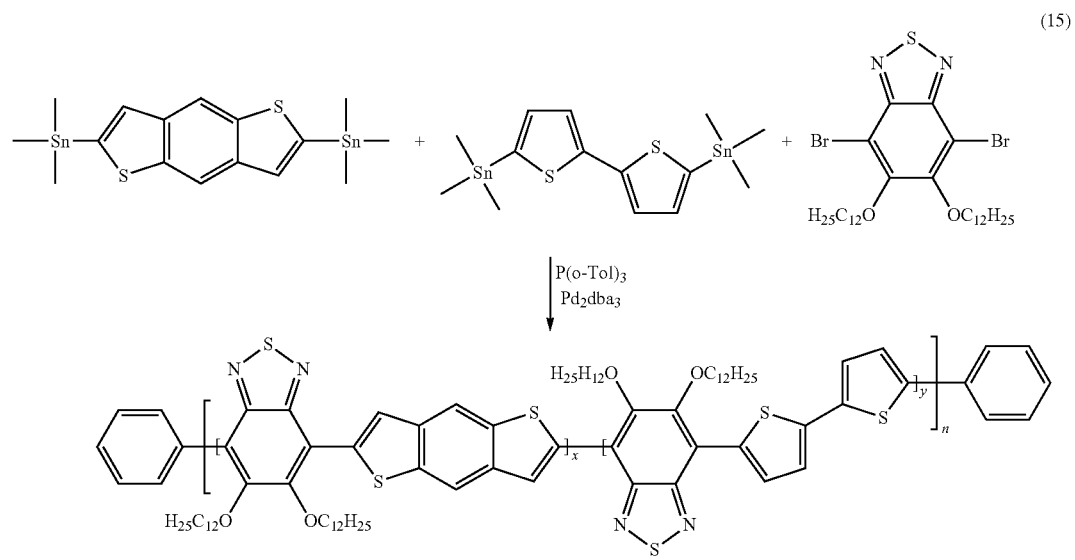

Following the general polymerisation reaction, 2,6-bis-trimethylstannanyl-benzo[1,2-b;4,5-b']dithiophene (206.4 mg; 0.4000 mmol; 1.000 eq.), 4,7-dibromo-5,6-bis-dodecyloxy-benzo[1,2,5]thiadiazole (530.1 mg; 0.8000 mmol; 2.000 eq.), 5,5'-bis-trimethylstannanyl-[2,2']bithiophenyl (196.8 mg; 0.4000 mmol; 1.000 eq.), tri-o-tolyl-phosphine (19.5 mg; 64.0 µmol; 0.160 eq.), tris(dibenzylideneacetone) dipalladium(0) (14.7 mg; 16.0 µmol; 0.0400 eq.) and chlorobenzene (5.0 cm$^3$) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 175° C. for 600 seconds each time. After the reaction completion, the polymer is precipitated collected, washed and subjected to Soxhlet extraction. Methanol (200 cm$^3$) is added dropwise to the chloroform fraction (150 cm$^3$) and the resulting precipitate collected by filtration and dried in vacuo to give a black solid (518 mg, Yield: 95%). GPC (140° C., 1,2,4-trichlorobenzene): $M_n$=28.8 kg·mol$^{-1}$; $M_w$=63.9 kg·mol$^{-1}$; PDI=2.22.

Example 16

Polymer 16

Following the general polymerisation reaction, 4,8-didodecyl-2,6-bis-trimethylstannanyl-benzo[1,2-b;4,5-b']dithiophene (255.8 mg; 0.3000 mmol; 1.000 eq.), 4,7-dibromo-5,6-bis-octyloxy-benzo[1,2,5]thiadiazole (495.3 mg; 0.9000 mmol; 3.000 eq.), 2,5-bis-trimethylstannanyl-thiophene (245.9 mg; 0.6000 mmol; 2.000 eq.), tri-o-tolyl-phosphine (14.6 mg; 48.0 µmol; 0.160 eq.), tris(dibenzylideneacetone) dipalladium(0) (11.0 mg; 12.0 µmol; 0.0400 eq.) and chlorobenzene (5.0 cm$^3$) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.20 cm$^3$; 0.60 mmol; 2.0 eq.) and bromobenzene (0.10 cm$^3$; 0.9 mmol; 3.0 eq.) at 175° C. for 600 seconds each time. After the reaction completion, the polymer is precipitated, collected and subjected to Soxhlet extraction. Isopropyl alcohol (200 cm$^3$) is added dropwise to the cyclohexane fraction (150 cm$^3$) and the resulting precipitate collected by filtration and dried in vacuo to give a black solid (463 mg, Yield: 83%). GPC (140° C., 1,2,4-trichlorobenzene): $M_n$=28.8 kg·mol$^{-1}$; $M_w$=78.0 kg·mol$^{-1}$; PDI=1.74.

(16)

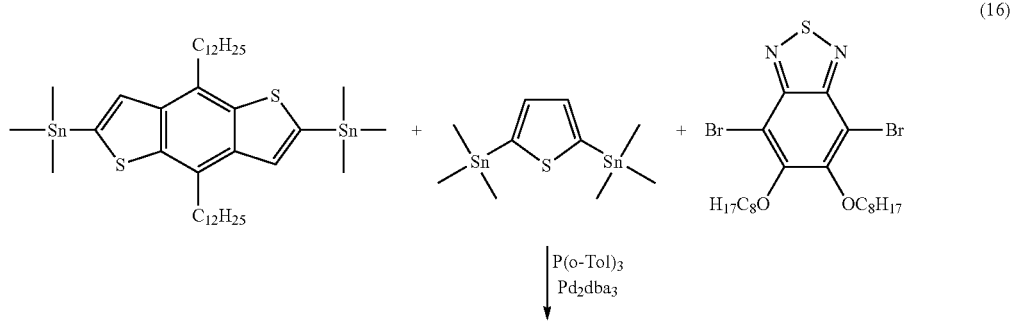

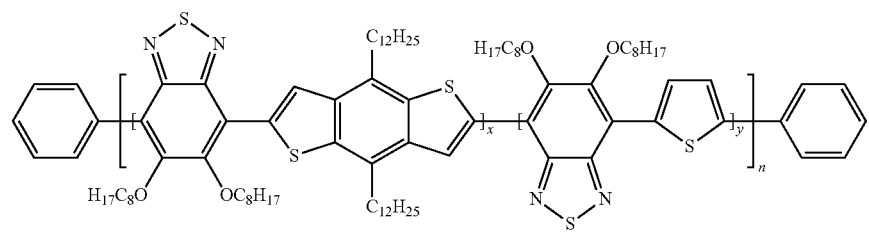

Example 17

Polymer 17

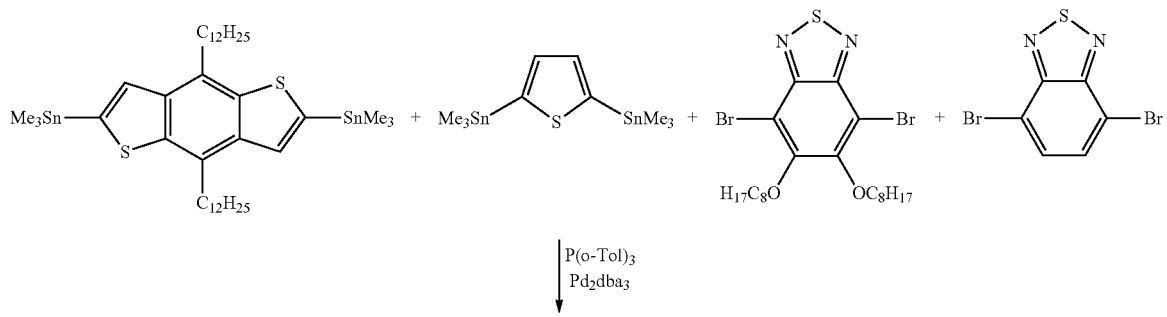

(17)

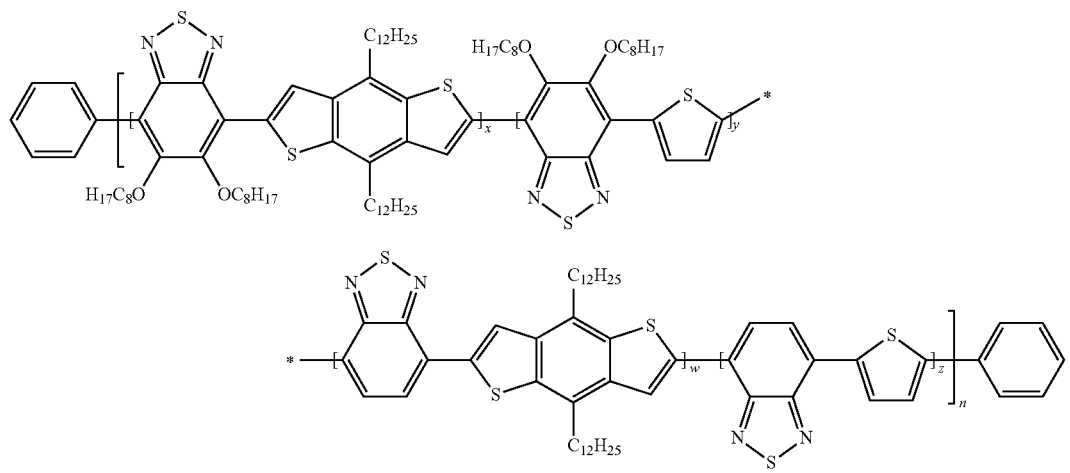

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 4,7-dibromo-benzo[1,2,5]thiadiazole (117.6 mg; 0.4000 mmol; 1.000 eq.), 2,5-bis-trimethylstannanyl-thiophene (327.8 mg; 0.8000 mmol; 2.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.000 cm$^3$) are heated at 140° C. (60 minutes) with an oil bath. The reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 140° C. for 60 minutes each time. After the reaction completion, the polymer is precipitated, collected and subjected to Soxhlet extraction. Methanol (200 cm$^3$) is added dropwise to the chloroform fraction (150 cm$^3$) and the resulting precipitate is collected by filtration and dried in vacuo to give a black solid (628 mg, Yield: 98%). GPC (140° C., 1,2,4-trichlorobenzene): $M_n$=41.0 kg·mol$^{-1}$; $M_w$=92.7 kg·mol$^{-1}$; PDI=2.26.

Example 18

Polymer 18

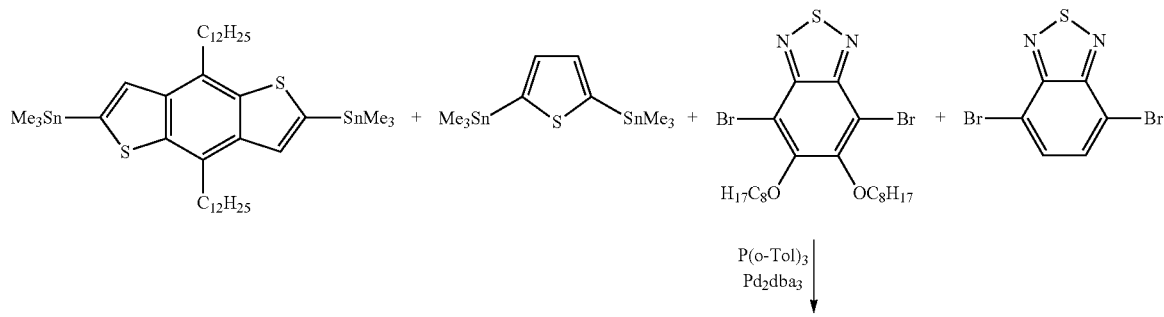

(18)

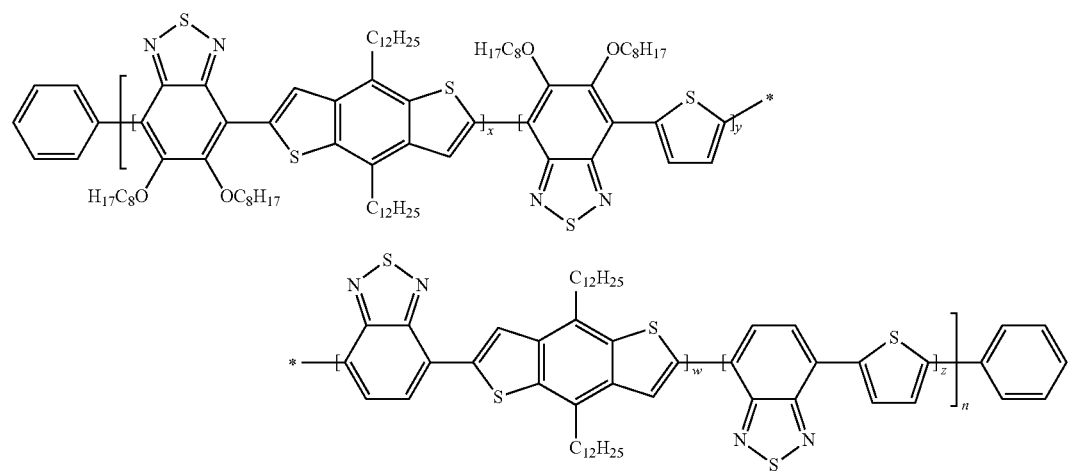

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (396.3 mg, 0.720 mmol, 1.800 eq.), 4,7-dibromo-benzo[1,2,5]thiadiazole (23.5 mg, 0.080 mmol, 0.200 eq.), 2,5-bis-trimethylstannanyl-thiophene (163.9 mg, 0.400 mmol, 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.000 cm³) are heated at 140° C. (60 seconds), 160° C. (60 seconds) and 175° C. (1800 seconds) in a microwave reactor (Biotage Initiator). The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. (60 minutes) each time. After the reaction completion, the polymer is precipitated, collected and subjected to Soxhlet extraction. The cyclohexane fraction is reduced in vacuo, redissolved in chloroform (150 cm³) and precipitated into stirred methanol (250 cm³), and collected by filtration and dried in vacuo to give a black solid (440 mg, Yield: 82%). GPC (140° C., 1,2,4-trichlorobenzene): $M_n$=21.3 kg·mol⁻¹; $M_w$=42.0 kg·mol⁻¹; PDI=1.97.

Example 19

Polymer 19

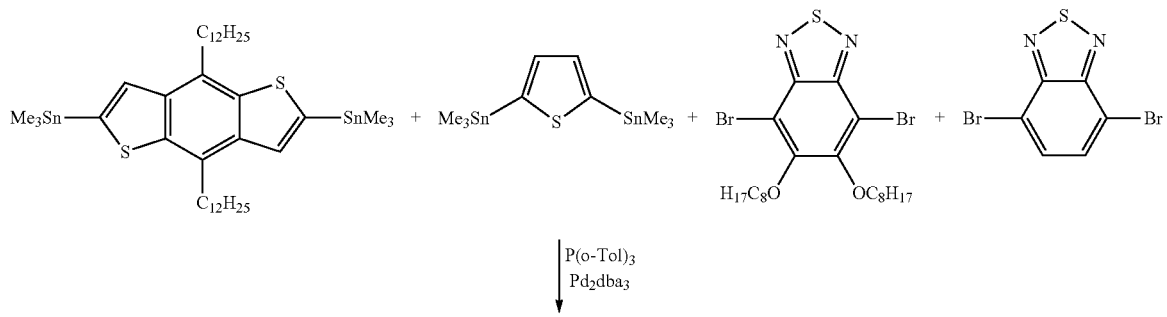

(19)

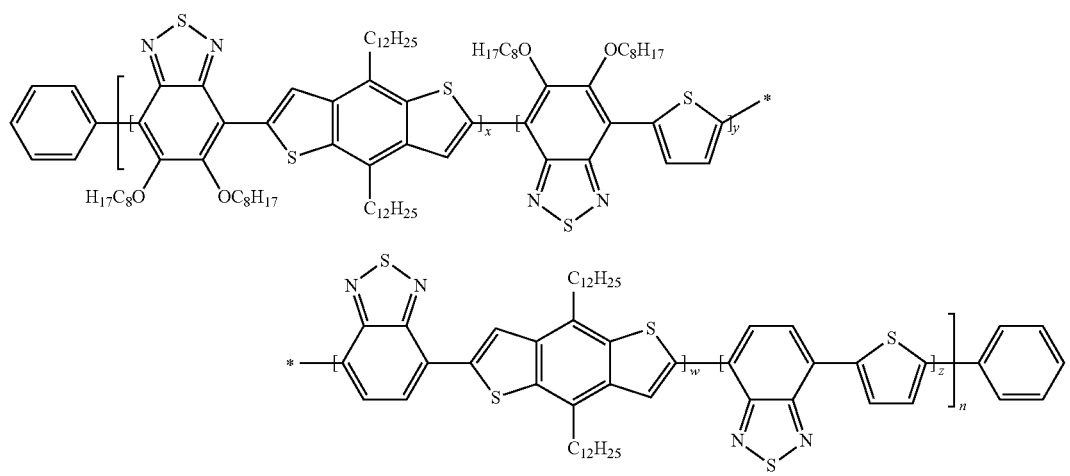

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (220.2 mg, 0.4000 mmol, 1.000 eq.), 4,7-dibromo-benzo[1,2,5]thiadiazole (117.6 mg, 0.400 mmol, 1.000 eq.), 2,5-bis-trimethylstannanyl-thiophene (163.9 mg, 0.400 mmol, 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.000 cm³) are heated at 140° C. (60 seconds), 160° C. (60 seconds) and 175° C. (1800 seconds) in a microwave reactor (Biotage Initiator).

The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and dried in vacuo to give a black solid (420 mg, Yield: 93%). GPC (50° C., chlorobenzene): $M_n$=3.0 kg·mol⁻1; $M_w$=7.8 kg·mol⁻¹; PDI=2.59.

Example 20

Polymer 20

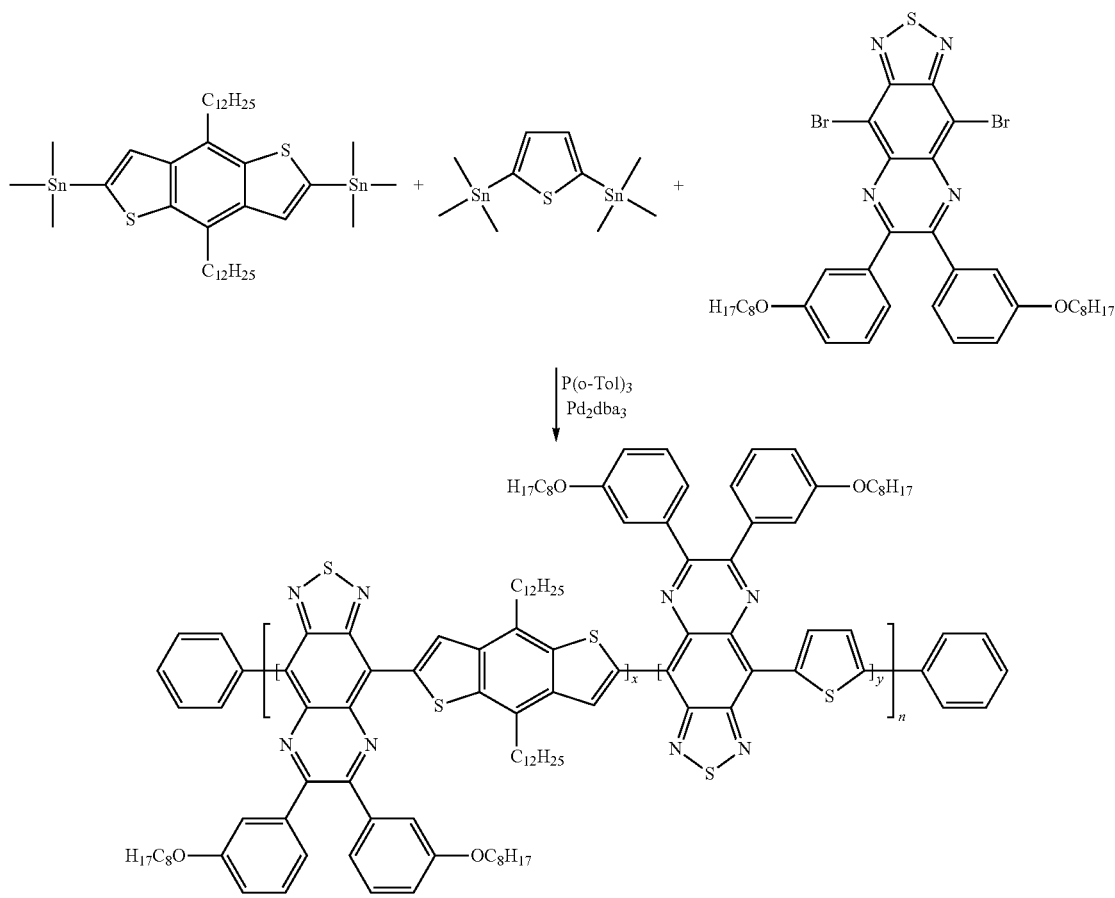

(20)

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,9-dibromo-6,7-bis-(3-octyloxy-phenyl)-2-thia-1,3,5,8-tetraazacyclopenta[b]naphthalene (603.7 mg; 0.8000 mmol; 2.000 eq.), 2,5-bis-trimethylstannanyl-thiophene (163.9 mg; 0.4000 mmol; 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.0 cm³) are heated at 140° C. (120 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (706 mg, Yield: 98%). GPC (140° C., 1,2,4-trichlorobenzene): $M_n$=9.4 kg·mol$^{-1}$; $M_w$=23.1 kg·mol$^{-1}$; PDI=2.43.

Example 21

Polymer 21

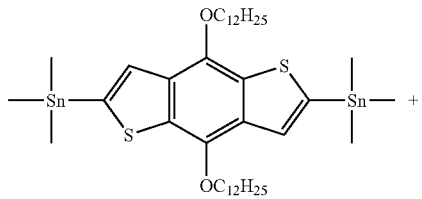

(21)

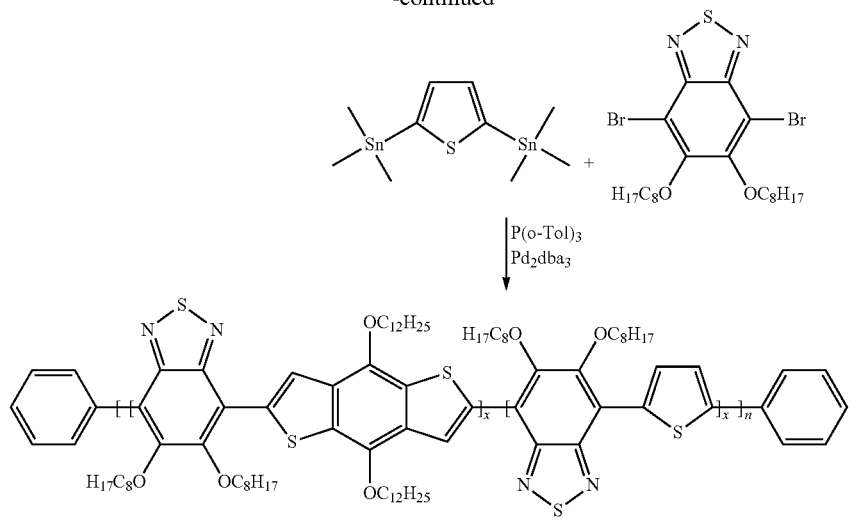

Following the general polymerisation reaction, 4,8-bis-dodecyloxy-2,6-bis-trimethylstannanyl-benzo[1,2-b;4,5-b']dithiophene (353.8 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 2,5-bis-trimethylstannanyl-thiophene (163.9 mg; 0.4000 mmol; 1.000 eq.), tri-o-tolyl-phosphine (19.5 mg; 64.0 µmol; 0.160 eq.), tris(dibenzylide-neacetone)dipalladium(0) (14.7 mg; 16.0 µmol; 0.0400 eq.) and chlorobenzene (5.0 cm³) are heated at 140° C. (135 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction comple-tion, the polymer is precipitated, collected and subjected to Soxhlet extraction with acetone, petroleum ether (40-60° C.) and toluene. Methanol (200 cm³) is added dropwise to the toluene fraction (150 cm³) and the resulting precipitate collected by filtration and dried in vacuo to give a black solid (532 mg, Yield: 94%). GPC (140° C., 1,2,4-trichloroben-zene): $M_n$=35.5 kg·mol$^{-1}$; $M_w$=81.2 kg·mol$^{-1}$; PDI=2.29.

Example 22

Polymer 22

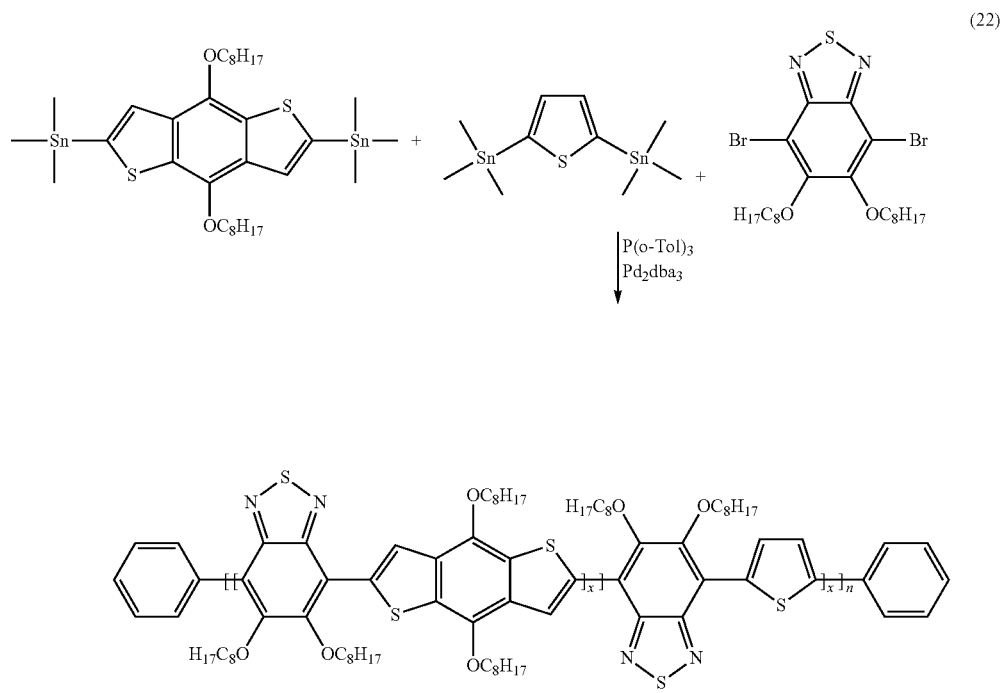

Following the general polymerisation reaction, 4,8-bis-octyloxy-2,6-bis-trimethylstannanyl-benzo[1,2-b;4,5-b']dithiophene (308.9 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 2,5-bis-trimethylstannanyl-thiophene (163.9 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm³) are heated at 140° C. (135 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated into, collected and subjected to Soxhlet extraction with acetone, petroleum ether (40-60° C.) and toluene. Methanol (200 cm³) is added dropwise to the toluene fraction (150 cm³) and the resulting precipitate collected by filtration and dried in vacuo to give a black solid (488 mg, Yield: 94%). GPC (140° C., 1,2,4-trichlorobenzene): $M_n$=37.4 kg·mol$^{-1}$; $M_w$=86.8 kg·mol$^{-1}$; PDI=2.32.

Example 23

Example 23.1

4,8-Bis-(1-dodecyl-tridecyloxy)-benzo[1,2-b;4,5-b']dithiophene

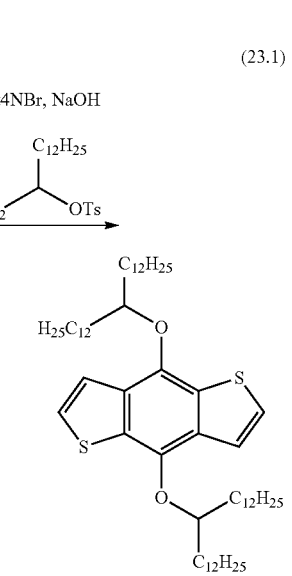

(23.1)

Benzo[1,2-b;4,5-b']dithiophene-4,8-dione (2.50 g; 11.4 mmol; 1.00 eq.), zinc powder (1.93 g; 29.5 mmol; 2.60 eq.), tetrabutylammonium bromide (1.14 g; 3.53 mmol; 0.311 eq.), sodium hydroxide (6.82 g; 170 mmol; 15.0 eq.) and water (34 cm³) are placed in a 100 cm³ flask. The reaction mixture is stirred and heated to 105° C. for 1 hour, then toluene-4-sulfonic acid 1-dodecyl-tridecyl ester (17.8 g; 34.1 mmol; 3.00 eq.) is added. The reaction is further stirred for 2 hours at 105° C. and an additional amount of zinc powder (0.682 g; 10.4 mmol; 0.919 eq.) is added. The mixture is maintained at 105° C. for 16 hours, cooled down, poured into water and extracted with diethyl ether (3×100 cm³), dried over magnesium sulfate, filtered and the solvent evaporated. The crude product is purified by column chromatography using petroleum ether (40-60° C.) until the first product is eluated then using a 90:10 mixture of petroleum ether (40-60° C.) and dichloromethane to give a colourless oil (3.65 g, Yield: 35%). $^1$H NMR (300 MHz, CDCl$_3$): δ 7.46 (d, J=5.7 Hz, 2H), 7.32 (d, J=5.6 Hz, 2H), 4.56 (quin, J=5.7 Hz, 2H), 1.63-1.75 (m, 8H), 1.40-1.51 (m, 8H), 1.19-1.32 (m, 72H), 0.88 (t, J=6.7 Hz, 12H).

Example 23.2

4,8-Bis-(1-dodecyl-tridecyloxy)-2,6-bis-trimethyl-stannanyl-benzo[1,2-b;4,5-b']dithiophene

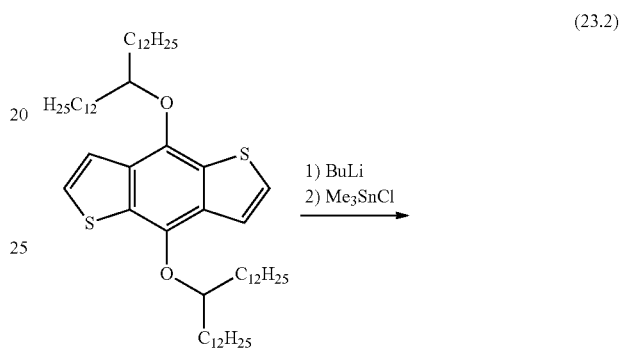

(23.2)

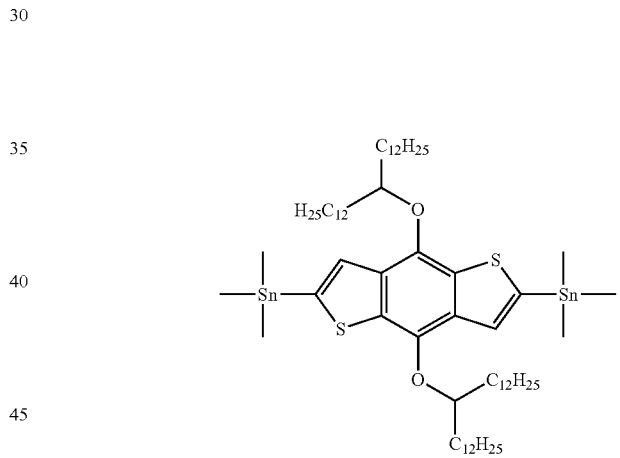

4,8-Bis-(1-dodecyl-tridecyloxy)-benzo[1,2-b;4,5-b']dithiophene (4.200 g; 4.547 mmol; 1.000 eq.) is dissolved into tetrahydrofuran anhydrous (90 cm³) and the solution cooled down to −78° C. A 2.5 M solution of n-butyllithium in hexanes (5.50 cm³; 13.6 mmol; 3.00 eq.) is added dropwise over 10 minutes. The resulting mixture is stirred at −78° C. for 30 minutes and at 23° C. for 30 minutes, cooled down back to −78° C. and a 1.0 M solution of trimethyltinchloride in hexanes (14.6 cm³; 14.6 mmol; 3.20 eq.) added in one portion. The cooling bath is removed and the resulting solution stirred at 23° C. for 60 minutes. The reaction mixture is poured into water (100 cm³) and extracted with diethyl ether (3×150 cm³). The combined organic fractions are dried over sodium sulfate and removed in vacuo to give a greenish oil which is used without further purification (5.243 g, Yield: 92%). $^1$H NMR (300 MHz, CDCl$_3$): δ 7.51 (s, 2H), 4.61 (quin, J=5.6 Hz, 2H), 1.61-1.86 (m, 8H), 1.47-1.59 (m, 8H), 1.25 (s, 72H), 0.88 (t, J=6.7 Hz, 12H), 0.43 (s, 18H).

Example 23.3

Polymer 23

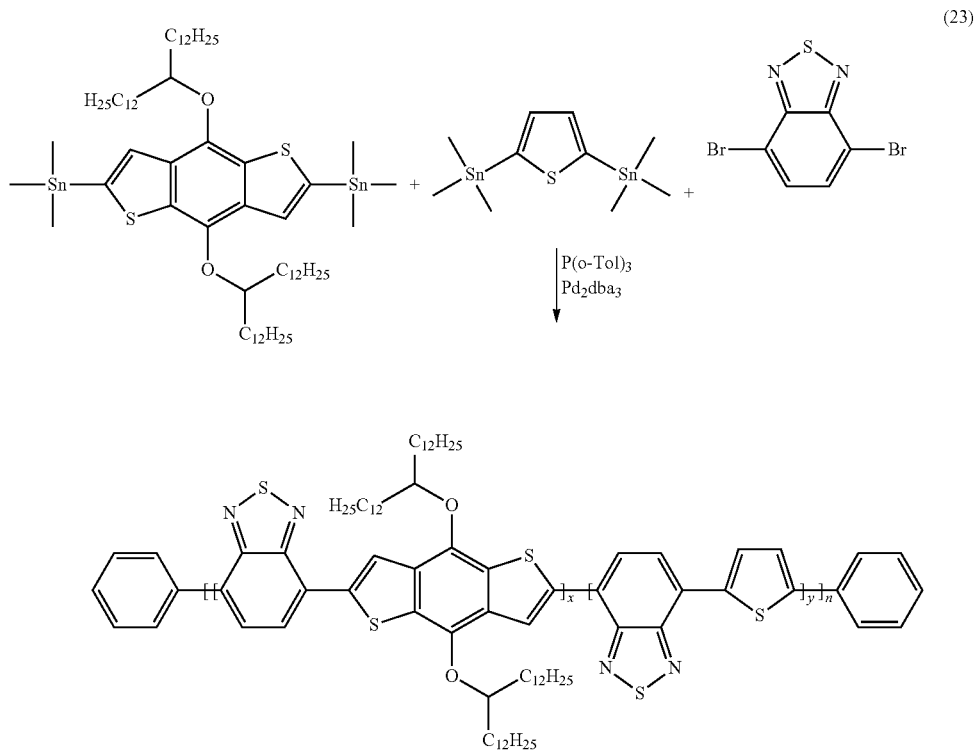

Following the general polymerisation reaction, 4,8-bis-(1-dodecyl-tridecyloxy)-2,6-bis-trimethylstannanyl-benzo[1,2-b;4,5-b']dithiophene (480.6 mg; 0.3847 mmol; 1.000 eq.), 4,7-dibromo-benzo[1,2,5]thiadiazole (226.2 mg; 0.7694 mmol; 2.000 eq.), 2,5-Bis-trimethylstannanyl-thiophene (157.6 mg; 0.3847 mmol; 1.000 eq.), tri-o-tolyl-phosphine (18.7 mg; 61.6 µmol; 0.160 eq.), tris(dibenzylideneacetone)dipalladium(0) (14.1 mg; 15.4 µmol; 0.0400 eq) and chlorobenzene (4.9 cm$^3$) are heated at 140° C. (135 minutes) with a preheated oil bath. The reaction is end-capped with tributyl-phenyl-stannane (0.25 cm$^3$; 0.77 mmol; 2.0 eq.) and bromobenzene (0.12 cm$^3$; 1.1 mmol; 3.0 eq.) at 140° C. for 60 minutes each time. After the reaction completion, the polymer is precipitated, collected and subjected to Soxhlet extraction with acetone, petroleum ether (40-60° C.) and toluene. Methanol (200 cm$^3$) is added dropwise to the toluene fraction (150 cm$^3$) and the resulting precipitate collected by filtration and dried in vacuo to give a black solid (443 mg, Yield: 91%). GPC (140° C., 1,2,4-trichlorobenzene): $M_n$=18.2 kg·mol$^{-1}$; $M_w$=38.3 kg·mol$^{-1}$; PDI=2.10.

Example 24

Example 24.1

4,8-Bis-(1-octyl-nonyloxy)-benzo[1,2-b;4,5-b']dithiophene

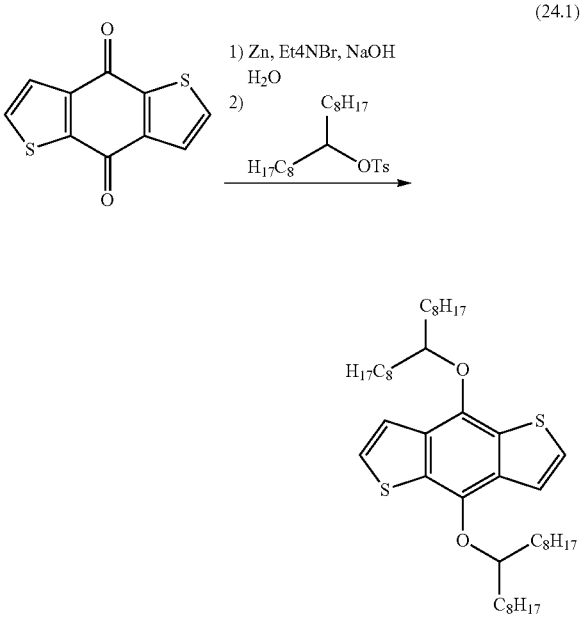

Benzo[1,2-b;4,5-b']dithiophene-4,8-dione (3.00 g; 13.6 mmol; 1.00 eq.), zinc powder (2.32 g; 35.5 mmol; 2.60 eq.), tetrabutylammonium bromide (1.37 g; 4.24 mmol; 0.311 eq.), sodium hydroxide (8.18 g; 205 mmol; 15.0 eq.) and water (41 cm³) are placed in a 100 cm³ flask. The reaction mixture is stirred and heated to 105° C. for 1 hour, then toluene-4-sulfonic acid 1-octyl-nonyl ester (22.4 g; 54.5 mmol; 4.00 eq.) is added. The reaction is further stirred for 2 hours at 105° C. and an additional amount of zinc powder (0.818 g; 12.5 mmol; 0.919 eq.) is added. The mixture is maintained at 105° C. for 16 hours, cooled down, poured into water and extracted with diethyl ether (3×100 cm³), dried over magnesium sulfate, filtered and the solvent evaporated. The crude product is purified by column chromatography using petroleum ether (40-60° C.) until the first product is eluated then using a 90:10 mixture of petroleum ether (40-60° C.) and dichloromethane to give a colourless oil (4.34 g, Yield: 46%). ¹H NMR (300 MHz, CDCl₃): δ 7.46 (d, J=5.6 Hz, 2H), 7.32 (d, J=5.6 Hz, 1H), 4.56 (quin, J=5.7 Hz, 2H), 1.61-1.78 (m, 8H), 1.36-1.59 (m, 8H), 1.25 (m, 40H), 0.87 (t, J=6.7 Hz, 12H).

Example 24.2

4,8-Bis-(1-octyl-nonyloxy)-2,6-bis-trimethylstannanyl-benzo[1,2-b;4,5-b']dithiophene

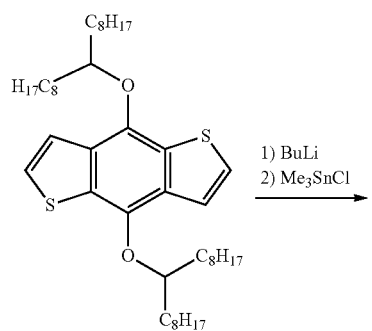

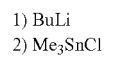

4,8-Bis-(1-octyl-nonyloxy)-benzo[1,2-b;4,5-b']dithiophene (5.000 g; 7.151 mmol; 1.000 eq.) is dissolved into tetrahydrofuran anhydrous (142 cm³) and the solution cooled down to −78° C. A 2.5 M solution of n-butyllithium in hexanes (8.58 cm³; 21.5 mmol; 3.00 eq.) is added dropwise over 10 minutes. The resulting mixture is stirred at −78° C. for 30 minutes and at 23° C. for 30 minutes, cooled down back to −78° C. and a 1.0 M solution of trimethyltinchloride in hexanes (22.9 cm³; 22.9 mmol; 3.20 eq.) added in one portion. The cooling bath is removed and the resulting solution stirred at 23° C. for 60 minutes. The reaction mixture is poured into water (100 cm³) and extracted with diethyl ether (3×150 cm³). The combined organic fractions are dried over sodium sulfate and removed in vacuo to give a greenish oil which is used without further purification (7.020 g, Yield: 96%). ¹H NMR (300 MHz, CDCl₃): δ 7.44 (s, 2H), 4.58 (quin, J=5.7 Hz, 2H), 1.58-1.72 (m, 8H), 1.31-1.55 (m, 8H), 1.14-1.31 (m, 40H), 0.83 (t, J=6.4 Hz, 12H), 0.40 (s, 18H).

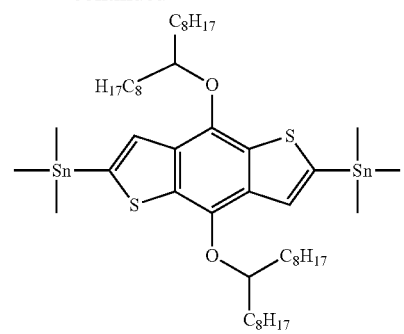

Example 24.3

Polymer 24

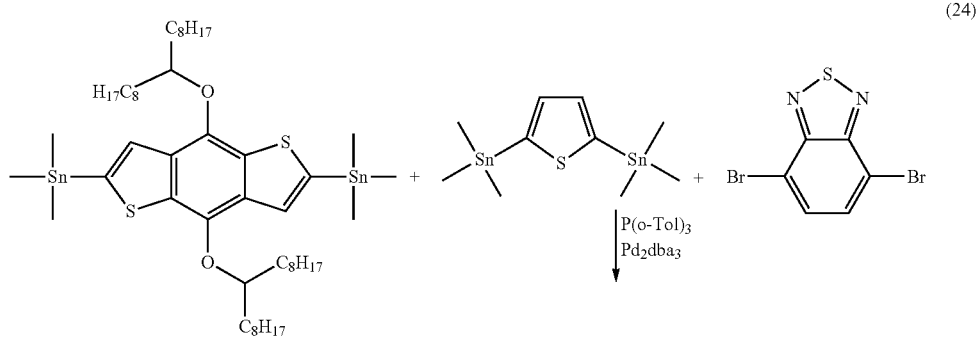

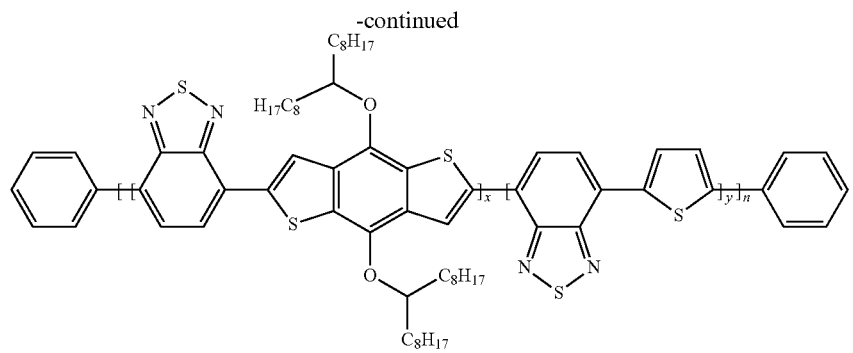

Following the general polymerisation reaction, 4,8-bis-(1-octyl-nonyloxy)-2,6-bis-trimethylstannanyl-benzo[1,2-b;4,5-b']dithiophene (407.4 mg; 0.3975 mmol; 1.000 eq.), 4,7-dibromo-benzo[1,2,5]thiadiazole (233.7 mg; 0.7951 mmol; 2.000 eq.), 2,5-bis-trimethylstannanyl-thiophene (162.9 mg; 0.3975 mmol; 1.000 eq.), tri-o-tolyl-phosphine (19.4 mg; 63.6 µmol; 0.160 eq.), tris(dibenzylideneacetone)dipalladium(0) (14.6 mg; 15.9 µmol; 0.0400 eq.) and chlorobenzene (5.0 cm³) are heated at 140° C. (135 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction with acetone, petroleum ether (40-60° C.) and toluene. Methanol (200 cm³) is added dropwise to the toluene fraction (150 cm³) and the resulting precipitate collected by filtration and dried in vacuo to give a black solid (369 mg, Yield: 89%). GPC (140° C., 1,2,4-trichlorobenzene): $M_n$=15.2 kg·mol$^{-1}$; $M_w$=36.9 kg·mol$^{-1}$; PDI=2.43.

Example 25

Polymer 25

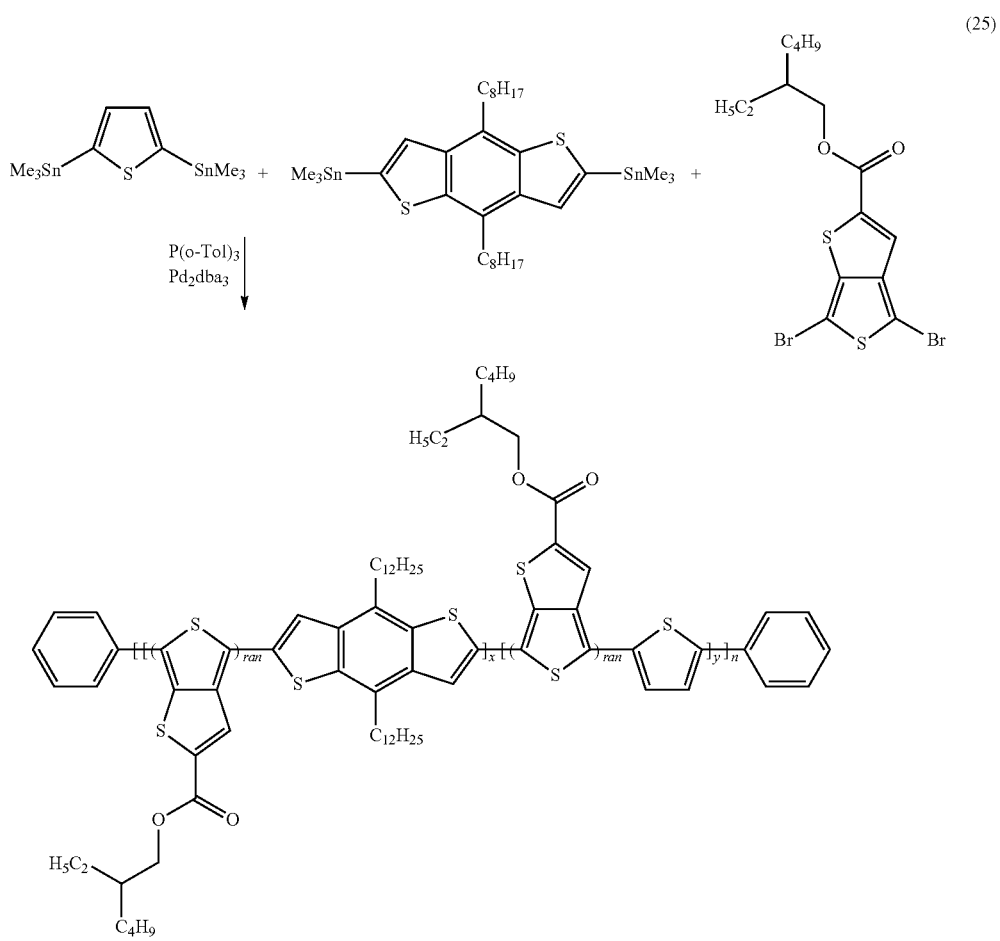

Following the general polymerisation reaction, 4,8-dioctyl-2,6-bis-trimethylstannanyl-benzo[1,2-b;4,5-b']dithiophene (381.0 mg; 0.5146 mmol; 1.000 eq.), 2,5-bis-trimethylstannanyl-thiophene (210.9 mg; 0.5146 mmol; 1.000 eq.), 4,6-dibromo-thieno[3,4-b]thiophene-2-carboxylic acid 2-ethyl-hexyl ester (467.5 mg; 1.029 mmol; 2.000 eq.), tri-o-tolyl-phosphine (25.1 mg; 82.3 µmol; 0.160 eq.), tris(dibenzylideneacetone)dipalladium(0) (18.8 mg; 20.6 µmol; 0.0400 eq.) and chlorobenzene (6.4 cm³) are heated at 140° C. (48 hours) with a preheated oil bath. The reaction is end-capped with tributyl-phenyl-stannane (0.17 cm³; 0.52 mmol; 1.0 eq.) and bromobenzene (0.081 cm³; 0.77 mmol; 1.5 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (490 mg, Yield: 88%). GPC (140° C., 1,2,4-trichlorobenzene): $M_n$=3.5 kg·mol⁻¹; $M_w$=6.5 kg·mol⁻¹; PDI=1.84.

Example 26

Polymer 26

Following the general polymerisation reaction, 4,8-didodecyloxy-2,6-bis-trimethylstannanyl-benzo[1,2-b;4,5-b']dithiophene (335.2 mg; 0.3790 mmol; 1.000 eq.), 2,5-bis-trimethylstannanyl-thiophene (155.3 mg; 0.3790 mmol; 1.000 eq.), 4,6-dibromo-thieno[3,4-b]thiophene-2-carboxylic acid 2-ethyl-hexyl ester (344.3 mg, 0.7580 mmol; 2.000 eq.), tri-o-tolyl-phosphine (18.5 mg, 60.6 µmol; 0.160 eq.), tris(dibenzylideneacetone)dipalladium(0) (13.9 mg; 20.6 µmol; 0.0400 eq.) and chlorobenzene (4.7 cm³) are heated at 140° C. (100 minutes) with a preheated oil bath. The reaction is end-capped with tributyl-phenyl-stannane (0.12 cm³; 0.38 mmol; 1.0 eq.) and bromobenzene (0.060 cm³; 0.57 mmol; 1.5 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (450 mg, Yield: 97%). GPC (140° C., 1,2,4-trichlorobenzene): $M_n$=5.9 kg·mol⁻¹; $M_w$=9.7 kg·mol⁻¹; PDI=1.63.

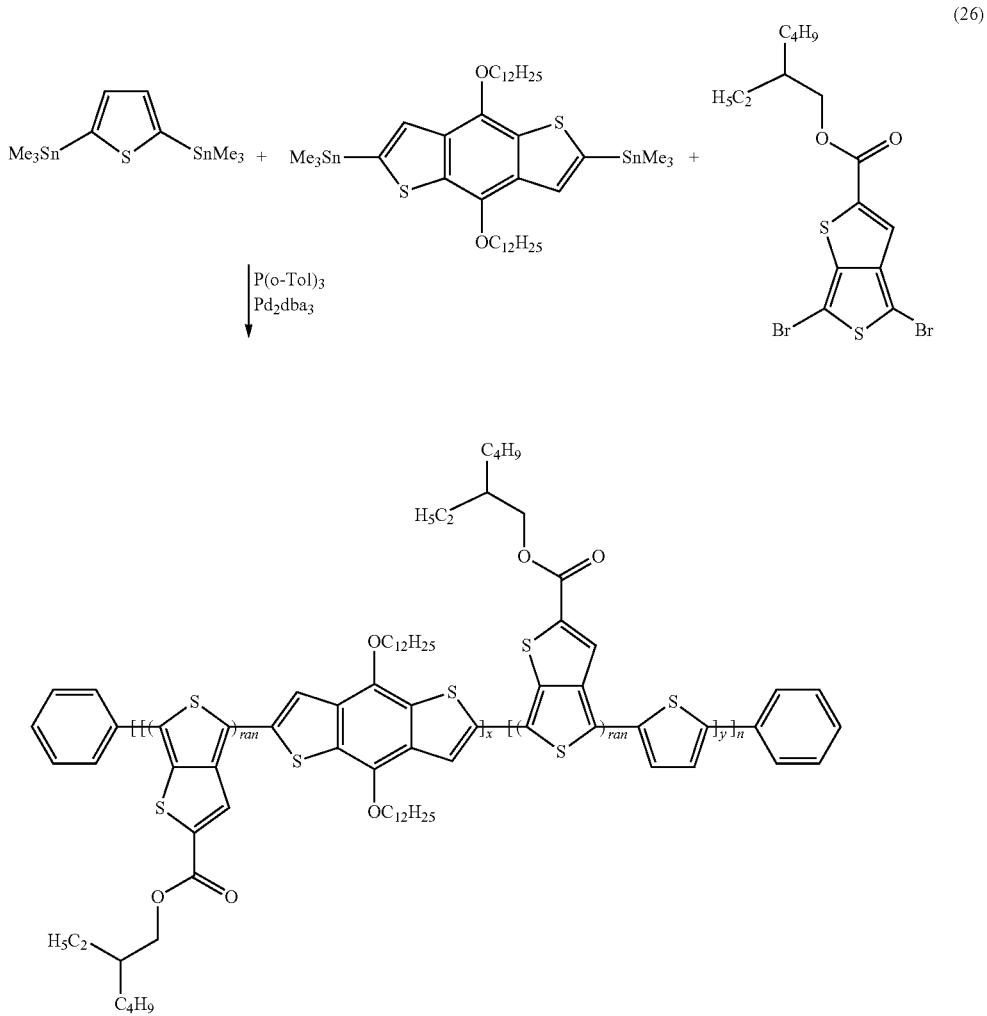

Example 27

Polymer 27

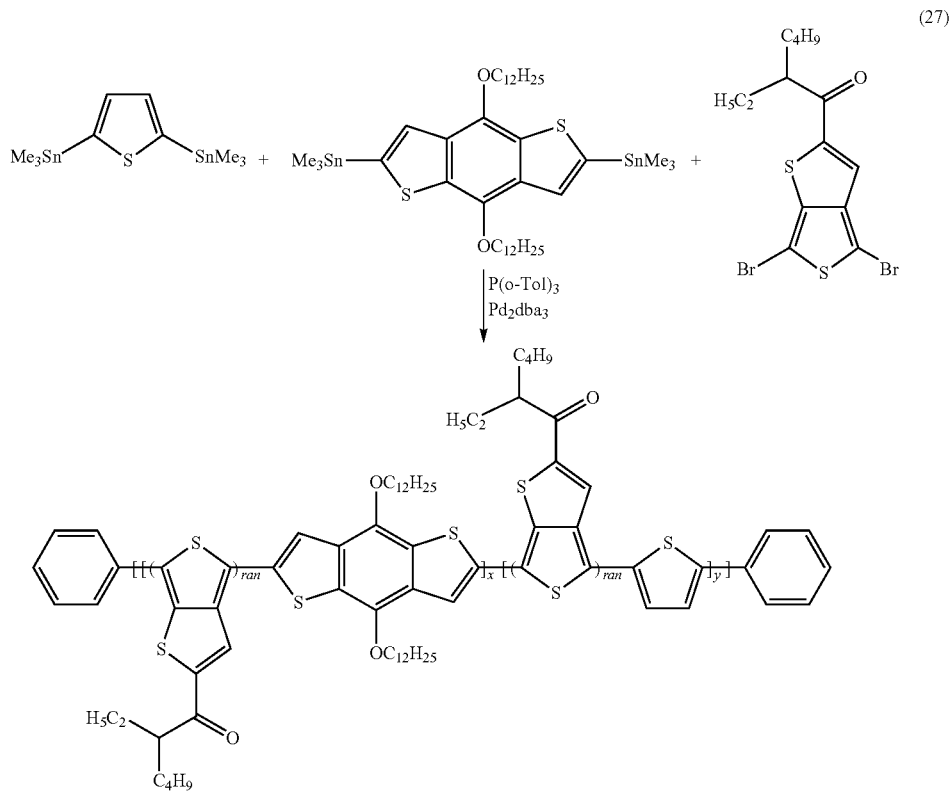

Following the general polymerisation reaction, 4,8-didodecyloxy-2,6-bis-trimethylstannanyl-benzo[1,2-b;4,5-b']dithiophene (408.3 mg; 0.4616 mmol; 1.000 eq.), 2,5-bis-trimethylstannanyl-thiophene (189.1 mg; 0.4616 mmol; 1.000 eq.), 1-(4,6-dibromo-thieno[3,4-b]thiophen-2-yl)-2-ethyl-hexan-1-one (391.6 mg; 0.9231 mmol; 2.000 eq.), tri-o-tolyl-phosphine (22.5 mg; 73.8 μmol; 0.160 eq.), tris(dibenzylideneacetone)dipalladium(0) (16.9 mg; 18.5 μmol; 0.0400 eq.) and chlorobenzene (5.7 cm³) are heated at 140° C. (160 minutes) with a preheated oil bath. The reaction is end-capped with tributyl-phenyl-stannane (0.15 cm³; 0.46 mmol; 1.0 eq.) and bromobenzene (0.073 cm³; 0.69 mmol; 1.5 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (485 mg, Yield: 90%). GPC (50° C., chlorobenzene): $M_n$=10.6 kg·mol$^{-1}$; $M_w$=27.8 kg·mol$^{-1}$; PDI=2.62.

Example 28

Polymer 28

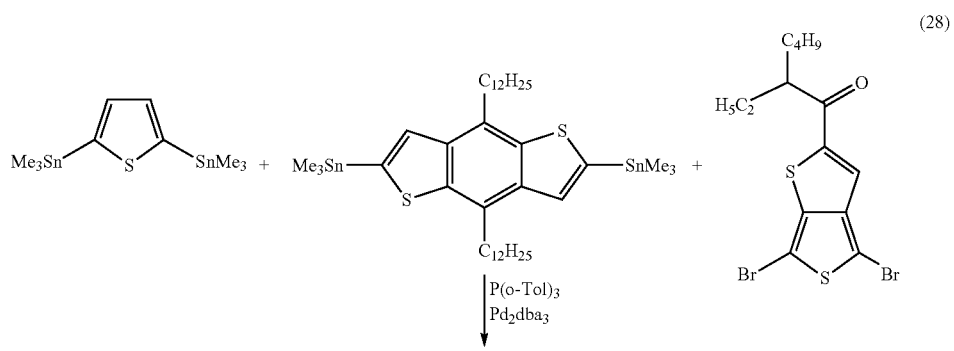

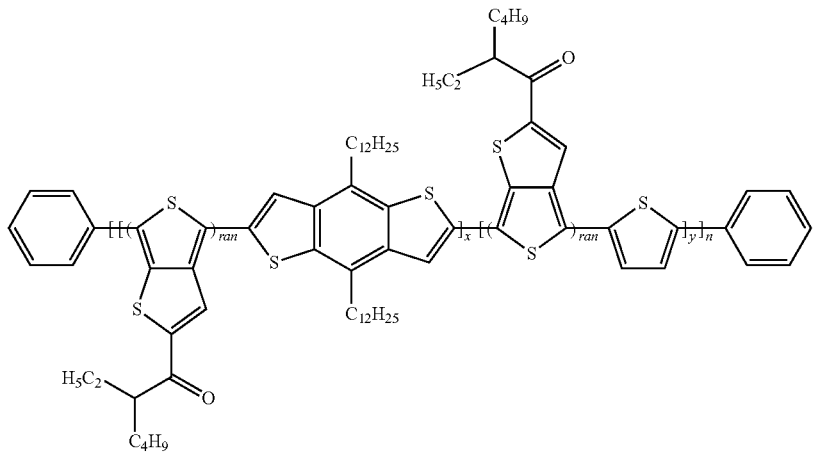

Following the general polymerisation reaction, 4,8-didodecyl-2,6-bis-trimethylstannanyl-benzo[1,2-b;4,5-b']dithiophene (447.0 mg; 0.5243 mmol; 1.000 eq.), 2,5-bis-trimethylstannanyl-thiophene (214.8 mg; 0.5243 mmol; 1.000 eq.), 1-(4,6-dibromo-thieno[3,4-b]thiophen-2-yl)-2-ethyl-hexan-1-one (444.8 mg; 1.049 mmol; 2.000 eq.), tri-o-tolyl-phosphine (25.5 mg, 83.8 µmol; 0.160 eq.), tris(dibenzylideneacetone)dipalladium(0) (19.2 mg; 21.0 µmol; 0.0400 eq.) and chlorobenzene (6.5 cm³) are heated at 140° C. (160 minutes) with a preheated oil bath. The reaction is end-capped with tributyl-phenyl-stannane (0.17 cm³; 0.52 mmol; 1.0 eq.) and bromobenzene (0.083 cm³; 0.79 mmol; 1.5 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (490 mg, Yield: 82%). GPC (50° C., chlorobenzene): $M_n$=16.3 kg·mol⁻¹; $M_w$=53.1 kg·mol⁻¹; PDI=3.25.

Example 29

Polymer 29

(29)

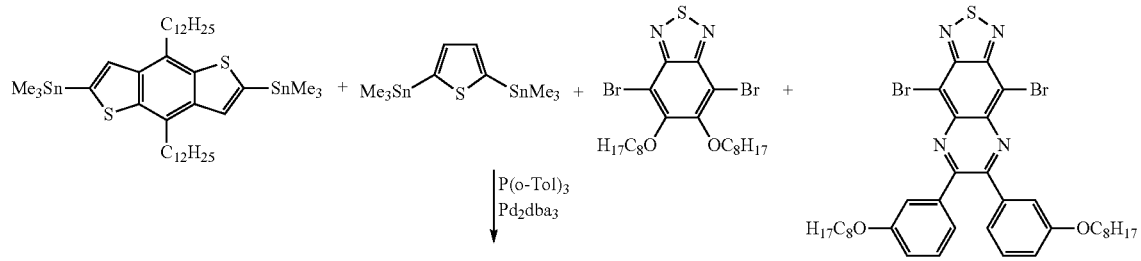

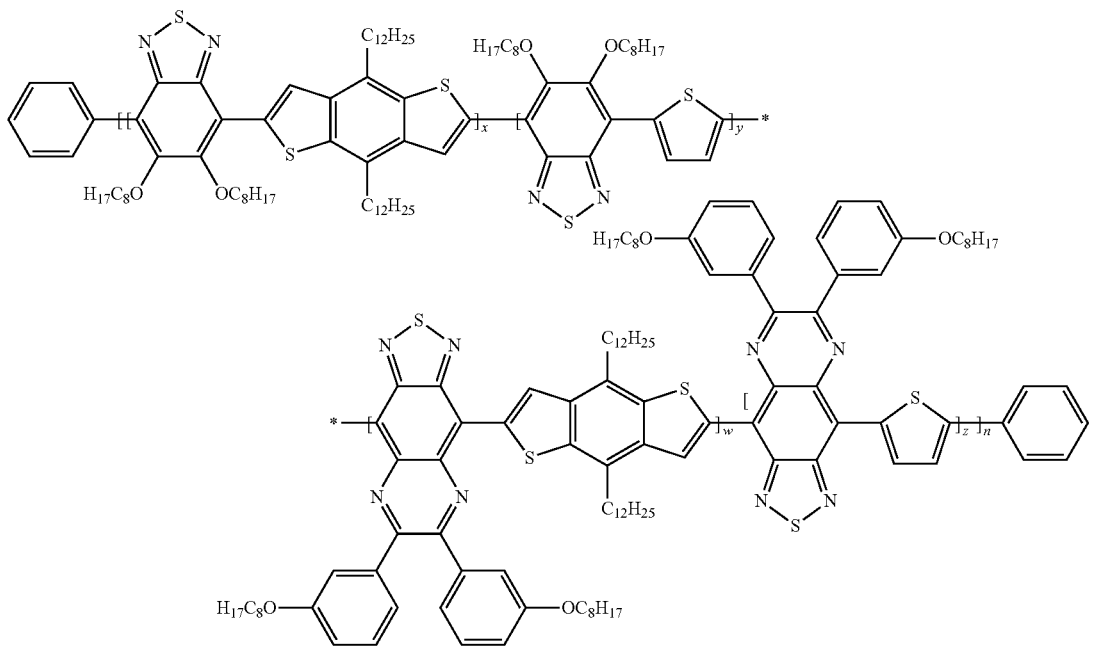

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (396.3 mg, 0.7200 mmol, 1.800 eq.), 4,9-dibromo-6,7-bis-(3-octyloxy-phenyl)-2-thia-1,3,5,8-tetraaza-cyclopenta[b]naphthalene (60.4 mg, 0.0800 mmol; 0.200 eq.), 2,5-bis-trimethylstannanyl-thiophene (163.9 mg, 0.400 mmol, 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.000 cm³) are heated at 140° C. (60 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. The cyclohexane fraction is reduced in vacuo, redissolved in chloroform (150 cm³) and precipitated into stirred methanol, and collected by filtration to give a black solid (545 mg, Yield: 86%). GPC (140° C., 1,2,4-chlorobenzene): $M_n$=35.1 kg·mol$^{-1}$; $M_w$=100.1 kg·mol$^{-1}$; PDI=2.85.

Example 30

Polymer 30

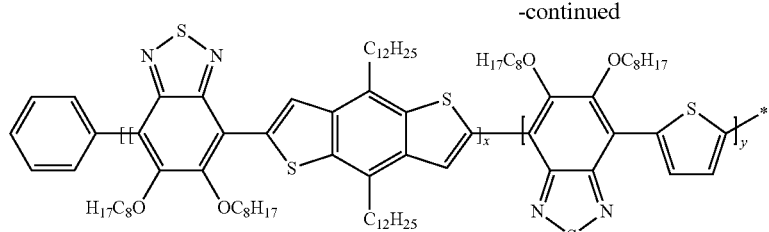

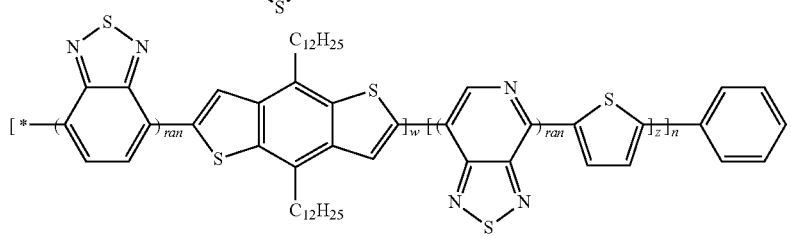

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (396.3 mg, 0.7200 mmol, 1.800 eq.), 4,7-dibromo-[1,2,5]thiadiazolo[3,4-c]pyridine (23.6 mg, 0.0800 mmol, 0.200 eq.), 2,5-bis-trimethylstannanyl-thiophene (163.9 mg, 0.400 mmol, 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.000 cm³) are heated at 140° C. (160 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (510 mg, Yield: 95%). GPC (140° C., 1,2,4-trichlorobenzene): $M_n$=23.0 kg·mol$^{-1}$; $M_w$=87.0 kg·mol$^{-1}$; PDI=3.78.

Example 31

Polymer 31

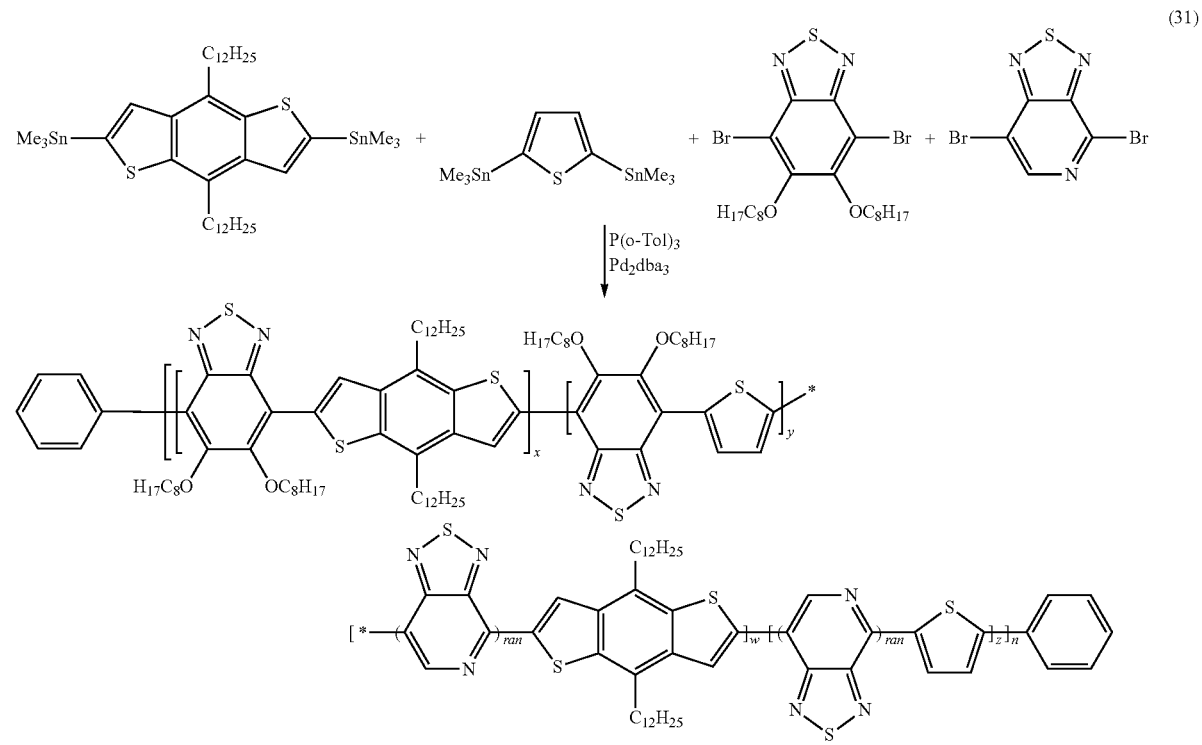

(31)

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5, 6-bis-octyloxy-benzo[1,2,5]thiadiazole (352.3 mg, 0.6400 mmol, 1.600 eq.), 4,7-dibromo-[1,2,5]thiadiazolo[3,4-c]pyridine (47.2 mg, 0.160 mmol, 0.400 eq.), 2,5-bis-trimethylstannanyl-thiophene (163.9 mg, 0.400 mmol, 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.000 cm³) are heated at 140° C. (160 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (477 mg, Yield: 93%). GPC (140° C., 1,2,4-trichlorobenzene): $M_n$=36.5 kg·mol⁻¹; $M_w$=81.7 kg·mol⁻¹; PDI=2.24.

Example 32

Polymer 32 mmol; 2.000 eq.), 2,6-bis-trimethylstannanyl-selenophene (182.7 mg; 0.4000 mmol; 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.0 cm³) are heated at 140° C. (135 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. The cyclohexane fraction is reduced in vacuo, redissolved in chloroform (150 cm³), precipitated into stirred methanol, and collected by filtration to give a black solid (532 mg, Yield: 93%). GPC (140° C., 1,2,4-trichlorobenzene): $M_n$=47.4 kg·mol⁻¹; $M_w$=107.7 kg·mol⁻¹; PDI=2.27.

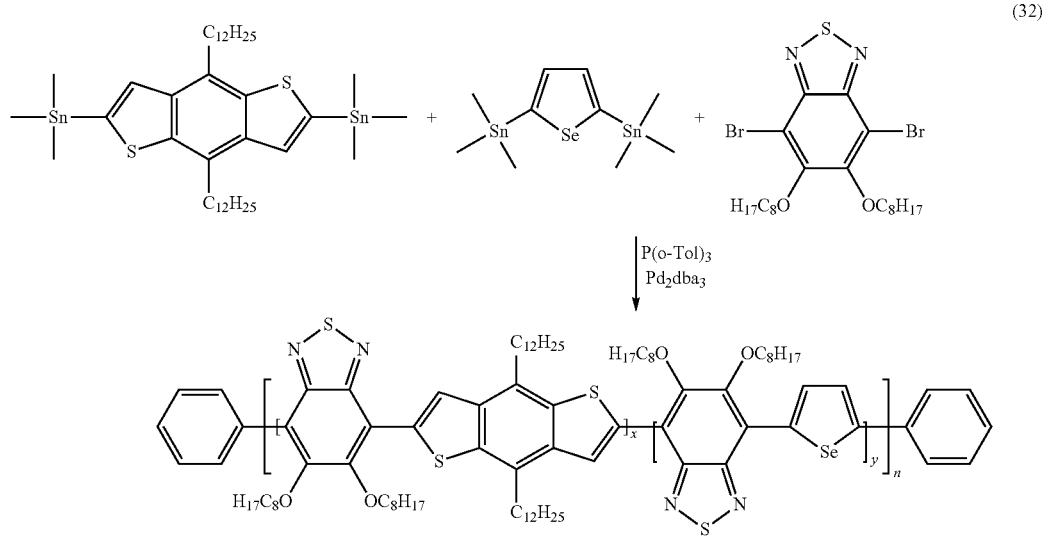

(32)

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (440.3 mg; 0.8000

Example 33

Polymer 33

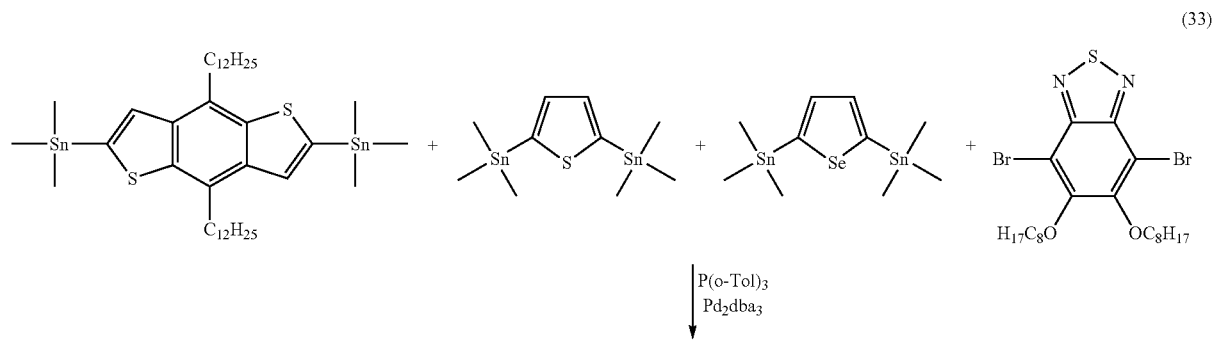

(33)

-continued

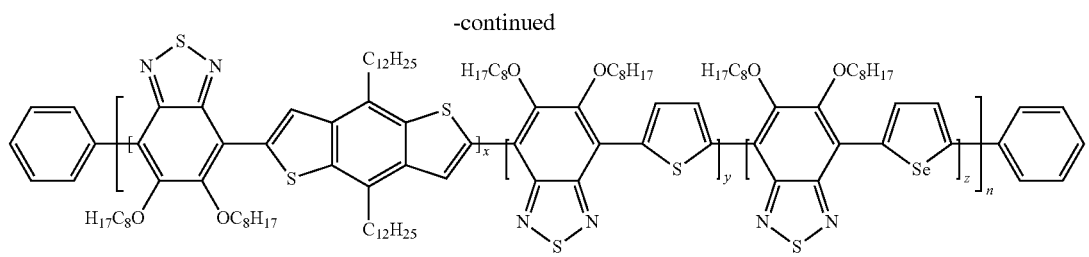

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 2,5-bis-trimethylstannanyl-thiophene (82.0 mg; 0.200 mmol; 0.500 eq.), 2,6-bis-trimethylstannanyl-selenophene (91.3 mg; 0.200 mmol; 0.500 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm³) are heated at 140° C. (145 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. The cyclohexane fraction is reduced in vacuo, redissolved in chloroform (150 cm³), precipitated into stirred methanol and collected by filtration to give a black solid (547 mg, Yield: 97%). GPC (140° C., 1,2,4-trichlorobenzene): $M_n$=50.2 kg·mol$^{-1}$; $M_w$=116.9 kg·mol$^{-1}$; PDI=2.33.

Example 34

Polymer 34

Following the general polymerisation reaction, 4,8-didodecyl-2,6-bis-trimethylstannanyl-benzo[1,2-b;4,5-b']dithiophene (170.5 mg; 0.2000 mmol; 0.5000 eq.), 2,6-bis-trimethylstannanyl-benzo[1,2-b;4,5-b']dithiophene (103.2 mg; 0.2000 mmol; 0.5000 eq.), 4,7-dibromo-5,6-bis-octyloxy-benzo[1,2,5]thiadiazole (440.3 mg; 0.8000 mmol; 2.000 eq.), 2,5-bis-trimethylstannanyl-thiophene (163.9 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm³) are heated at 140° C. (145 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (403 mg, Yield: 83%). GPC (140° C., 1,2,4-trichlorobenzene): $M_n$=41.7 kg·mol$^{-1}$; $M_w$=93.5 kg·mol$^{-1}$; PDI=-2.24.

(34)

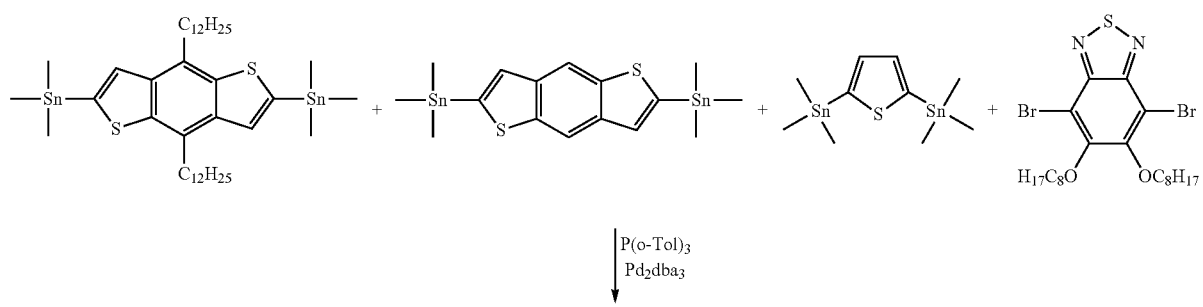

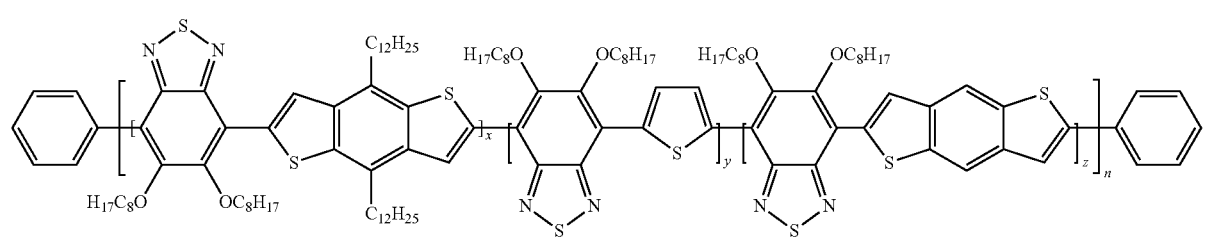

Example 35

Polymer 35

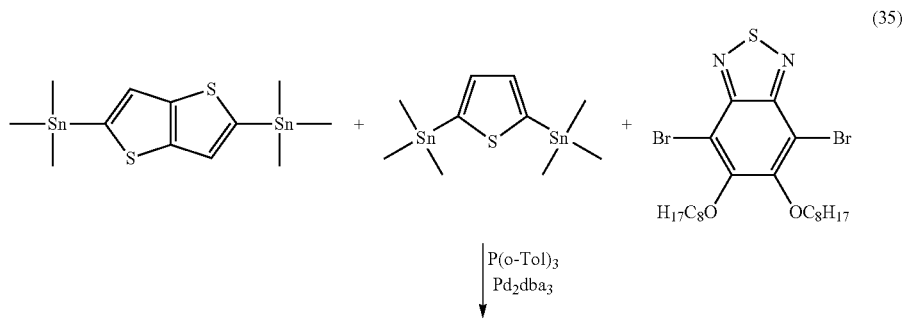

(35)

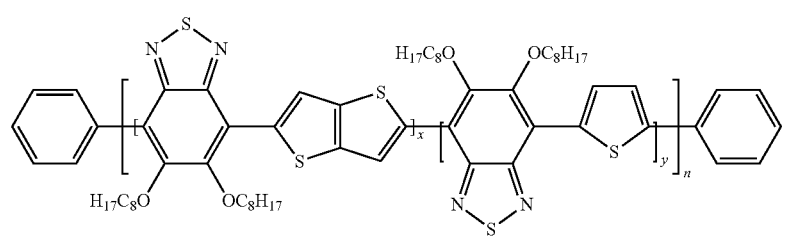

Following the general polymerisation reaction, 2,5-bis-trimethylstannanyl-thieno[3,2-b]thiophene (186.4 mg; 0.4000 mmol; 1.000 eq.), 4,7-dibromo-5,6-bis-octyloxy-benzo[1,2,5]thiadiazole (440.3 mg; 0.8000 mmol; 2.000 eq.), 2,5-bis-trimethylstannanyl-thiophene (163.9 mg; 0.4000 mmol; 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.0 cm³) are heated at 140° C. (210 minutes) with a preheated oil bath. The reaction is end-capped with tributylphenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (360 mg, Yield: 90%). GPC (140° C., 1,2,4-trichlorobenzene): $M_n$=30.0 kg·mol⁻¹; $M_w$=63.6 kg·mol⁻¹; PDI=2.12.

Example 36

Polymer 36

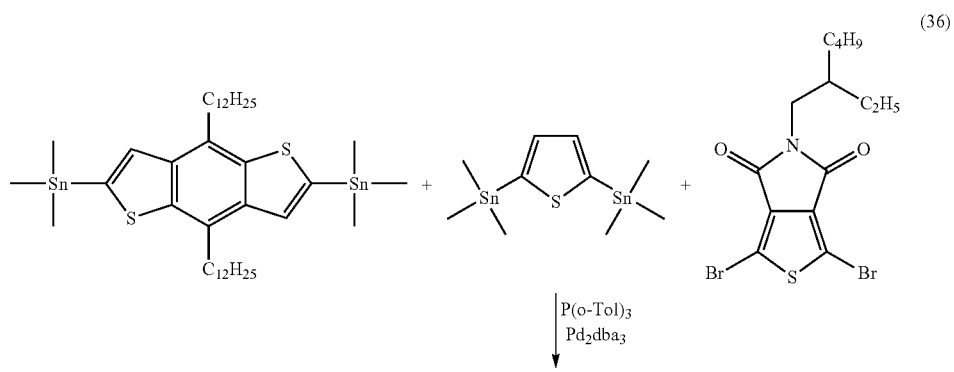

(36)

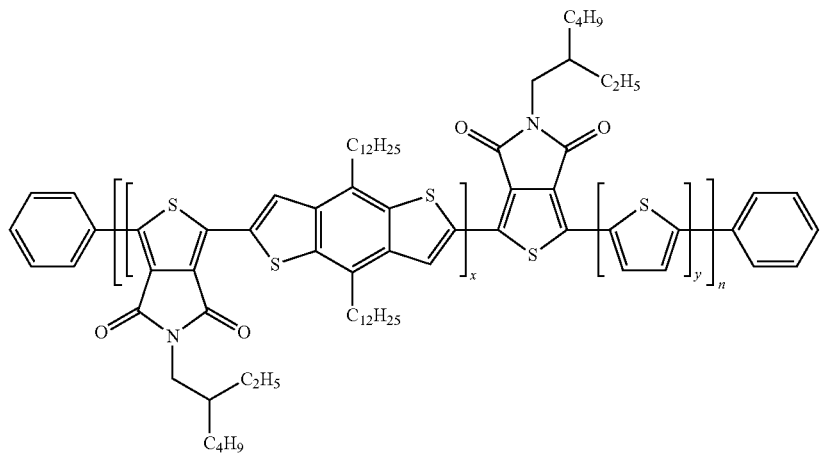

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 1,3-dibromo-5-(2-ethyl-hexyl)-thieno[3,4-c]pyrrole-4,6-dione (338.7 mg; 0.8000 mmol; 2.000 eq.), 2,5-bis-trimethylstannanyl-thiophene (163.9 mg; 0.4000 mmol; 1.000 eq.), tri-o-tolylphosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm$^3$) are heated at 140° C. (210 minutes) with a preheated oil bath. The reaction is end-capped with tributyl-phenyl-stannane (0.26 cm$^3$; 0.80 mmol; 2.0 eq.) and bromobenzene (0.13 cm$^3$; 1.2 mmol; 3.0 eq.) at 140° C. for 60 minutes each time. After the reaction completion, the polymer is precipitated, collected and subjected to Soxhlet extraction. Methanol (200 cm$^3$) is added dropwise to the chloroform fraction (150 cm$^3$) and the resulting precipitate collected by filtration and dried in vacuo to give a black solid (290 mg, Yield: 64%). GPC (140° C., 1,2,4-trichlorobenzene): $M_n$=12.4 kg·mol$^{-1}$; $M_w$=39.3 kg·mol$^{-1}$; PDI=3.19.

Example 37

Polymer 37

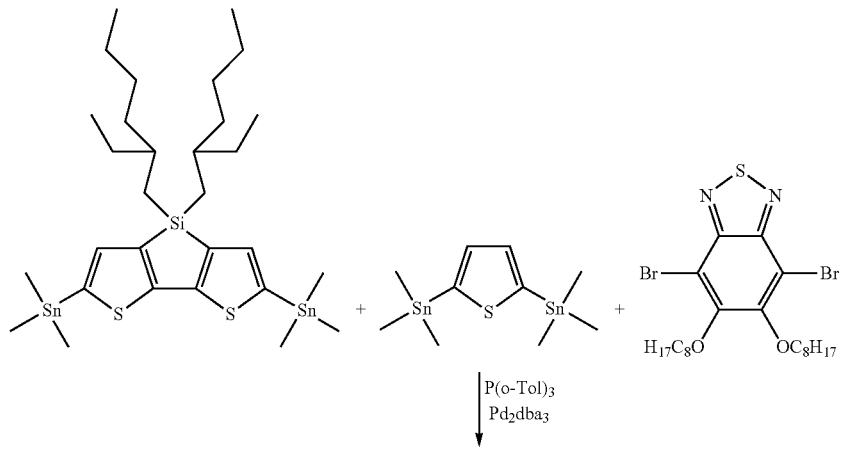

(37)

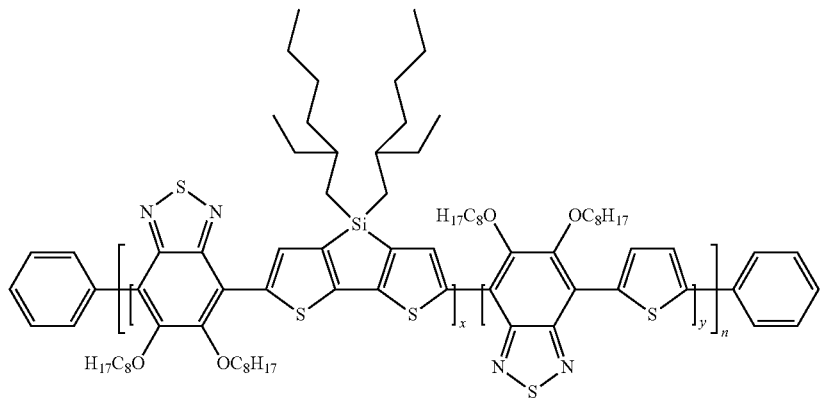

Following the general polymerisation reaction, 7,7-bis-(2-ethyl-hexyl)-2,5-bis-trimethylstannanyl-7H-3,4-dithia-7-sila-cyclopenta[a]pentalene (297.3 mg; 0.3994 mmol; 1.000 eq.), 4,7-dibromo-5,6-bis-octyloxy-benzo[1,2,5]thiadiazole (439.6 mg; 0.7987 mmol; 2.000 eq.), 2,5-bis-trimethylstannanyl-thiophene (163.7 mg; 0.3995 mmol; 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.0 cm³) are heated at 140° C. (210 minutes) with a preheated oil bath. The reaction is end-capped with tributyl-phenyl-stannane (0.27 cm³; 0.82 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (370 mg, Yield: 72%). GPC (140° C., 1,2,4-trichlorobenzene): $M_n$=8.5 kg·mol⁻¹; $M_w$=15.6 kg·mol⁻¹; PDI=1.83.

Example 38

Polymer 38

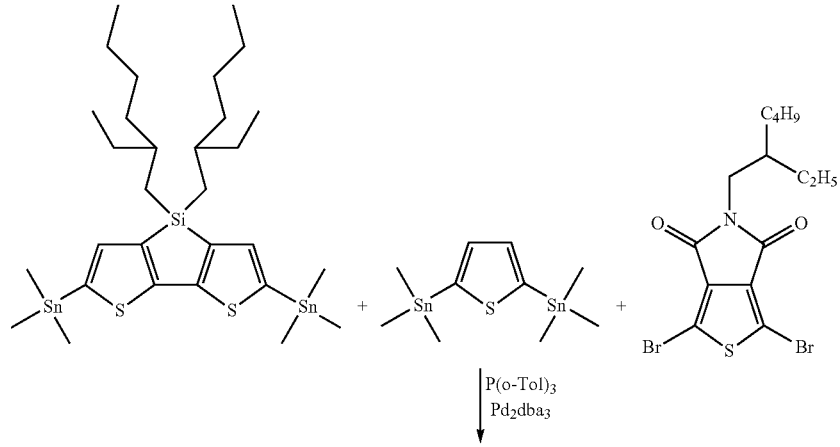

(38)

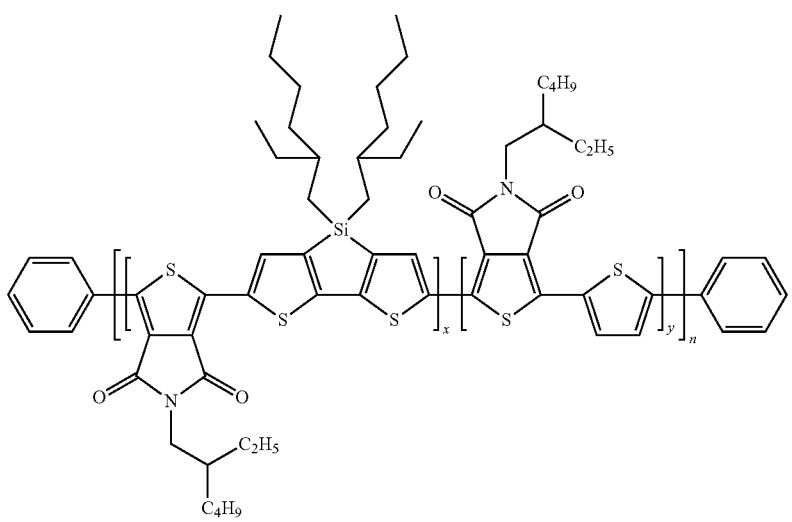

Following the general polymerisation reaction, 7,7-bis-(2-ethyl-hexyl)-2,5-bis-trimethylstannanyl-7H-3,4-dithia-7-sila-cyclopenta[a]pentalene (298.9 mg; 0.4017 mmol; 1.000 eq.), 1,3-dibromo-5-(2-ethyl-hexyl)-thieno[3,4-c]pyrrole-4,6-dione (340.0 mg; 0.8035 mmol; 2.000 eq.), 2,5-bis-trimethylstannanyl-thiophene (164.6 mg; 0.4017 mmol; 1.000 eq.), tri-o-tolyl-phosphine (19.5 mg; 64.0 μmol; 0.160 eq.), tris(dibenzylideneacetone)dipalladium(0) (14.7 mg; 16.0 μmol; 0.0400 eq.) and chlorobenzene (5.0 cm³) are heated at 140° C. (210 minutes) with a preheated oil bath. The reaction is end-capped with tributyl-phenyl-stannane (0.27 cm³; 0.82 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. Methanol (200 cm³) is added dropwise to the chloroform fraction (150 cm³) and the resulting precipitate collected by filtration and dried in vacuo to give a black solid (190 mg, Yield: 46%). GPC (140° C., 1,2,4-trichlorobenzene): $M_n$=7.4 kg·mol⁻¹; $M_w$=10.8 kg·mol⁻¹; PDI=1.47.

Example 39

Polymer 39

(39)

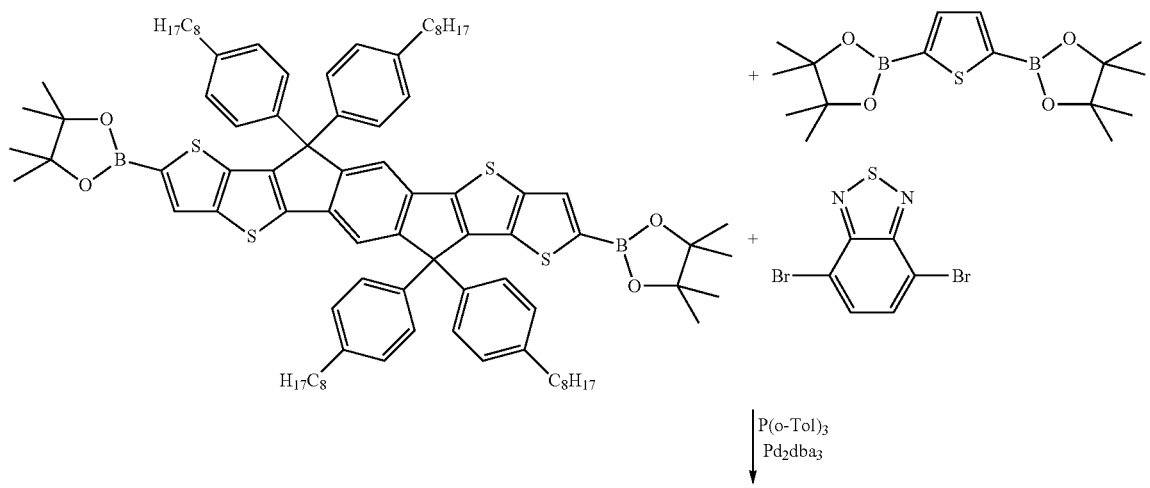

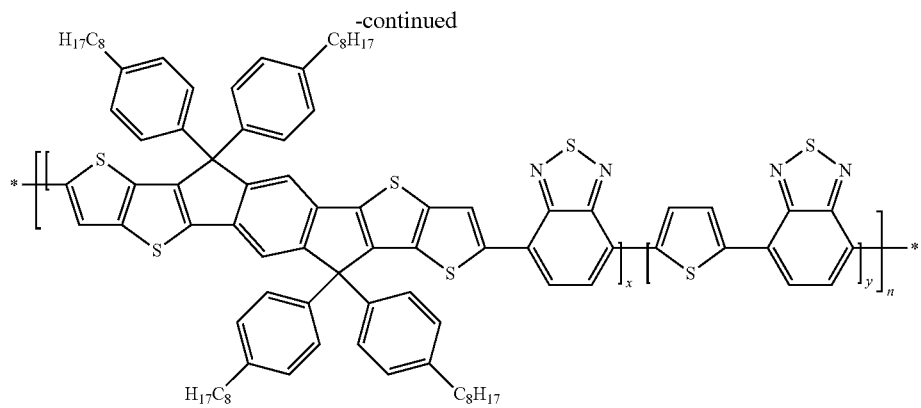

2,8-Dibromo-6,6,12,12-tetra(4'-octylphenyl)-6,12-dihydro-dithieno[2,3-d:2',3'-d']-s-indaceno[1,2-b:5,6-b']dithiophene (364.2 mg; 0.2824 mmol; 1.000 eq.), 2,5-dibromothiophene (68.3 mg; 0.282 mmol; 1.000 eq.), 4,7-bis-(4,4,5,5-tetramethyl-[1,3,2]dioxaborolan-2-yl)-benzo[1,2,5]thiadiazole (219.2 mg; 0.5648 mmol; 2.000 eq.), tri-o-tolyl phosphine (13.8 mg, 45.2 μmol, 0.160 eq.), tris(dibenzylideneacetone)dipalladium(0) (10.3 mg, 11.3 μmol, 0.0400 eq) and aliquat 336 (50 mg) are added to a sealed 50 cm³ round bottom flask equipped with a condensed. The flask is evacuated and then refilled with nitrogen three times and then degassed toluene (11 cm³) and degassed 2 M aqueous solution of sodium carbonate (1.7 cm³; 3.4 mmol; 6.0 eq) is added to the flask. The solution is slowly heated to 100° C. and reacted for 48 hours. The contents of the vessel is precipitated in 10:1 methanol:water (175 cm³), filtered and further washed with methanol (2×100 cm³) to give a solid. The polymer is subjected to sequential Soxhlet extraction with acetone, petroleum ether (40-60° C.), cyclohexane and chloroform. Methanol (200 cm³) is added dropwise to the chloroform fraction (150 cm³) and the resulting precipitate is collected by filtration and dried in vacuo to give a black solid (239 mg, Yield: 57%). GPC (50° C., chlorobenzene): $M_n$=8.2 kg·mol⁻¹; $M_w$=35.2 kg·mol⁻¹; PDI=4.29.

Example 40

Example 40.1

2,6-Bis-(4,4,5,5-tetramethyl-[1,3,2]dioxaborolan-2-yl)-benzo[1,2-b;4,5-b']dithiophene-4,8-dicarboxylic acid didodecyl ester

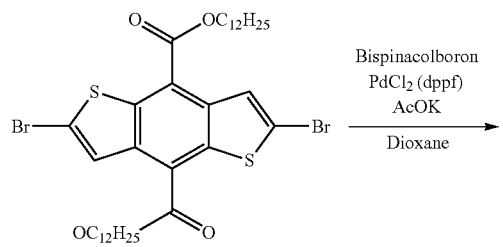

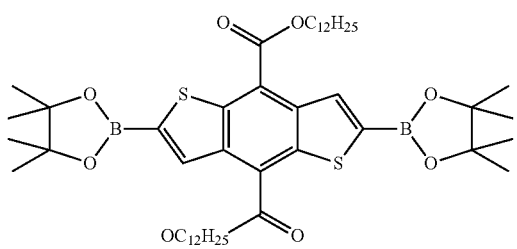

Anhydrous dioxane is degassed for 60 minutes by bubbling nitrogen into the stirred solvent. To a mixture of 2,6-dibromo-benzo[1,2-b;4,5-b']dithiophene-4,8-dicarboxylic acid didodecyl ester (10 g; 13 mmol), 4,4,5,5,4',4',5',5'-octamethyl-[2,2']bi([1,3,2]dioxaborolanyl) (7.6 g; 30 mmol), [1,1'-bis(diphenylphosphino)ferrocene]dichloropalladium (II) (1.9 g; 2.3 mmol) and potassium acetate anhydrous (7.6 g; 78 mmol) under nitrogen in a oven dried schlenk tube is added the predegassed anhydrous dioxane (38 cm³). The mixture is then further degassed for 30 minutes and then heated at 80° C. for 17 hours. The mixture is allowed to cool, water (100 cm³) added and the product extracted with dichloromethane (4×150 cm³). The combined organic extracts are dried over anhydrous magnesium sulfate, filtered and the solvent removed in vacuo to give a brown yellow solid. The crude product is purified by multiple hot filtrations in acetonitrile followed by multiple recrystallizations to afford the desired product as yellow needles (4.9 g, 44%). ¹H NMR (300 MHz, CDCl₃): δ 8.79 (s, 2H); 4.58 (t, J=6.7 Hz, 4H); 1.88-1.99 (m, 4H); 1.50-1.61 (m, 4H); 1.34-1.45 (m, 32H); 1.17-1.34 (m, 24H); 0.88 (t, J=6.9 Hz, 6H).

Example 40.2

Polymer 40

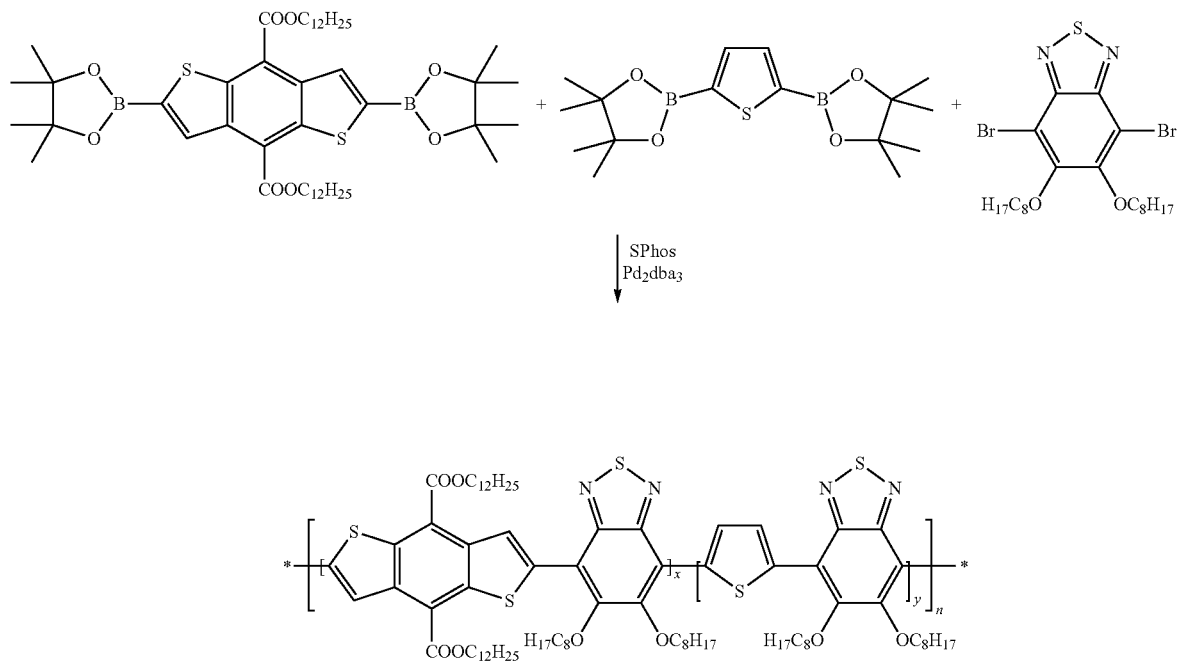

(40)

2,6-Bis-(4,4,5,5-tetramethyl-[1,3,2]dioxaborolan-2-yl)-benzo[1,2-b;4,5-b']dithiophene-4,8-dicarboxylic acid didodecyl ester (433.4 mg; 0.5000 mmol; 1.000 eq.), 2,2'-(2,5-thiophenediyl)bis[4,4,5,5-tetramethyl-1,3,2-dioxaborolane] (168.0 mg; 0.5000 mmol; 1.000 eq.), 4,7-dibromo-5,6-bis-octyloxy-benzo[1,2,5]thiadiazole (550.4 mg; 1.000 mmol; 2.000 eq.), and dicyclohexyl-(2',6'-dimethoxy-biphenyl-2-yl)-phosphane (SPhos) (32.8 mg; 0.0800 mmol; 0.160 eq.) are added to a 20 cm³ microwave tube. The flask is sealed and evacuated and then refilled with nitrogen three times then degassed toluene (4.0 cm³) added. In the mean time, a second 5 cm³ microwave tube is filled with tris(dibenzylideneacetone)dipalladium(0) (18.3 mg; 0.0200 mmol, 0.0400 eq.), sealed, evacuated and then refilled with nitrogen three times then degassed toluene (1.0 cm³) added. Both resulting solutions are further degassed for 15-20 minutes individually. The monomer solution is heated to 100° C. then a degassed solution of potassium phosphane (509.4 mg; 2.400 mol; 4.800 eq) in deionised water (0.80 cm³) and the degassed palladium catalyst solution are quickly added in order. The solution is reacted for 48 hours at 100° C. The contents of the vessel is precipitated in 10:1 methanol:water (175 cm³), filtered and further washed with methanol (2×100 cm³) to give a solid. The polymer is subjected to sequential Soxhlet extraction with acetone, petroleum ether (40-60° C.) and cyclohexane. Isopropanol (200 cm³) is added dropwise to the cyclohexane fraction (100 cm³) and the resulting precipitate is collected by filtration and dried in vacuo to give a black solid (51 mg, Yield: 6.9%). GPC (50° C., chlorobenzene): $M_n$=9.9 kg·mol⁻¹; $M_w$=26.7 kg·mol⁻¹; PDI=2.70.

Example 41

Polymer 41

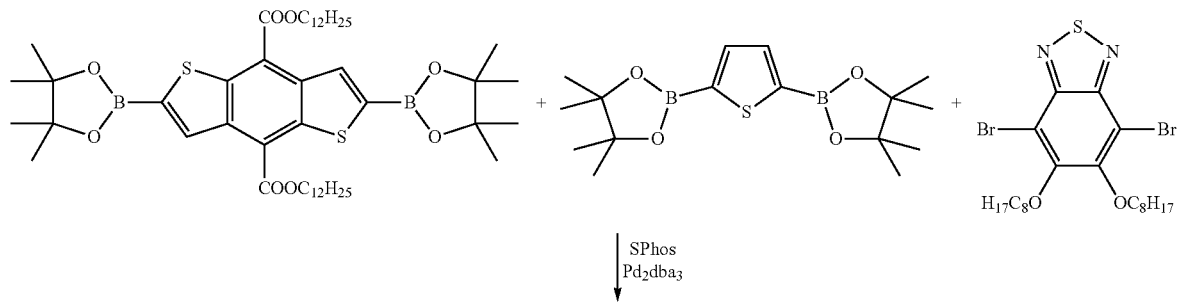

(41)

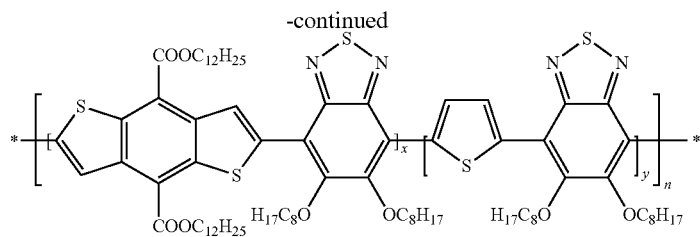

Following the polymerisation reaction used for polymer 40, 2,6-bis-(4,4,5,5-tetramethyl-[1,3,2]dioxaborolan-2-yl)-benzo[1,2-b;4,5-b']dithiophene-4,8-dicarboxylic acid didodecyl ester (624.1 mg; 0.7200 mmol; 0.9000 eq.), 2,2'-(2,5-thiophenediyl)bis[4,4,5,5-tetramethyl-1,3,2-dioxaborolane] (26.9 mg; 0.0800 mmol; 0.100 eq.), 4,7-dibromo-5,6-bis-octyloxy-benzo[1,2,5]thiadiazole (440.314 mg; 0.8000 mmol; 1.000 eq.) and dicyclohexyl-(2',6'-dimethoxy-biphenyl-2-yl)-phosphane (SPhos) (52.5 mg; 0.1280 mmol; 0.160 eq.) in toluene (4.0 cm³), tris(dibenzylideneacetone)dipalladium(0) (29.3 mg; 0.0320 mmol; 0.0400 eq.) in toluene (1.0 cm³), potassium phosphate (815 mg; 3.84 mmol; 4.80 eq.) in Water (0.800 cm³) are reacted for 96 hours at 100° C. The polymer is precipitate, filtered and subjected to sequential Soxhlet extraction with acetone, petroleum ether (40-60° C.) and cyclohexane. Isopropanol (200 cm³) is added dropwise to the cyclohexane fraction (100 cm³) and the resulting precipitate is collected by filtration and dried in vacuo to give a black solid (516 mg, Yield: 68%). GPC (50° C., chlorobenzene): $M_n$=13.8 kg·mol⁻¹; $M_w$=34.1 kg·mol⁻¹; PDI=2.47.

Example 42

Polymer 42

Following the general polymerisation reaction, 4,8-didodectyl-2,6-bis-trimethylstannanyl-benzo[1,2-b;4,5-b']dithiophene (613.8 mg, 0.7200 mmol; 0.9000 eq.), 4,7-dibromo-5,6-bis-octyloxy-benzo[1,2,5]thiadiazole (440.3 mg; 0.8000 mmol; 1.000 eq.), 2,5-bis-trimethylstannanyl-thiophene (32.8 mg, 0.0800 mmol; 0.100 eq.), tri-o-tolyl-phosphine (19.5 mg; 64.0 μmol; 0.0800 eq.), tris(dibenzylideneacetone)dipalladium(0) (14.7 mg; 16.0 μmol; 0.0200 eq.) and chlorobenzene (5.0 cm³) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm³; 0.80 mmol; 1.0 eq.) and bromobenzene (0.13 cm³; 1.2 mmol; 1.5 eq.) at 175° C. for 600 seconds each time. After the reaction completion, the polymer is precipitated into, collected and subjected to Soxhlet extraction. Methanol (200 cm³) is added dropwise to the chloroform fraction (150 cm³) and the resulting precipitate collected by filtration and dried in vacuo to give a black solid (180 mg, 26% yield). GPC, chlorobenzene (50° C.): $M_n$=24.4 kg·mol⁻¹, $M_w$=64.9 kg·mol⁻¹, PDI=2.66

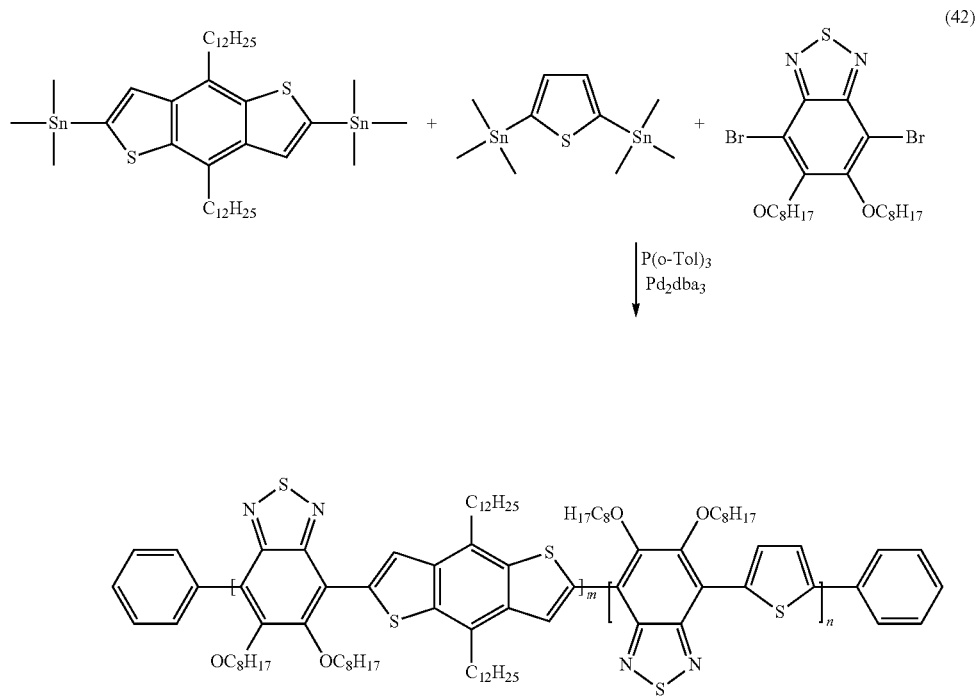

Example 43

Polymer 43

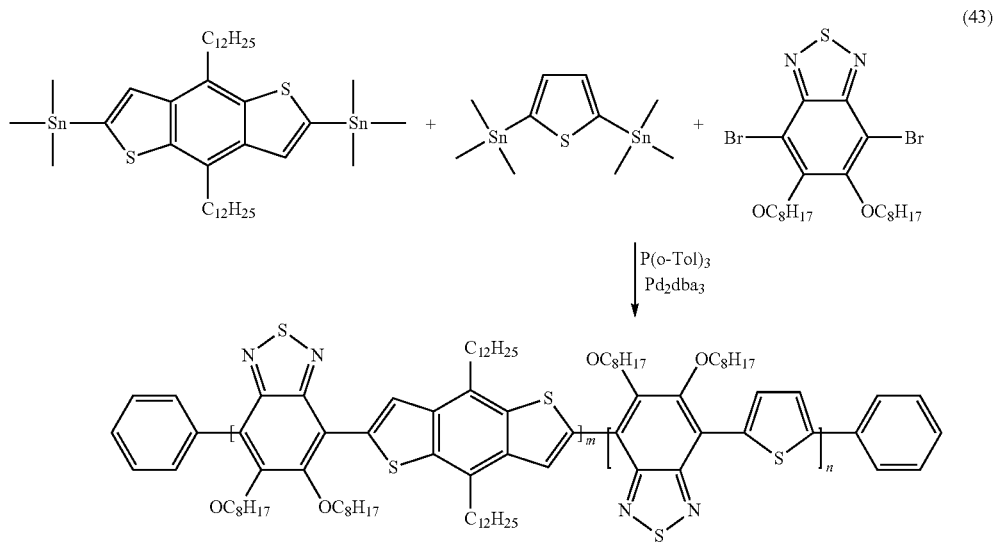

(43)

Following the general polymerisation reaction, 4,8-didodectyl-2,6-bis-trimethylstannanyl-benzo[1,2-b;4,5-b']dithiophene (409.2 mg, 0.4800 mmol; 0.6000 eq.), 4,7-dibromo-5,6-bis-octyloxy-benzo[1,2,5]thiadiazole (440.3 mg; 0.8000 mmol; 1.000 eq.), 2,5-bis-trimethylstannanyl-thiophene (131.1 mg, 0.3200 mmol; 0.4000 eq.), tri-o-tolyl-phosphine (19.5 mg; 64.0 µmol; 0.0800 eq.), tris(dibenzylideneacetone)dipalladium(0) (14.7 mg; 16.0 µmol; 0.0200 eq.) and chlorobenzene (5.0 cm$^3$) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm$^3$; 0.80 mmol; 1.0 eq.) and bromobenzene (0.13 cm$^3$; 1.2 mmol; 1.5 eq.) at 175° C. for 600 seconds each time. After the reaction completion, the polymer is precipitated into, collected and subjected to Soxhlet extraction. The cyclohexane fraction is reduced in vacuo, redissolved in chloroform (150 cm$^3$), precipitated into stirred methanol collected by filtration and dried in vacuo to give a black solid (490 mg, 83% yield). GPC, trichlorobenzene (140° C.): $M_n$=30.0 kg·mol$^{-1}$, $M_w$=65.0 kg·mol$^{-1}$, PDI=2.16

Example 44

Polymer 44

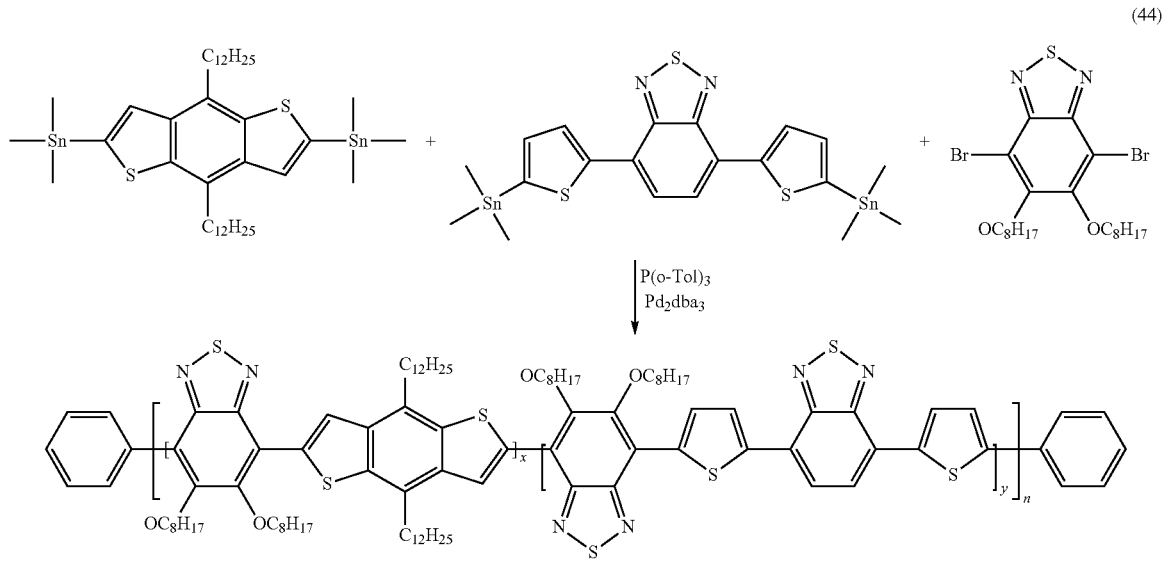

(44)

Following the general polymerisation reaction, 4,8-didodectyl-2,6-bis-trimethylstannanyl-benzo[1,2-b;4,5-b']dithiophene (409.2 mg, 0.4000 mmol; 1.000 eq.), 4,7-dibromo-5,6-bis-octyloxy-benzo[1,2,5]thiadiazole (440.3 mg; 0.8000 mmol; 2.000 eq.), 4,7-bis-(5-trimethylstannanyl-thiophen-2-yl)-benzo[1,2,5]thiadiazole (250.4 mg; 0.4000 mmol; 1.000 eq.), tri-o-tolyl-phosphine (19.5 mg; 64.0 µmol; 0.160 eq.), tris(dibenzylideneacetone)dipalladium(0) (14.7 mg; 16.0 µmol; 0.0400 eq.) and chlorobenzene (5.0 cm³) are heated sequentially at 140° C. (60 seconds), 160° C. (60 seconds) and 175° C. (1800 seconds) in a microwave reactor (Biotage Initiator). The reaction is end-capped with tributyl-phenyl-stannane (0.26 cm³; 0.80 mmol; 2.0 eq.) and bromobenzene (0.13 cm³; 1.2 mmol; 3.0 eq.) at 175° C. for 600 seconds each time. After the reaction completion, the polymer is precipitated into, collected and subjected to Soxhlet extraction. The cyclohexane fraction is reduced in vacuo, redissolved in chloroform (150 cm³), precipitated into stirred methanol collected by filtration and dried in vacuo to give a black solid (166 mg, 26% yield). GPC, trichlorobenzene (140° C.): $M_n$=14.0 kg·mol⁻¹, $M_w$=35.2 kg·mol⁻¹, PDI=2.51

Example 45

Polymer 45

Following the general polymerisation reaction, 4,8-didodecyl-2,6-bis-trimethylstannanyl-benzo[1,2-b;4,5-b']dithiophene (341.0 mg; 0.4000 mmol; 1.000 eq.), 4,7-dibromo-5,6-bis-octyloxy-benzo[1,2,5]thiadiazole (396.3 mg, 0.7200 mmol, 1.800 eq.), 3,6-bis-(5-bromo-thiophen-2-yl)-2,5-bis-(2-decyl-tetradecyl)-2,5-dihydro-pyrrolo[3,4-c]pyrrole-1,4-dione (90.5 mg, 0.0800 mmol, 0.200 eq.), 2,5-bis-trimethylstannanyl-thiophene (163.9 mg, 0.400 mmol, 1.000 eq.), tri-o-tolyl-phosphine (19.5 mg; 64.0 µmol; 0.160 eq.), tris (dibenzylideneacetone)dipalladium(0) (14.7 mg; 16.0 µmol; 0.0400 eq.) and chlorobenzene (5.0 cm³) are heated at 140° C. (140 minutes) with a preheated oil bath. The reaction is end-capped with tributyl-phenyl-stannane (0.26 cm³; 0.80 mmol; 2.0 eq.) and bromobenzene (0.13 cm³; 1.2 mmol; 3.0 eq.) at 140° C. for 60 minutes each time. After the reaction completion, the polymer is precipitated, collected and subjected to Soxhlet extraction. Isopropyl alcohol (200 cm³) is added dropwise to the cyclohexane fraction (150 cm³) and the resulting precipitate collected by filtration and dried in vacuo to give a black solid (520 mg, Yield: 86%). GPC (140° C., 1,2,4-trichlorobenzene): $M_n$=47.3 kg·mol⁻¹; $M_w$=98.9 kg·mol⁻¹; PDI=2.09.

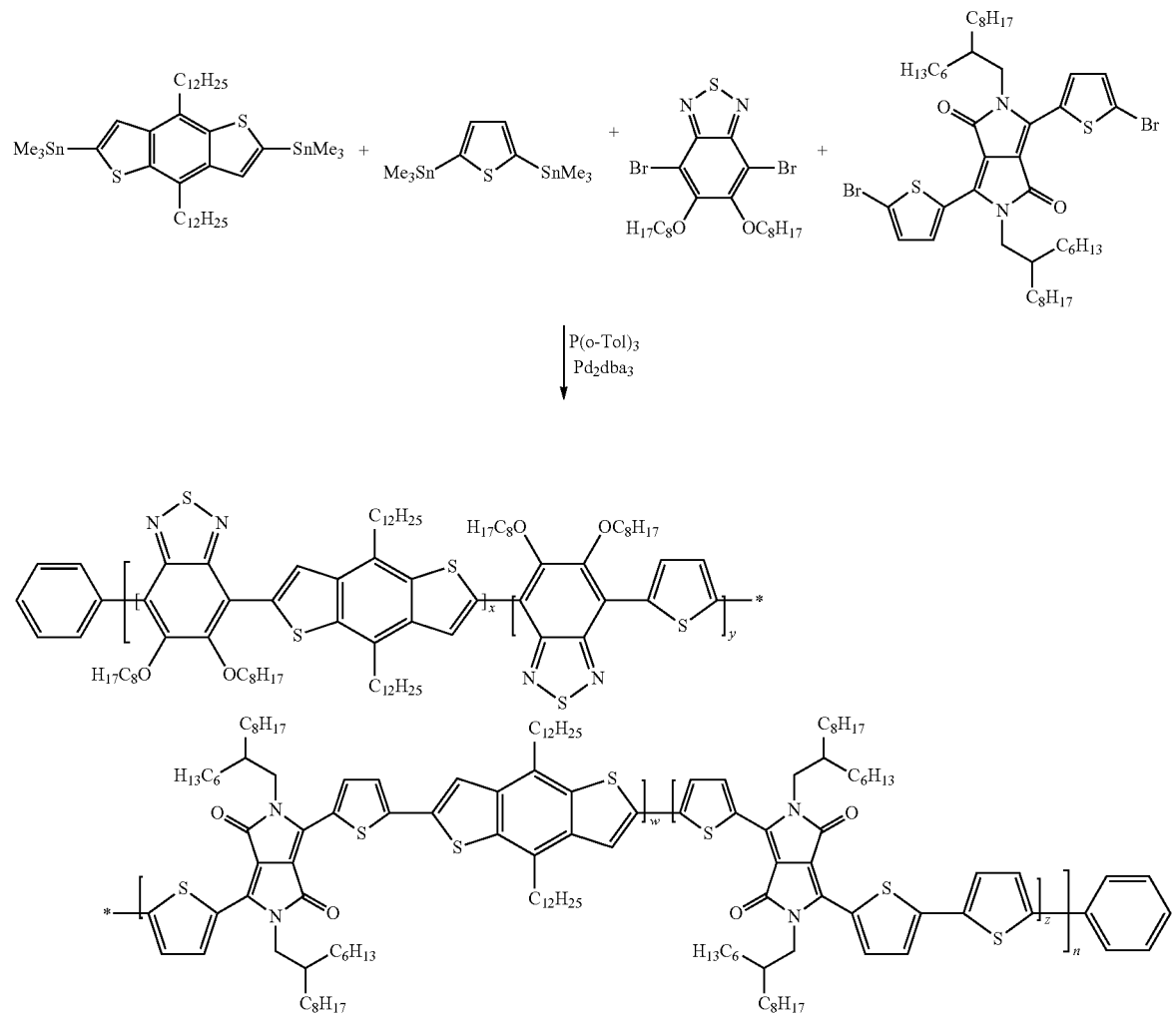

(45)

B) Use Examples

Bulk Heterojunction Organic Photovoltaic Devices (OPVs) for Polymer 1-39

Organic photovoltaic (OPV) devices are fabricated on pre-patterned ITO-glass substrates (13 Ω/sq.) purchased from LUMTEC Corporation. Substrates were cleaned using common solvents (acetone, iso-propanol, deionized-water) in an ultrasonic bath. A conducting polymer poly(ethylene dioxythiophene) doped with poly(styrene sulfonic acid) [Clevios VPAI 4083 (H.C. Starck)] is mixed in a 1:1 ratio with deionized-water. This solution was filtered using a 0.45 μm filter before spin-coating to achieve a thickness of 20 nm. Substrates were exposed to ozone prior to the spin-coating process to ensure good wetting properties. Films were then annealed at 140° C. for 30 minutes in a nitrogen atmosphere where they were kept for the remainder of the process. Active material solutions (i.e. polymer+PCBM) were prepared and stirred overnight to fully dissolve the solutes. Thin films were either spin-coated or blade-coated in a nitrogen atmosphere to achieve active layer thicknesses between 100 and 500 nm as measured using a profilometer. A short drying period followed to ensure removal of any residual solvent.

Typically, spin-coated films were dried at 23° C. for 10 minutes and blade-coated films were dried at 70° C. for 2 minutes on a hotplate. For the last step of the device fabrication, Ca (30 nm)/Al (125 nm) cathodes were thermally evaporated through a shadow mask to define the cells. Current-voltage characteristics were measured using a Keithley 2400 SMU while the solar cells were illuminated by a Newport Solar Simulator at 100 mW·cm-2 white light. The Solar Simulator was equipped with AM1.5G filters. The illumination intensity was calibrated using a Si photodiode. All the device preparation and characterization is done in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV device characteristics for a blend of polymer and $PC_6{}^1BM$ coated from a o-dichlorobenzene solution at a total solid concentration are shown in Table 1.

TABLE 1

Photovoltaic cell characteristics.

| Polymer | ratio Polymer: PCBM | conc$^n$ mg·ml$^{-1}$ | Voc mV | Jsc mA·cm$^{-2}$ | FF % | PCE % |
|---|---|---|---|---|---|---|
| Polymer 1 | 1.00:2.00 | 30 | 800 | −9.04 | 67 | 5.05 |
| Polymer 2 | 1.00:2.00 | 30 | 800 | −10.56 | 64 | 5.40 |
| Polymer 3 | 1.00:2.00 | 30 | 776 | −2.22 | 56 | 0.97 |
| Polymer 4 | 1.00:2.00 | 20 | 793 | −3.56 | 60 | 1.68 |
| Polymer 5 | 1.00:1.50 | 30 | 843 | −5.46 | 56 | 2.56 |

TABLE 1-continued

Photovoltaic cell characteristics.

| Polymer | ratio Polymer: PCBM | conc$^n$ mg·ml$^{-1}$ | Voc mV | Jsc mA·cm$^{-2}$ | FF % | PCE % |
|---|---|---|---|---|---|---|
| Polymer 6 | 1.00:1.50 | 30 | 844 | −8.50 | 60 | 4.29 |
| Polymer 8 | 1.00:2.00 | 30 | 800 | −4.42 | 50 | 1.76 |
| Polymer 9 | 1.00:2.00 | 30 | 811 | −2.51 | 59 | 1.20 |
| Polymer 10 | 1.00:1.50 | 30 | 940 | −10.74 | 55 | 5.50 |
| Polymer 11 | 1.00:1.50 | 30 | 956 | −9.85 | 44 | 4.11 |
| Polymer 12 | 1.00:2.00 | 30 | 952 | −8.42 | 48 | 3.80 |
| Polymer 13 | 1.00:2.00 | 30 | 875 | −10.24 | 65 | 5.77 |
| Polymer 14 | 1.00:3.00 | 30 | 882 | −8.54 | 54 | 4.05 |
| Polymer 15 | 1.00:2.00 | 30 | 704 | −7.37 | 69 | 3.57 |
| Polymer 16 | 1.00:1.50 | 30 | 956 | −8.45 | 45 | 3.64 |
| Polymer 17 | 1.00:3.00 | 30 | 800 | −11.75 | 51 | 4.82 |
| Polymer 18 | 1.00:1.50 | 30 | 908 | −11.47 | 60 | 6.20 |
| Polymer 20 | 1.00:2.00 | 20 | 292 | −0.91 | 50 | 0.13 |
| Polymer 21 | 1.00:2.00 | 30 | 754 | −4.58 | 40 | 1.37 |
| Polymer 22 | 1.00:1.50 | 30 | 740 | −3.38 | 38 | 0.94 |
| Polymer 23 | 1.00:2.00 | 20 | 769 | −1.92 | 59 | 0.87 |
| Polymer 24 | 1.00:2.00 | 30 | 760 | −4.46 | 58 | 1.96 |
| Polymer 25 | 1.00:3.00 | 30 | 315 | −1.93 | 33 | 0.20 |
| Polymer 26 | 1.00:3.00 | 30 | 344 | −2.27 | 39 | 0.37 |
| Polymer 27 | 1.00:3.00 | 30 | 416 | −1.74 | 42 | 0.30 |
| Polymer 28 | 1.00:1.50 | 30 | 422 | −1.18 | 35 | 0.17 |
| Polymer 29 | 1.00:2.00 | 30 | 713 | −2.66 | 37 | 0.70 |
| Polymer 30 | 1.00:2.00 | 20 | 845 | −6.96 | 56 | 3.29 |
| Polymer 31 | 1.00:2.00 | 20 | 646 | −8.83 | 44 | 2.51 |
| Polymer 32 | 1.00:1.50 | 30 | 860 | −8.51 | 60 | 4.37 |
| Polymer 33 | 1.00:2.00 | 30 | 880 | −12.00 | 52 | 5.42 |
| Polymer 34 | 1.00:3.00 | 30 | 893 | −11.25 | 42 | 4.24 |
| Polymer 35 | 1.00:1.50 | 30 | 834 | −9.07 | 46 | 3.35 |
| Polymer 36 | 1.00:3.00 | 30 | 783 | −6.20 | 42 | 2.05 |
| Polymer 37 | 1.00:3.00 | 30 | 616 | −3.94 | 29 | 0.73 |
| Polymer 38 | 1.00:1.50 | 30 | 858 | −1.75 | 40 | 0.60 |
| Polymer 39 | 1.00:3.00 | 30 | 810 | −5.29 | 34 | 1.48 |
| Polymer 40 | 1.00:3.00 | 30 | 844 | −1.53 | 47 | 0.68 |
| Polymer 41 | 1.00:2.00 | 30 | 943 | −1.88 | 56 | 0.99 |
| Polymer 42 | 1.00:1.00 | 30 | 890 | −9.40 | 68 | 5.70 |
| Polymer 43 | 1.00:2.00 | 30 | 914 | −10.77 | 69 | 6.82 |
| Polymer 45 | 1.00:2.00 | 30 | 790 | −8.68 | 58 | 3.96 |

Organic Photodetector Devices (OPDs) for Polymer 10, 20, 27, 28 and 29.

OPD Device for Polymer 10

The device is fabricated similarly to the bulk heterojunction organic photovoltaic devices (OPVs). A 23 mg·cm$^{-3}$ material solution of polymer 10 and $PC_{60}BM$ (1.0:2.0 ratio) is blade-coated in a nitrogen atmosphere at 50° C. to achieve 300 nm active layer thicknesses measured using a profilometer.

The J-V curve obtained is shown in FIG. 1.

FIG. 1: J-V curve for a blend of polymer 10 and $PC_{60}BM$ (1.0:2.0 ratio) in an OPD device.

OPD Device for Polymer 20

The ITO glass substrates are cleaned by using a normal glass cleaning procedure: 30 minutes ultrasonic bath in Dycon 90 solution, followed by deionized-water washing 3 times and another 30 minutes ultrasonic bath in deionized-water. Then the ITO substrates are photo lithography patterned, formed dots with size of 50 mm², following a cleaning steps. The PEDOT-PSS layers are deposited by spin coating from PEDOT-PSS AL4083 solution (Sigma-Adrich) with 1% Zonyl 300 surfactant. The thickness is around 50 nm.

The active layer polymer 20:$PC_{70}BM$ (1:1.5) is deposited in sequence by blade coater (K101 Control Coater System) at 70° C. The distance between blade and substrate is set to 15-50 mm, and a speed 0.2 m·min$^{-1}$. The top 50 nm Al metal electrodes are thermally deposited through a shadow mask and the metal dots matching the bottom ITO dots.

Figure 2:
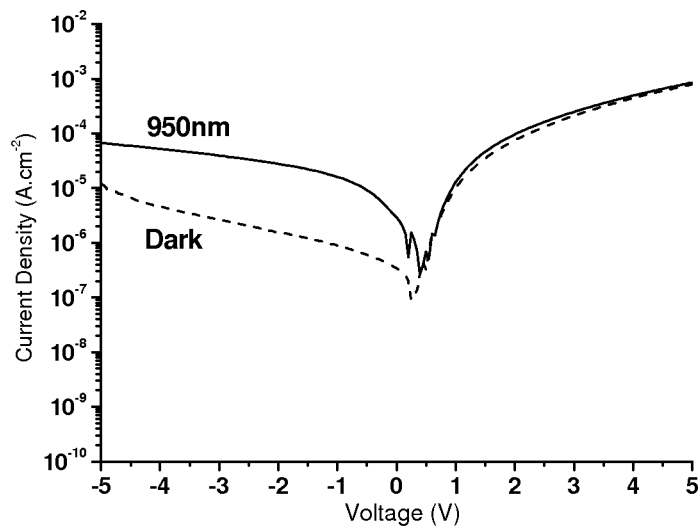
FIG. 2 shows the J-V curve for a blend of polymer 20 and $PC_{70}BM$ (1.0:1.5 ratio) in an OPD device according to the Examples.

The J-V curve obtained is shown in FIG. 2.

FIG. 2: J-V curve for a blend of polymer 20 and PC$_{70}$BM (1.0:1.5 ratio) in an OPD device.

OPV Device for Polymer 27

The device is fabricated similarly to the OPV device for polymer 20 using polymer 27 and PC$_{60}$BM.

Figure 3:
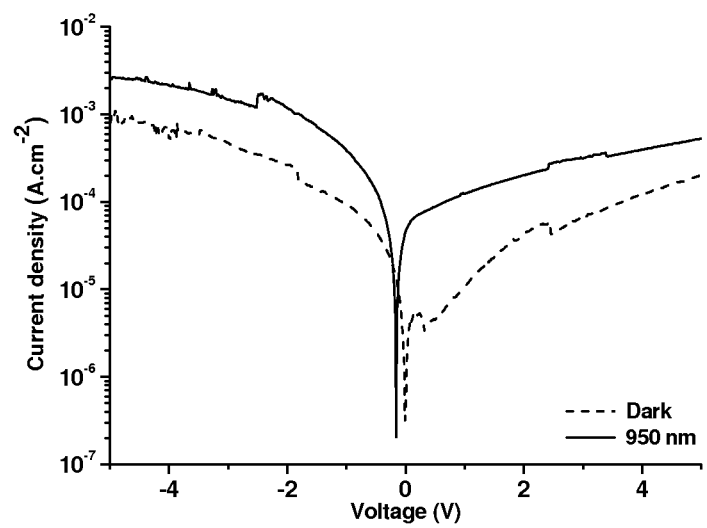
FIG. 3 shows the J-V curve for a blend of polymer 27 and $PC_{60}BM$ (1.0:1.5 ratio) in an OPD device according to the Examples.

The J-V curve obtained is shown in FIG. 3.

FIG. 3: J-V curve for a blend of polymer 27 and PC$_{60}$BM (1.0:1.5 ratio) in an OPD device.

OPV Device for Polymer 28

The device is fabricated similarly to the OPV device for polymer 20 using polymer 28 and PC$_{60}$BM.

Figure 4:
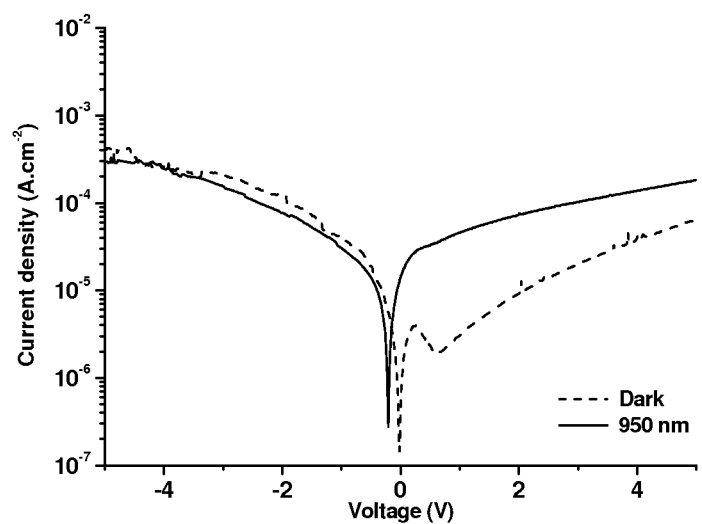
FIG. 4 shows the J-V curve for a blend of polymer 28 and $PC_{60}BM$ (1.0:1.5 ratio) in an OPD device according to the Examples.

The J-V curve obtained is shown in FIG. 4.

FIG. 4: J-V curve for a blend of polymer 28 and PC$_{60}$BM (1.0:1.5 ratio) in an OPD device.

OPV Device for Polymer 29

The device is fabricated similarly to the OPV device for polymer 20 using polymer 29 and PC$_{60}$BM.

Figure 5:
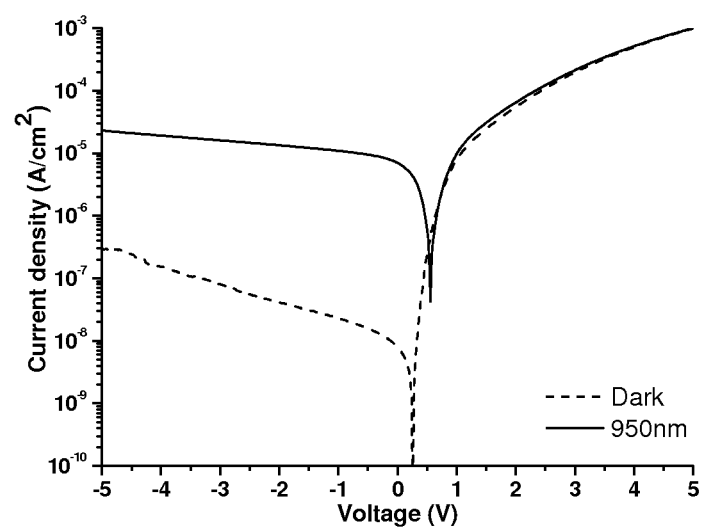
FIG. 5 shows the J-V curve for a blend of polymer 29 and PC$_{60}$BM (1.0:1.5 ratio) in an OPD device according to the Examples.

The J-V curve obtained is shown in FIG. 5.

FIG. 5: J-V curve for a blend of polymer 29 and PC$_{60}$BM (1.0:1.5 ratio) in an OPD device.

The invention claimed is:

1. A conjugated polymer that comprises in its backbone one or more electron donor units $D^i$ and one or more electron acceptor units $A^i$, and optionally one or two terminal or endcap units T, wherein each donor unit $D^i$ in the polymer backbone is flanked by two acceptor units $A^i$ to form a triad $A^i$-$D^i$-$A^i$, except for $D^i$ units adjacent to a terminal or endcap group T, which polymer fulfils the condition $f \leq s/2+2$, wherein f is the total number of units $D^i$ in the polymer backbone, s is the total number of units $A^i$ in the polymer backbone and s is at least 2, and excluding polymers comprising repeating units [A-D-A] wherein A is optionally substituted pyrazolone and D is optionally substituted benzo[1,2-b:4,5-b']dithiophene.

2. The conjugated polymer according to claim 1, which comprises in its backbone one or more spacer units $Sp^i$ linking the triads $A^i$-$D^i$-$A^i$, wherein said one or more spacer units $Sp^i$ are different from $D^i$ and are selected such that they do not act as electron acceptor towards the donor unit $D^i$.

3. The conjugated polymer according to claim 1, which comprises in its backbone one or more repeating units, sequences, segments or blocks selected from the group consisting of the formulae -[A$^1$-D$^1$]$_x$-[A$^2$-Sp$^1$]$_y$- and -[A$^1$-D$^1$-A$^2$-Sp$^1$]- wherein A$^1$ and A$^2$ denote independently of each other an acceptor unit, D$^1$ denotes a donor unit, and Sp$^1$ denotes a spacer unit which is not acting as electron acceptor towards D$^1$ and is different from D$^1$.

4. The conjugated polymer according to claim 3, wherein 0<x<1, 0<y<1, x+y=1, wherein x is the molar ratio of the segments A$^1$-D$^1$ and y is the molar ratio of the segments A$^2$-Sp$^1$.

5. The conjugated polymer according to claim 1, wherein the donor units $D^i$ are selected from the group consisting of benzo[1,2-b:4,5-b']dithiophene-2,6-diyl,
7H-3,4-dithia-7-sila-cyclopenta[a]pentalene-di-2,5-diyl, and
4H-cyclopenta[2,1-b;3,4-b']dithiophene-2,6-diyl.

6. The conjugated polymer according to claim 1, wherein the donor units $D^i$ and the acceptor units $A^i$ are selected from the group consisting of arylene and heteroarylene units, which are monocyclic or polycyclic and are unsubstituted or substituted.

7. The conjugated polymer according to claim 6, wherein the donor units $D^i$ are selected from the group consisting of the following formulae:

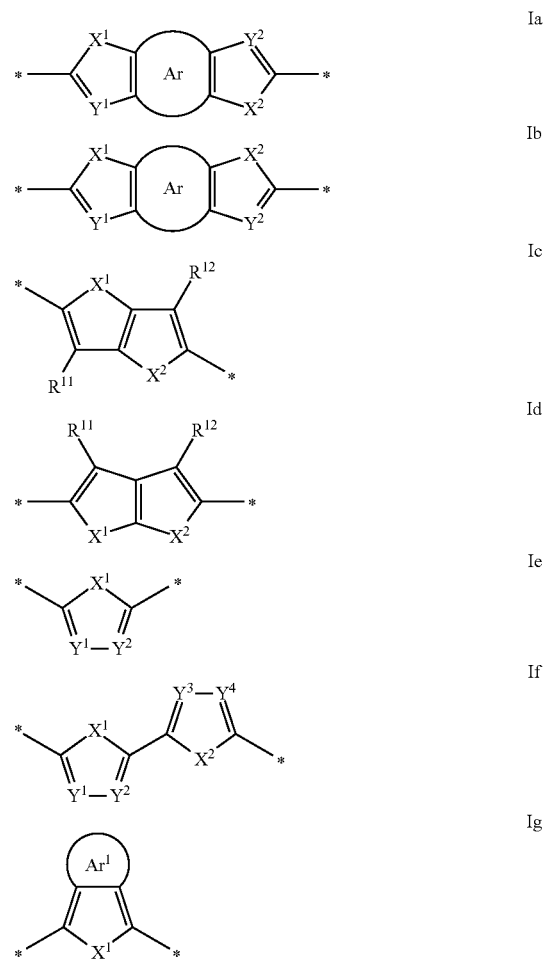

wherein
Ar denotes a carbocyclic, heterocyclic, aromatic or heteroaromatic group, which comprises one or more saturated or unsaturated rings that are covalently linked or fused, which is fused to the terminal five-membered rings in formula Ia or Ib to form a conjugated system, and which is unsubstituted or substituted, Ar$^1$ denotes a carbocyclic, heterocyclic, aromatic or heteroaromatic group, which comprises one or more saturated or unsaturated rings that are covalently linked or fused, which is fused to the divalent five-membered ring in formula Ig, and which is unsubstituted or substituted, X$^1$ and X$^2$ denote independently of each other O, S, Se, Si or NR$^1$, Y$^{1-4}$ denote independently of each other CR$^1$ or N, R$^1$ denotes H, halogen, or an optionally substituted carbyl or hydrocarbyl group, wherein one or more C atoms are optionally replaced by a hetero atom, and R$^{11}$ and R$^{12}$ independently of each other have one of the meanings of R$^1$.

8. The conjugated polymer according to claim 7, wherein Ar and Ar$^1$ in formula Ia, Ib and Ig are selected from the group consisting of benzene, pyrazine, 2H-pyran, 1,4-dioxane, naphthalene, anthracene, cyclopentadiene, thiophene, pyrrole, furan, 1H-silole, thieno[3,2-b]thiophene, thieno[2,3-b]thiophene, 1,5-dihydro-s-indacene, 1,7-dihydro-s-indacene, 1,5-disila-s-indacene, 1,7-disila-s-indacene, pyrrolo

[3,2-f]indole, and pyrrolo[2,3-f]indole, all of which are unsubstituted or substituted by one or more groups R¹, which denotes H, halogen, or an optionally substituted carbyl or hydrocarbyl group wherein one or more C atoms are optionally replaced by a hetero atom.

9. The conjugated polymer according to claim 1, wherein the donor units D$^i$ are selected from the group consisting of the following formulae and their mirror images:

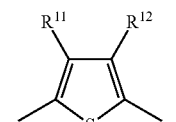
(D1)

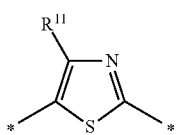
(D2)

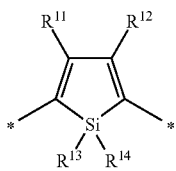
(D3)

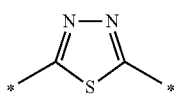
(D4)

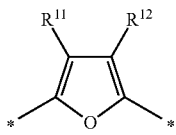
(D5)

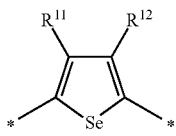
(D6)

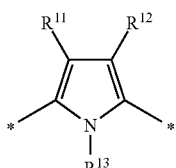
(D7)

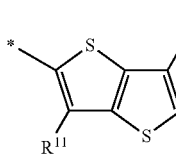
(D8)

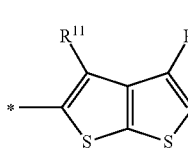
(D9)

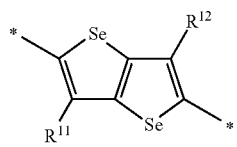
(D10)

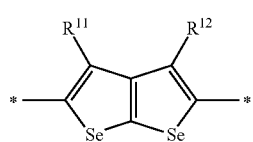
(D11)

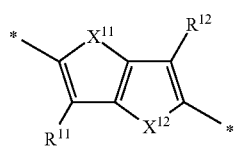
(D12)

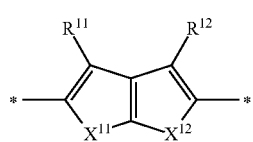
(D13)

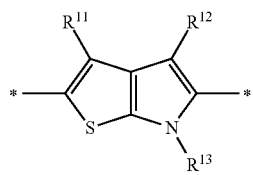
(D14)

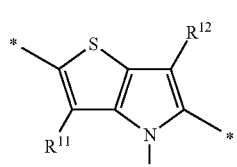
(D15)

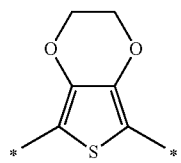
(D16)

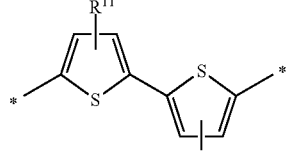
(D17)

(D18)

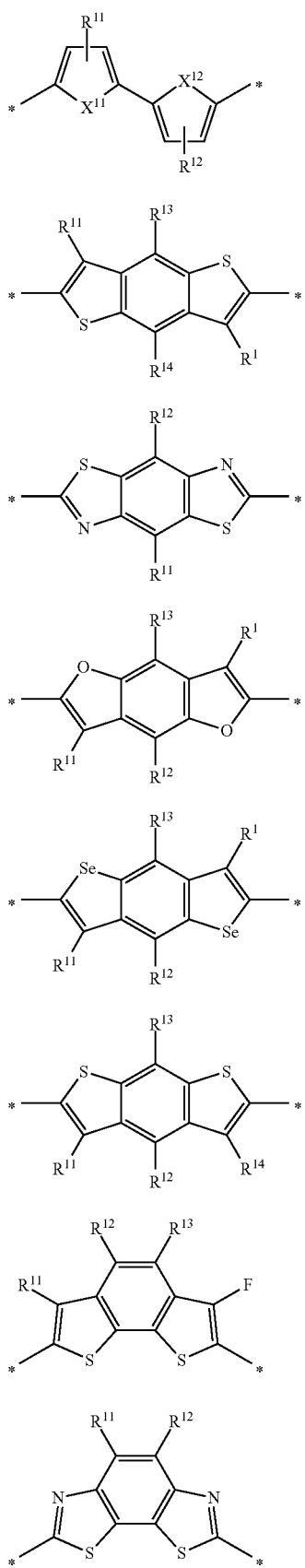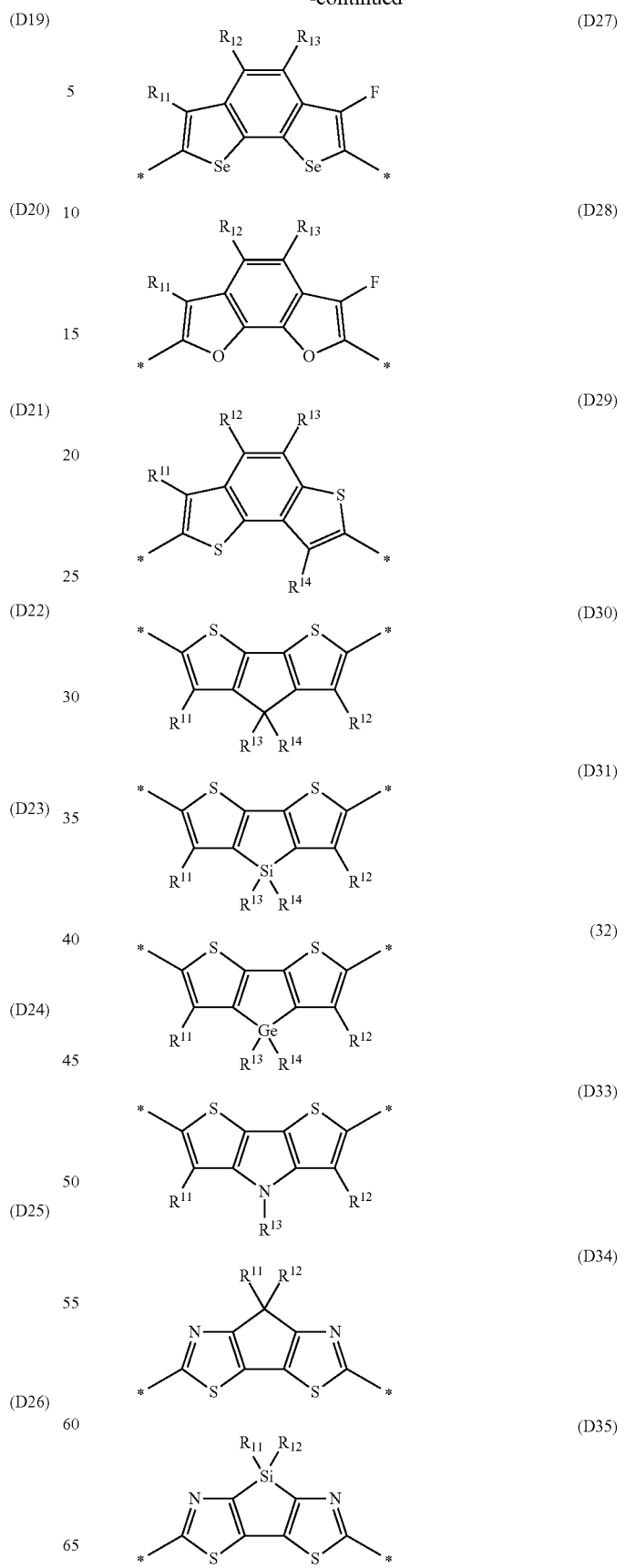

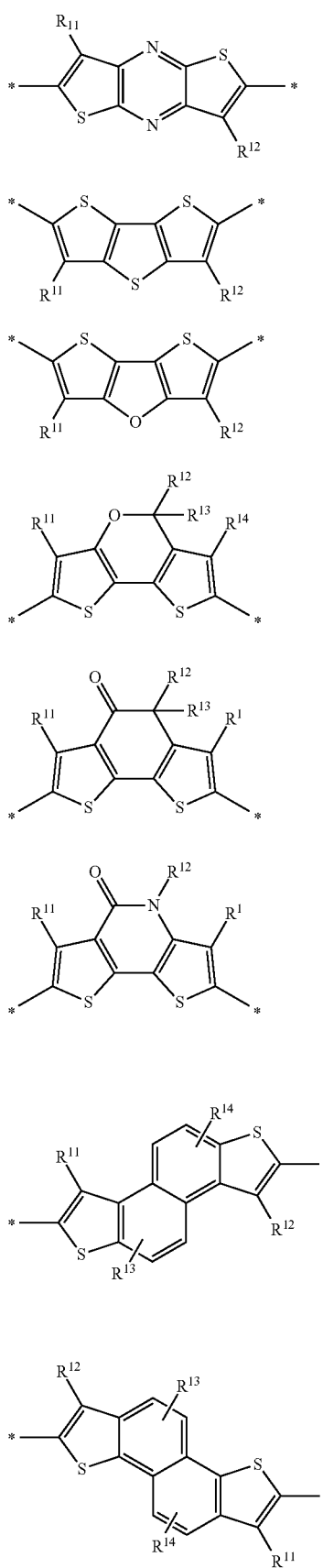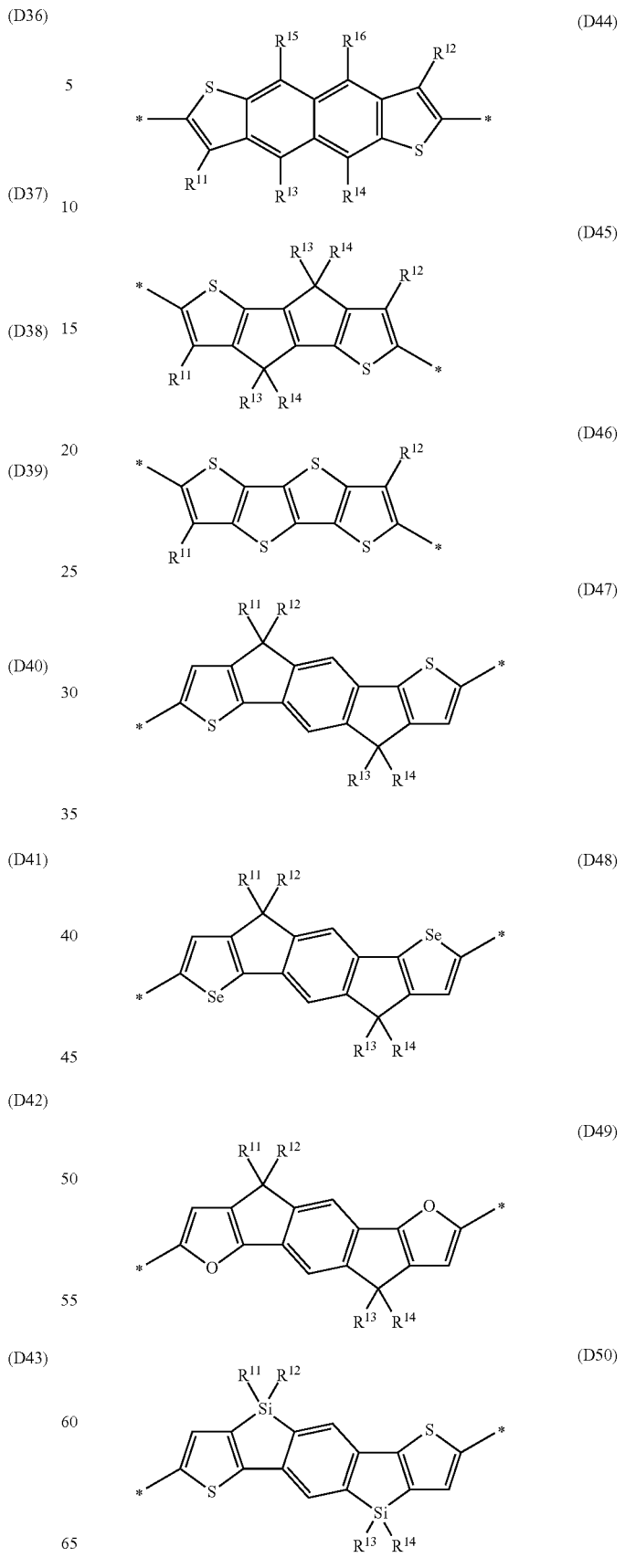

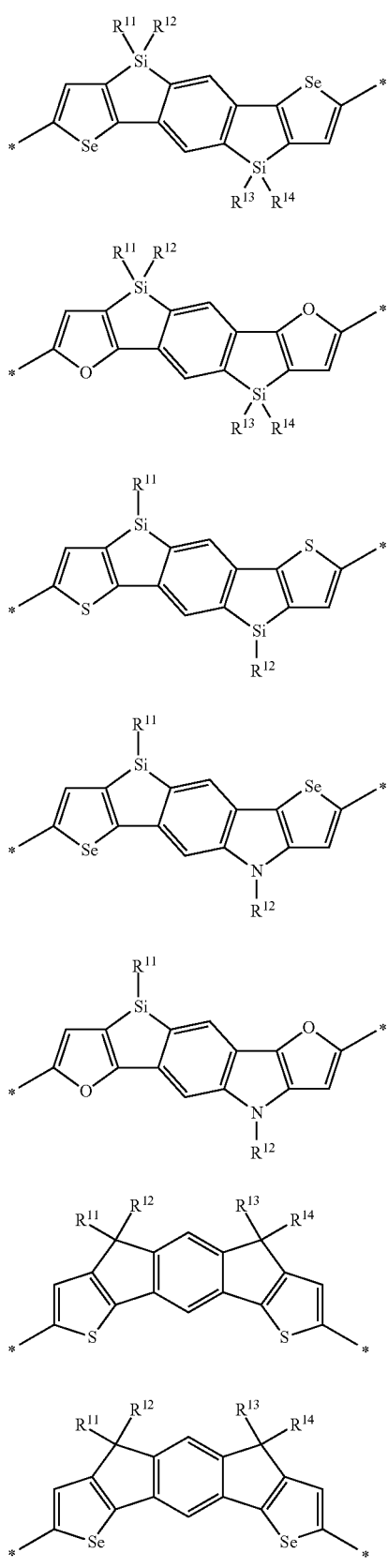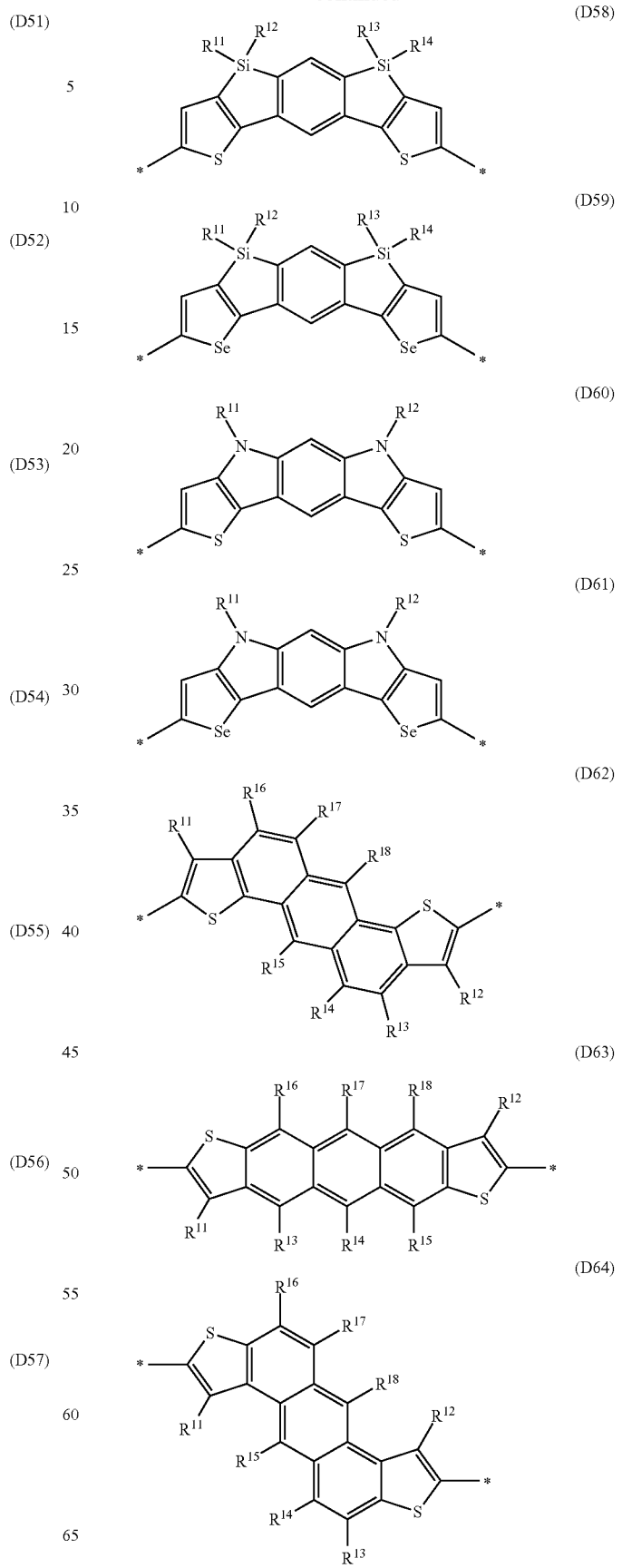

-continued (D65) 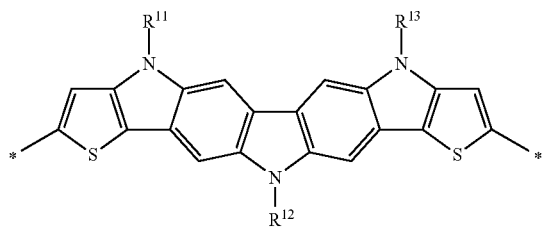

(D66) 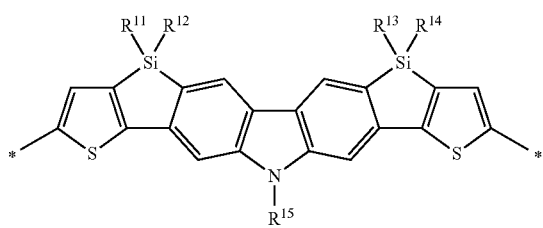

(D67) 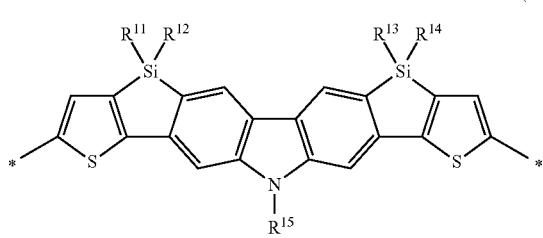

(D68) 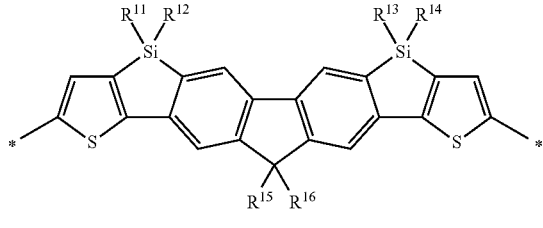

(D69) 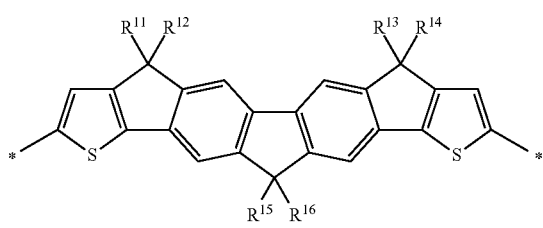

(D70) 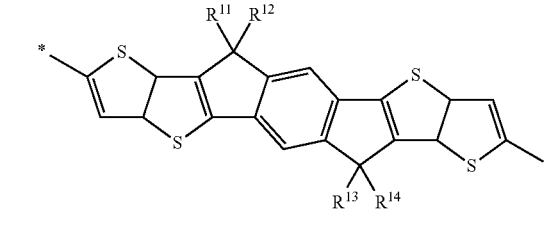

-continued (D71) 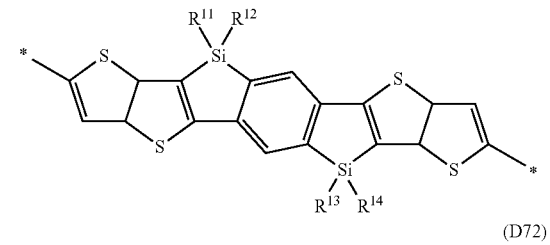

(D72) 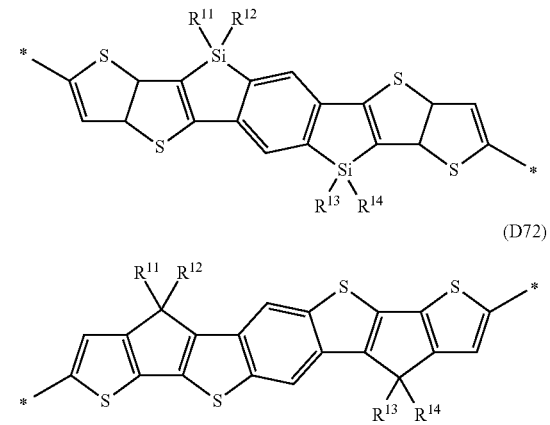

wherein one of $X^{11}$ and $X^{12}$ is S and the other is Se, and $R^{11}$, $R^{12}$, $R^{13}$, $R^{14}$, $R^{15}$, $R^{16}$, $R^{16}$, $R^{17}$ and $R^{18}$ independently of each other denote H, halogen, or an optionally substituted carbyl or hydrocarbyl group wherein one or more C atoms are optionally replaced by a hetero atom.

10. The conjugated polymer according to claim 1, wherein the donor units $D^i$ are selected from the group consisting of the following formulae Ia1 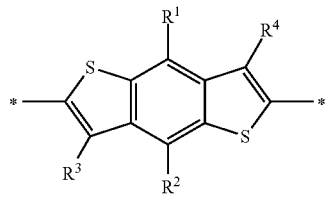

Ia2 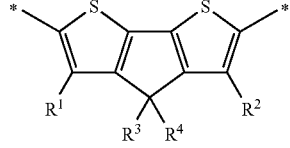

Ia3 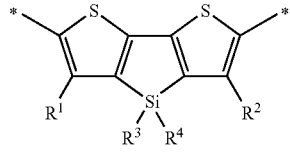

wherein $R^{1-4}$ independently of each other denote H, halogen, or an optionally substituted carbyl or hydrocarbyl group wherein one or more C atoms are optionally replaced by a hetero atom.

11. The conjugated polymer according to claim 1, wherein the donor units $D^i$ are selected from the group consisting of the following formulae

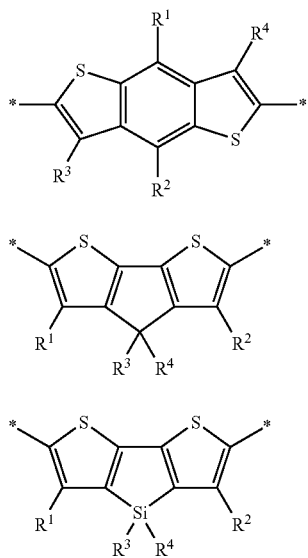

wherein $R^{1-4}$ independently of each other denote H, halogen, straight-chain, branched or cyclic alkyl with 1 to 30 C atoms, in which one or more non-adjacent $CH_2$ groups are optionally replaced by —O—, —S—, —C(O)—, —C(O)—O—, —O—C(O)—, —O—C(O)—O—, —SO$_2$—, —SO$_3$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, or denote aryl or heteroaryl that is optionally substituted and has 4 to 30 ring atoms, wherein $R^0$ and $R^{00}$ are independently of each other H or optionally substituted $C_{1-40}$ carbyl or hydrocarbyl, and $Y^1$ and $Y^2$ denote H, F or CN.

12. The conjugated polymer according to claim 1, wherein the acceptor units $A^i$ are selected from the group consisting of the following formulae and their mirror images:

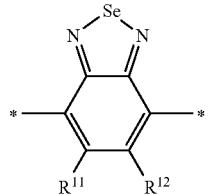

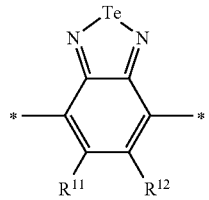

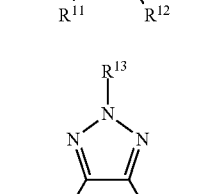

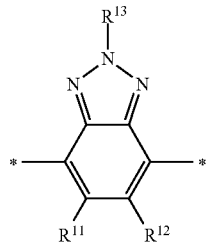

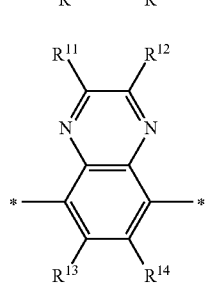

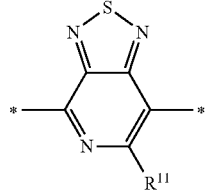

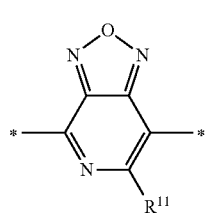

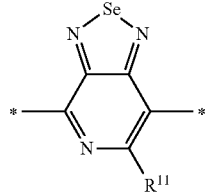

-continued
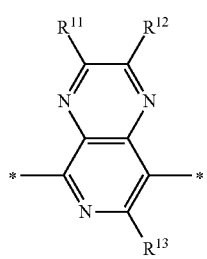 (A10)
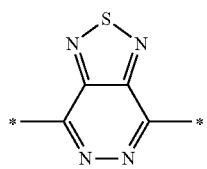 (A11)
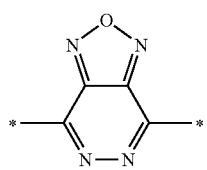 (A12)
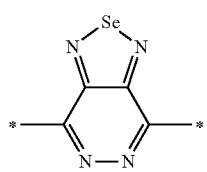 (A13)
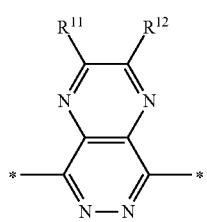 (A14)
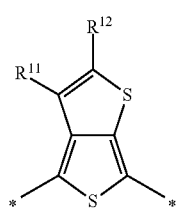 (A15)
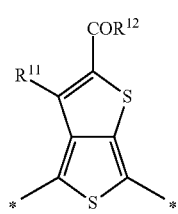 (A16)
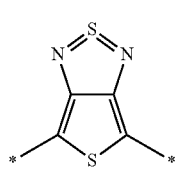 (A17)
-continued
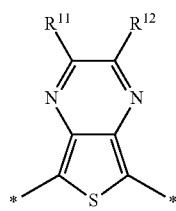 (A18)
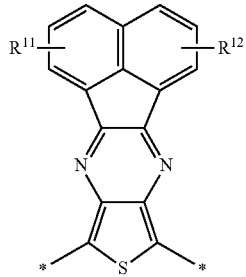 (A19)
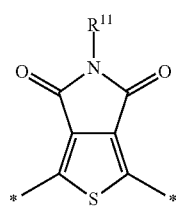 (A20)
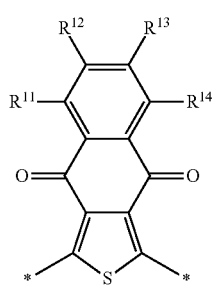 (A21)
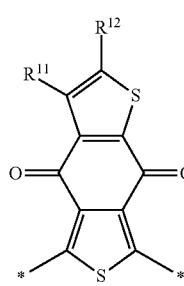 (A22)
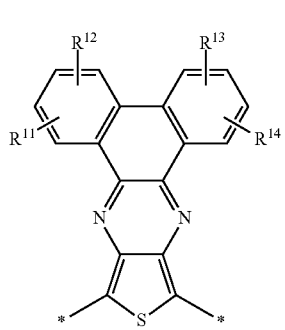 (A23)

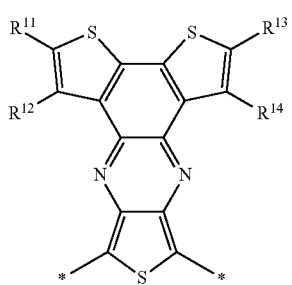
(A24)
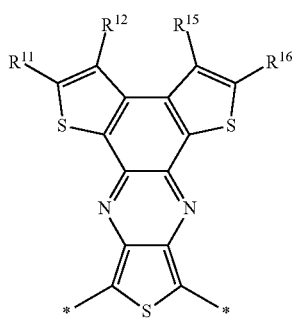
(A25)
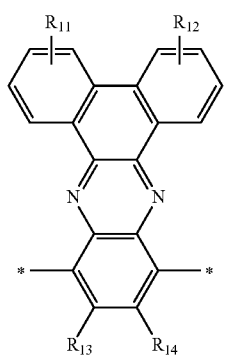
(A26)
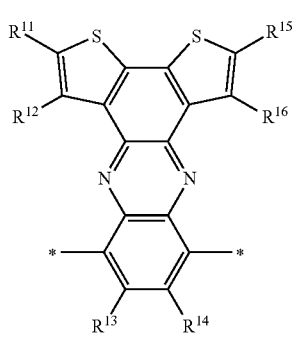
(A27)
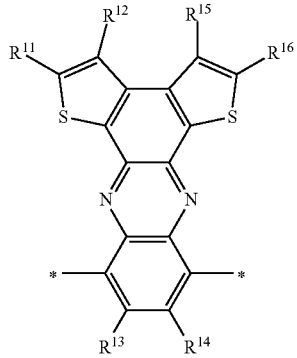
(A28)
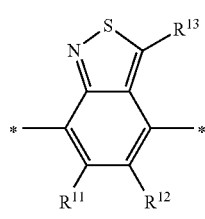
(A29)
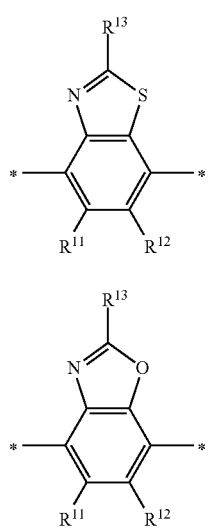
(A30)
(A31)
(A32)
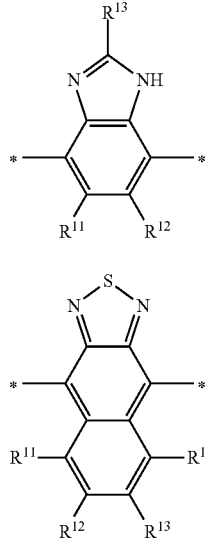
(A33)

-continued
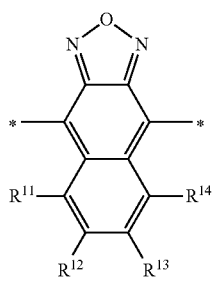 (A34)
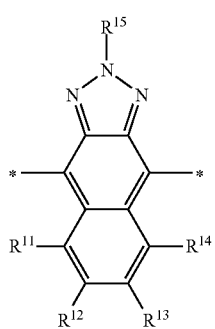 (A35)
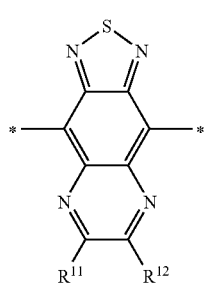 (A36)
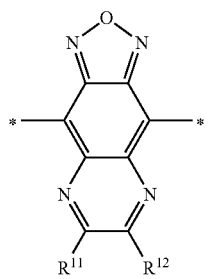 (A37)
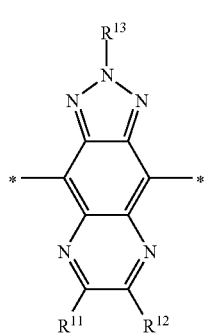 (A38)
-continued
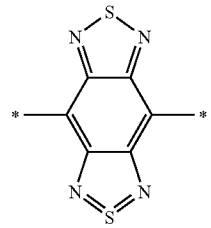 (A39)
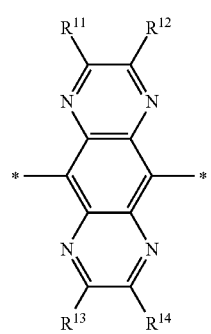 (A40)
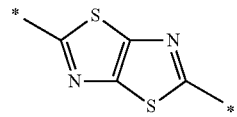 (A41)
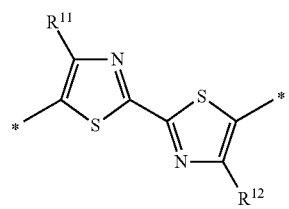 (A42)
(A43)
(A44)
(A45)
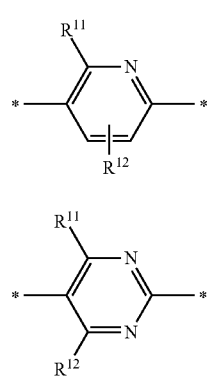 (A45)
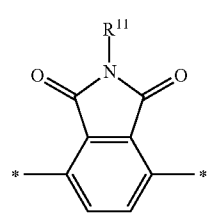 (A46)

(A47) 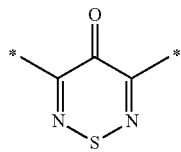
(A48) 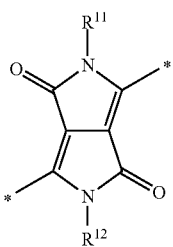
(A49) 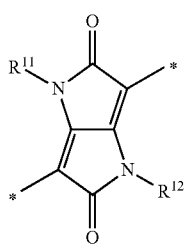
(A50) 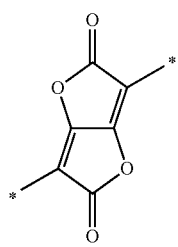
(A51) 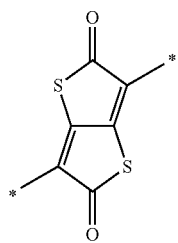
(A52) 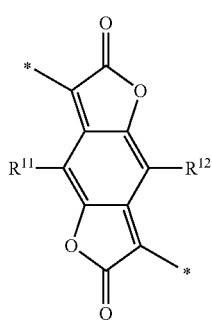
(A53) 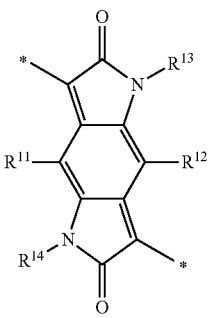
(A54) 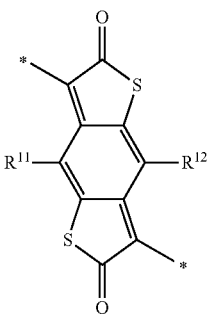
(A55) 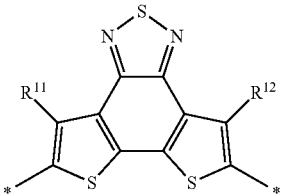
(A56) 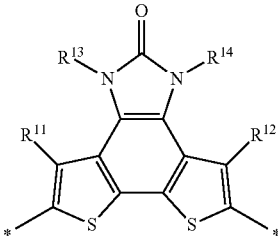
(A57) 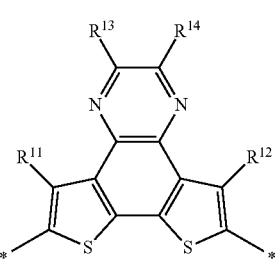

-continued
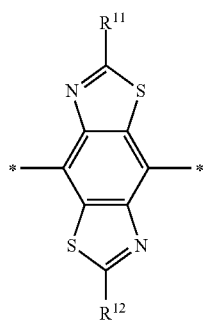 (A58)
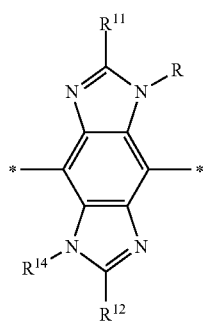 (A59)
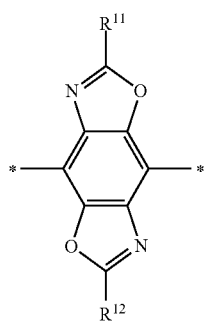 (A60)
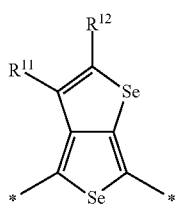 (A61)
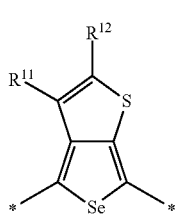 (A62)
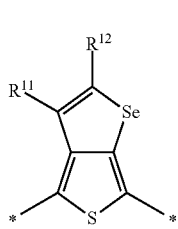 (A63)
-continued
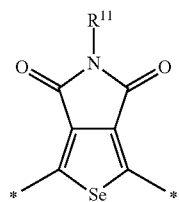 (A64)
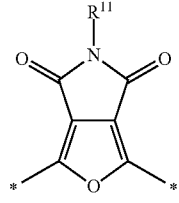 (A65)
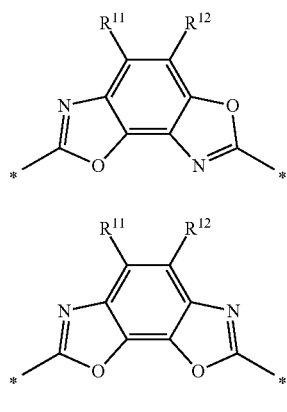 (A66)
(A67)
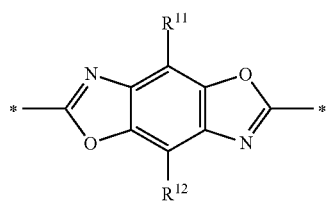 (A68)
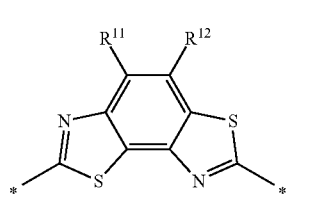 (A69)
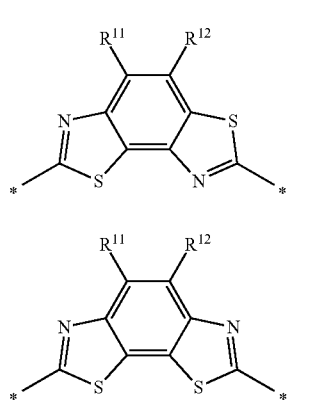 (A70)
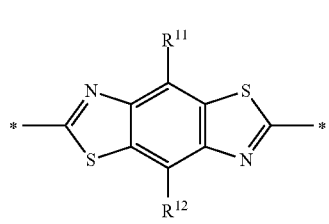 (A71)

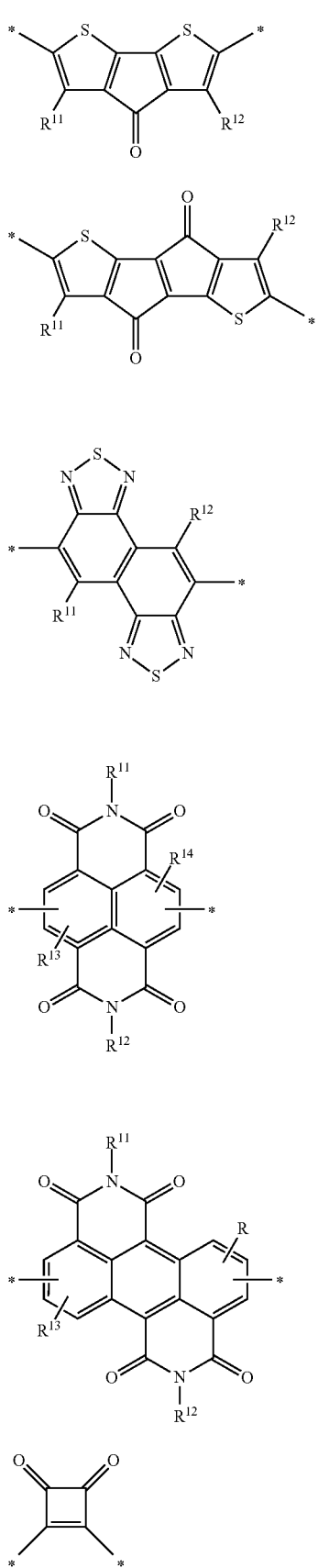
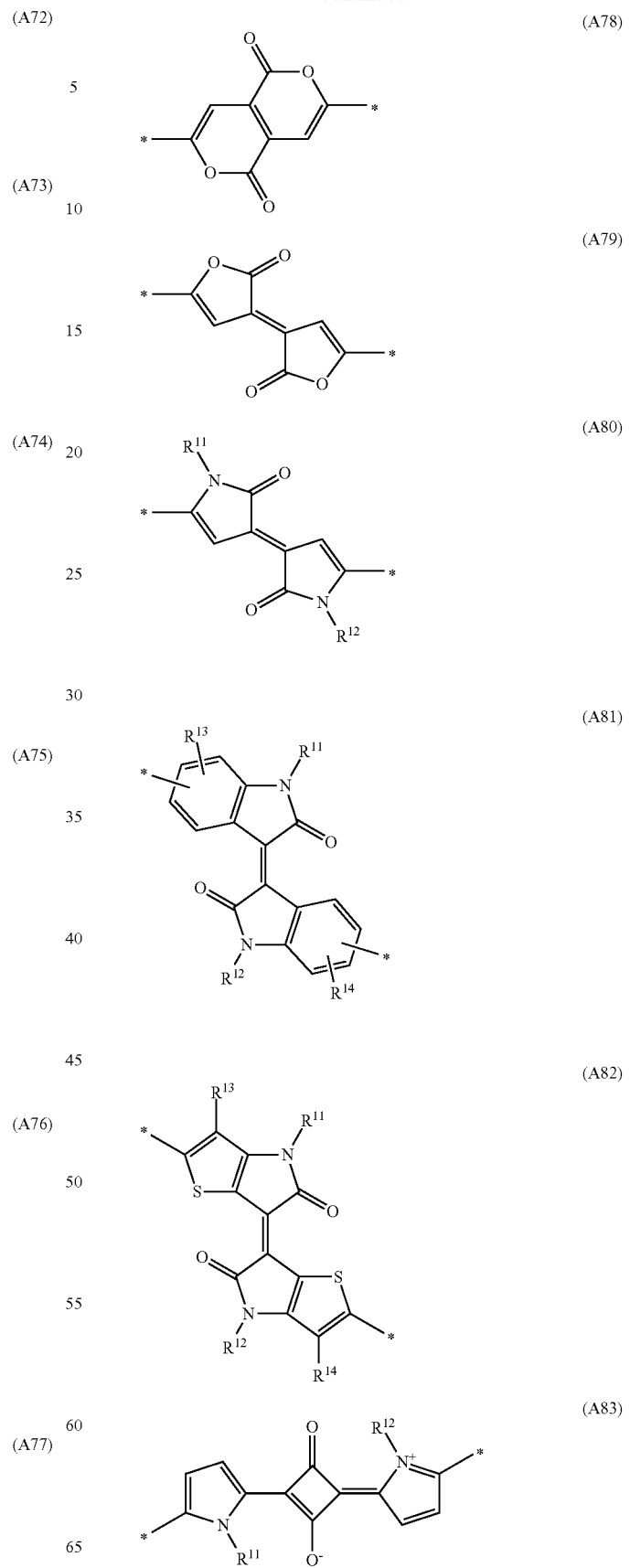

-continued
(A84) 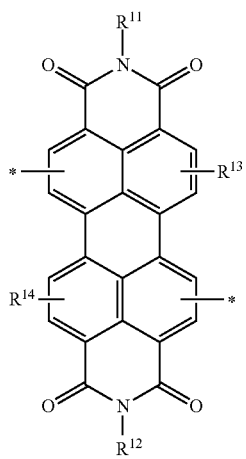
(A85) 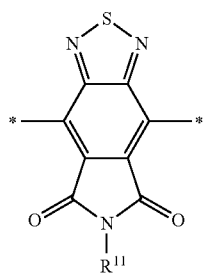
(A86) 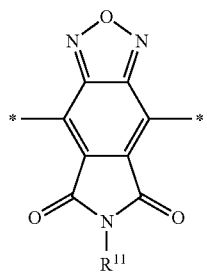
(A87) 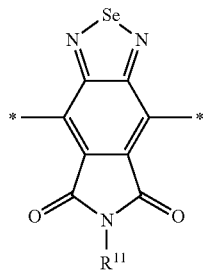
(A88) 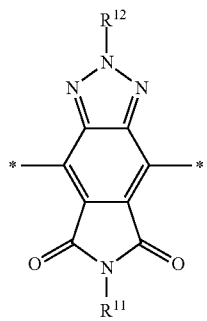
-continued
(A89) 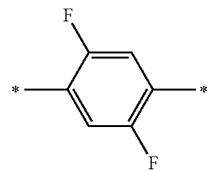
(A90) 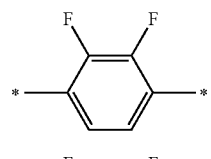
(A91) 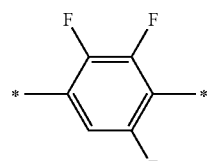
(A92) 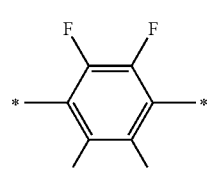
(A93) 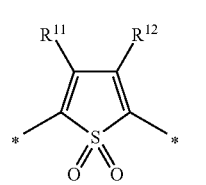
(A94) 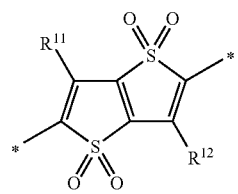
(A95) 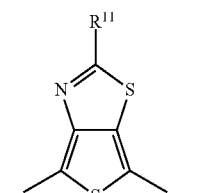
(A96) 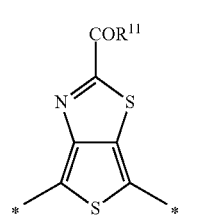
wherein $R^{11}$, $R^{12}$, $R^{13}$ and $R^{14}$ independently of each denote H, halogen, or an optionally substituted carbyl or hydrocarbyl group wherein one or more C atoms are optionally replaced by a hetero atom.
13. The conjugated polymer according to claim 12, which comprises one or more acceptor units $A^i$ selected from the group consisting of formulae A1, A2, A3, A7, A15, A16, A20, A21, A36, A39, A40, A74 and A85.

14. The conjugated polymer according to claim 1, which comprises one or more spacer units $Sp^i$ that are different from the donor and acceptor units $D^i$ and $A^i$, and are each independently a divalent, mono- or polycyclic, and optionally substituted, arylene or heteroarylene, —$CY^1$=$CY$— or —C≡C—, wherein $Y^1$ and Y independently of each other denote H, F, Cl or CN.

15. The conjugated polymer according to claim 14, wherein the spacer units $Sp^i$ are selected from the group consisting of the following formulae and their mirror images:

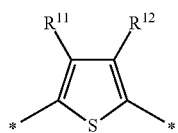

(D1)

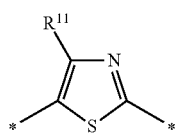

(D2)

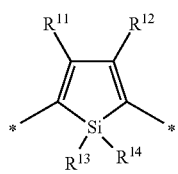

(D3)

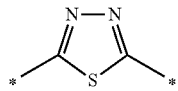

(D4)

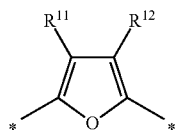

(D5)

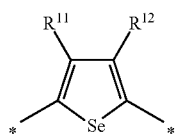

(D6)

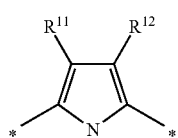

(D7)

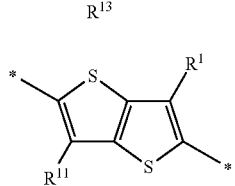

(D8)

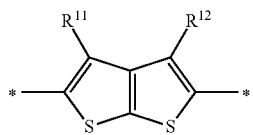

(D9)

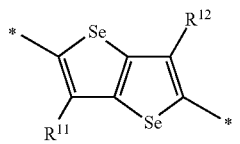

(D10)

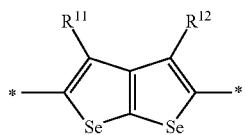

(D11)

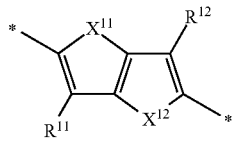

(D12)

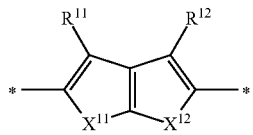

(D13)

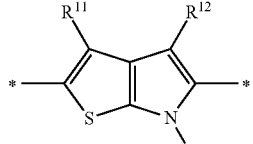

(D14)

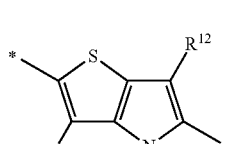

(D15)

(D16)

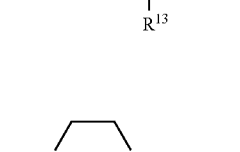

(D17)

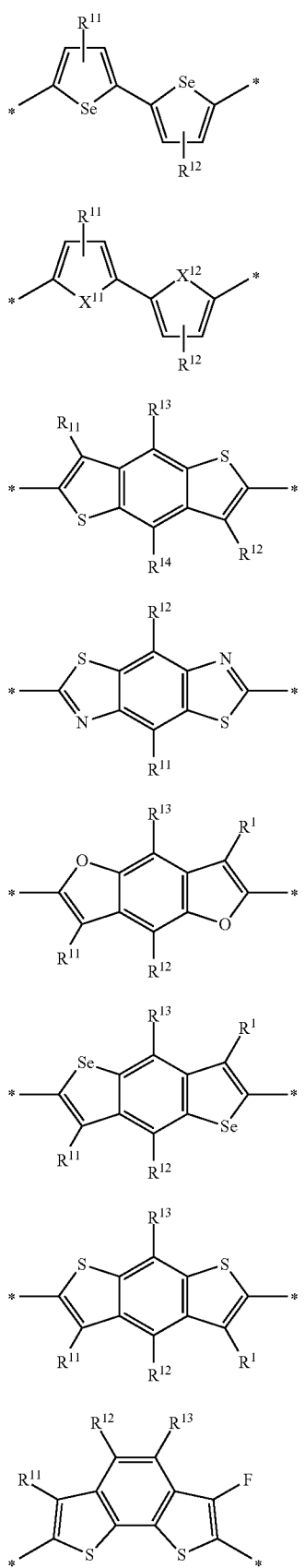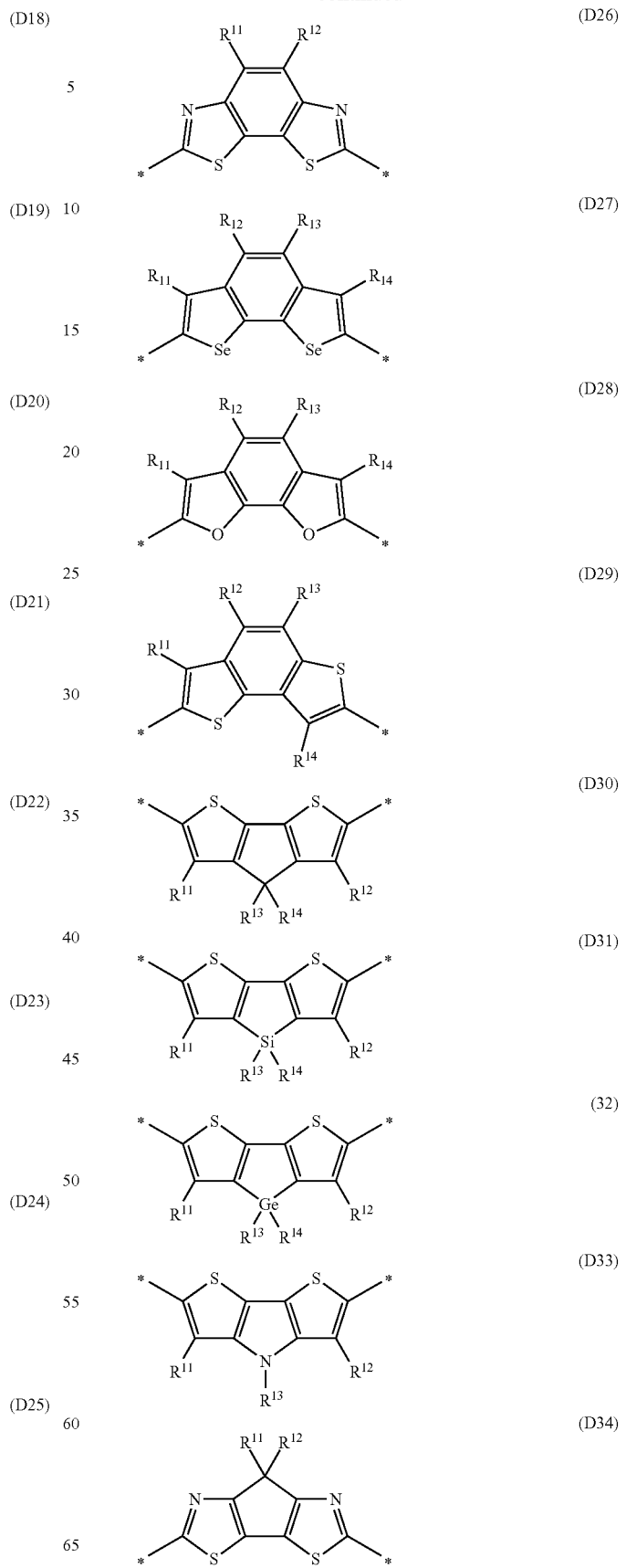

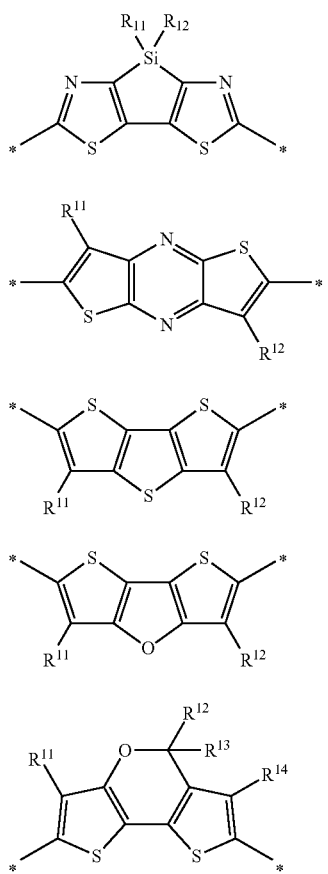
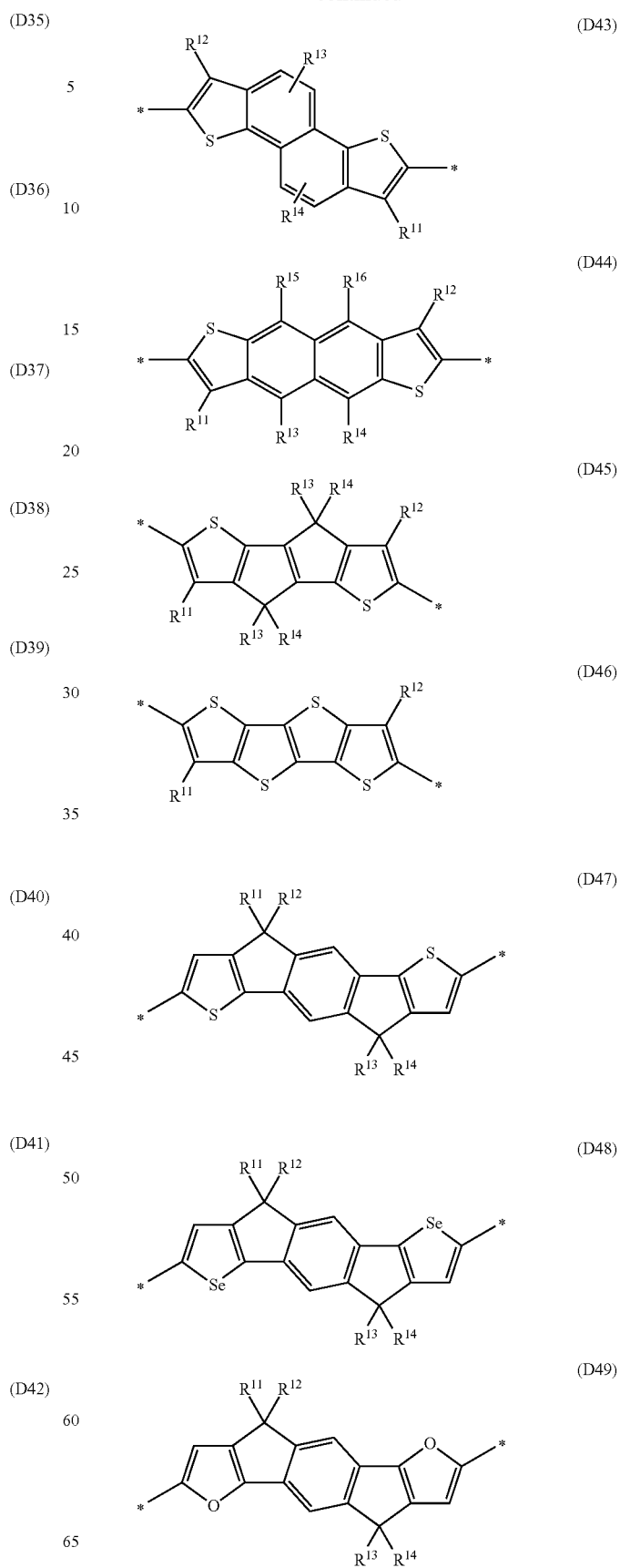

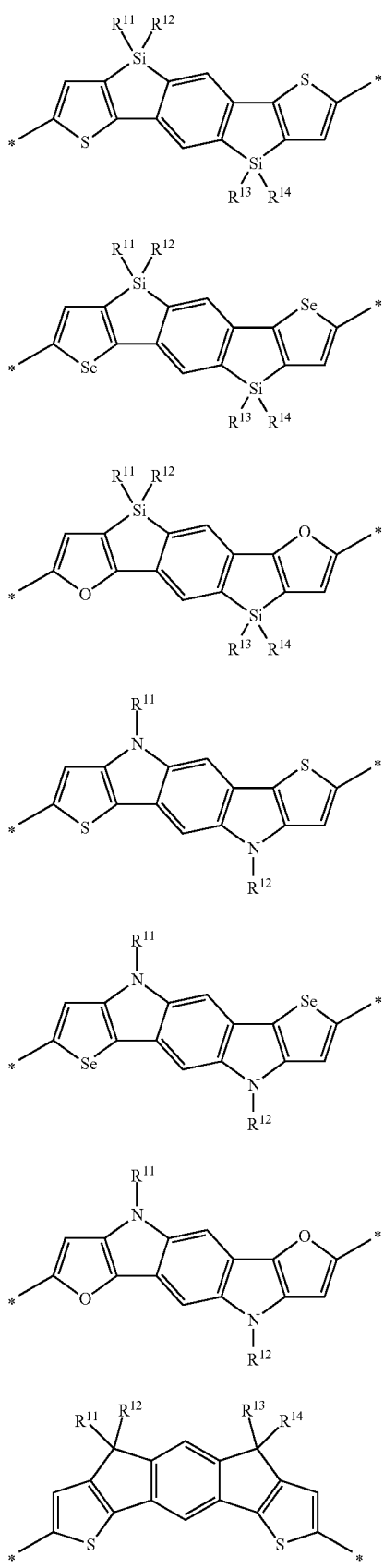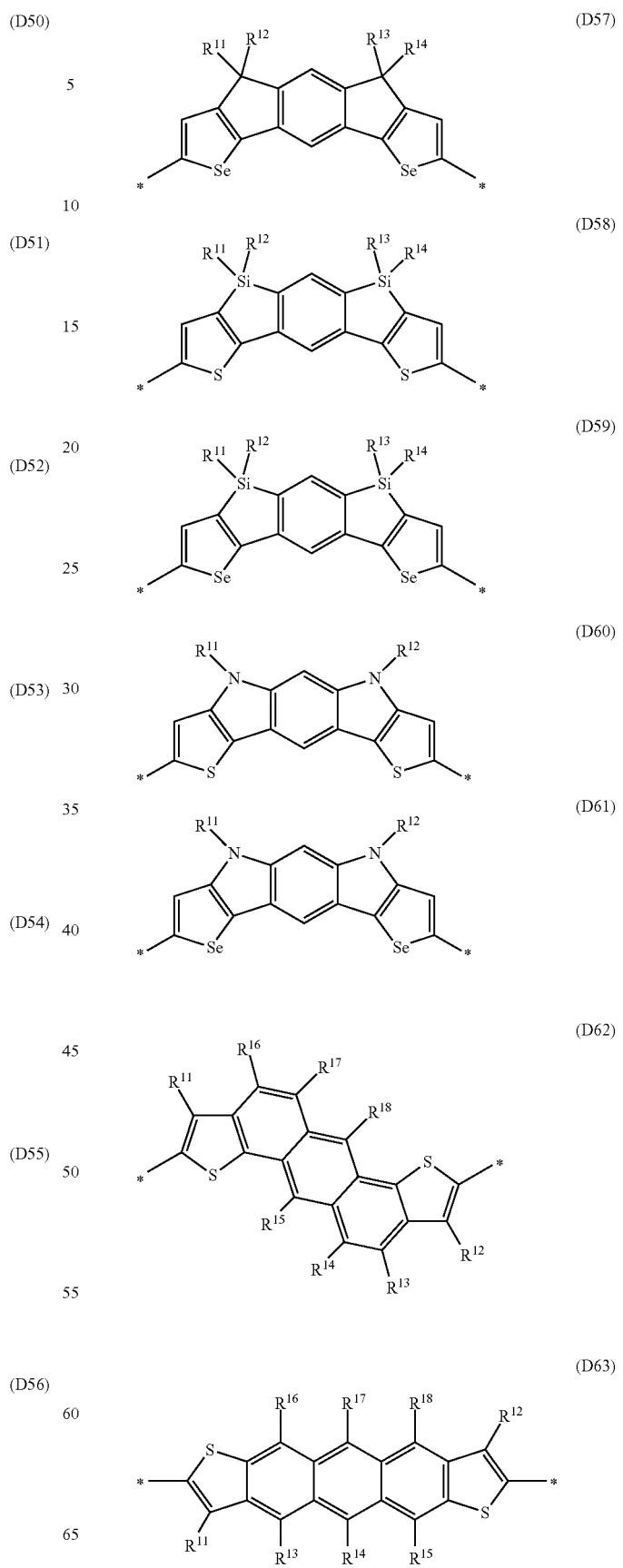

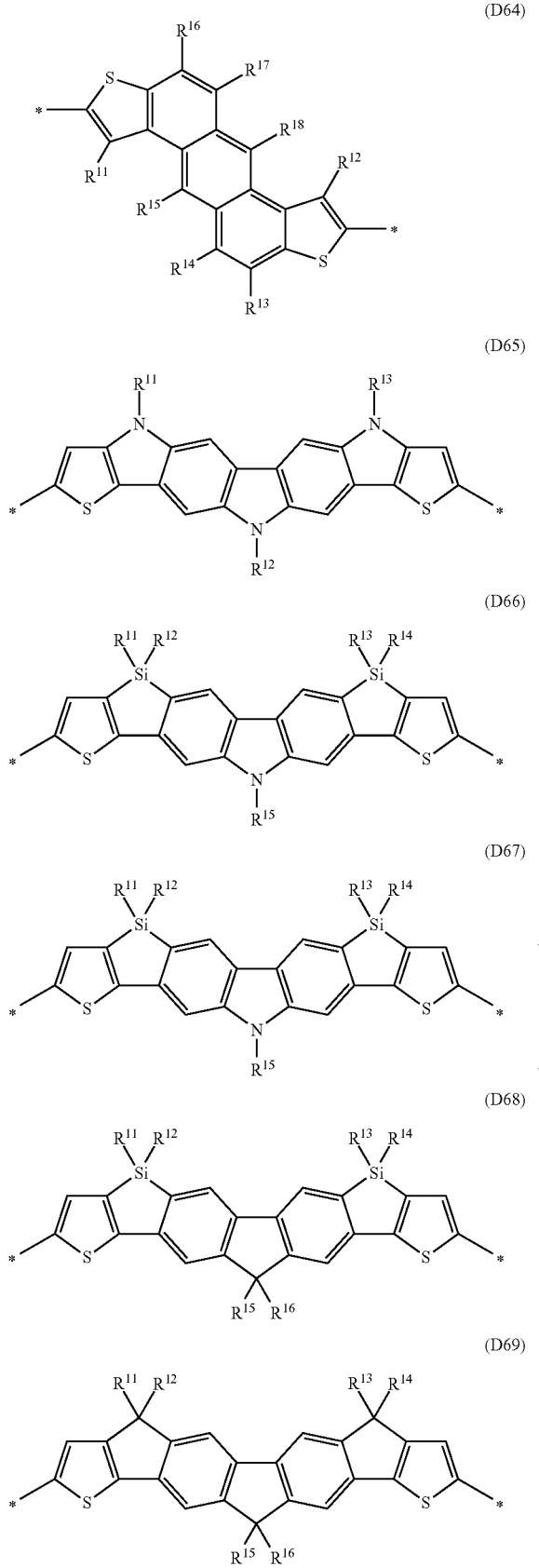

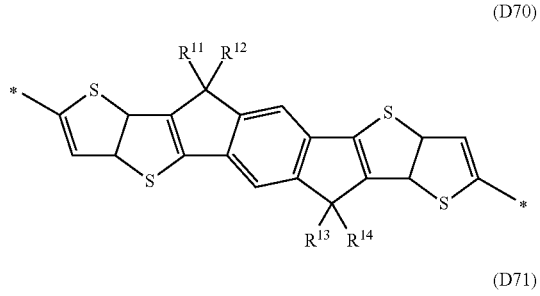

wherein one of $X^{11}$ and $X^{12}$ is S and the other is Se, and $R^{11}$, $R^{12}$, $R^{13}$, $R^{14}$, $R^{15}$, $R^{16}$, $R^{16}$, $R^{17}$ and $R^{18}$ independently of each other denote H, halogen, or an optionally substituted carbyl or hydrocarbyl group wherein one or more C atoms are optionally replaced by a hetero atom.

16. The conjugated polymer according to claim 14, which comprises one or more spacer units $Sp^i$ selected from the group consisting of the following formulae:

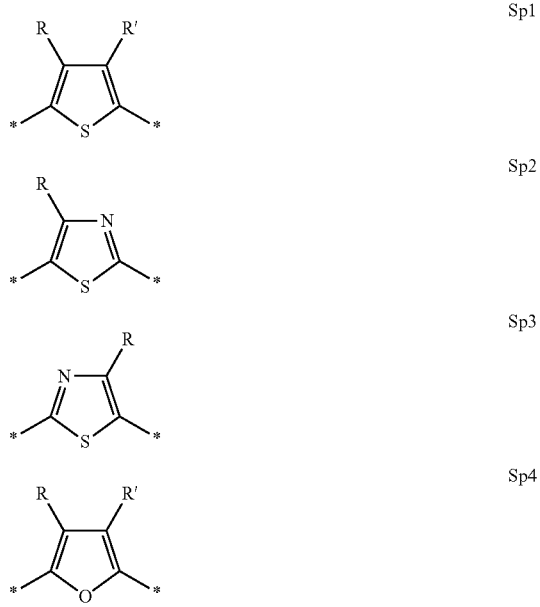

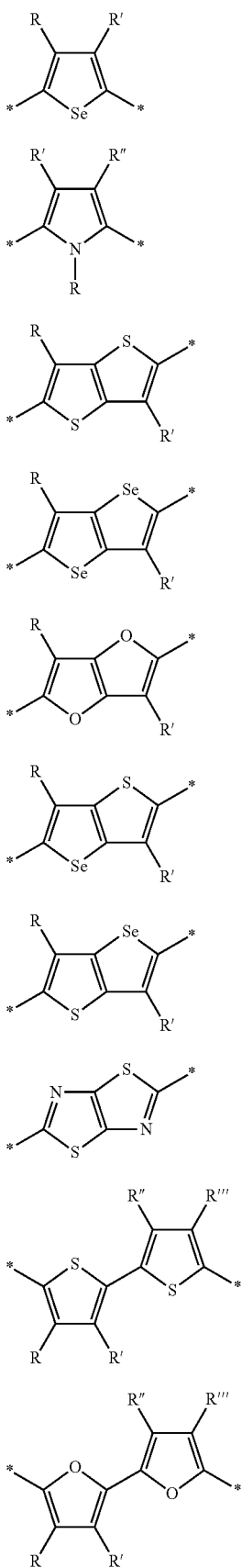
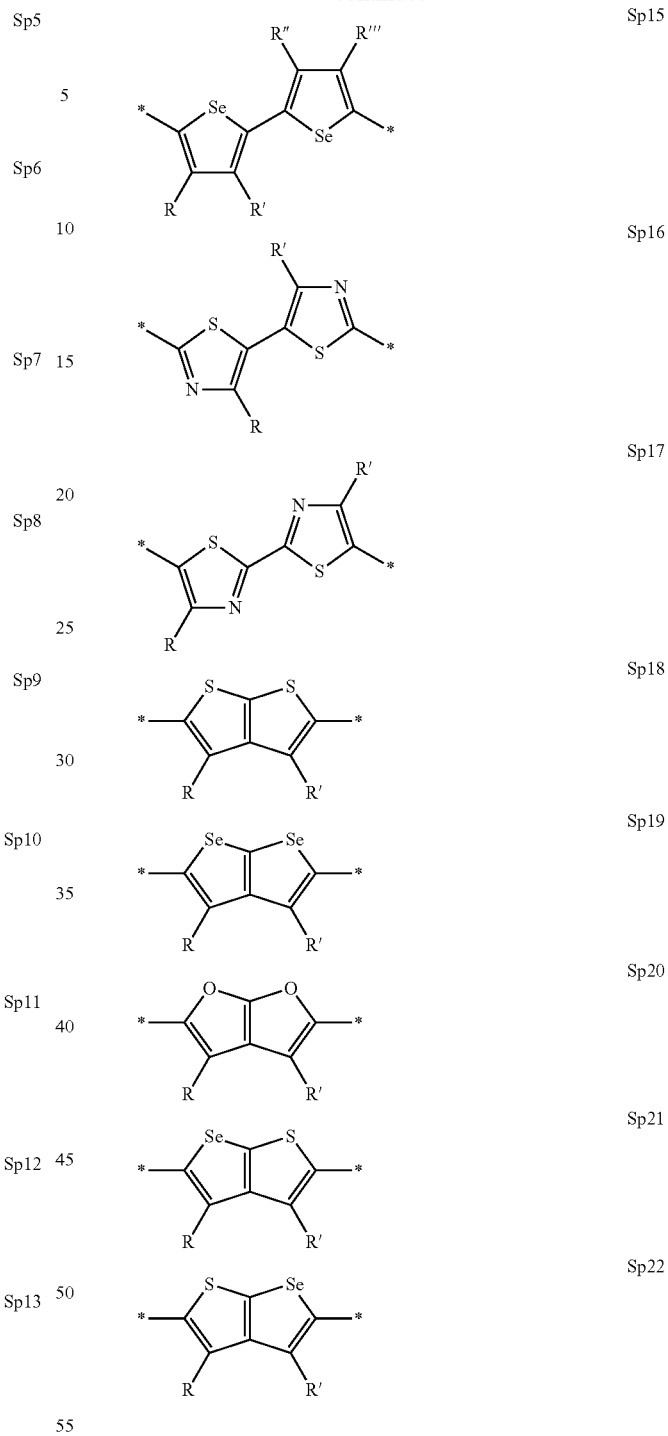

wherein R, R', R" and R'" independently of each other denote H, halogen, straight-chain, branched or cyclic alkyl with 1 to 30 C atoms, in which one or more non-adjacent CH$_2$ groups are optionally replaced by —O—, —S—, —C(O)—, —C(O)—O—, —O—C(O)—, —O—C(O)—O—, —SO$_2$—, —SO$_3$—, —NR$^o$—, —SiR$^o$R$^{oo}$—, —CF$_2$—, —CHR$^o$=CR$^{oo}$—, —CY$^1$=CY$^2$— or —C≡C— in such a manner that O and/or S atoms are not linked directly to one another, and in which one or more H atoms are optionally replaced by F, Cl, Br, I or CN, or denote aryl or heteroaryl that is optionally substituted and has 4 to 30 ring atoms, wherein R$^o$ and R$^{oo}$ are independently of each other H or optionally substituted $C_{1-40}$ carbyl or hydrocarbyl, and $Y^1$ and $Y^2$ denote H, F or CN.

17. The conjugated polymer according to claim 1, which comprises in its backbone one or more repeat units of formula II:

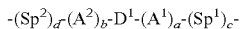   II wherein

D¹ is a first unit selected from the group consisting of formula Ia to Ig, Ia1, Ia2 and Ia3

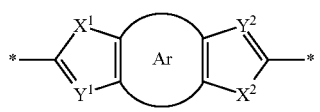   Ia

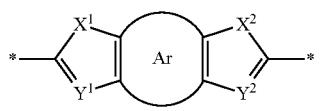   Ib

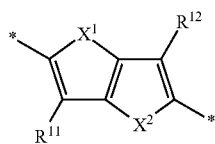   Ic

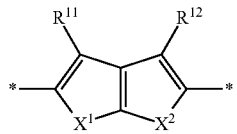   Id

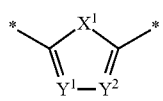   Ie

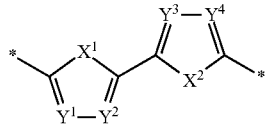   If

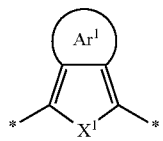   Ig wherein

Ar denotes a carbocyclic, heterocyclic, aromatic or heteroaromatic group, which comprises one or more saturated or unsaturated rings that are covalently linked or fused, which is fused to the terminal five-membered rings in formula Ia or Ib to form a conjugated system, and which is unsubstituted or substituted, Ar¹ denotes a carbocyclic, heterocyclic, aromatic or heteroaromatic group, which comprises one or more saturated or unsaturated rings that are covalently linked or fused, which is fused to the divalent five-membered ring in formula Ig, and which is unsubstituted or substituted, $X^1$ and $X^2$ denote independently of each other O, S, Se, Si or $NR^1$, $Y^{1-4}$ denote independently of each other $CR^1$ or N, $R^1$ denotes H, halogen, or an optionally substituted carbyl or hydrocarbyl group, wherein one or more C atoms are optionally replaced by a hetero atom, and $R^{11}$ and $R^{12}$ independently of each other have one of the meanings of $R^1$,

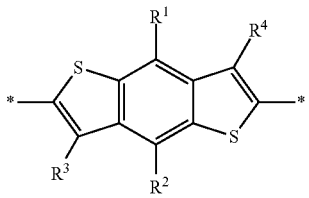   Ia1

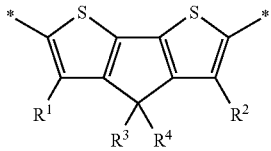   Ia2

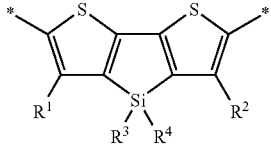   Ia3 wherein $R^{1-4}$ independently of each other denote H, halogen, or an optionally substituted carbyl or hydrocarbyl group wherein one or more C atoms are optionally replaced by a hetero atom $A^1$ and $A^2$ independently of each other denote an acceptor unit that is different from $D^1$, $Sp^1$ and $Sp^2$, and is arylene or heteroarylene that is mono- or polycyclic and optionally substituted, or is selected from the group consisting of the following formulae and their mirror images:

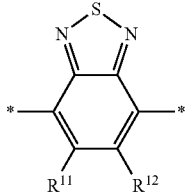   (A1)

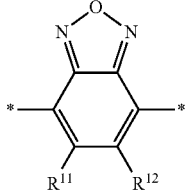   (A2)

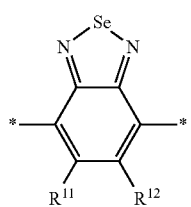 (A3)
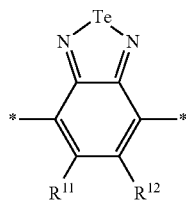 (A4)
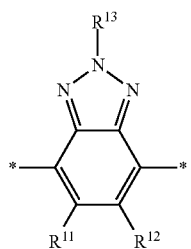 (A5)
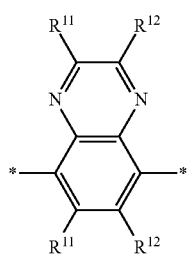 (A6)
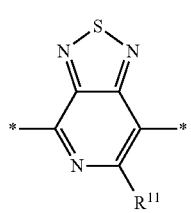 (A7)
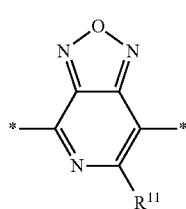 (A8)
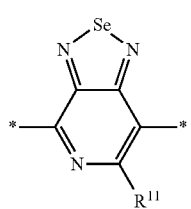 (A9)
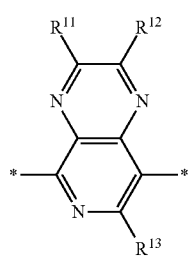 (A10)
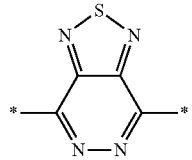 (A11)
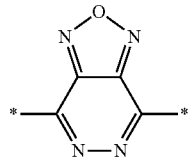 (A12)
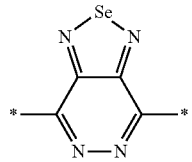 (A13)
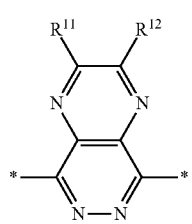 (A14)
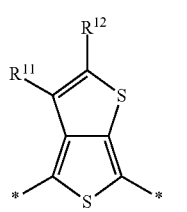 (A15)
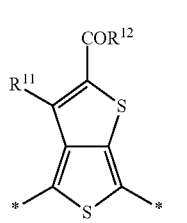 (A16)
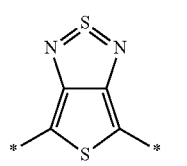 (A17)

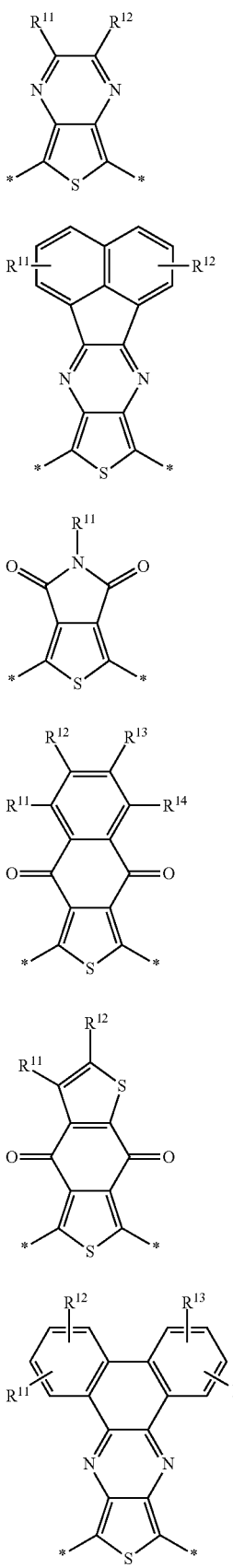
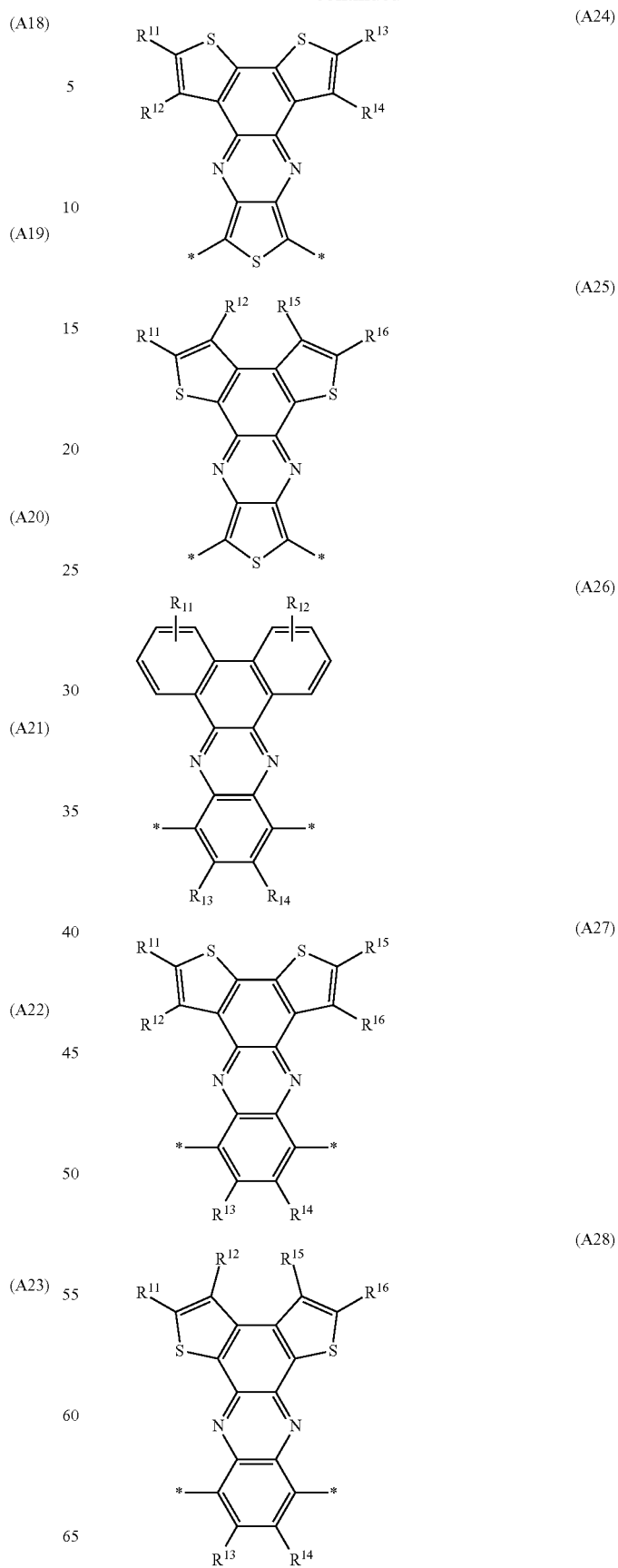

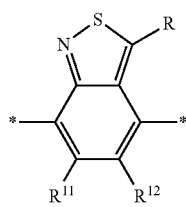
(A29)
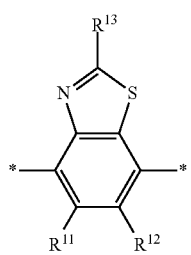
(A30)
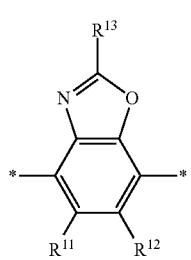
(A31)
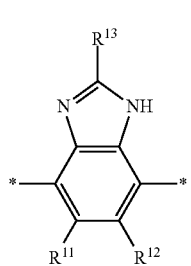
(A32)
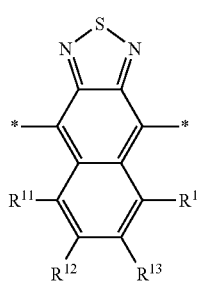
(A33)
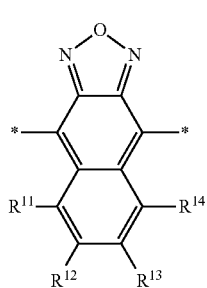
(A34)
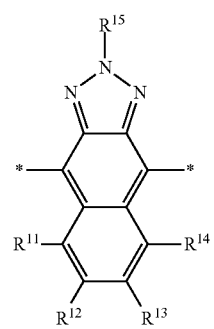
(A35)
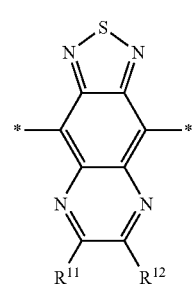
(A36)
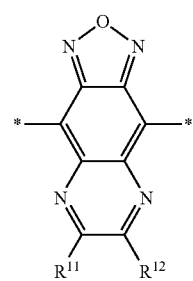
(A37)
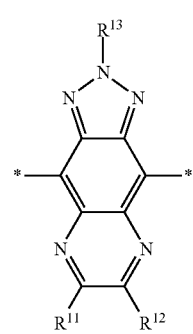
(A38)
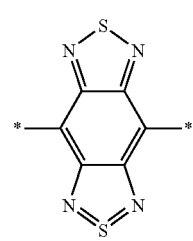
(A39)

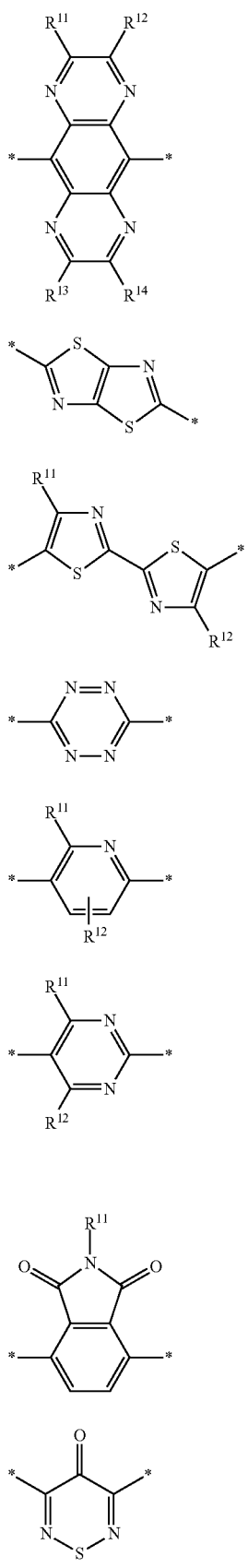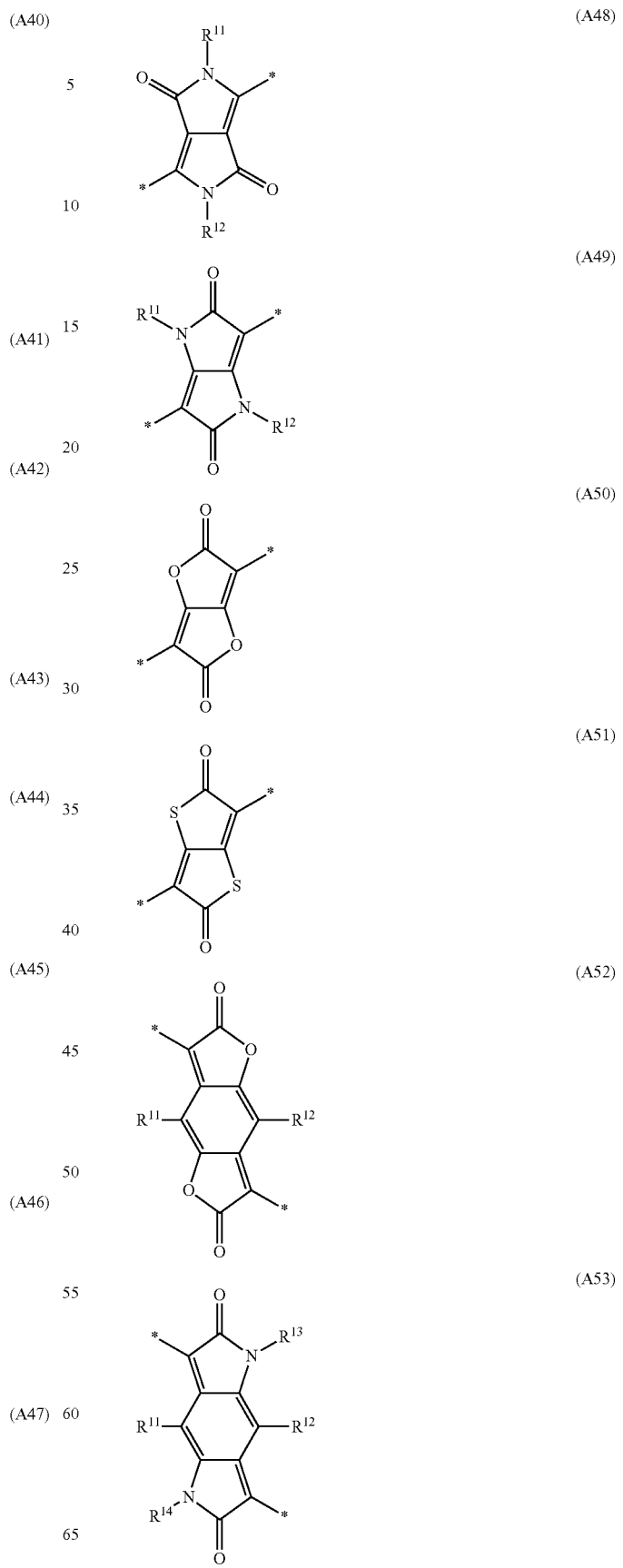

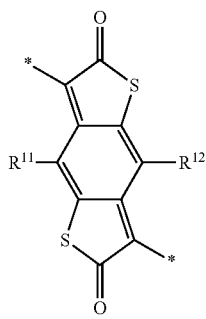
(A54)
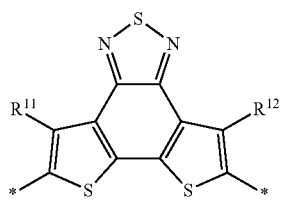
(A55)
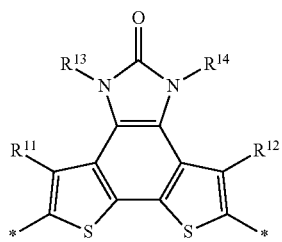
(A56)
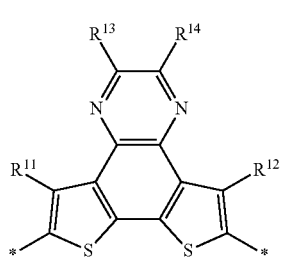
(A57)
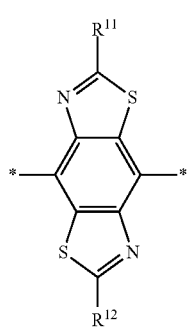
(A58)
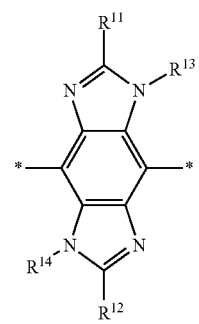
(A59)
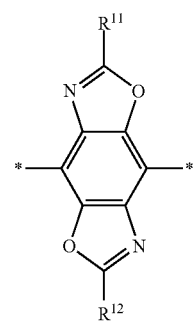
(A60)
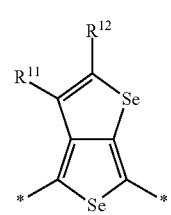
(A61)
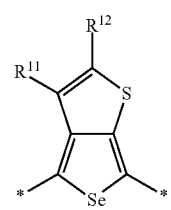
(A62)
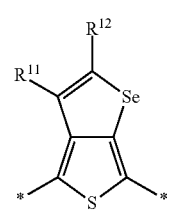
(A63)
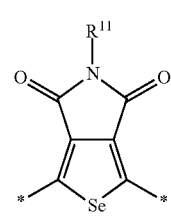
(A64)

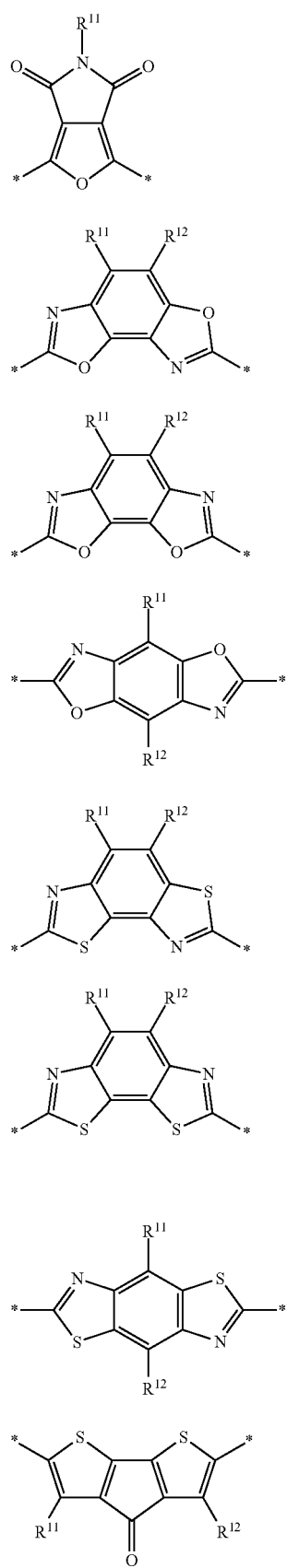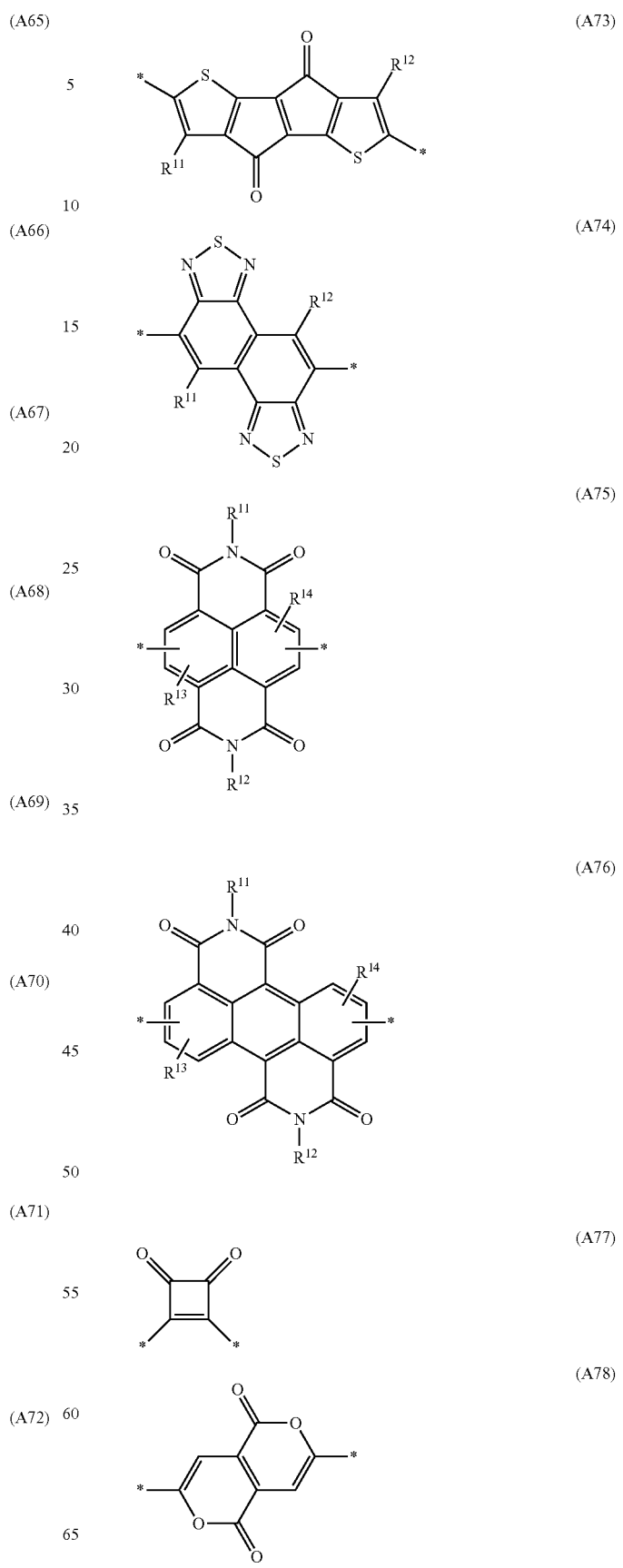

-continued
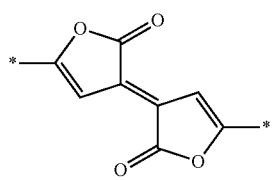
(A79)
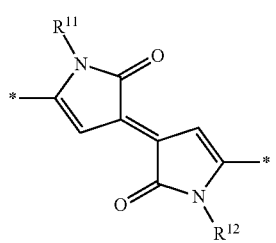
(A80)
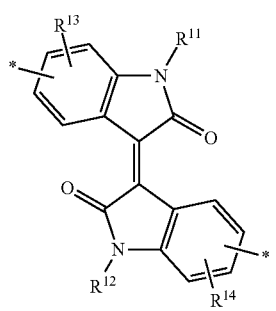
(A81)
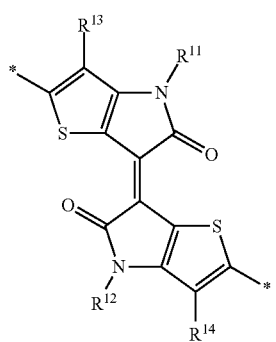
(A82)
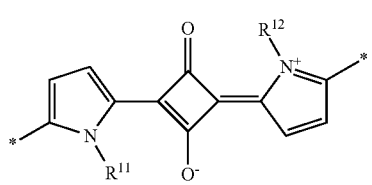
(A83)
-continued
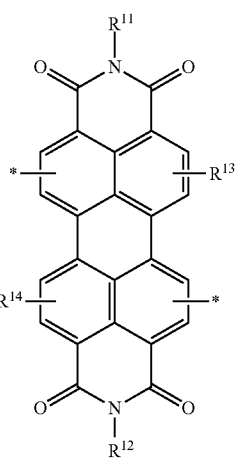
(A84)
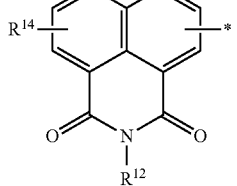
(A85)
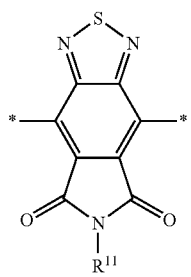
(A86)
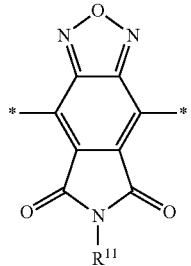
(A87)
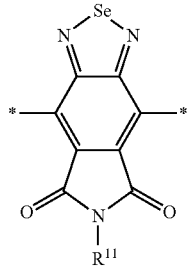
(A88)
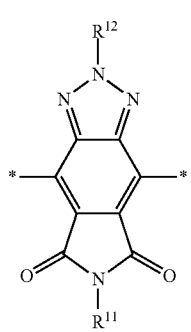

-continued

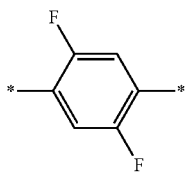
(A89)

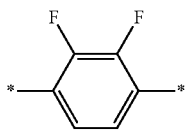
(A90)

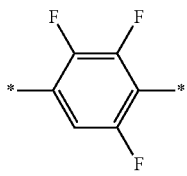
(A91)

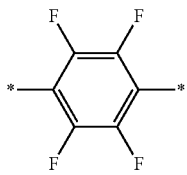
(A92)

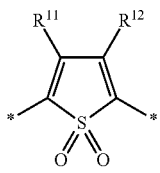
(A93)

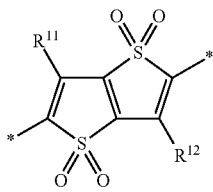
(A94)

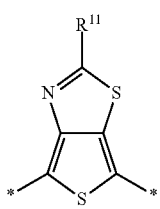
(A95)

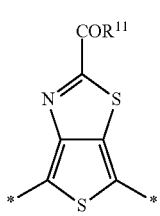
(A96)

wherein
$R^{11}$, $R^{12}$, $R^{13}$ and $R^{14}$ independently of each denote H, halogen, or an optionally substituted carbyl or hydrocarbyl group wherein one or more C atoms are optionally replaced by a hetero atom, $Sp^1$ and $Sp^2$ independently of each other denote a spacer unit, which is different from $D^1$, $A^1$ and $A^2$, and is arylene or heteroarylene that is mono- or polycyclic and is optionally substituted, or is selected from the group consisting of the following formulae and their mirror images:

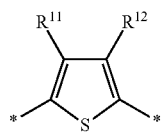
(D1)

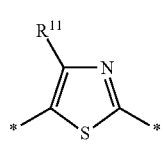
(D2)

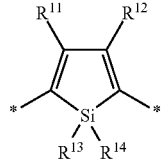
(D3)

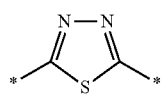
(D4)

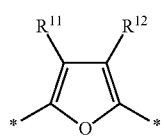
(D5)

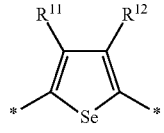
(D6)

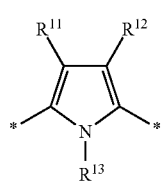
(D7)

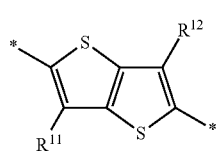
(D8)

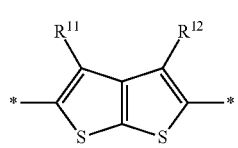
(D9)

-continued
(D10)
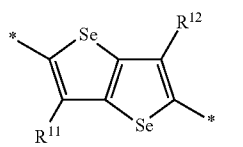
(D11)
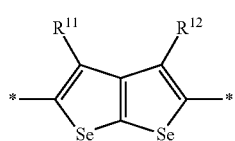
(D12)
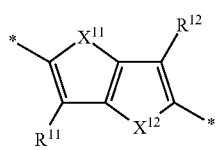
(D13)
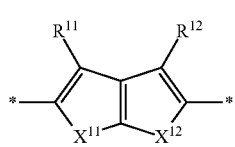
(D14)
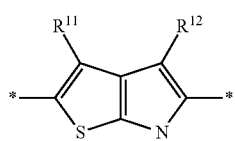
(D15)
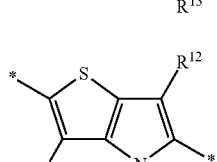
(D16)
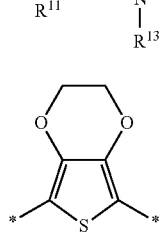
(D17)
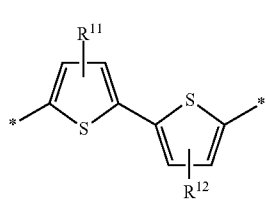
(D18)
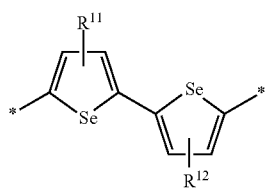
-continued
(D19)
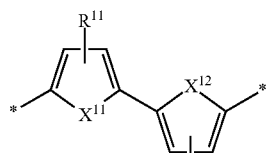
(D20)
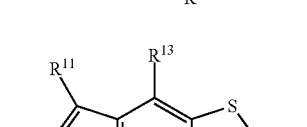
(D21)
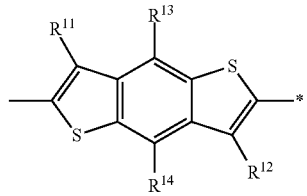
(D22)
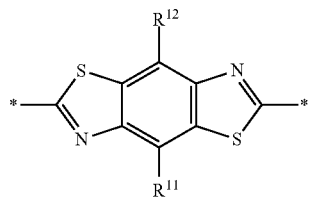
(D23)
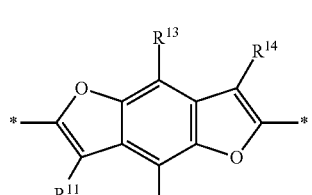
(D24)
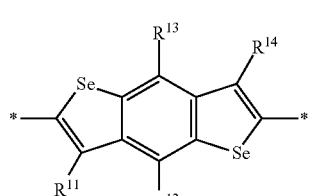
(D25)
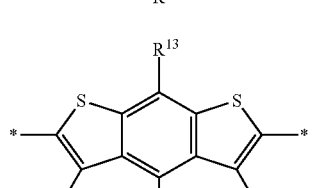
(D26)
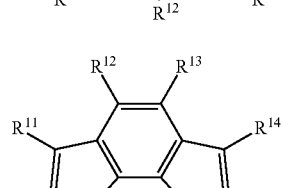
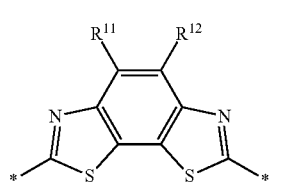

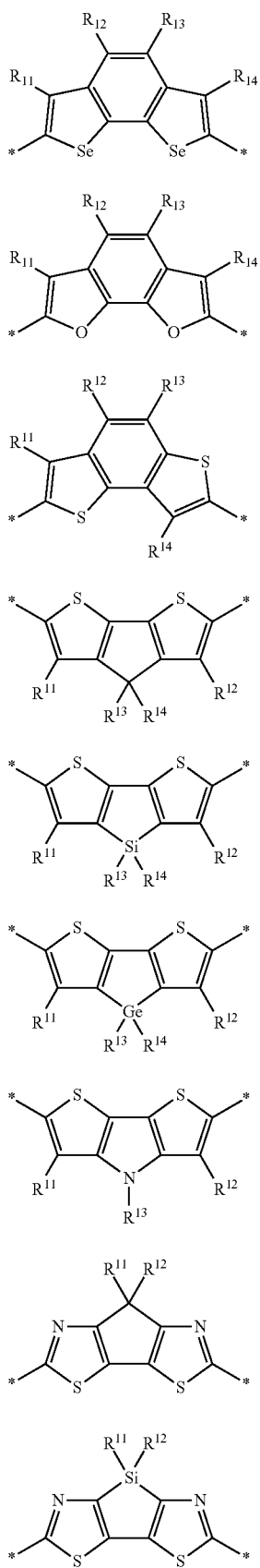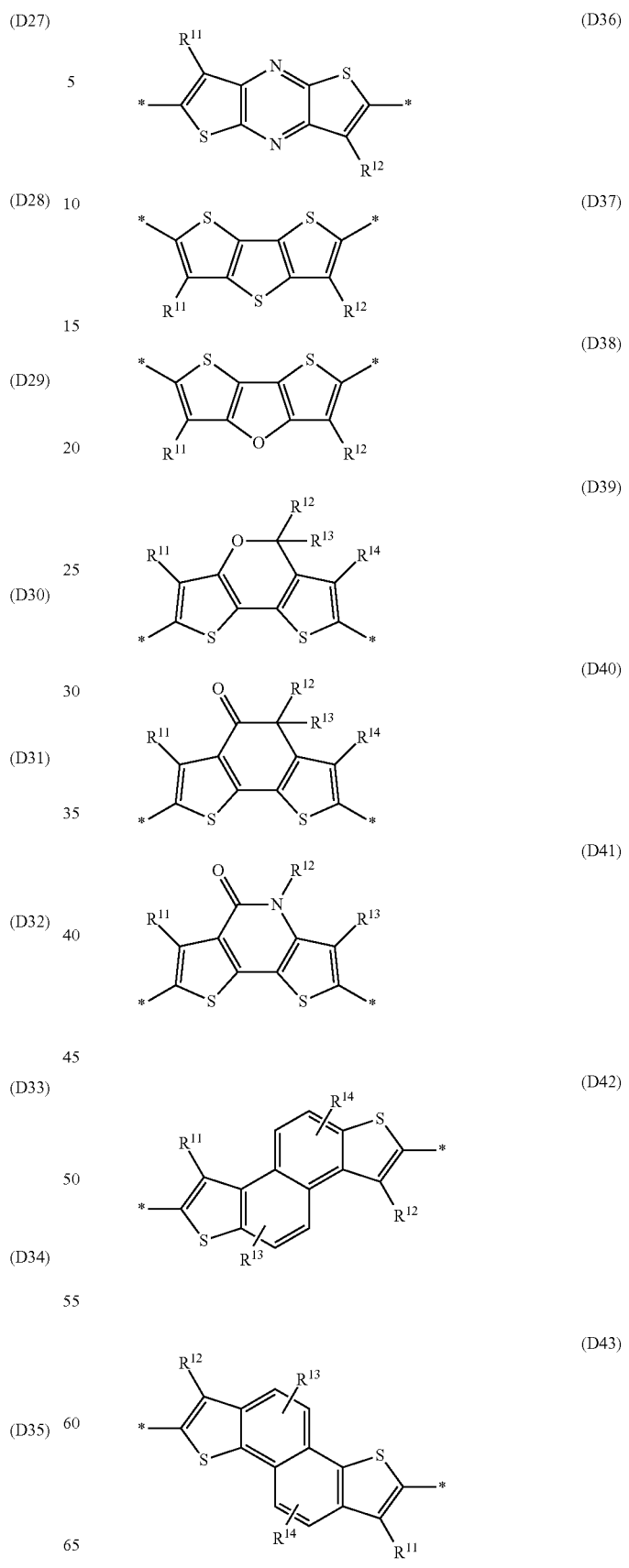

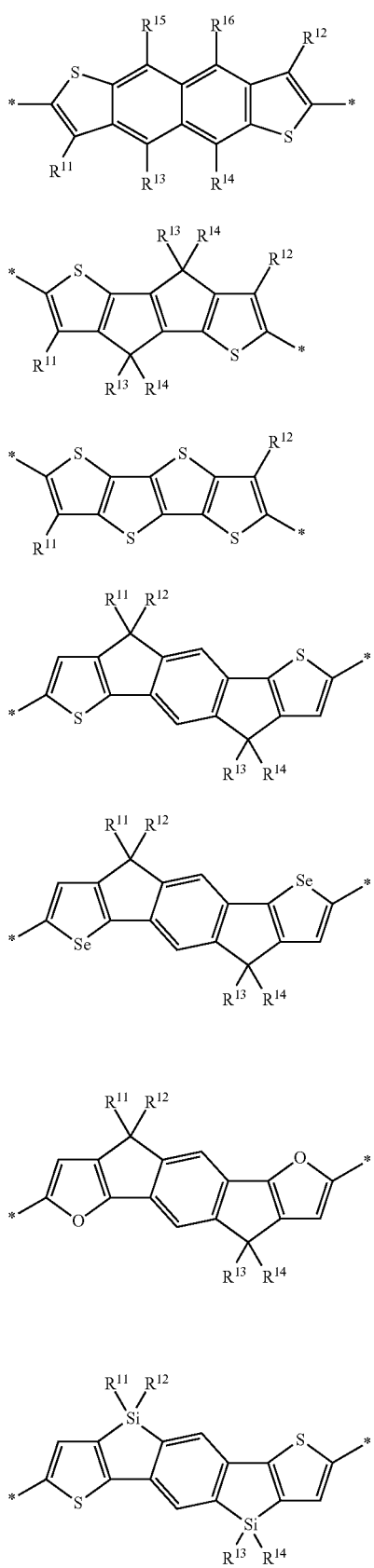
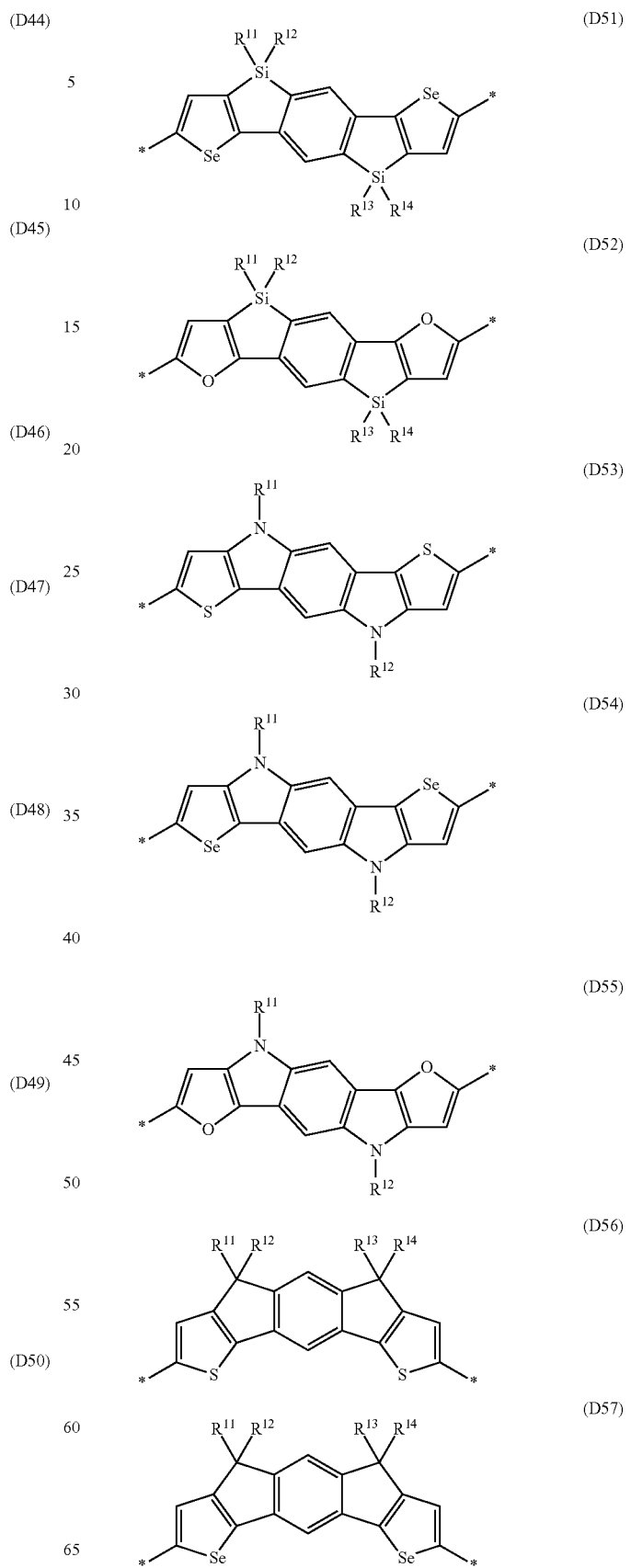

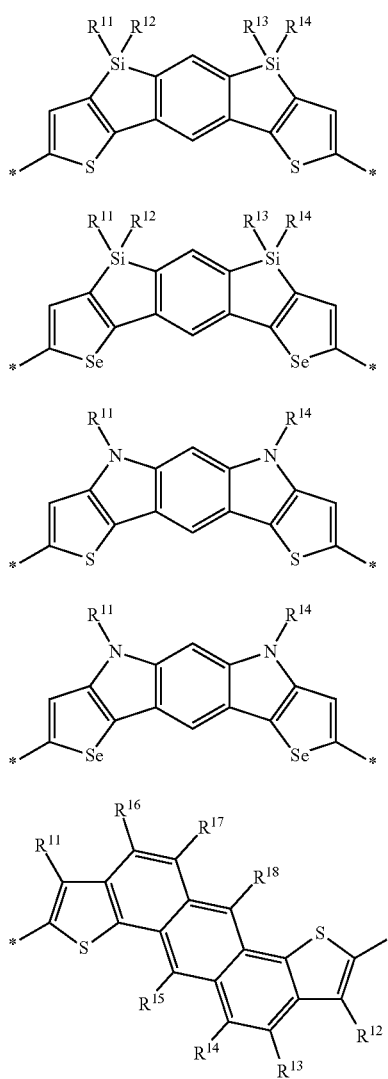
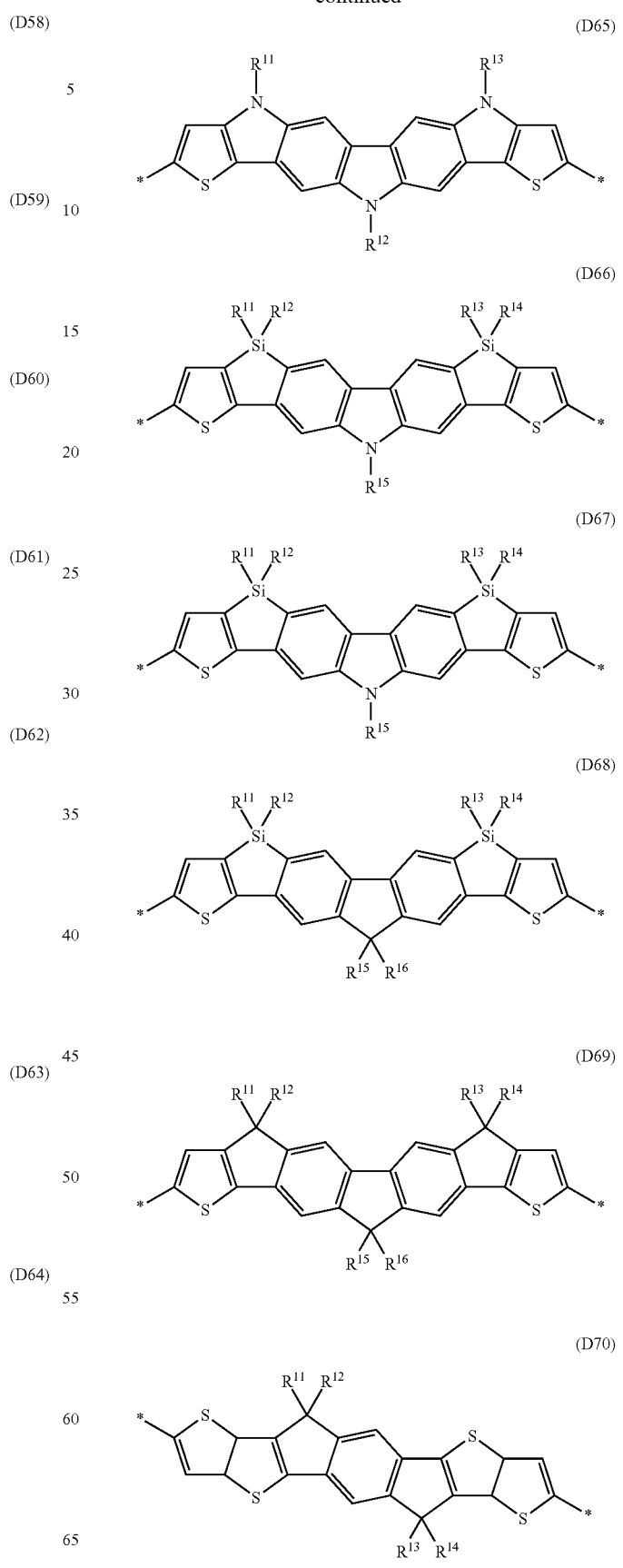

-continued (D71)
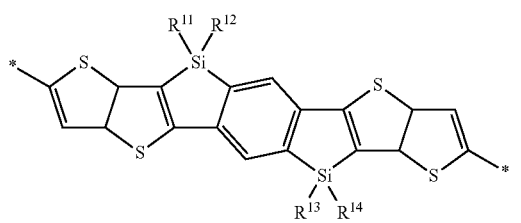

(D72)
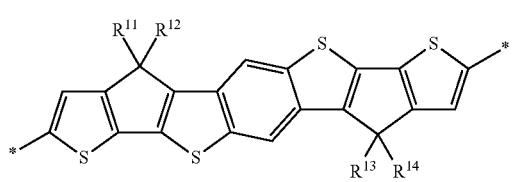

wherein
one of $X^{11}$ and $X^{12}$ is S and the other is Se, and
$R^{11}$, $R^{12}$, $R^{13}$, $R^{14}$, $R^{15}$, $R^{16}$, $R^{16}$, $R^{17}$ and $R^{18}$ independently of each other denote H, halogen, or an optionally substituted carbyl or hydrocarbyl group wherein one or more C atoms are optionally replaced by a hetero atom, or is selected from the group consisting of the following formulae:

Sp1
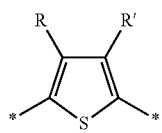

Sp2
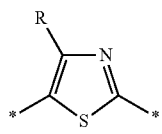

Sp3
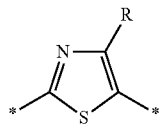

Sp4
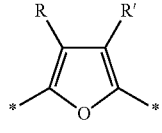

Sp5
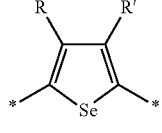

Sp6
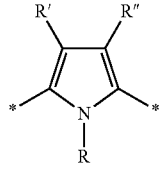

Sp7
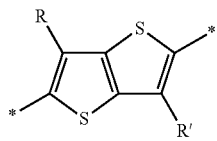

Sp8
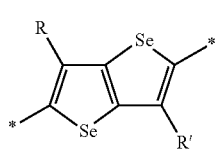

Sp9
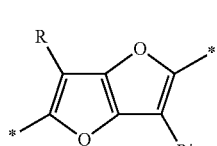

Sp10
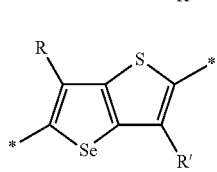

Sp11
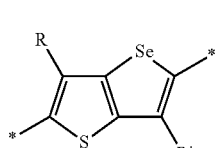

Sp12
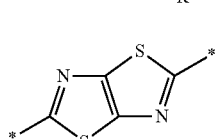

Sp13
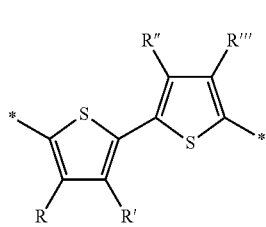

Sp14
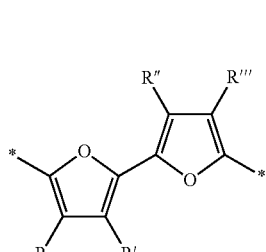

Sp15
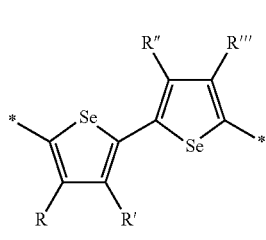

-continued

Sp16

Sp17

Sp18

Sp19

Sp20

Sp21

Sp22 wherein R, R', R'' and R''' independently of each other denote H, halogen, straight-chain, branched or cyclic alkyl with 1 to 30 C atoms, in which one or more non-adjacent CH$_2$ groups are optionally replaced by —O—, —S—, —C(O)—, —C(O)—O—, —O—C(O)—, —O—C(O)—O—, —SO$_2$—, —SO$_3$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, or denote aryl or heteroaryl that is optionally substituted and has 4 to 30 ring atoms, wherein R$^0$ and R$^{00}$ are independently of each other H or optionally substituted C$_{1-40}$ carbyl or hydrocarbyl, and Y$^1$ and Y$^2$ denote H, F or CN, or denote —CY$^1$=CY$^2$— or —C≡C—, wherein Y$^1$ and Y$^2$ independently of each other denote H, F, Cl or CN, a, b independently of each other denote 1, 2, 3 or 4, and c, d independently of each other denote 0, 1, 2, 3 or 4.

18. The conjugated polymer according to claim 1, which comprises in its backbone one or more repeat units selected from the group consisting of formulae III1, III2, III3 and III4, and optionally one or more repeat units of formulae III5 or III6, or their respective mirror images:

-D$^1$-(A$^1$)$_a$-   III1

(A$^1$)$_a$-D$^1$-(A$^2$)$_b$-   III2

-(A$^1$)$_a$-D$^1$-(A$^2$)$_b$-(Sp$^1$)$_c$-   III3

-(A$^1$)$_a$-D$^1$-(A$^2$)$_b$-(Sp$^1$)$_c$-(A$^1$)$_a$-(Sp$^2$)$_d$-   III4

-(Sp$^1$)$_c$-(A$^1$)$_a$-(Sp$^2$)$_d$-   III5

-(Sp$^1$)$_c$-(A$^1$)$_a$-   III6 wherein a unit D$^1$ is not linked to a unit Sp$^1$, and

D$^1$ is a first unit selected from the group consisting of formula Ia to Ig, Ia1, Ia2 and Ia3

Ia

Ib

Ic

Id

Ie

If

Ig wherein

Ar denotes a carbocyclic, heterocyclic, aromatic or heteroaromatic group, which comprises one or more saturated or unsaturated rings that are covalently linked or fused, which is fused to the terminal five-membered rings in formula Ia or Ib to form a conjugated system, and which is unsubstituted or substituted, Ar¹ denotes a carbocyclic, heterocyclic, aromatic or heteroaromatic group, which comprises one or more saturated or unsaturated rings that are covalently linked or fused, which is fused to the divalent five-membered ring in formula Ig, and which is unsubstituted or substituted, X¹ and X² denote independently of each other O, S, Se, Si or NR¹, Y$^{1-4}$ denote independently of each other CR¹ or N, R¹ denotes H, halogen, or an optionally substituted carbyl or hydrocarbyl group, wherein one or more C atoms are optionally replaced by a hetero atom, and R¹¹ and R¹² independently of each other have one of the meanings of R¹,

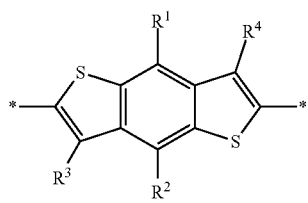

(Ia1)

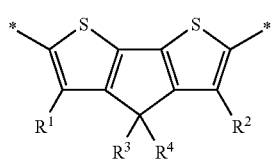

(Ia2)

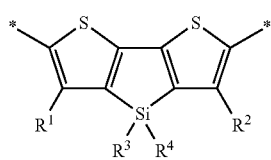

(Ia3)

wherein

R$^{1-4}$ independently of each other denote H, halogen, or an optionally substituted carbyl or hydrocarbyl group wherein one or more C atoms are optionally replaced by a hetero atom, A¹ and A² independently of each other denote an acceptor unit that is different from D¹, Sp¹ and Sp², and is arylene or heteroarylene that is mono- or polycyclic and optionally substituted, or is selected from the group consisting of the following formulae and their mirror images:

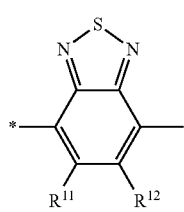

(A1)

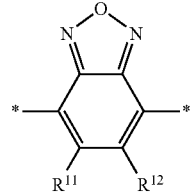

(A2)

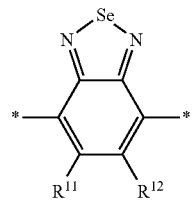

(A3)

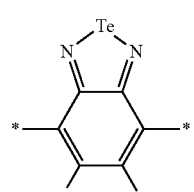

(A4)

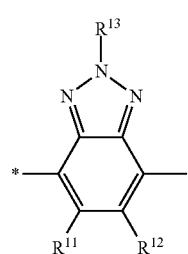

(A5)

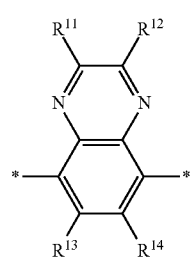

(A6)

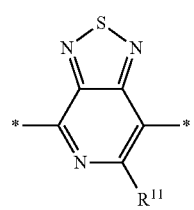

(A7)

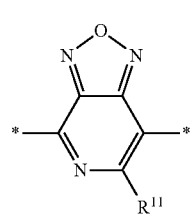

(A8)

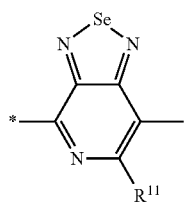
(A9)
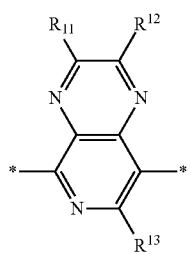
(A10)
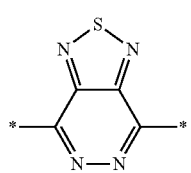
(A11)
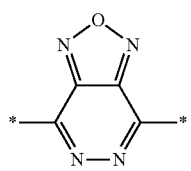
(A12)
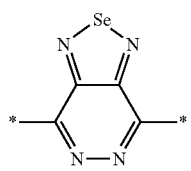
(A13)
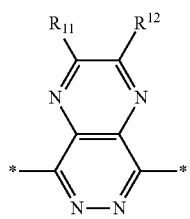
(A14)
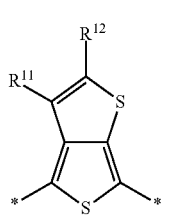
(A15)
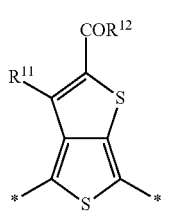
(A16)
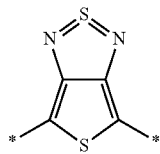
(A17)
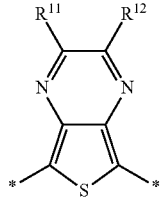
(A18)
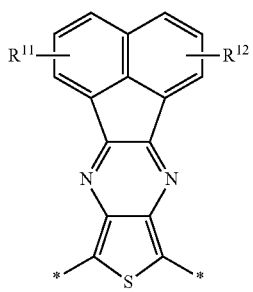
(A19)
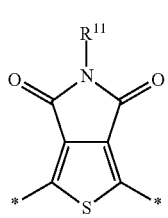
(A20)
(A21)
(A22)

-continued (A23)

(A24)

(A25)

(A26)

(A27)

-continued (A28)

(A29)

(A30)

(A31)

(A32)

(A33)

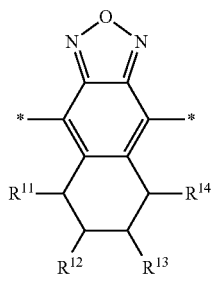 (A34)
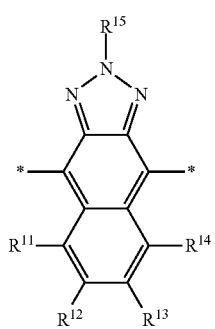 (A35)
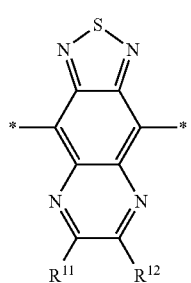 (A36)
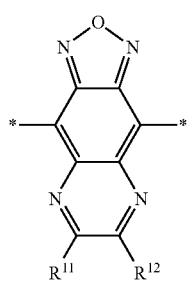 (A37)
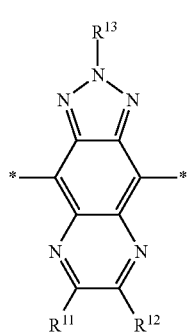 (A38)
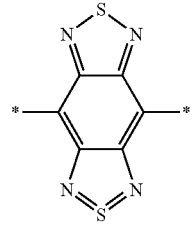 (A39)
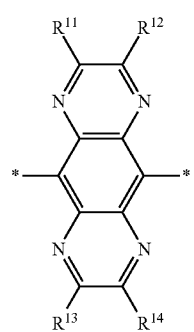 (A40)
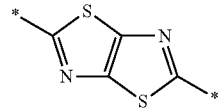 (A41)
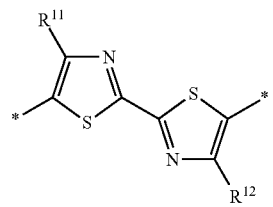 (A42)
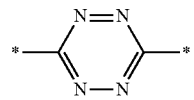 (A43)
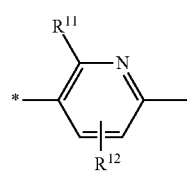 (A44)
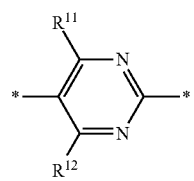 (A45)
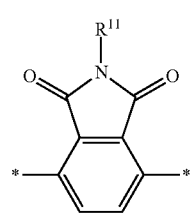 (A46)

-continued
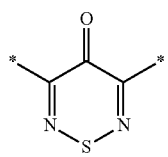 (A47)
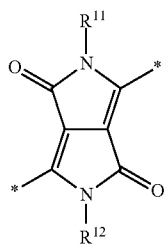 (A48)
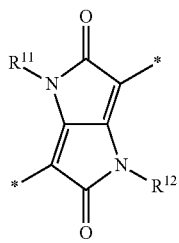 (A49)
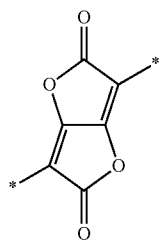 (A50)
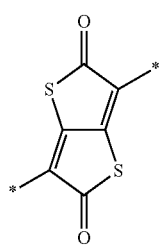 (A51)
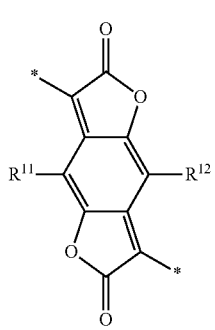 (A52)
-continued
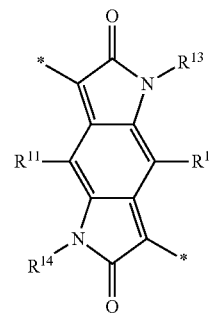 (A53)
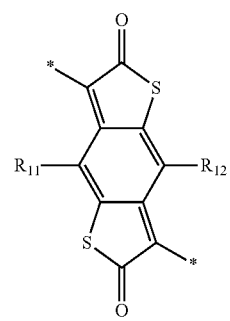 (A54)
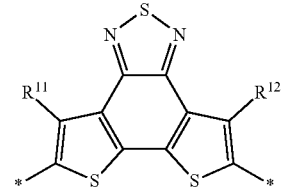 (A55)
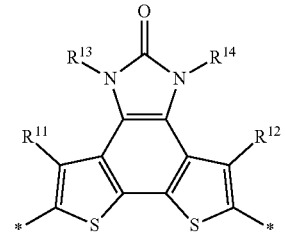 (A56)
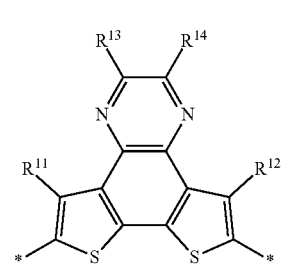 (A57)

-continued
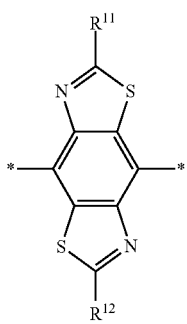 (A58)
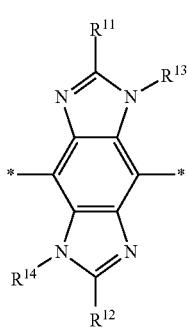 (A59)
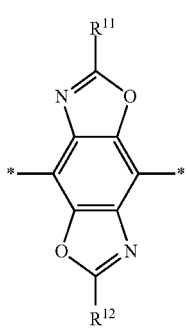 (A60)
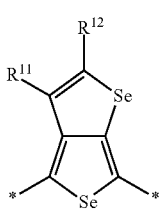 (A61)
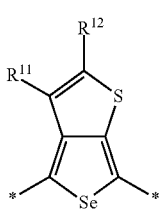 (A62)
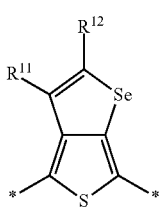 (A63)
-continued
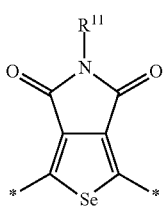 (A64)
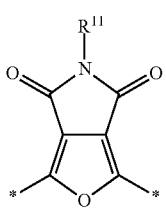 (A65)
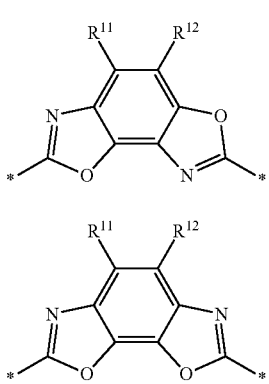 (A66)
(A67)
(A68)
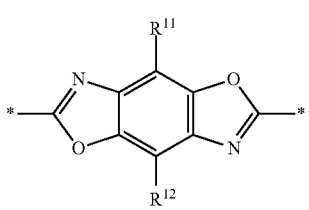 (A69)
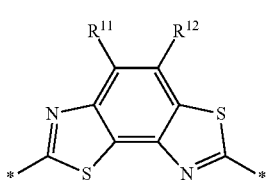 (A70)
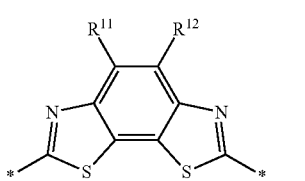 (A71)

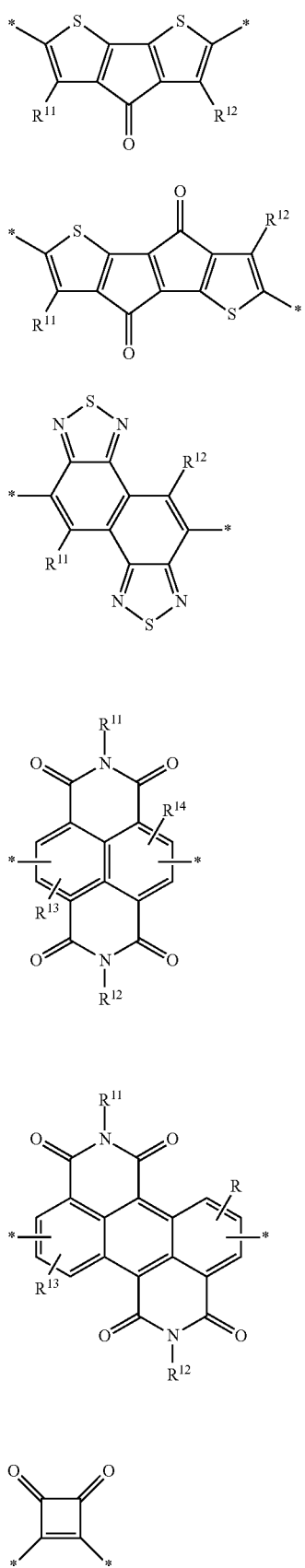
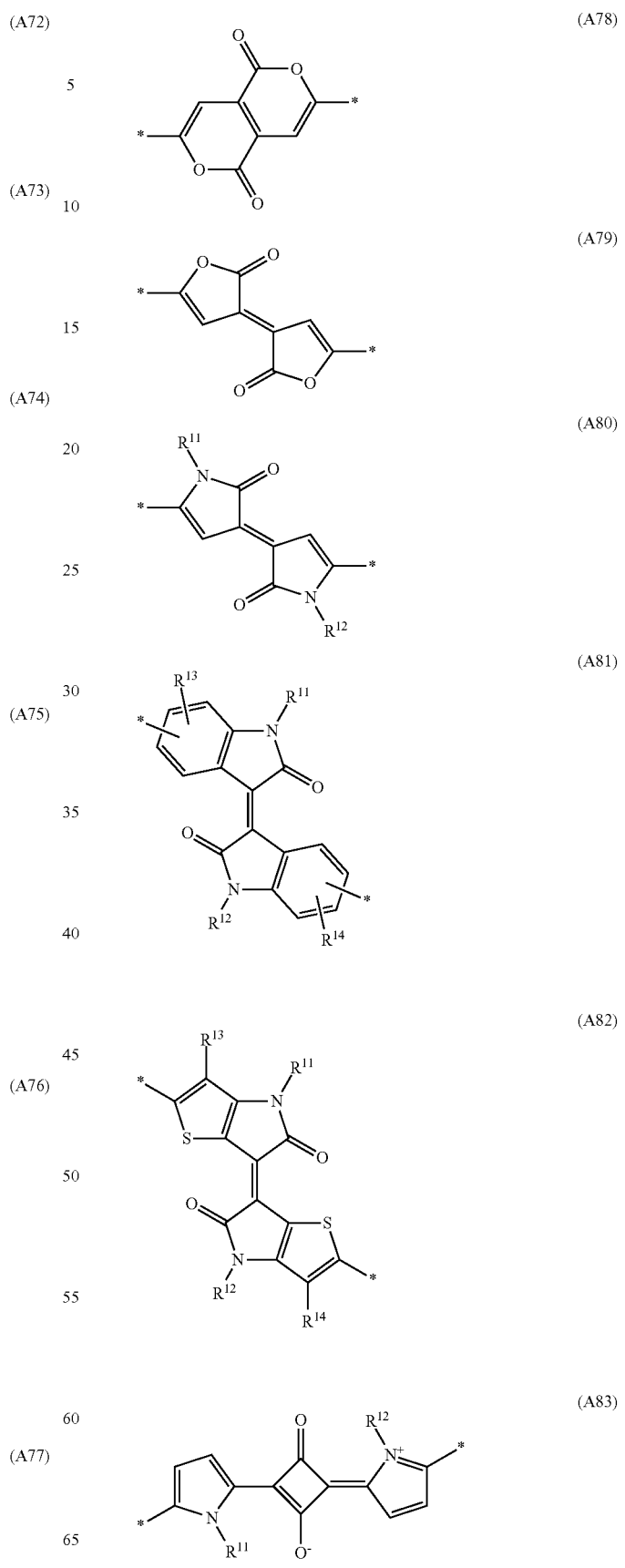

-continued
(A84) 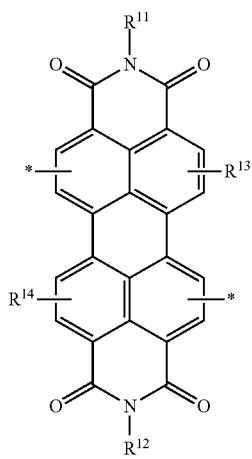
(A85) 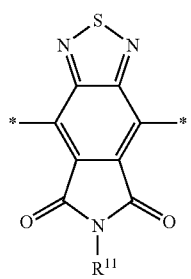
(A86) 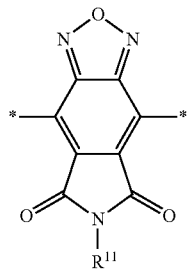
(A87) 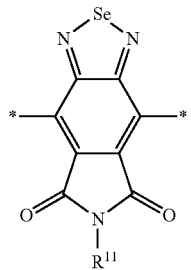
(A88) 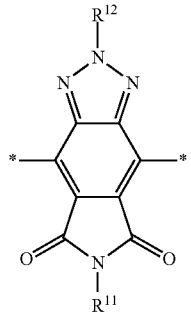
-continued
(A89) 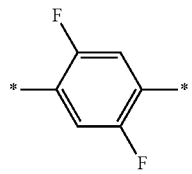
(A90) 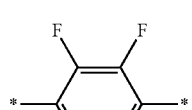
(A91) 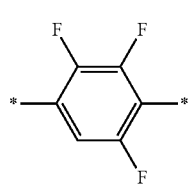
(A92) 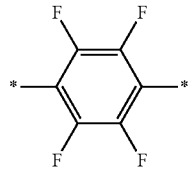
(A93) 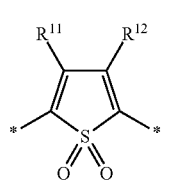
(A94) 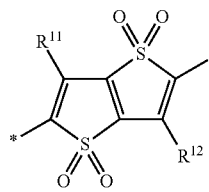
(A95) 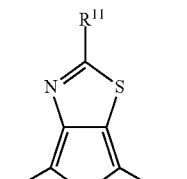
(A96) 
wherein
$R^{11}$, $R^{12}$, $R^{13}$ and $R^{14}$ independently of each denote H, halogen, or an optionally substituted carbyl or hydrocarbyl group wherein one or more C atoms are optionally replaced by a hetero atom, Sp¹ and Sp² independently of each other denote a spacer unit, which is different from D¹, A¹ and A², and is arylene or heteroarylene that is mono- or polycyclic and is optionally substituted, or is selected from the group consisting of the following formulae and their mirror images:
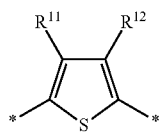 (D1)
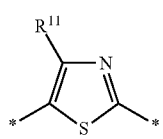 (D2)
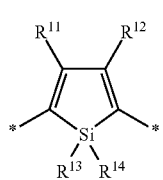 (D3)
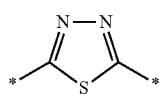 (D4)
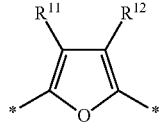 (D5)
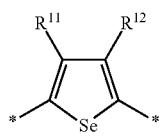 (D6)
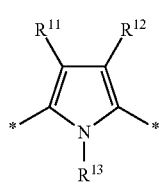 (D7)
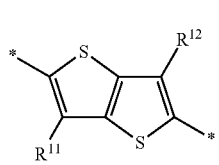 (D8)
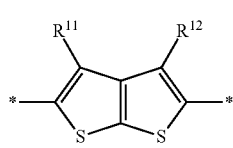 (D9)
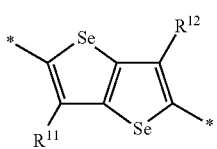 (D10)
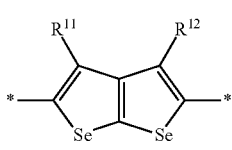 (D11)
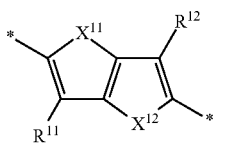 (D12)
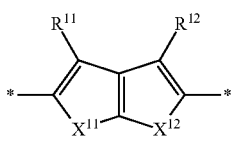 (D13)
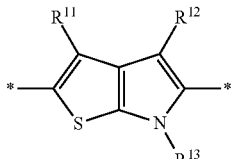 (D14)
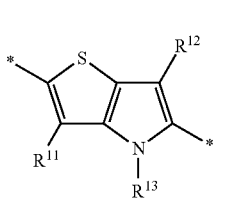 (D15)
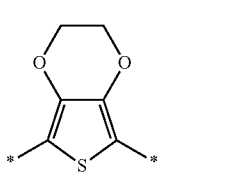 (D16)
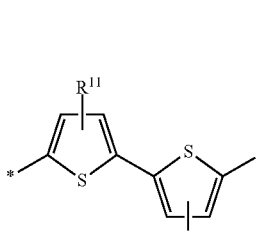 (D17)
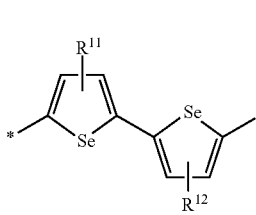 (D18)

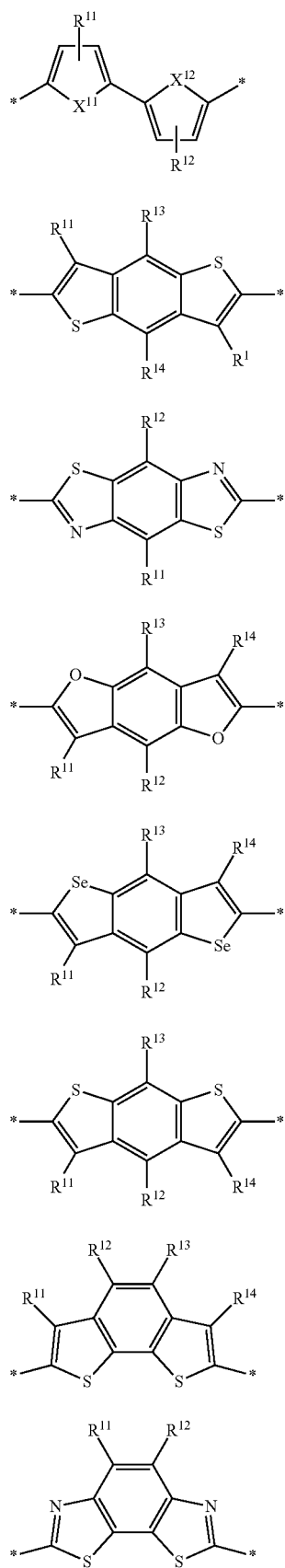
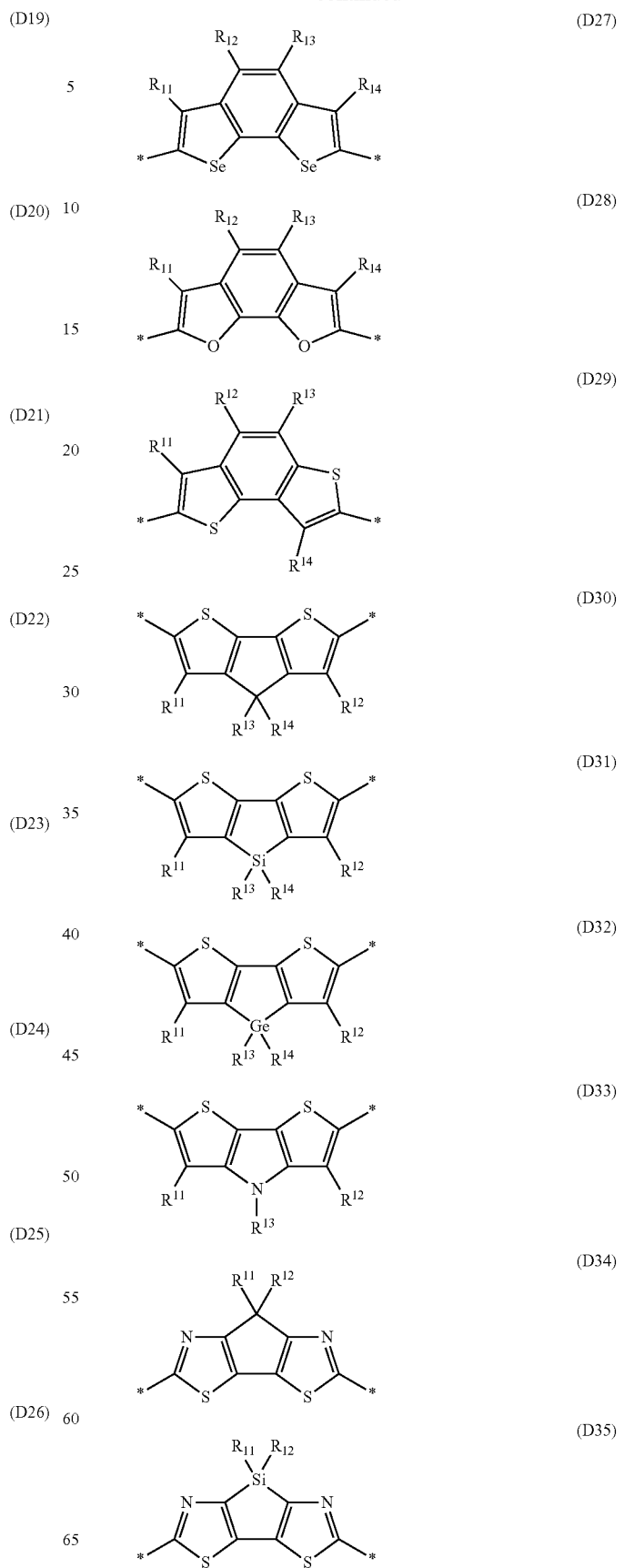

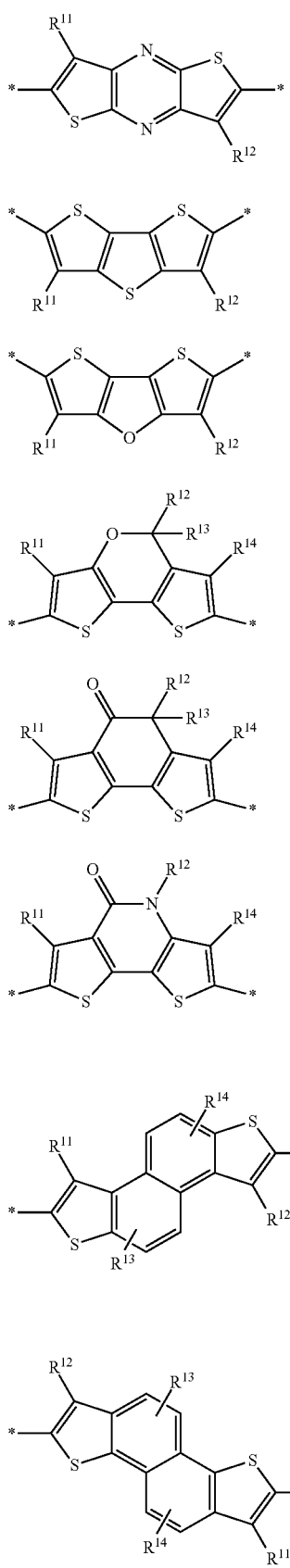 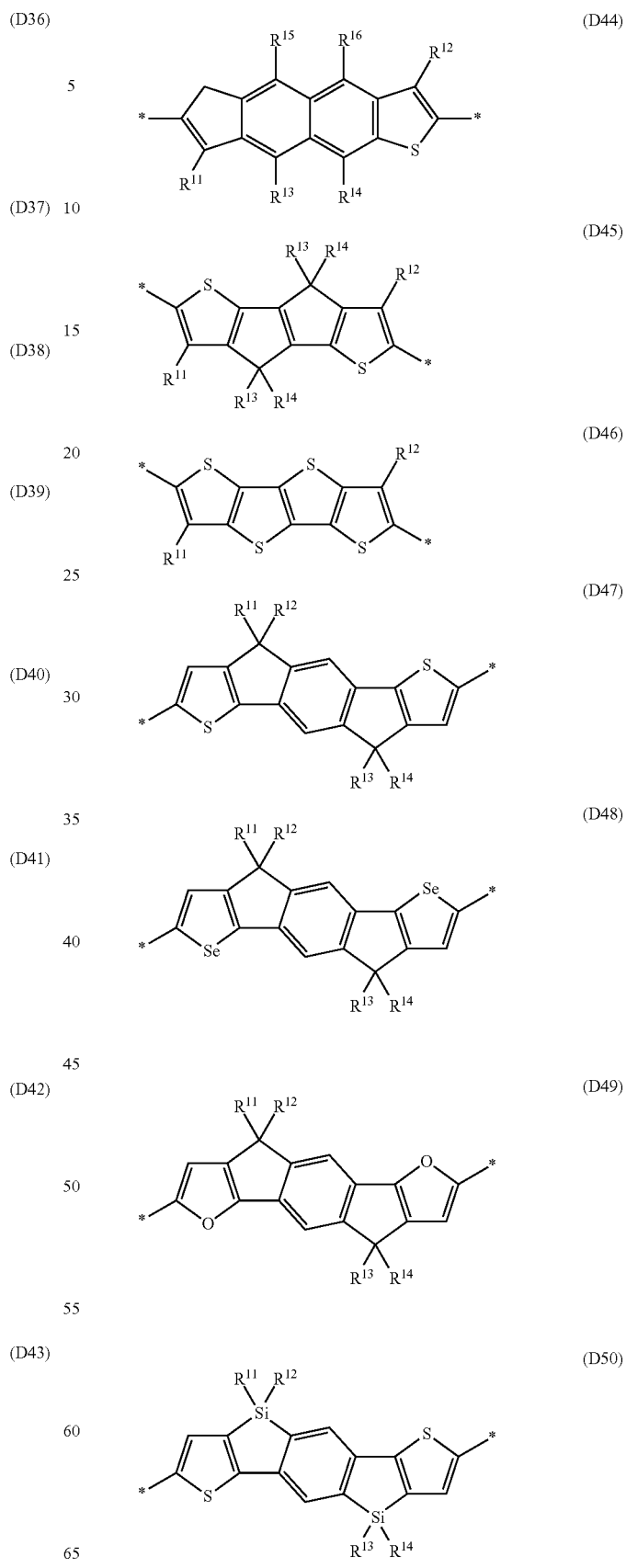

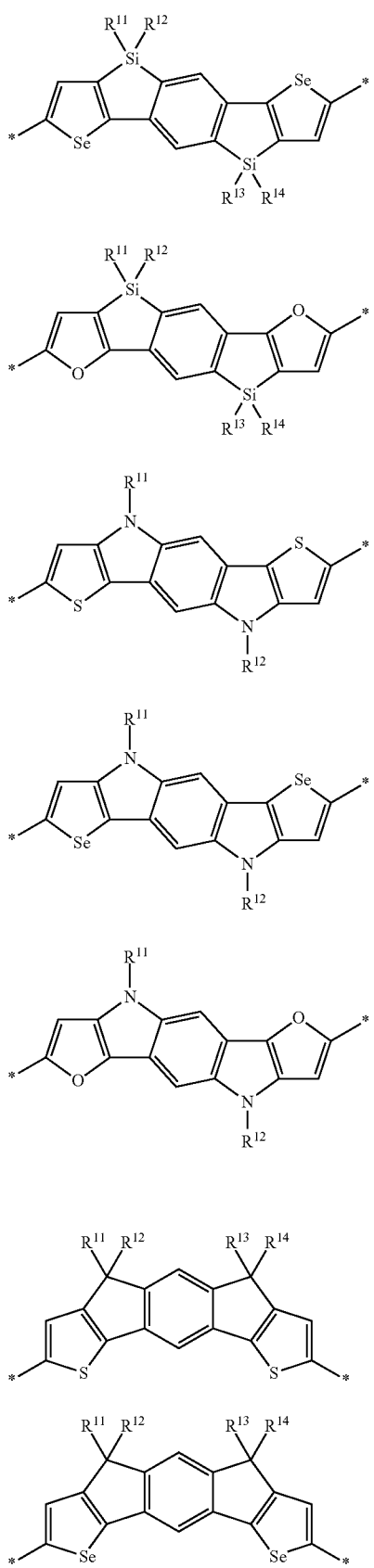
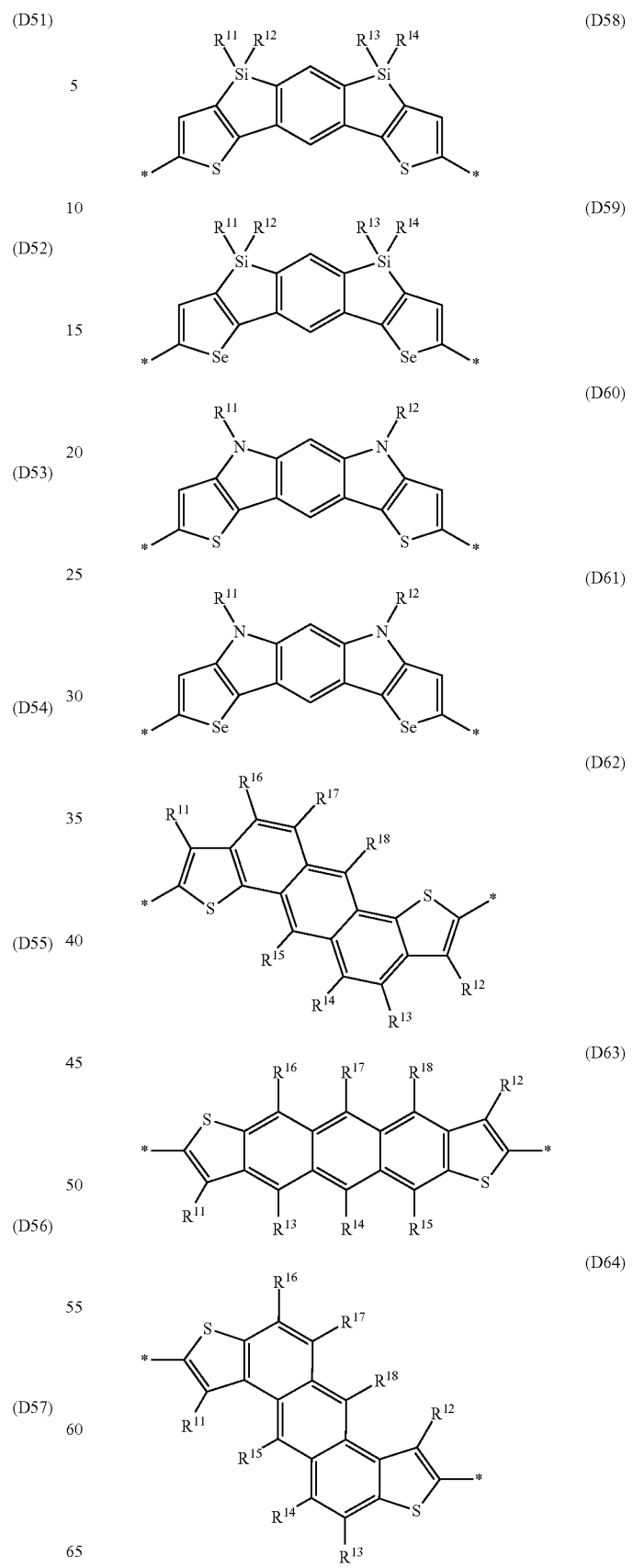

-continued (D65)
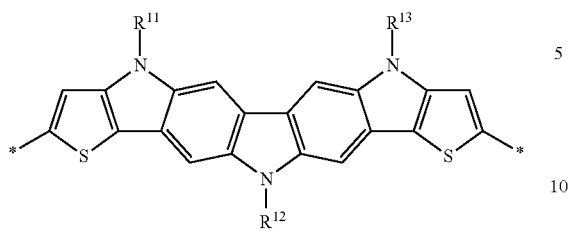

(D66)
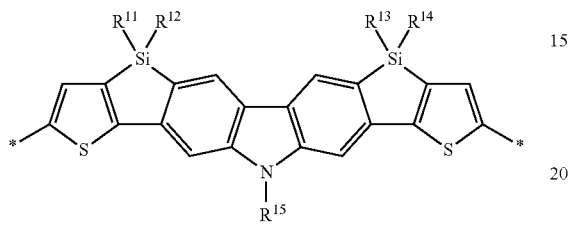

(D67)
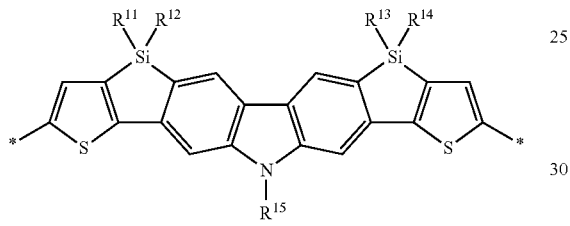

(D68)
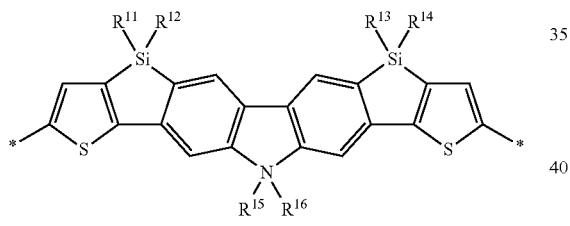

(D69)
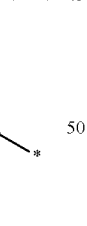

(D70)
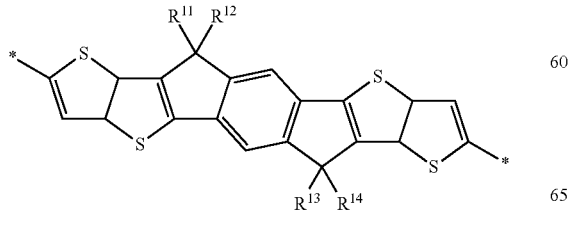

-continued (D71)
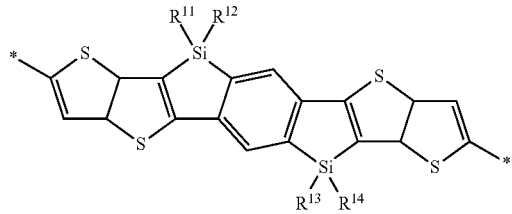

(D72)
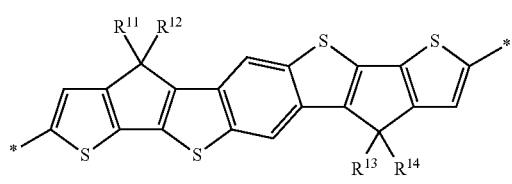

wherein one of $X^{11}$ and $X^{12}$ is S and the other is Se, and $R^{11}$, $R^{12}$, $R^{13}$, $R^{14}$, $R^{15}$, $R^{16}$, $R^{16}$, $R^{17}$ and $R^{18}$ independently of each other denote H, halogen, or an optionally substituted carbyl or hydrocarbyl group wherein one or more C atoms are optionally replaced by a hetero atom, or is selected from the group consisting of the following formulae:

Sp1
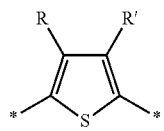

Sp2
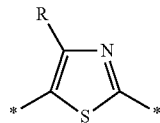

Sp3
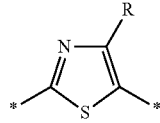

Sp4
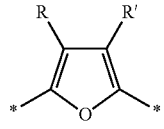

Sp5
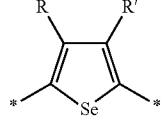

Sp6
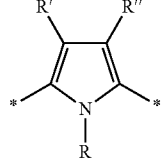

-continued

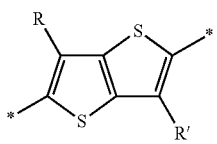
Sp7

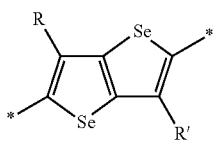
Sp8

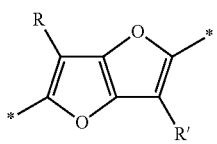
Sp9

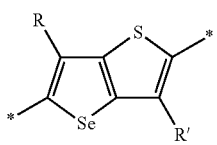
Sp10

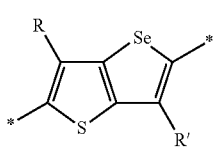
Sp11

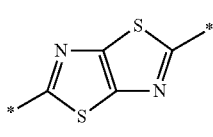
Sp12

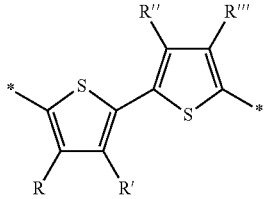
Sp13

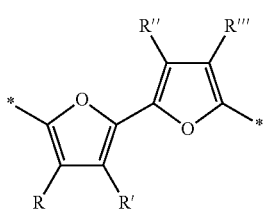
Sp14

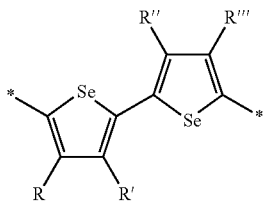
Sp15

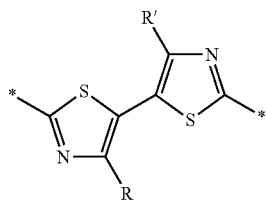
Sp16

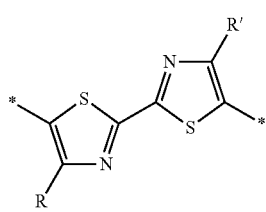
Sp17

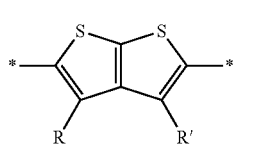
Sp18

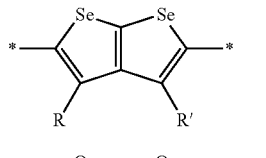
Sp19

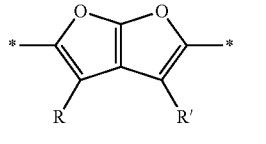
Sp20

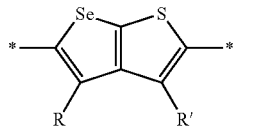
Sp21

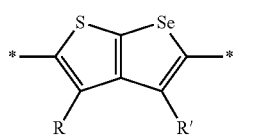
Sp22

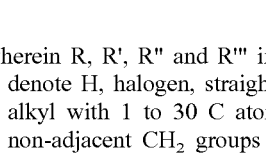

wherein R, R', R" and R'" independently of each other denote H, halogen, straight-chain, branched or cyclic alkyl with 1 to 30 C atoms, in which one or more non-adjacent CH$_2$ groups are optionally replaced by —O—, —S—, —C(O)—, —C(O)—O—, —O—C(O)—, —O—C(O)—O—, —SO$_2$—, —SO$_3$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, or denote aryl or heteroaryl that is optionally substituted and has 4 to 30 ring atoms, wherein R$^0$ and R$^{00}$ are independently of each other H or optionally substituted C$_{1-40}$ carbyl or hydrocarbyl, and Y$^1$ and Y$^2$ denote H, F or CN, or denote —CY$^1$=CY$^2$— or —C≡C—, wherein Y$^1$ and Y$^2$ independently of each other denote H, F, Cl or CN, a, b independently of each other denote 1, 2, 3 or 4, and
c, d independently of each other denote 0, 1, 2, 3 or 4.

19. The conjugated polymer according to claim 1, which is of formula IV1 or IV2:

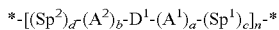 IV1

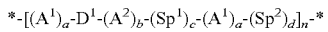 IV2 wherein
n is an integer >1,
$D^1$ is a first unit selected from the group consisting of formula Ia to Ig, Ia1, Ia2 and Ia3

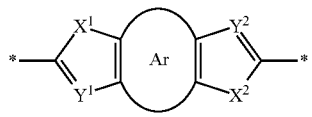 Ia

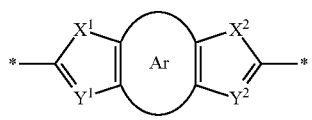 Ib

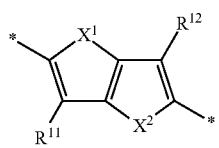 Ic

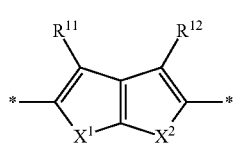 Id

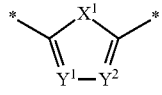 Ie

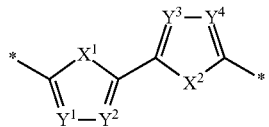 If

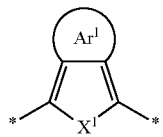 Ig wherein
Ar denotes a carbocyclic, heterocyclic, aromatic or heteroaromatic group, which comprises one or more saturated or unsaturated rings that are covalently linked or fused, which is fused to the terminal five-membered rings in formula Ia or Ib to form a conjugated system, and which is unsubstituted or substituted,
$Ar^1$ denotes a carbocyclic, heterocyclic, aromatic or heteroaromatic group, which comprises one or more saturated or unsaturated rings that are covalently linked or fused, which is fused to the divalent five-membered ring in formula Ig, and which is unsubstituted or substituted,
$X^1$ and $X^2$ denote independently of each other O, S, Se, Si or $NR^1$,
$Y^{1-4}$ denote independently of each other $CR^1$ or N,
$R^1$ denotes H, halogen, or an optionally substituted carbyl or hydrocarbyl group, wherein one or more C atoms are optionally replaced by a hetero atom, and
$R^{11}$ and $R^{12}$ independently of each other have one of the meanings of $R^1$,

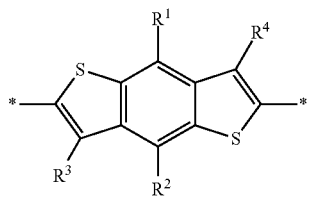 Ia1

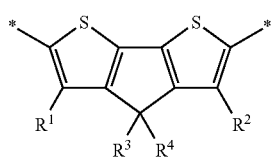 Ia2

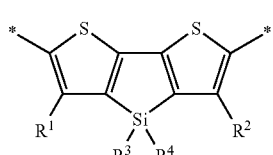 Ia3 wherein
$R^{1-4}$ independently of each other denote H, halogen, or an optionally substituted carbyl or hydrocarbyl group wherein one or more C atoms are optionally replaced by a hetero atom,
$A^1$ and $A^2$ independently of each other denote an acceptor unit that is different from $D^1$, $Sp^1$ and $Sp^2$, and is arylene or heteroarylene that is mono- or polycyclic and optionally substituted, or is selected from the group consisting of the following formulae and their mirror images:

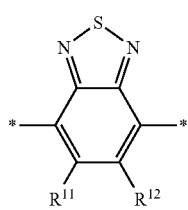 (A1)

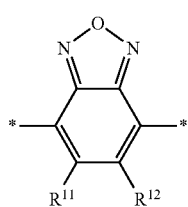 (A2)

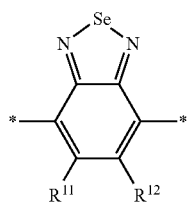 (A3)
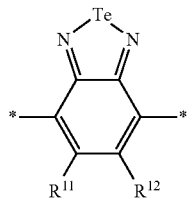 (A4)
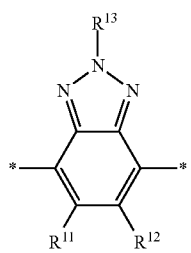 (A5)
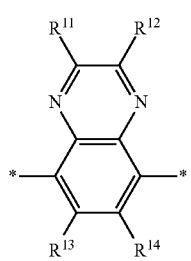 (A6)
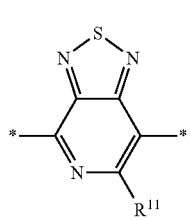 (A7)
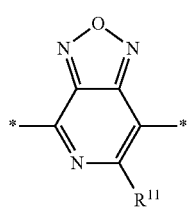 (A8)
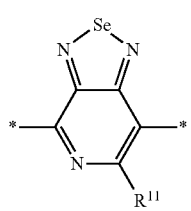 (A9)
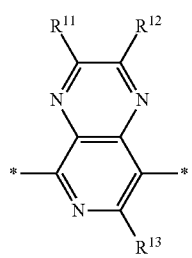 (A10)
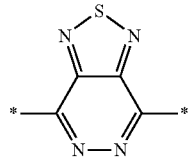 (A11)
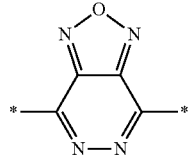 (A12)
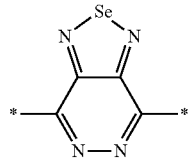 (A13)
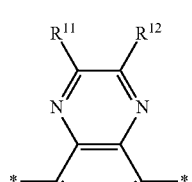 (A14)
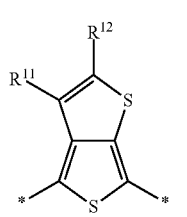 (A15)
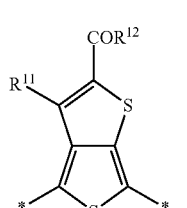 (A16)
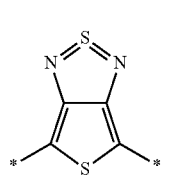 (A17)

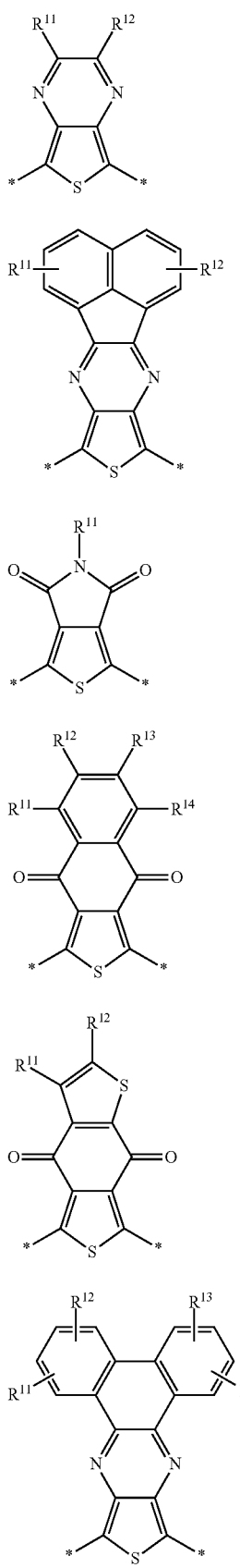

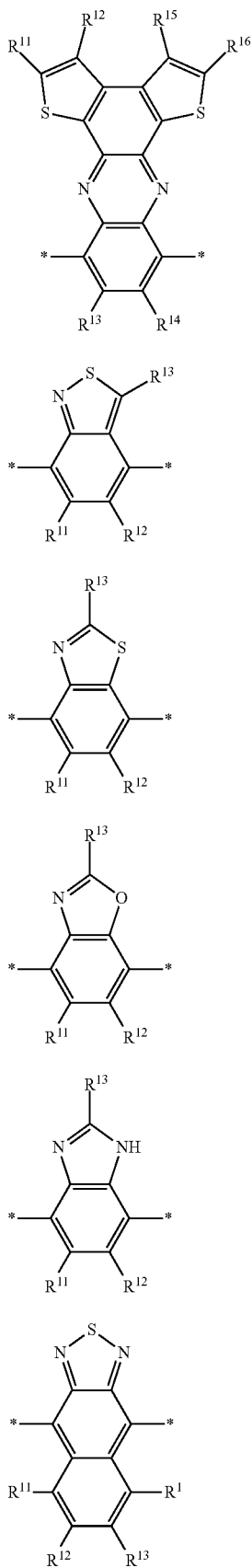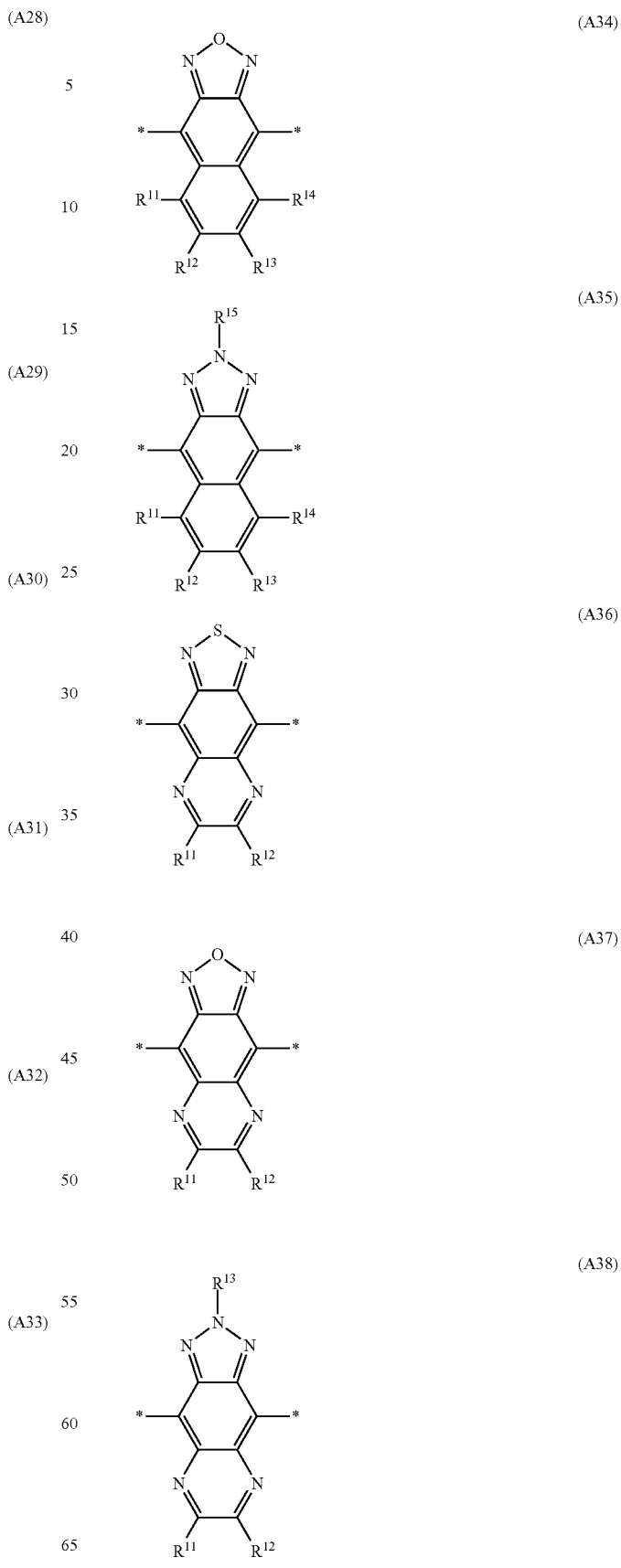

-continued
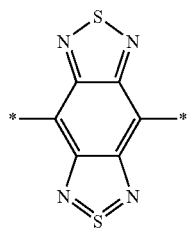 (A39)
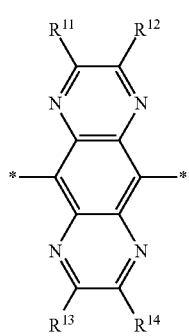 (A40)
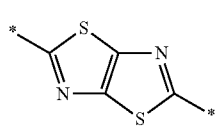 (A41)
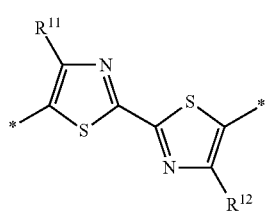 (A42)
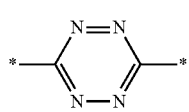 (A43)
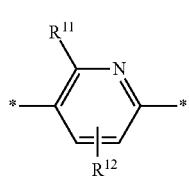 (A44)
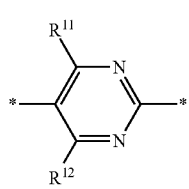 (A45)
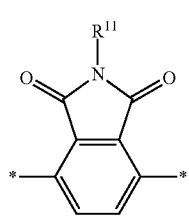 (A46)
-continued
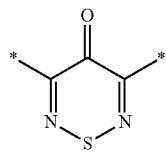 (A47)
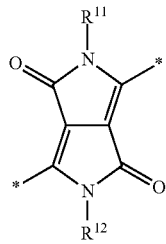 (A48)
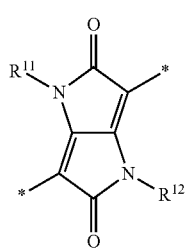 (A49)
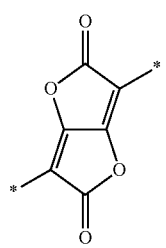 (A50)
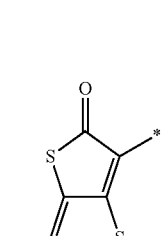 (A51)
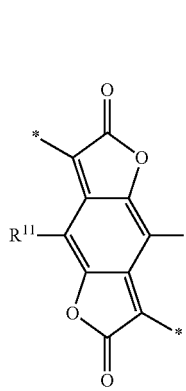 (A52)

-continued
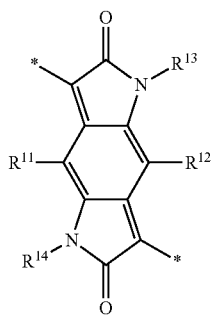
(A53)
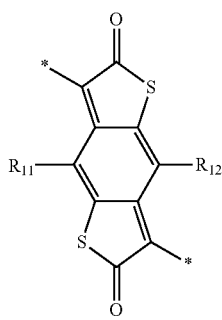
(A54)
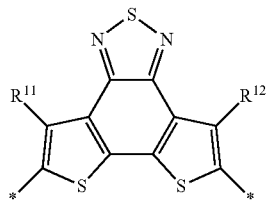
(A55)
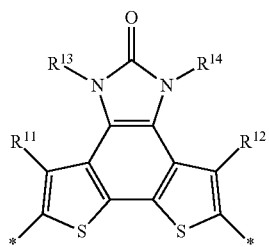
(A56)
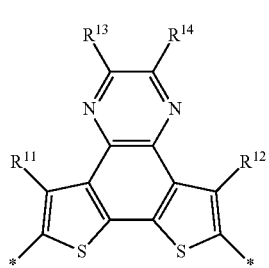
(A57)
-continued
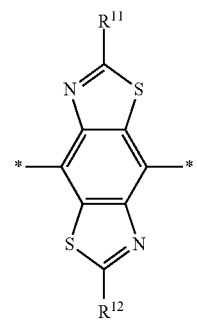
(A58)
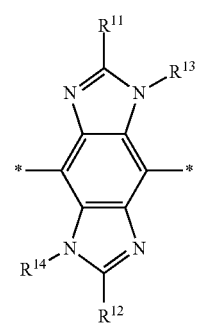
(A59)
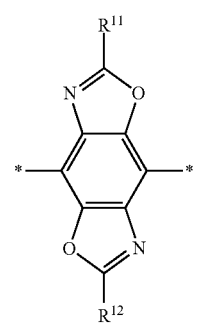
(A60)
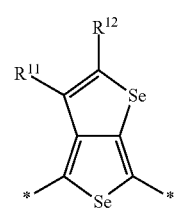
(A61)
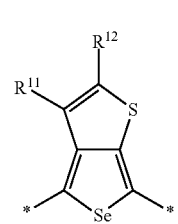
(A62)
(A63)

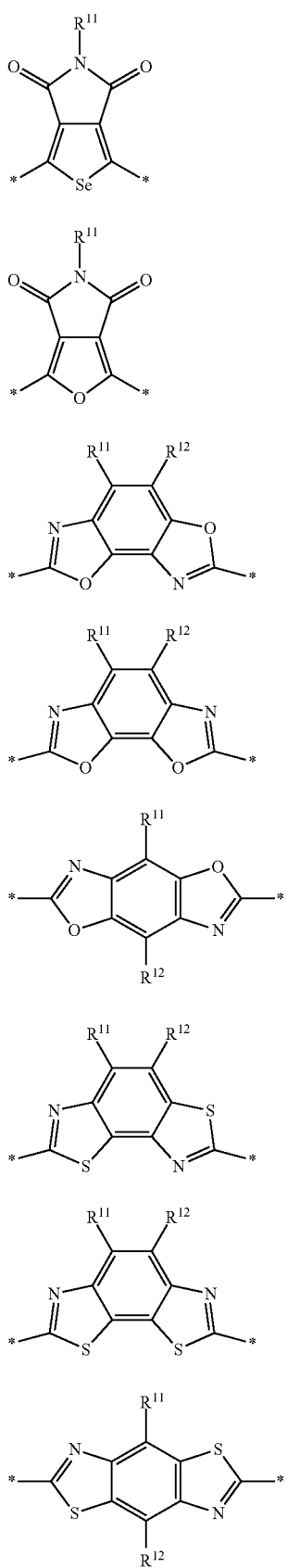
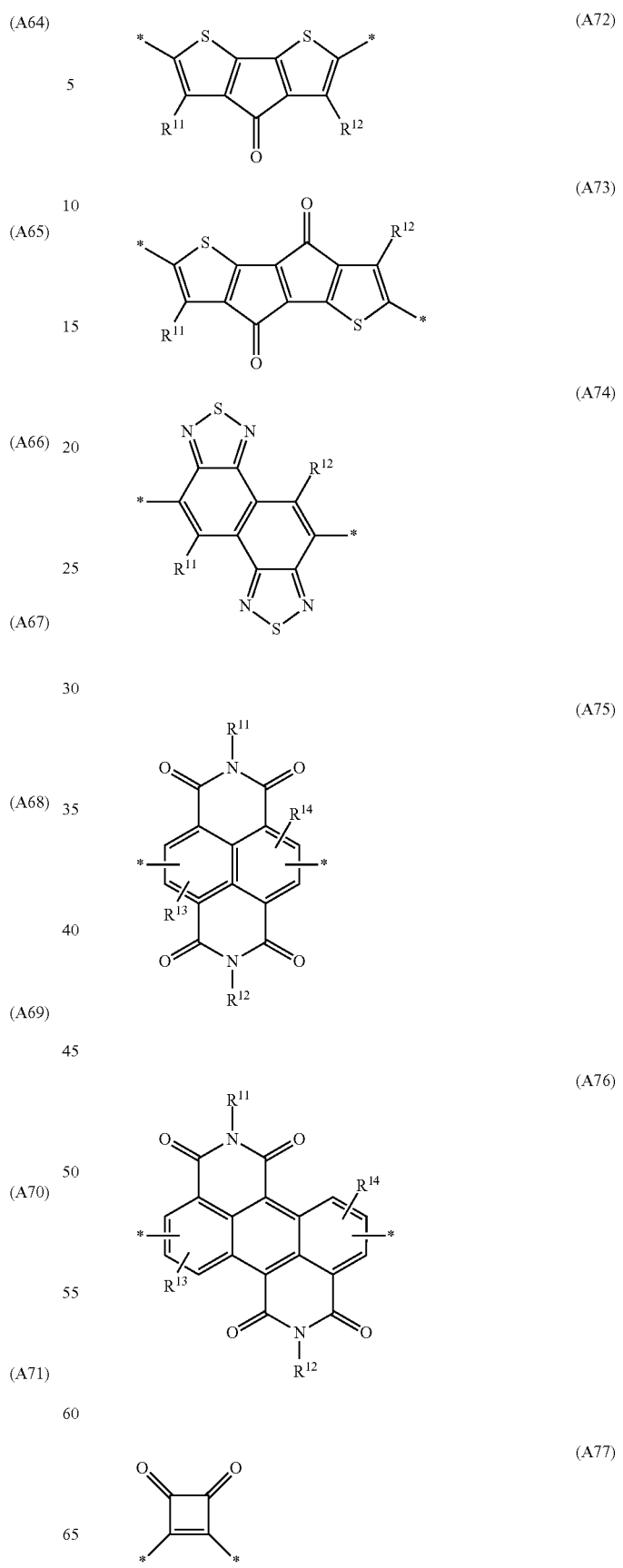

-continued
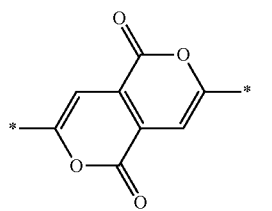
(A78)
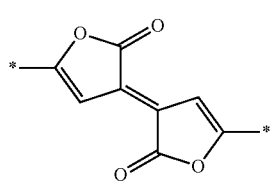
(A79)
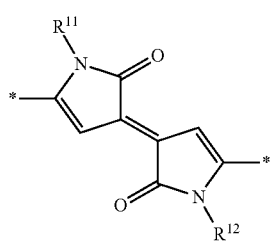
(A80)
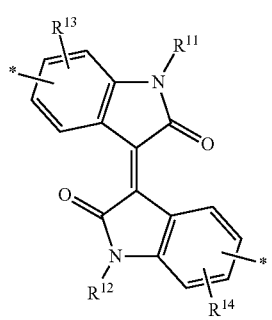
(A81)
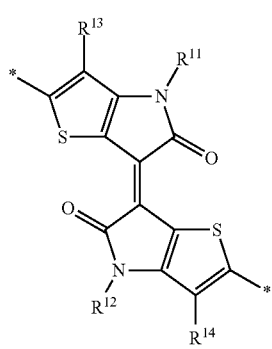
(A82)
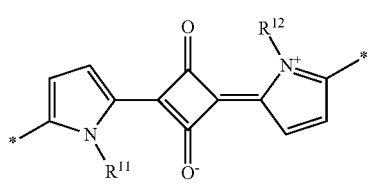
(A83)
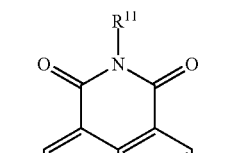
(A84)
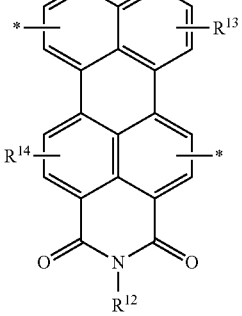
(A85)
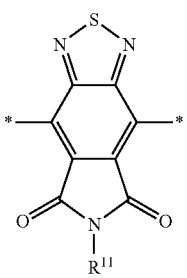
(A86)
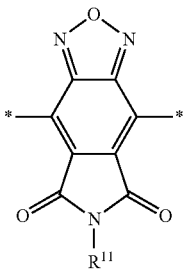
(A87)
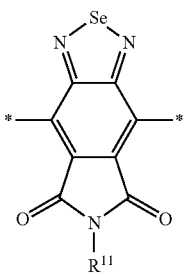
(A88)
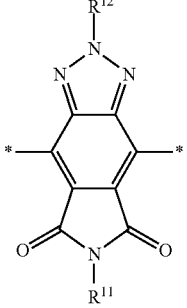

-continued

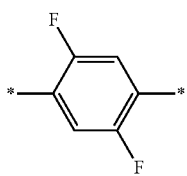 (A89)

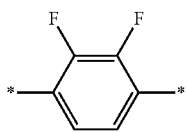 (A90)

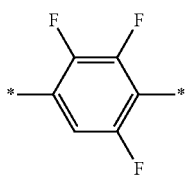 (A91)

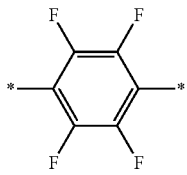 (A92)

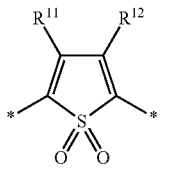 (A93)

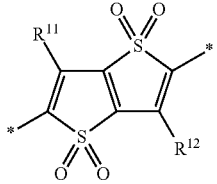 (A94)

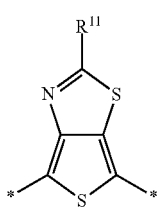 (A95)

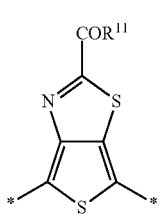 (A96)

wherein $R^{11}$, $R^{12}$, $R^{13}$ and $R^{14}$ independently of each other denote H, halogen, or an optionally substituted carbyl or hydrocarbyl group wherein one or more C atoms are optionally replaced by a hetero atom, $Sp^1$ and $Sp^2$ independently of each other denote a spacer unit, which is different from $D^1$, $A^1$ and $A^2$, and is arylene or heteroarylene that is mono- or polycyclic and is optionally substituted, or is selected from the group consisting of the following formulae and their mirror images:

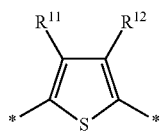 (D1)

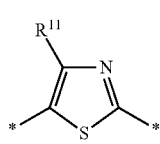 (D2)

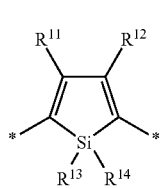 (D3)

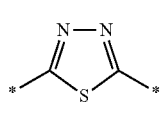 (D4)

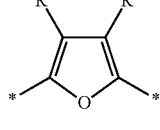 (D5)

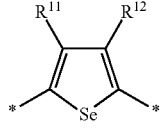 (D6)

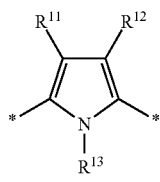 (D7)

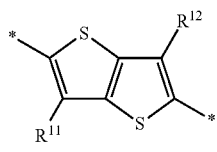 (D8)

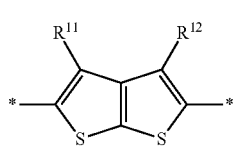 (D9)

-continued
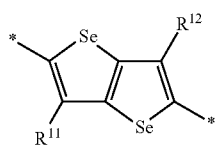 (D10)
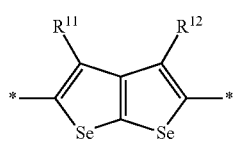 (D11)
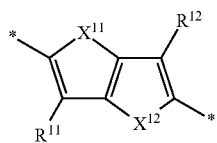 (D12)
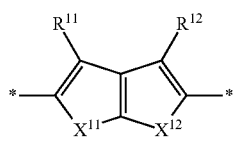 (D13)
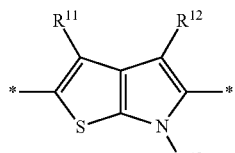 (D14)
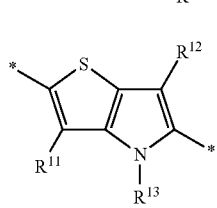 (D15)
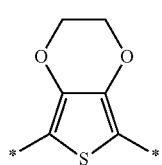 (D16)
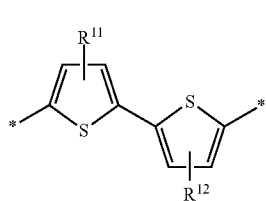 (D17)
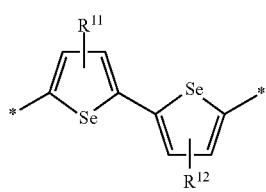 (D18)
-continued
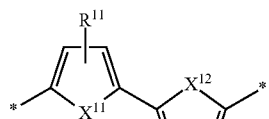 (D19)
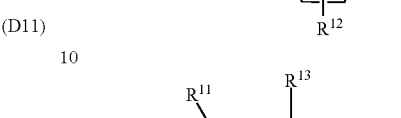 (D20)
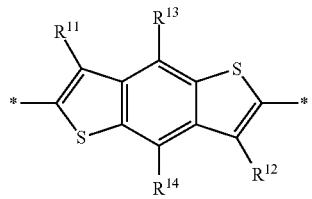 (D21)
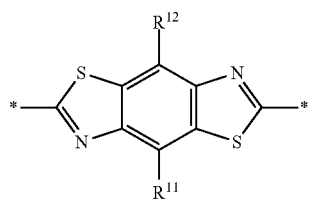 (D22)
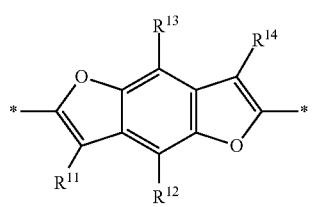 (D23)
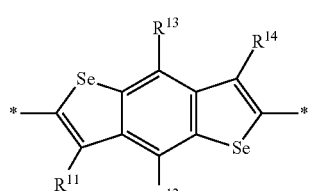 (D24)
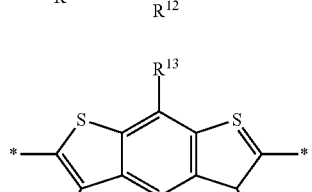 (D25)
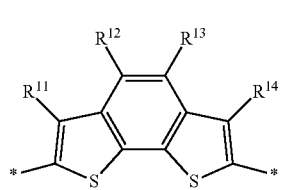 (D26)
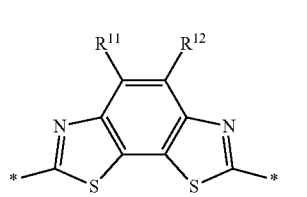

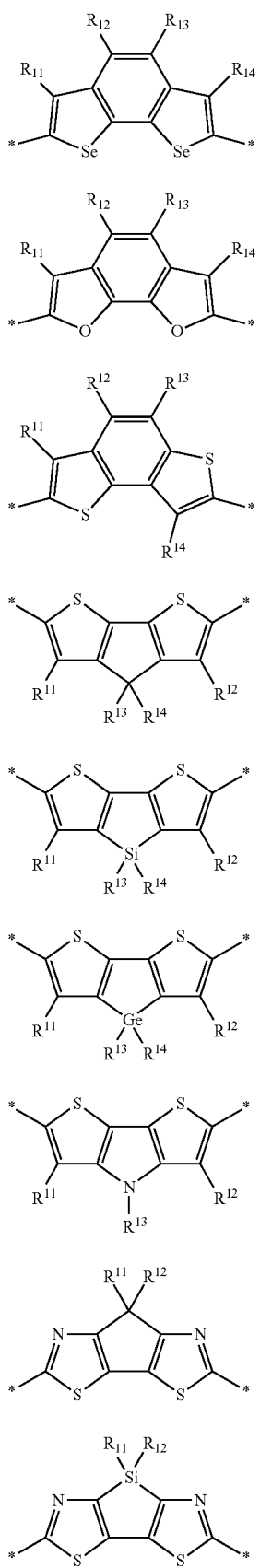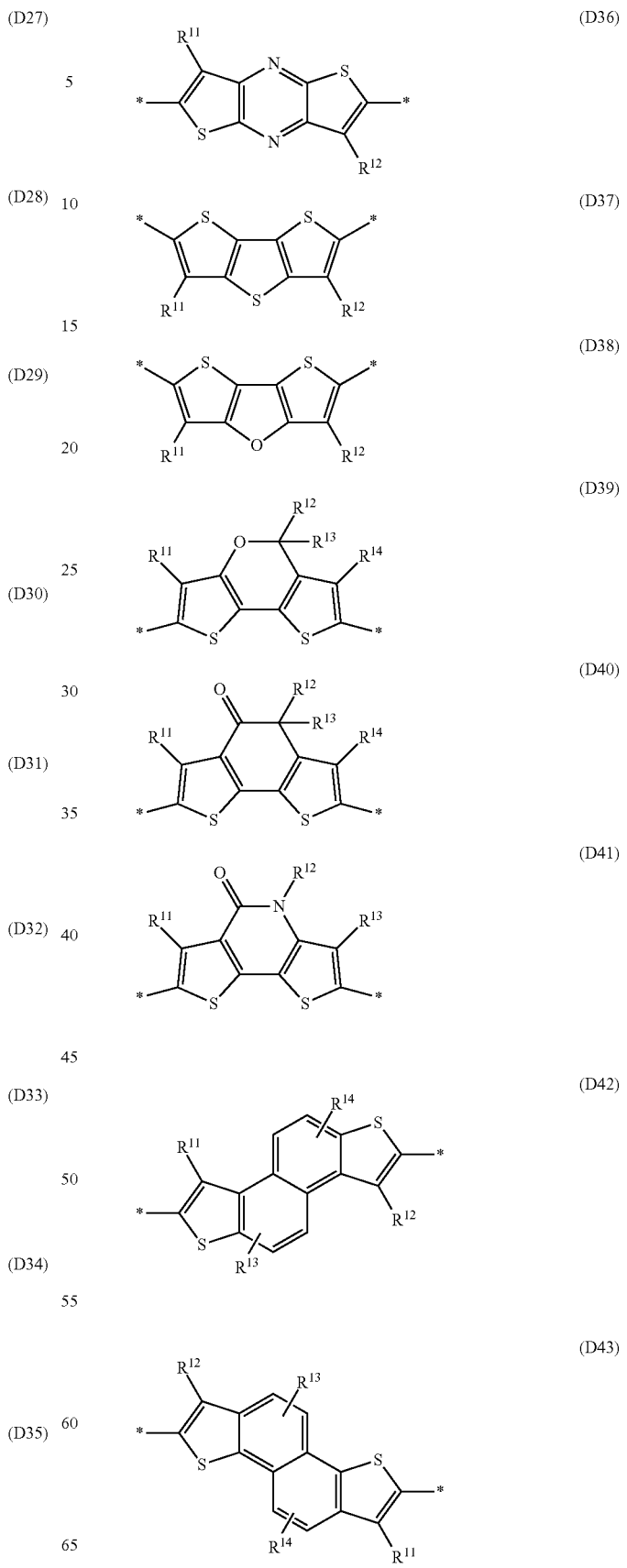

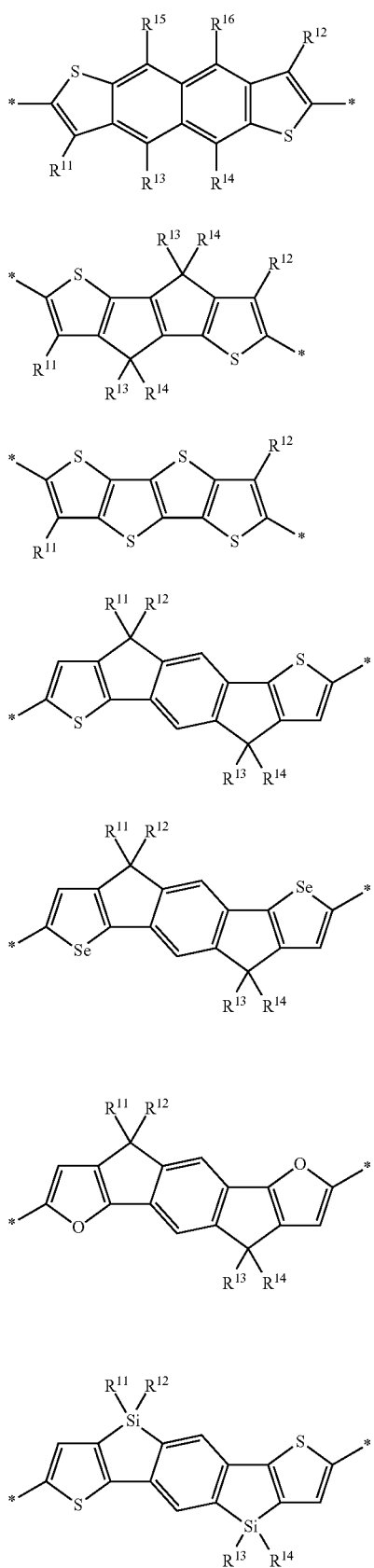
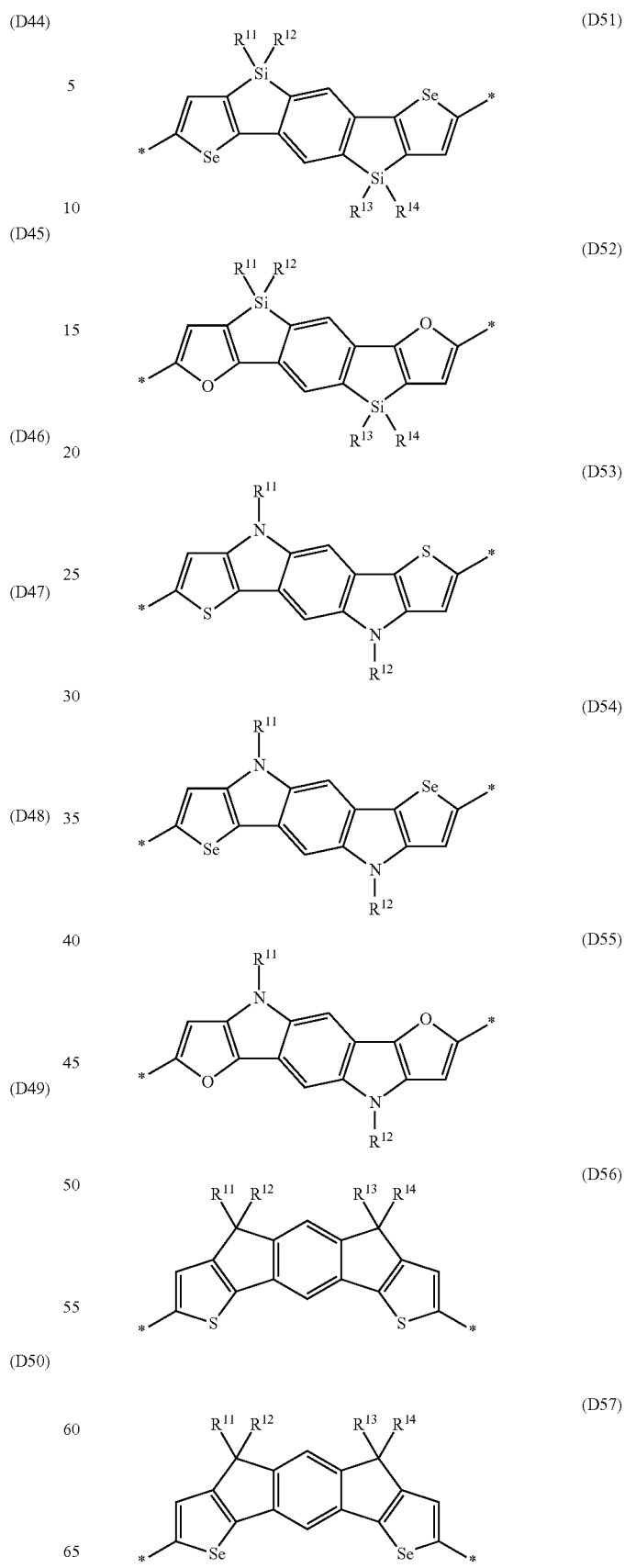

-continued
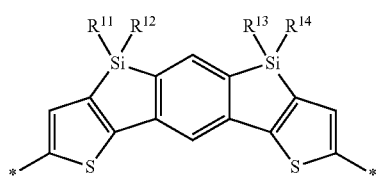
(D58)
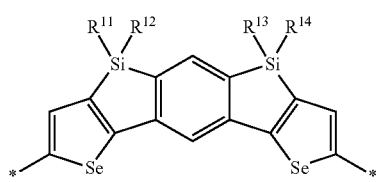
(D59)
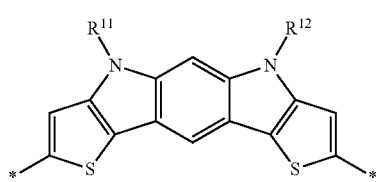
(D60)
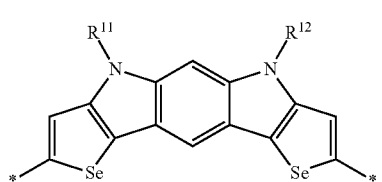
(D61)
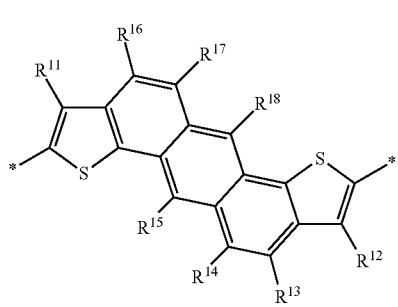
(D62)
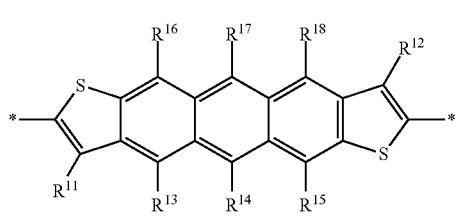
(D63)
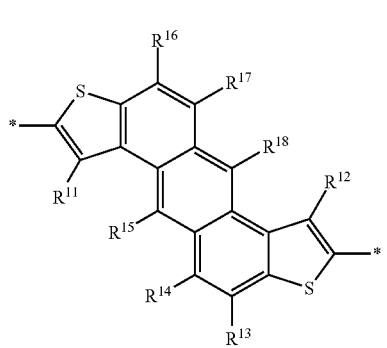
(D64)
-continued
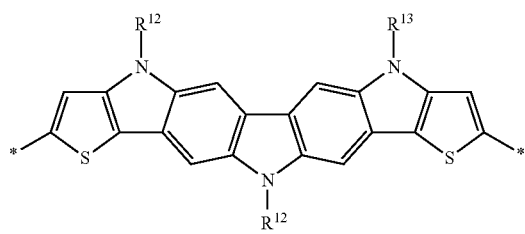
(D65)
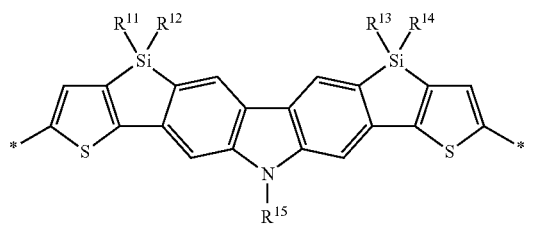
(D66)
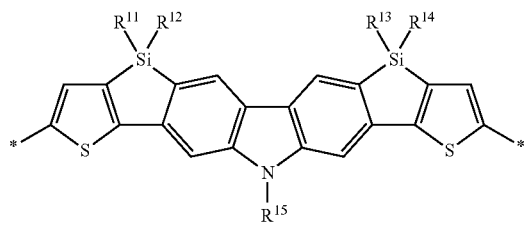
(D67)
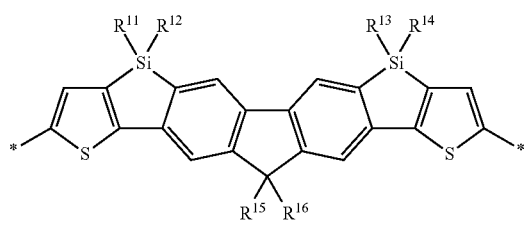
(D68)
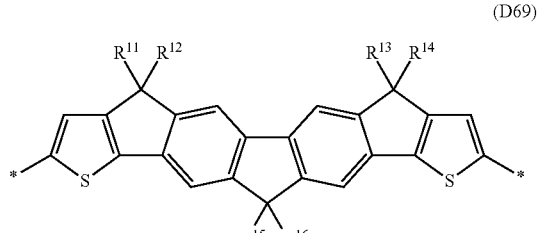
(D69)
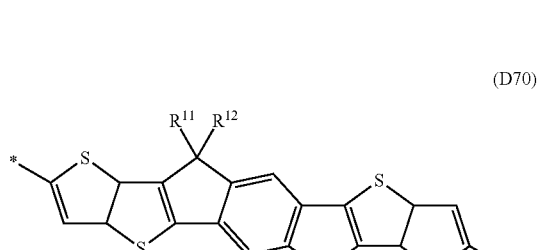
(D70)

-continued (D71)
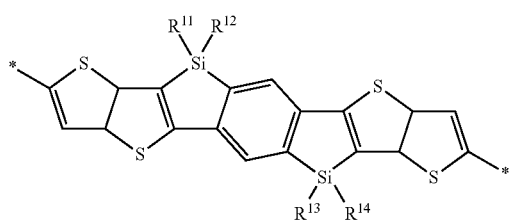

(D72)
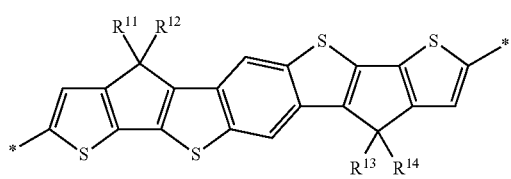

wherein one of $X^{11}$ and $X^{12}$ is S and the other is Se, and $R^{11}$, $R^{12}$, $R^{13}$, $R^{14}$, $R^{15}$, $R^{16}$, $R^{16}$, $R^{17}$ and $R^{18}$ independently of each other denote H, halogen, or an optionally substituted carbyl or hydrocarbyl group wherein one or more C atoms are optionally replaced by a hetero atom, or is selected from the group consisting of the following formulae:

Sp1
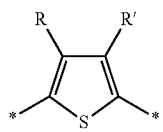

Sp2
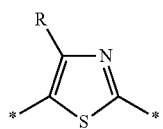

Sp3
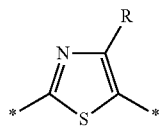

Sp4
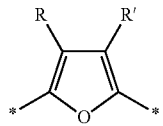

Sp5
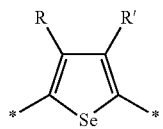

Sp6
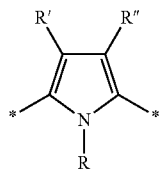

Sp7
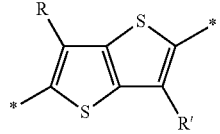

Sp8
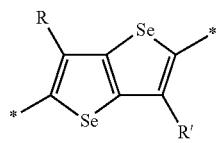

Sp9
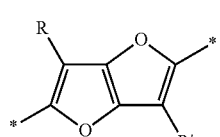

Sp10
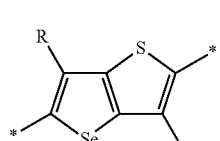

Sp11
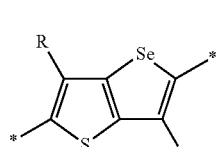

Sp12
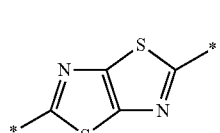

Sp13
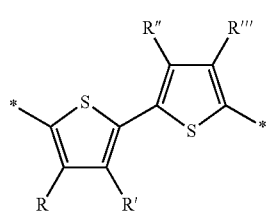

Sp14
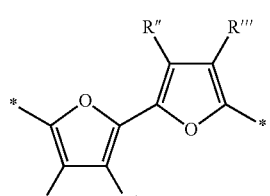

Sp15
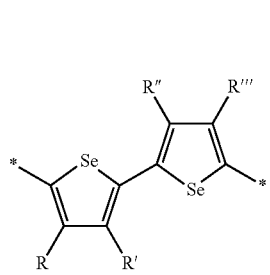

-continued

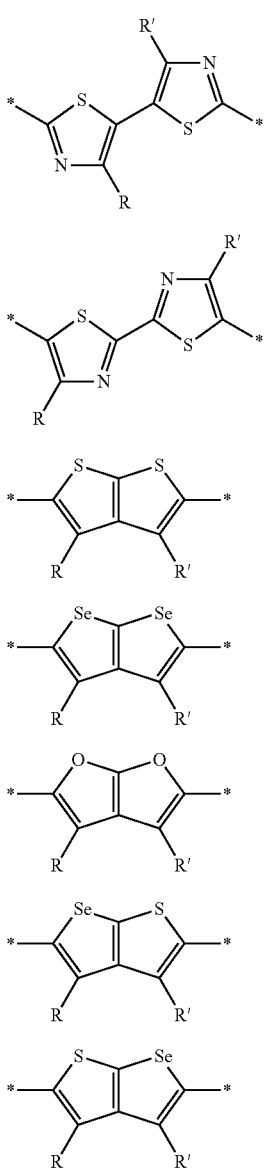

Sp16
Sp17
Sp18
Sp19
Sp20
Sp21
Sp22 wherein R, R', R" and R'" independently of each other denote H, halogen, straight-chain, branched or cyclic alkyl with 1 to 30 C atoms, in which one or more non-adjacent CH$_2$ groups are optionally replaced by —O—, —S—, —C(O)—, —C(O)—O—, —O—C (O)—, —O—C(O)—O—, —SO$_2$—, —SO$_3$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, or denote aryl or heteroaryl that is optionally substituted and has 4 to 30 ring atoms, wherein R$^0$ and R$^{00}$ are independently of each other H or optionally substituted C$_{1-40}$ carbyl or hydrocarbyl, and Y$^1$ and Y$^2$ denote H, F or CN, or denote —CY$^1$=CY$^2$— or —C≡C—, wherein Y$^1$ and Y$^2$ independently of each other denote H, F, Cl or CN, a, b independently of each other denote 1, 2, 3 or 4, and c, d independently of each other denote 0, 1, 2, 3 or 4.

20. The conjugated polymer according to claim 18, which is of the following formula $$*-[(A)_x-(B)_y-(C)_z]_n-* \quad V$$

wherein

A is a unit of formula III1, III2, III3 or III4 or its mirror image,

B and C are independently of each other a unit of formula III5 or III6 or its mirror image, x is >0 and <1, y is >0 and <1, z is ≥0 and >1, y≥x, x+y+z is 1, n is an integer >1, and wherein a unit D$^1$ is not linked to a unit Sp$^1$.

21. The conjugated polymer according to claim 20, which is of one of the following formulae $$*-\!\!+\!\!+\!\!D^1\!-\!(A^1)_a\!\!\xrightarrow{}_x\!\!+\!(Sp^1)_c\!-\!(A^1)_a\!\!\xrightarrow{}_y\!\!\xrightarrow{}_n\!\!-* \quad V1$$

$$*-\!\!+\!\!+\!\!(A^1)_a\!-\!D^1\!\!\xrightarrow{}_x\!\!+\!(A^1)_a\!-\!(Sp^1)_c\!\!\xrightarrow{}_y\!\!\xrightarrow{}_n\!\!-* \quad V2$$

$$*-\!\!+\!\!+\!\!(A^1)_a\!-\!D^1\!\!\xrightarrow{}_x\!\!+\!(A^1)_a\!-\!(Sp^1)_c\!\!\xrightarrow{}_y\!\!+\!(A^1)_a\!-\!(Sp^1)_c\!\!\xrightarrow{}_z\!\!\xrightarrow{}_n\!\!-* \quad V3$$

$$*-\!\!+\!\!+\!\!(A^1)_a\!-\!D^1\!-\!(A^1)_a\!-\!(Sp^1)_c\!\!\xrightarrow{}_x\!\!+\!(A^1)_a\!-\!(Sp^1)_c\!\!\xrightarrow{}_y\!\!\xrightarrow{}_n\!\!-* \quad V4$$

$$*-\!\!+\!\!+\!\!(A^1)_a\!-\!D^1\!-\!(A^1)_a\!\!\xrightarrow{}_x\!\!+\!(Sp^1)_c\!-\!(A^1)_a\!-\!(Sp^1)_c\!\!\xrightarrow{}_y\!\!\xrightarrow{}_n\!\!-*. \quad V5$$

22. The conjugated polymer according to claim 1, which is of one of the following formulae IV1a

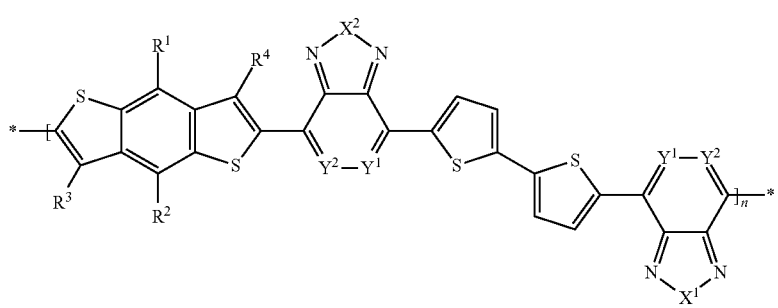

-continued
IV1b 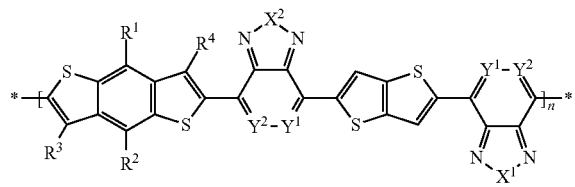 IV1c
IV1d 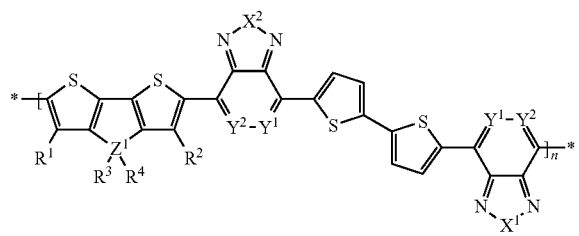 IV1e
IV1f 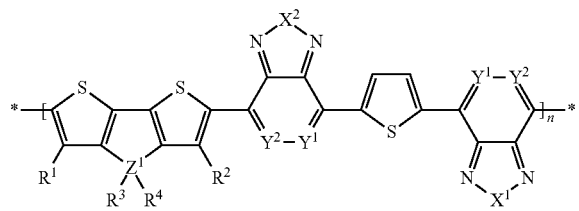 IV1g 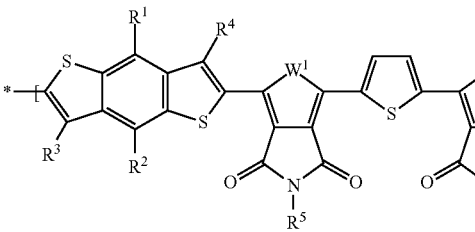
IV1h
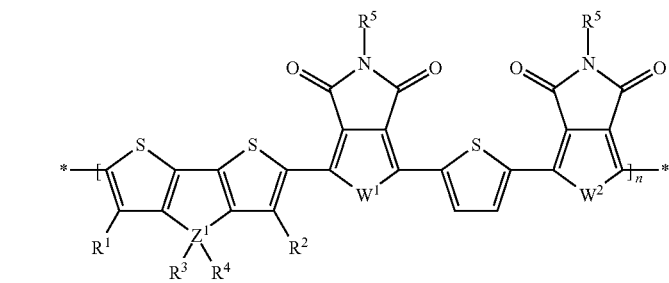
IV2a
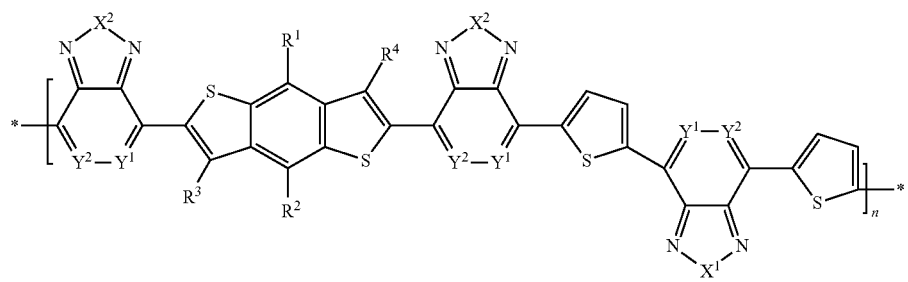
V1a
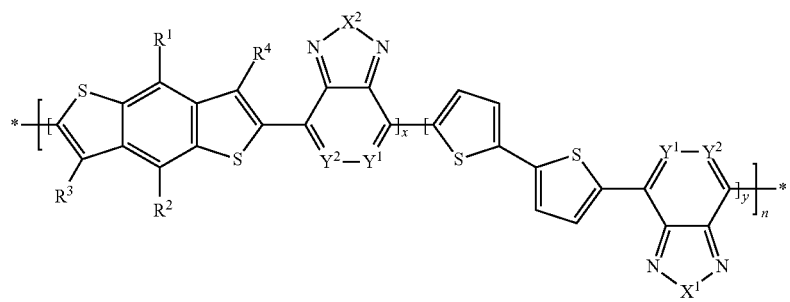

-continued
V1b
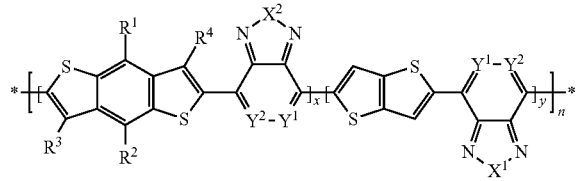
V1c
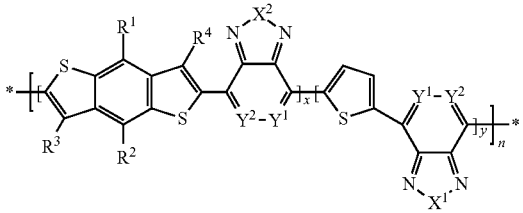
V1d
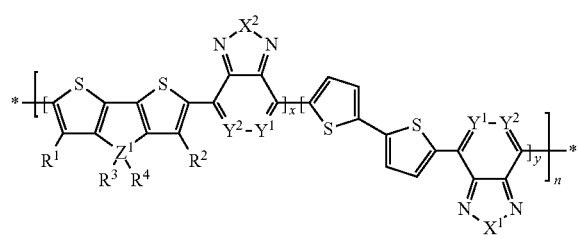
V1e
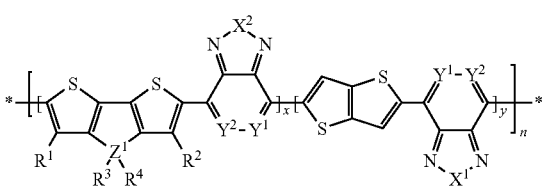
V1f
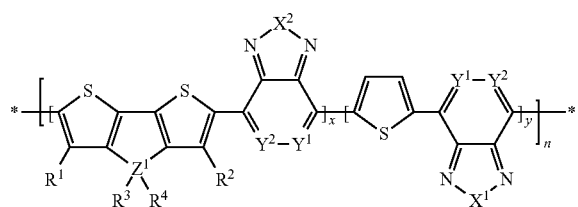
V1g
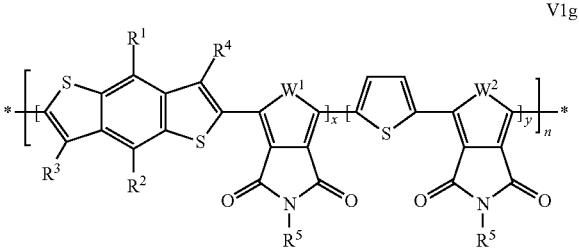
V1h
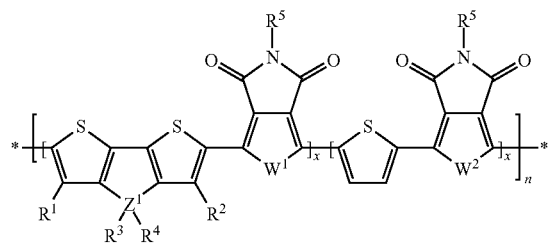
V2a
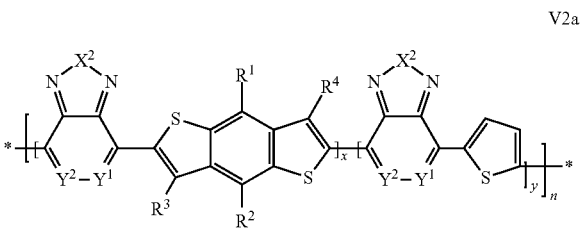
V3a
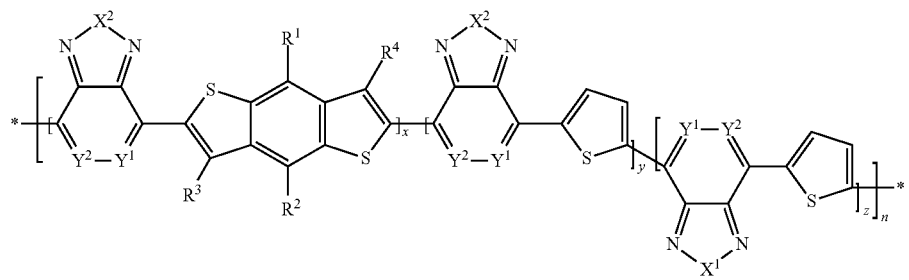
V4a
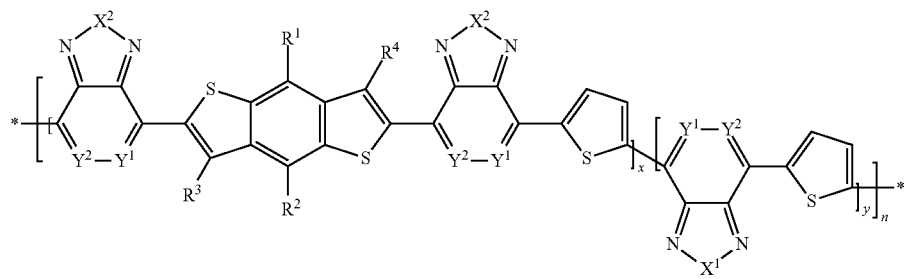

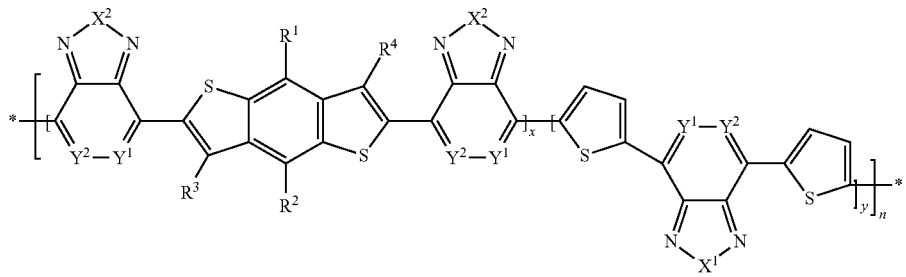

V5a wherein
X¹ and X² are independently of each other NR, O, S or Se,
Y¹ and Y² are independently of each other N, CH or CR,
Z¹ is independently of each other C, Si or Ge,
W¹ and W² are independently of each other O, S or Se,
$R^{1-4}$ denote H, halogen, or an optionally substituted carbyl or hydrocarbyl group wherein one or more C atoms are optionally replaced by a hetero atom,
R denotes H, halogen, or an optionally substituted carbyl or hydrocarbyl group wherein one or more C atoms are optionally replaced by a hetero atom, and x is >0 and <1,
y is >0 and <1,
z is ≥0 and >1,
y≥x,
x+y+z is 1,
n is an integer >1.

23. The conjugated polymer according to claim 22, which is of one of the following formulae

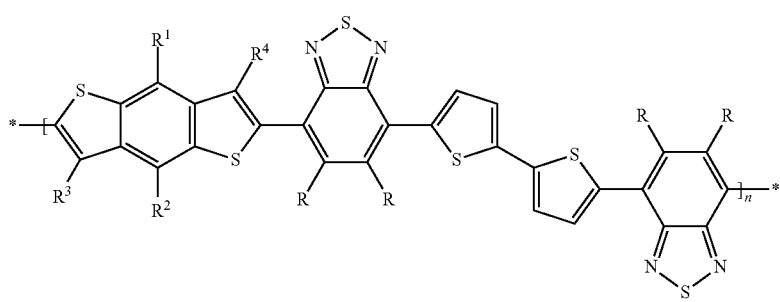

IV1a1

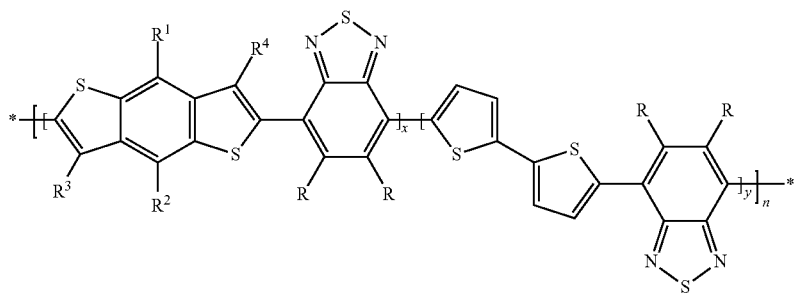

V1a1

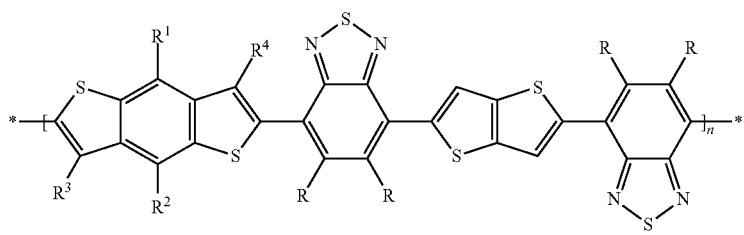

IV1b1

-continued
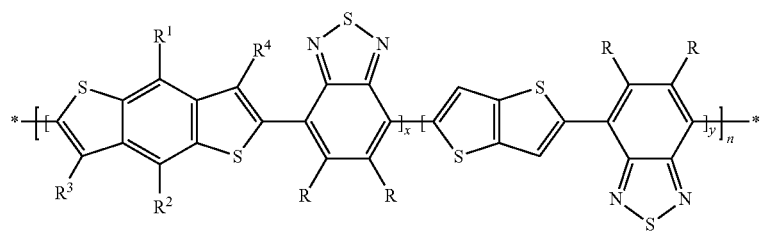
VIb1
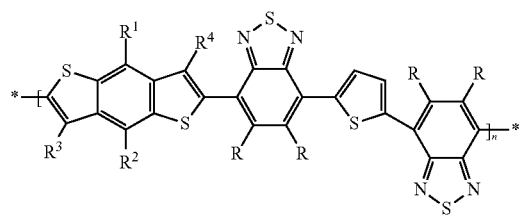
IV1c1
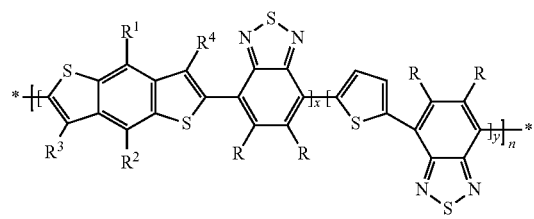
V1c1
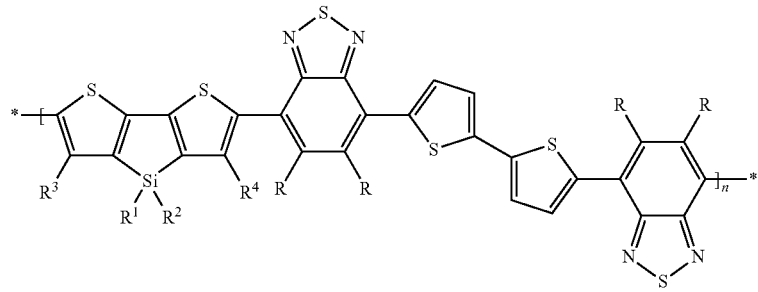
IV1d1
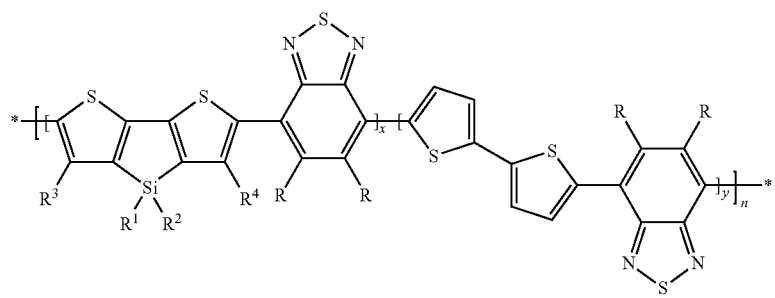
V1d1
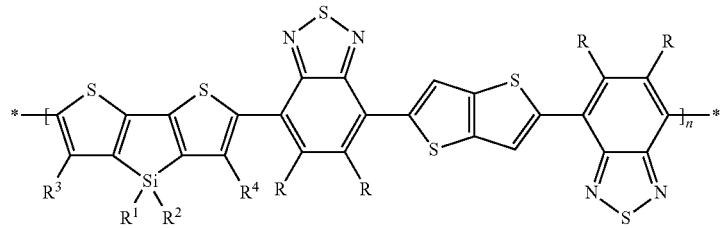
IV1e1
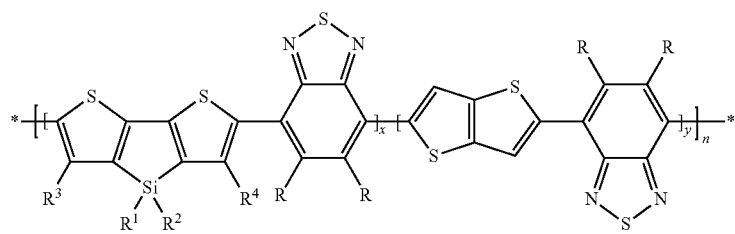
V1e1

-continued
| IV1f1 | V1f1 |
|---|---|
| 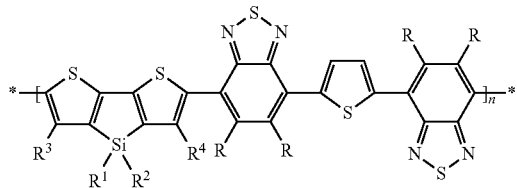 | 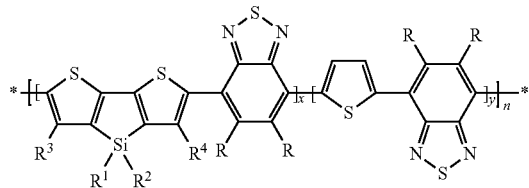 |
| IV1g1 | V1g1 |
| 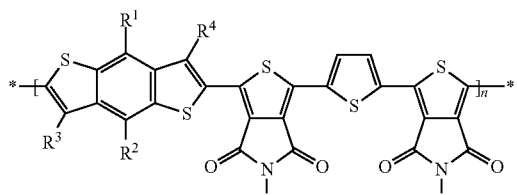 | 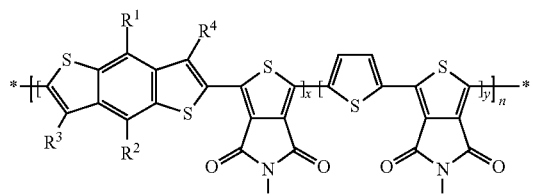 |
| IV1h1 | V1h1 |
| 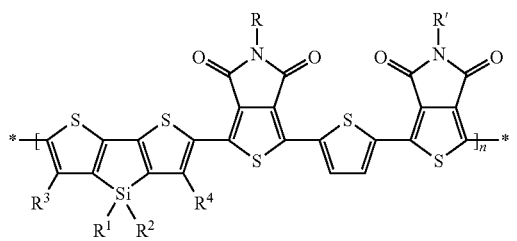 | |
V2a1
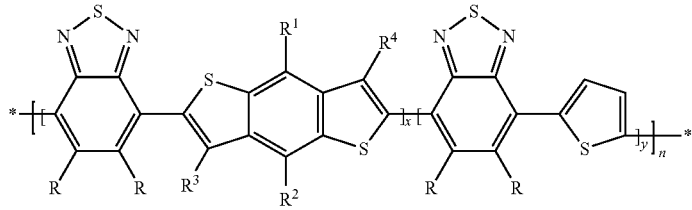
V3a1
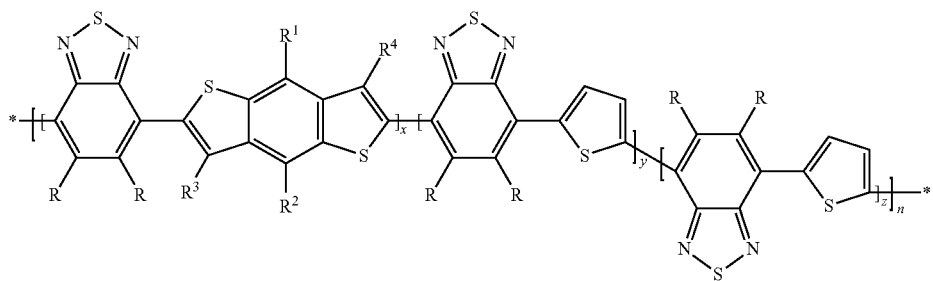
V4a1
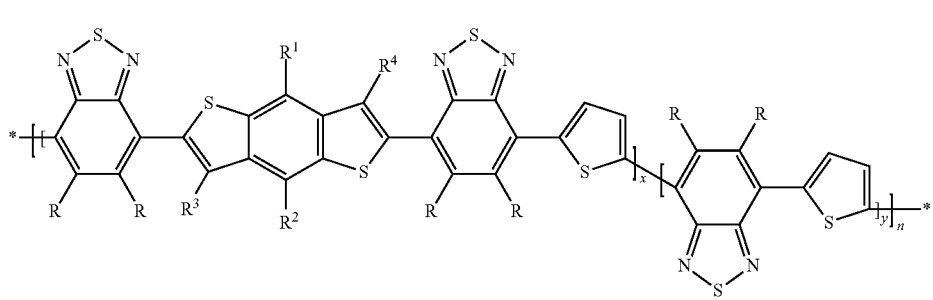

-continued
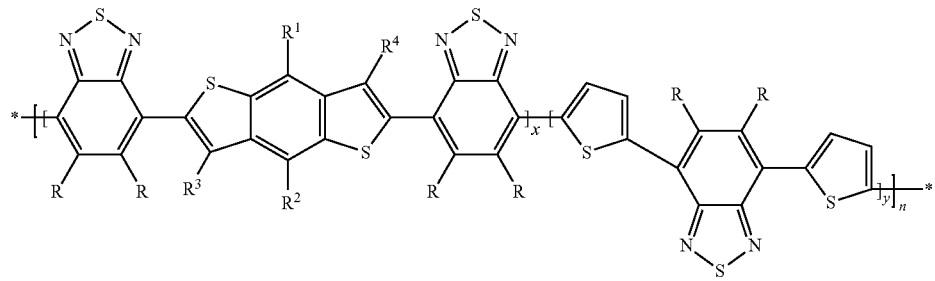
V5a1
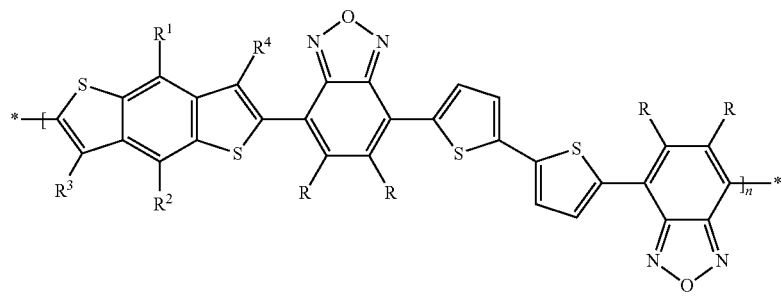
IV1a2
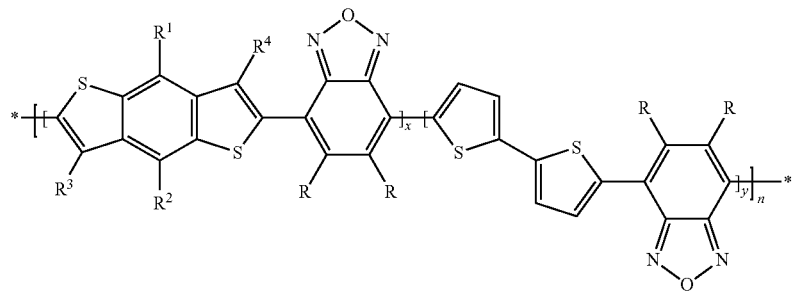
V1a2
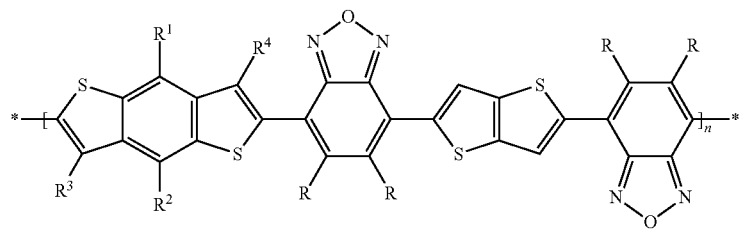
IV1b2
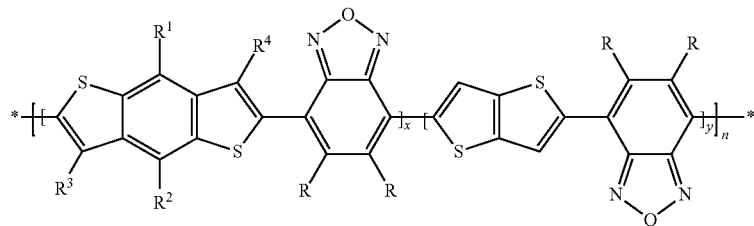
V1b2
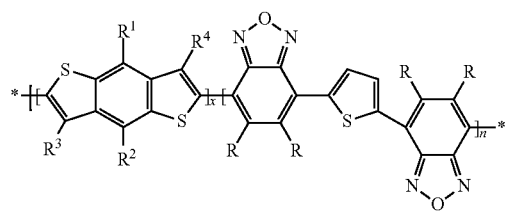
IV1c2
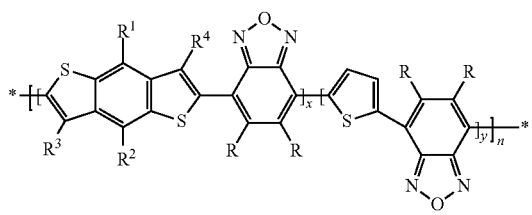
V1c2

-continued
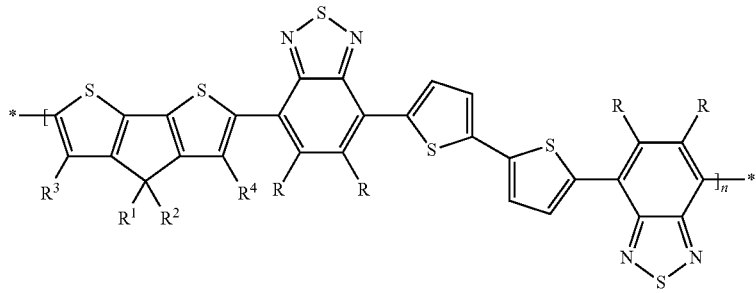
IV1d2
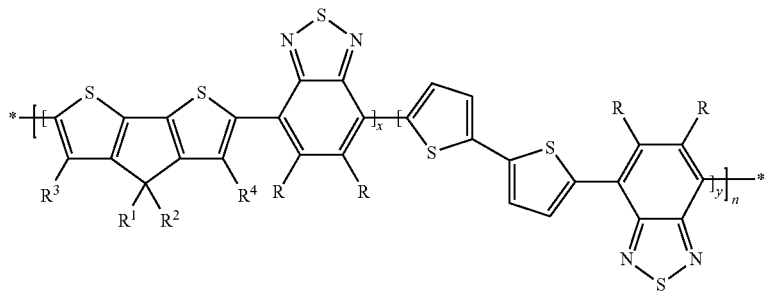
V1d2
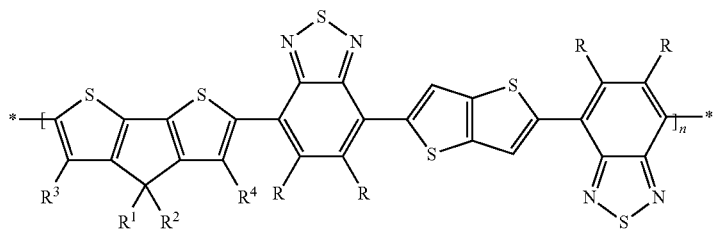
IV1e2
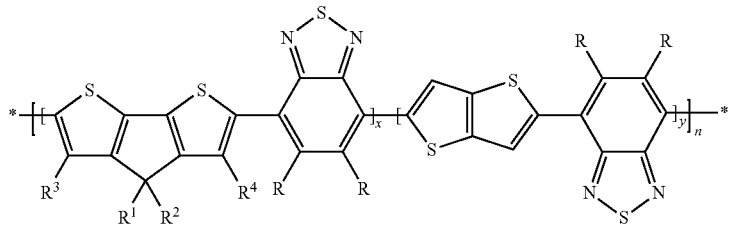
V1e2
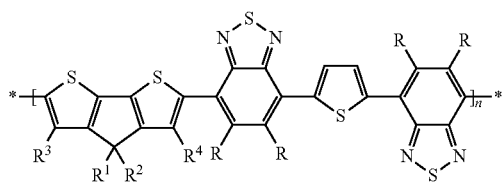
IV1f2
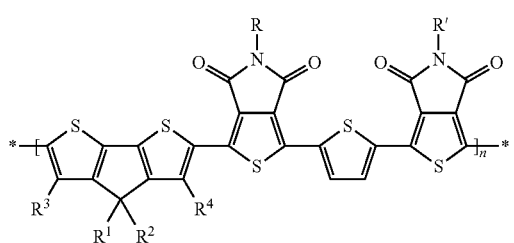
IV1h2
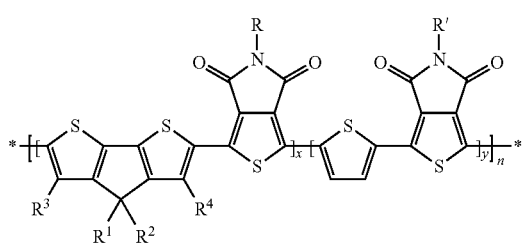
V1f2
V1h2

-continued
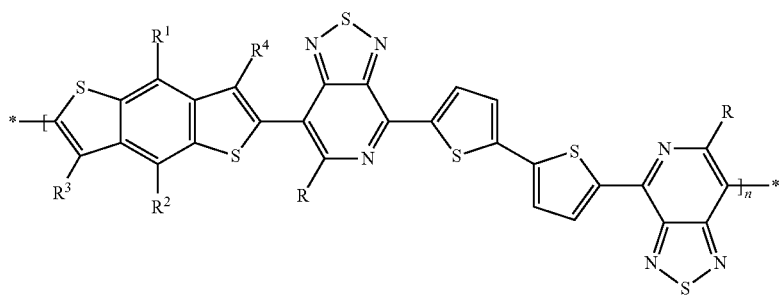
IV1a3
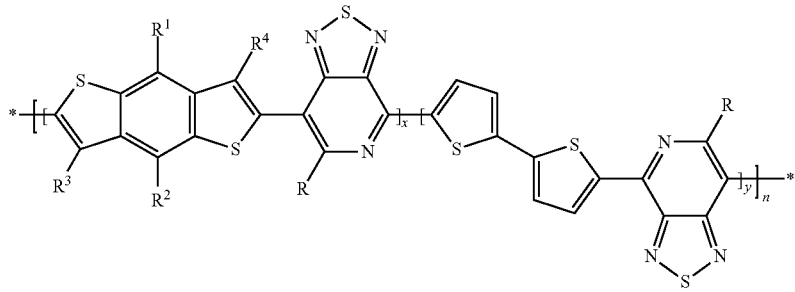
V1a3
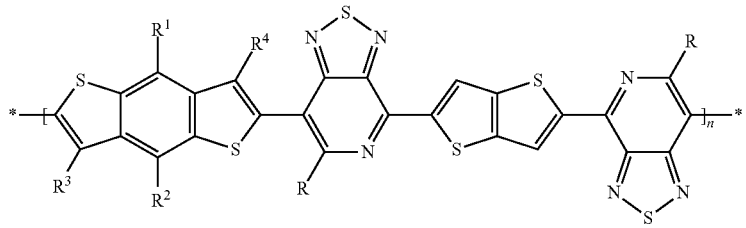
IV1b3
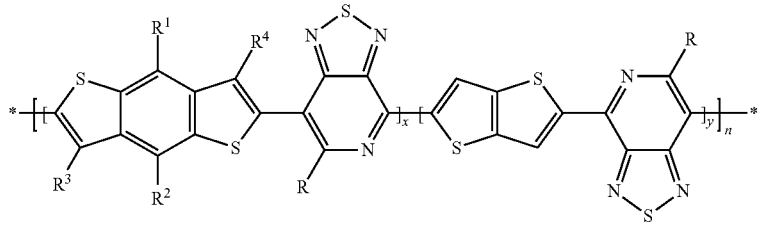
V1b3
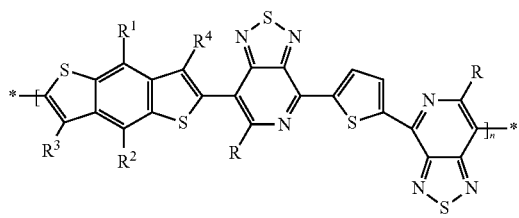
IV1c3
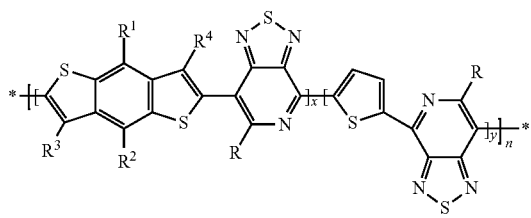
V1c3
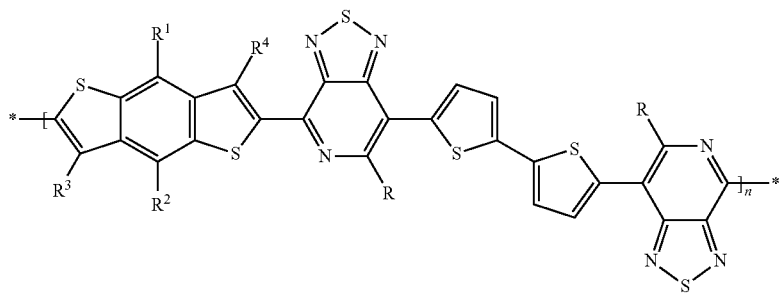
IV1a4

-continued
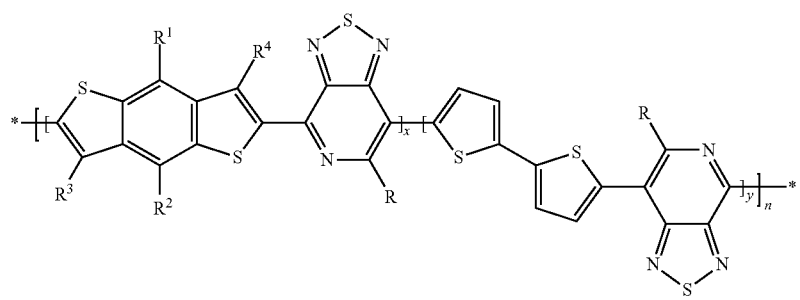
VIa4
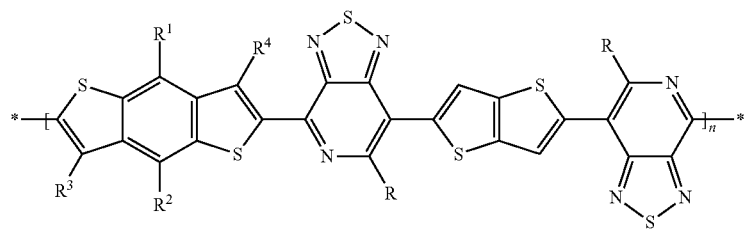
IVIb4
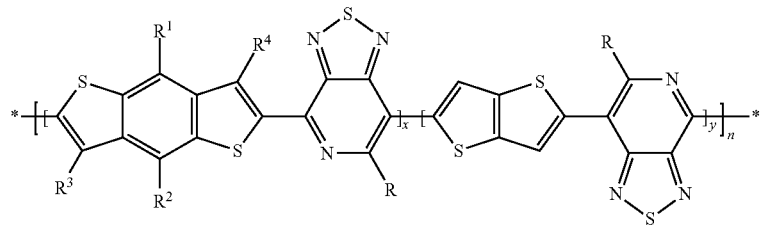
VIb4
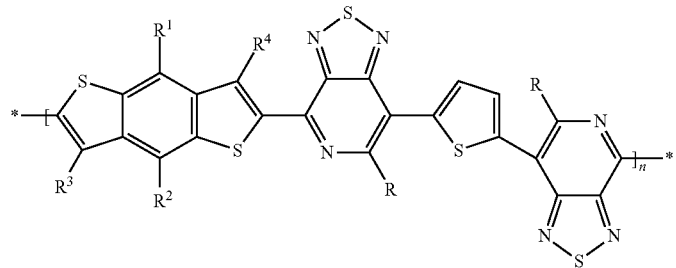
IVIc4
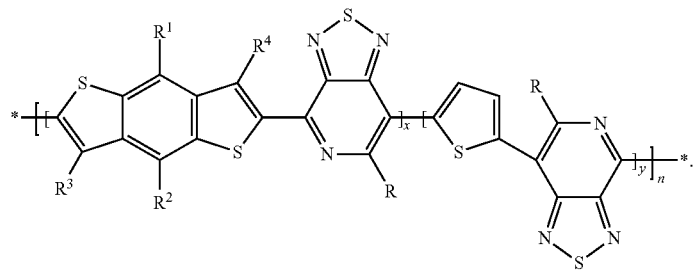
VIc4

24. The conjugated polymer according to claim 1, which is of formula VI

R⁵-chain-R⁶        VI wherein
chain denotes a polymer chain of formula IV1 or IV2 or V:

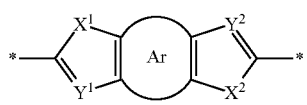        IV1

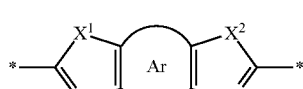        IV2

*-[(A)ₓ-(B)ᵧ-(C)_z]ₙ-*        V wherein
n is an integer >1,
D¹ is a first unit selected from the group consisting of formula Ia to Ig, Ia1, Ia2 and Ia3

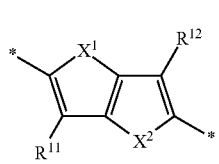        Ia

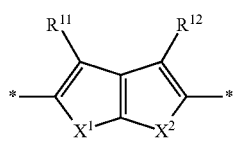        Ib

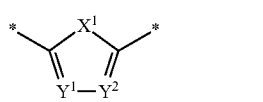        Ic

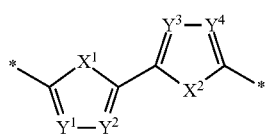        Id

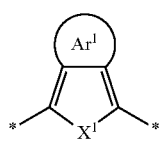        Ie

If

Ig wherein
Ar denotes a carbocyclic, heterocyclic, aromatic or heteroaromatic group, which comprises one or more saturated or unsaturated rings that are covalently linked or fused, which is fused to the terminal five-membered rings in formula Ia or Ib to form a conjugated system, and which is unsubstituted or substituted,
Ar¹ denotes a carbocyclic, heterocyclic, aromatic or heteroaromatic group, which comprises one or more saturated or unsaturated rings that are covalently linked or fused, which is fused to the divalent five-membered ring in formula Ig, and which is unsubstituted or substituted,
X¹ and X² denote independently of each other O, S, Se, Si or NR¹,
Y¹⁻⁴ denote independently of each other CR¹ or N,
R¹ denotes H, halogen, or an optionally substituted carbyl or hydrocarbyl group, wherein one or more C atoms are optionally replaced by a hetero atom, and
R¹¹ and R¹² independently of each other have one of the meanings of R¹,

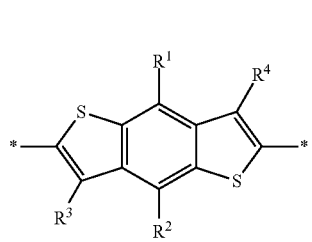        Ia1

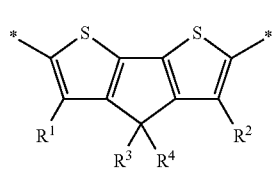        Ia2

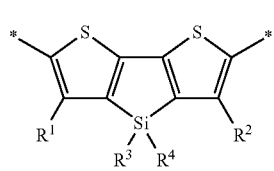        Ia3 wherein
R¹⁻⁴ independently of each other denote H, halogen, or an optionally substituted carbyl or hydrocarbyl group wherein one or more C atoms are optionally replaced by a hetero atom,
A¹ and A² independently of each other denote an acceptor unit that is different from D¹, Sp¹ and Sp², and is arylene or heteroarylene that is mono- or polycyclic and optionally substituted, or is selected from the group consisting of the following formulae and their mirror images:

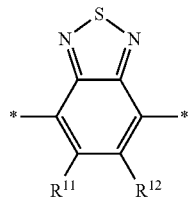        (A1)

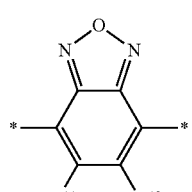        (A2)

(A3) 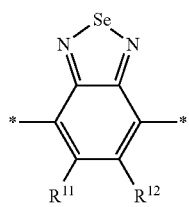
(A4) 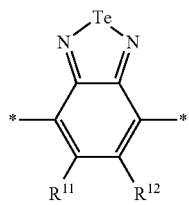
(A5) 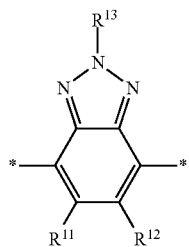
(A6) 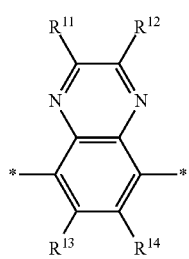
(A7) 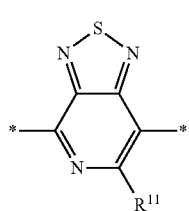
(A8) 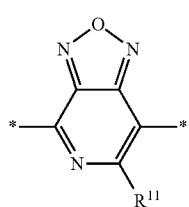
(A9) 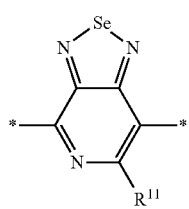
(A10) 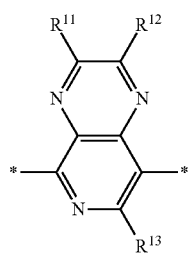
(A11) 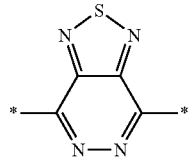
(A12) 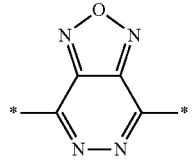
(A13) 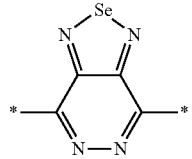
(A14) 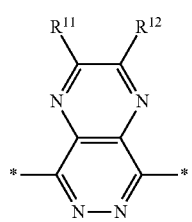
(A15) 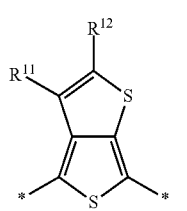
(A16) 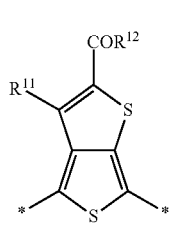
(A17) 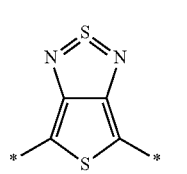

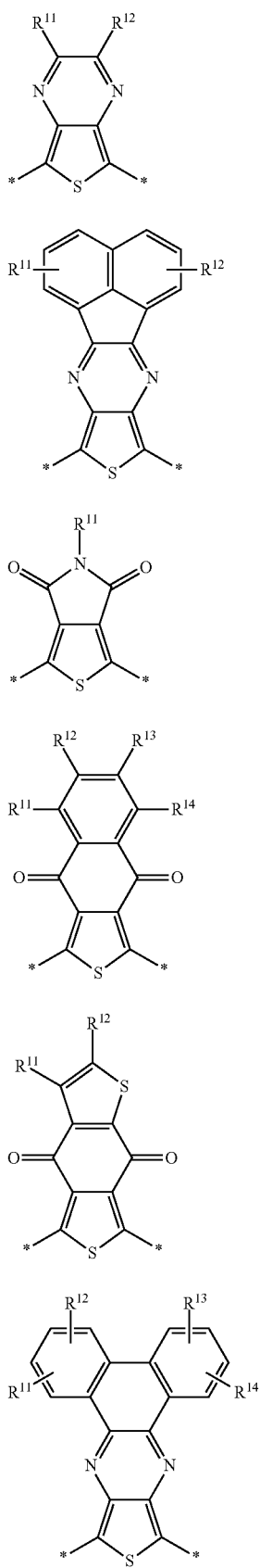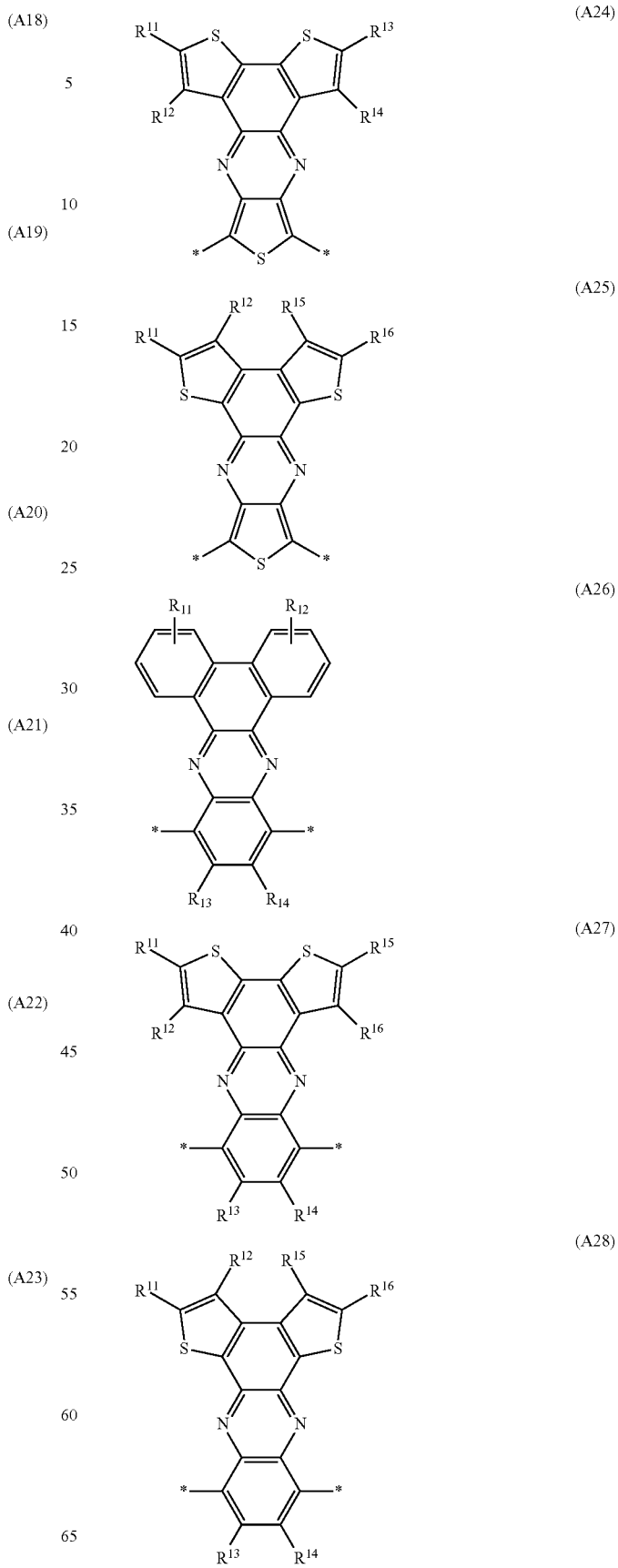

(A29) 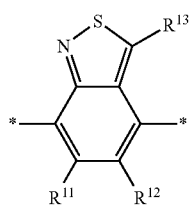
(A30) 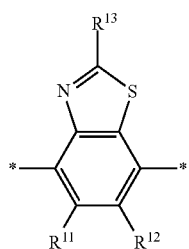
(A31) 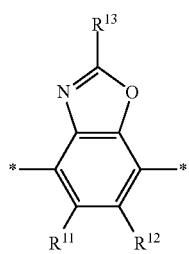
(A32) 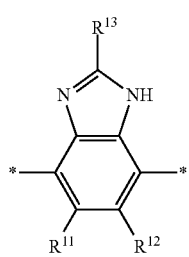
(A33) 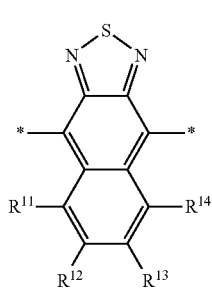
(A34) 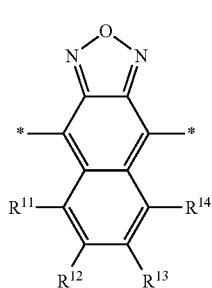
(A35) 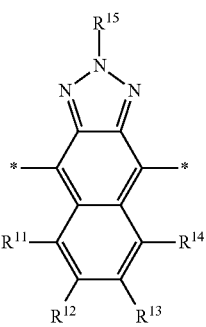
(A36) 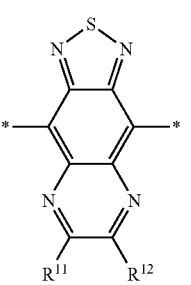
(A37) 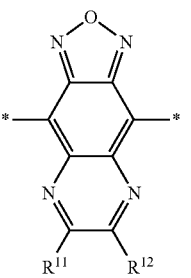
(A38) 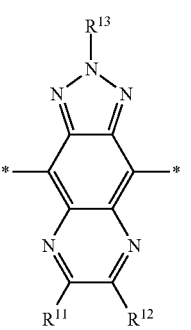
(A39) 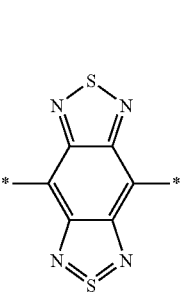

-continued (A40)

(A41)

(A42)

(A43)

(A44)

(A45)

(A46)

(A47)

-continued (A48)

(A49)

(A50)

(A51)

(A52)

(A53)

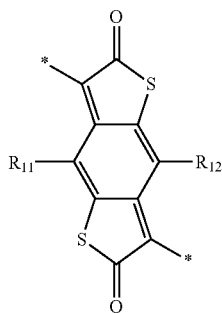
(A54)
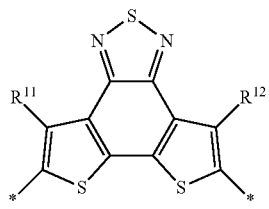
(A55)
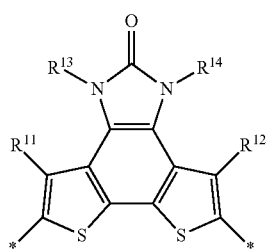
(A56)
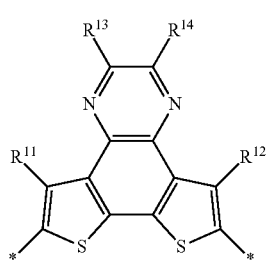
(A57)
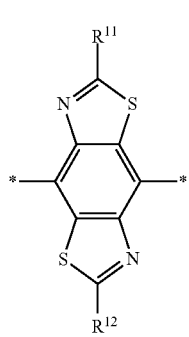
(A58)
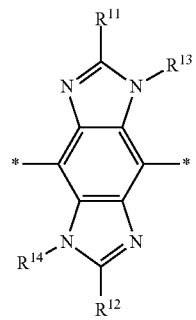
(A59)
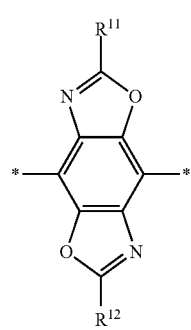
(A60)
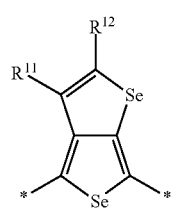
(A61)
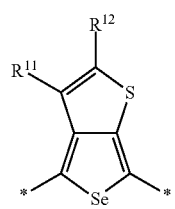
(A62)
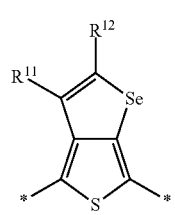
(A63)
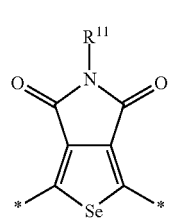
(A64)

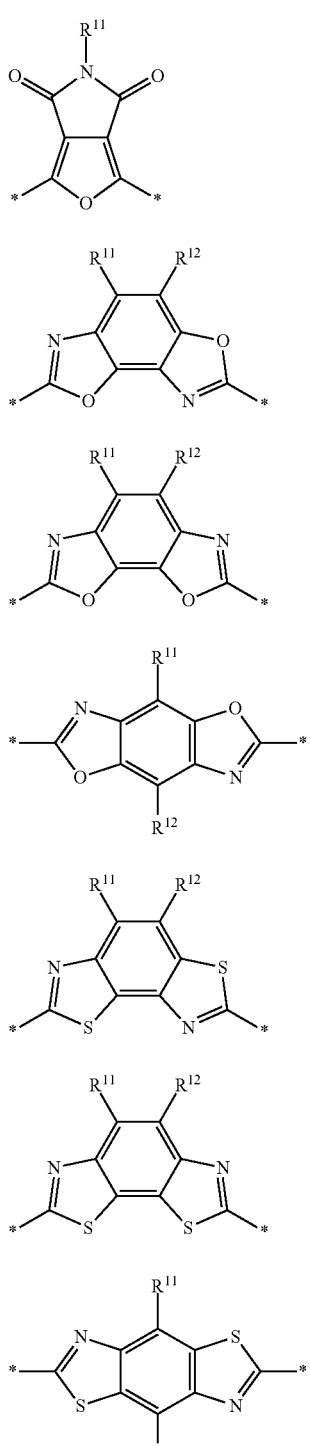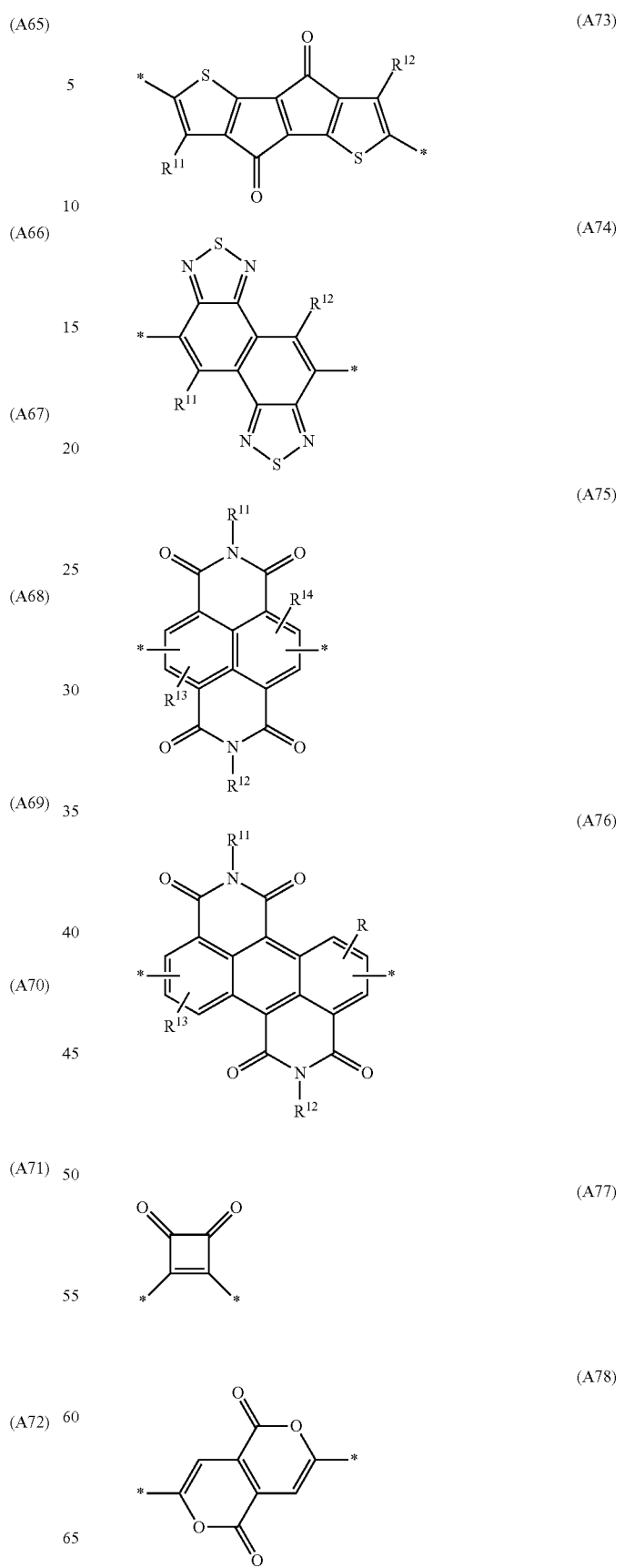

323
-continued
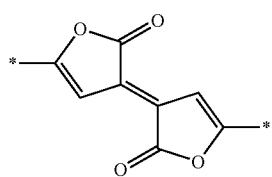
(A79)
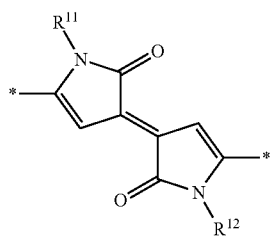
(A80)
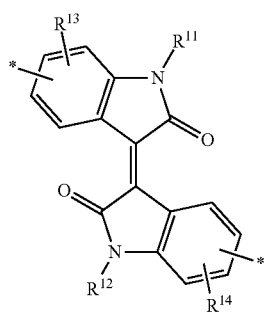
(A81)
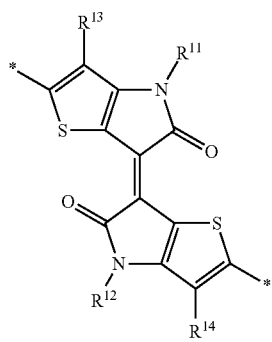
(A82)
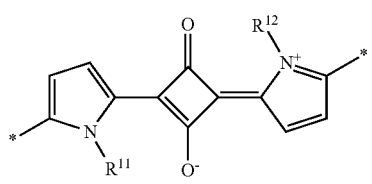
(A83)
324
-continued
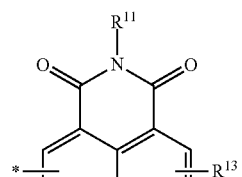
(A84)
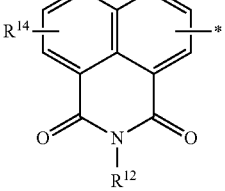
(A85)
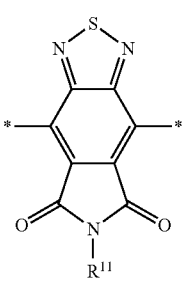
(A86)
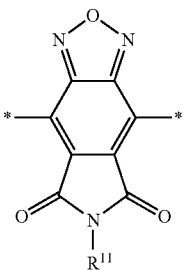
(A87)
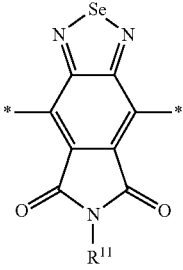
(A88)

-continued

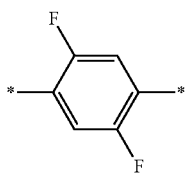 (A89)

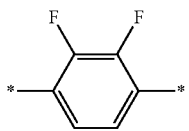 (A90)

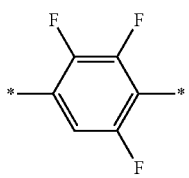 (A91)

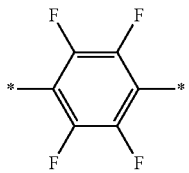 (A92)

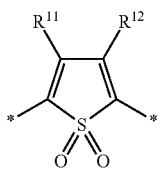 (A93)

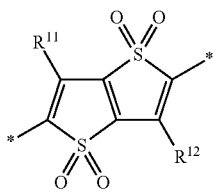 (A94)

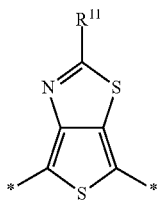 (A95)

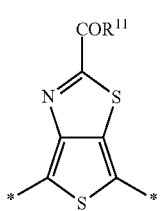 (A96)

wherein
$R^{11}$, $R^{12}$, $R^{13}$ and $R^{14}$ independently of each other denote H, halogen, or an optionally substituted carbyl or hydrocarbyl group wherein one or more C atoms are optionally replaced by a hetero atom, $Sp^1$ and $Sp^2$ independently of each other denote a spacer unit, which is different from $D^1$, $A^1$ and $A^2$, and is arylene or heteroarylene that is mono- or polycyclic and optionally substituted, or is selected from the group consisting of the following formulae and their mirror images:

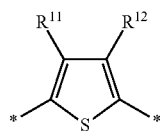 (D1)

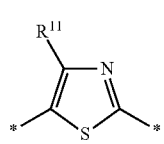 (D2)

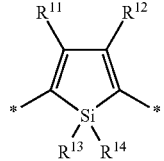 (D3)

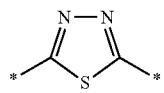 (D4)

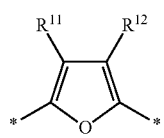 (D5)

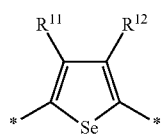 (D6)

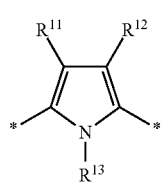 (D7)

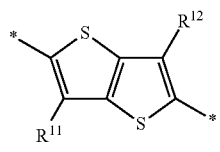 (D8)

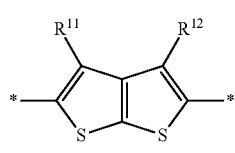 (D9)

-continued
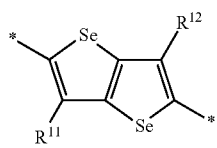 (D10)
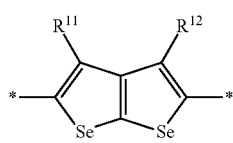 (D11)
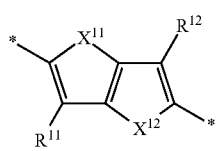 (D12)
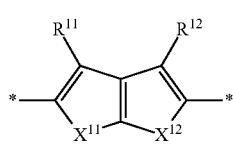 (D13)
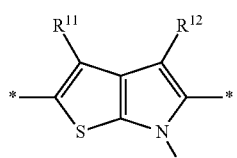 (D14)
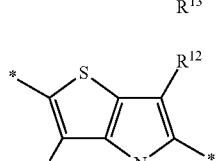 (D15)
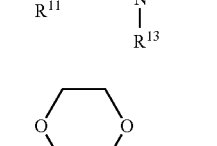 (D16)
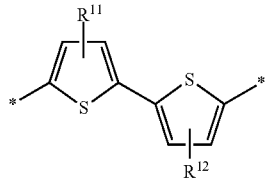 (D17)
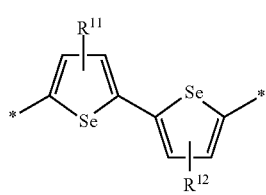 (D18)
-continued
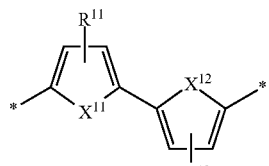 (D19)
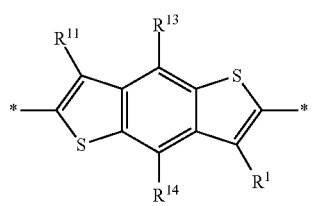 (D20)
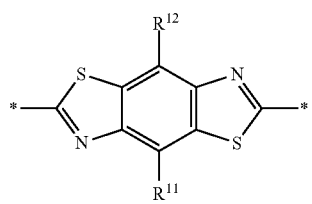 (D21)
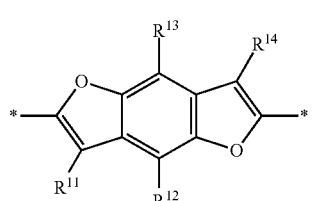 (D22)
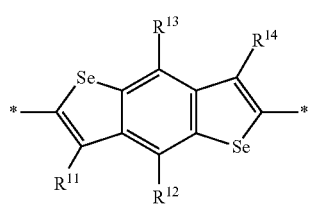 (D23)
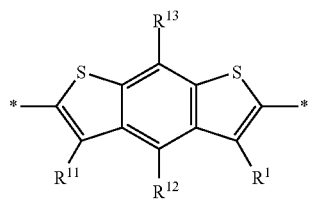 (D24)
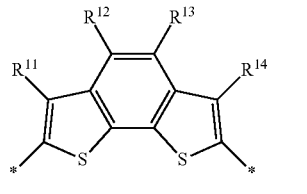 (D25)
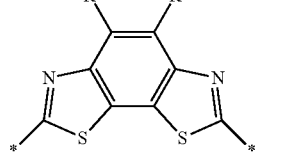 (D26)

-continued
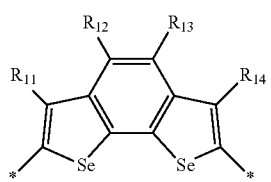
(D27)
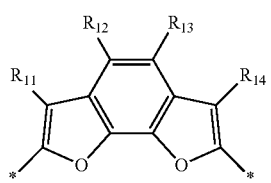
(D28)
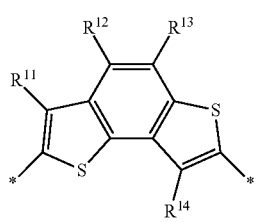
(D29)
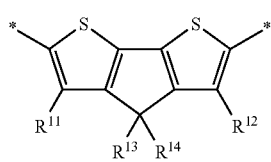
(D30)
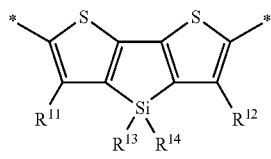
(D31)
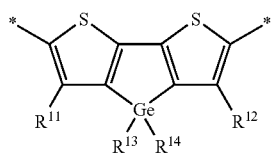
(D32)
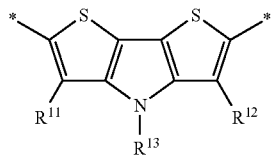
(D33)
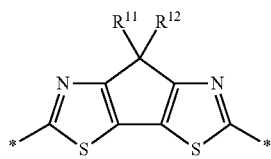
(D34)
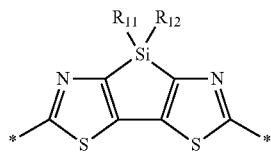
(D35)
-continued
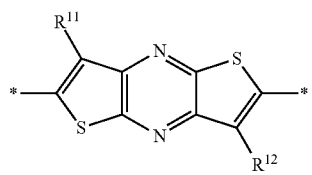
(D36)
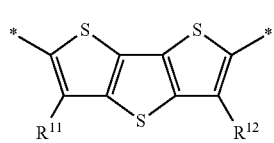
(D37)
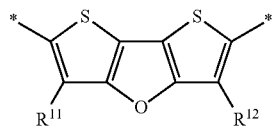
(D38)
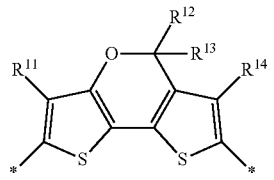
(D39)
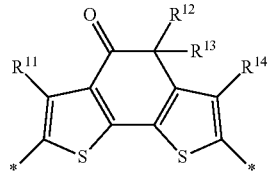
(D40)
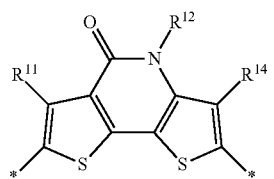
(D41)
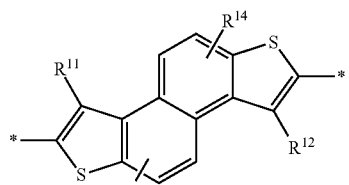
(D42)
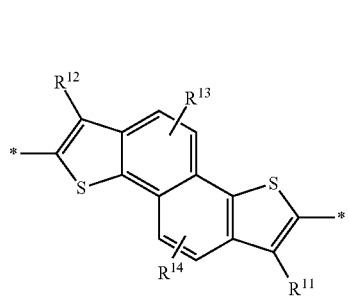
(D43)

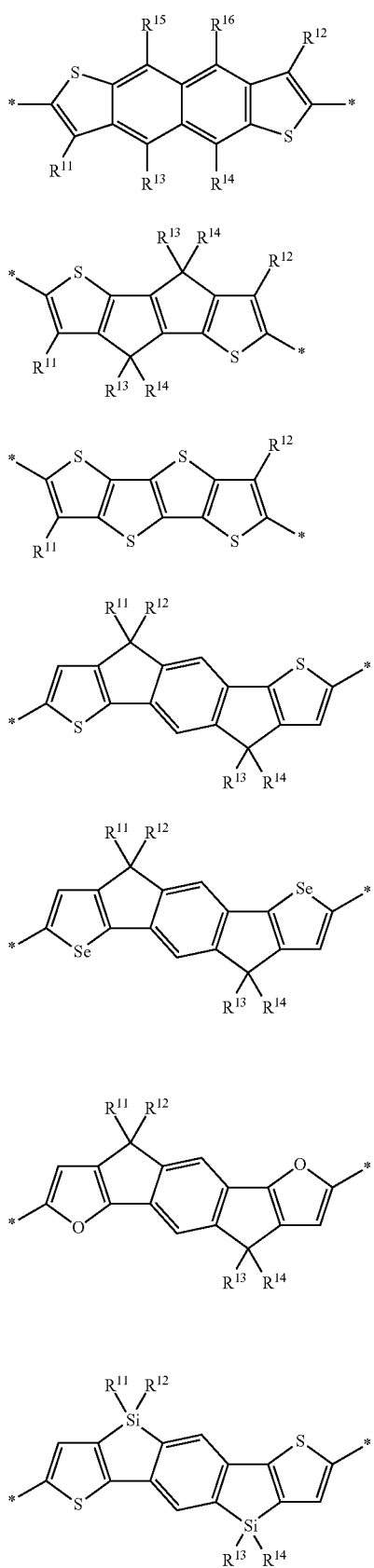
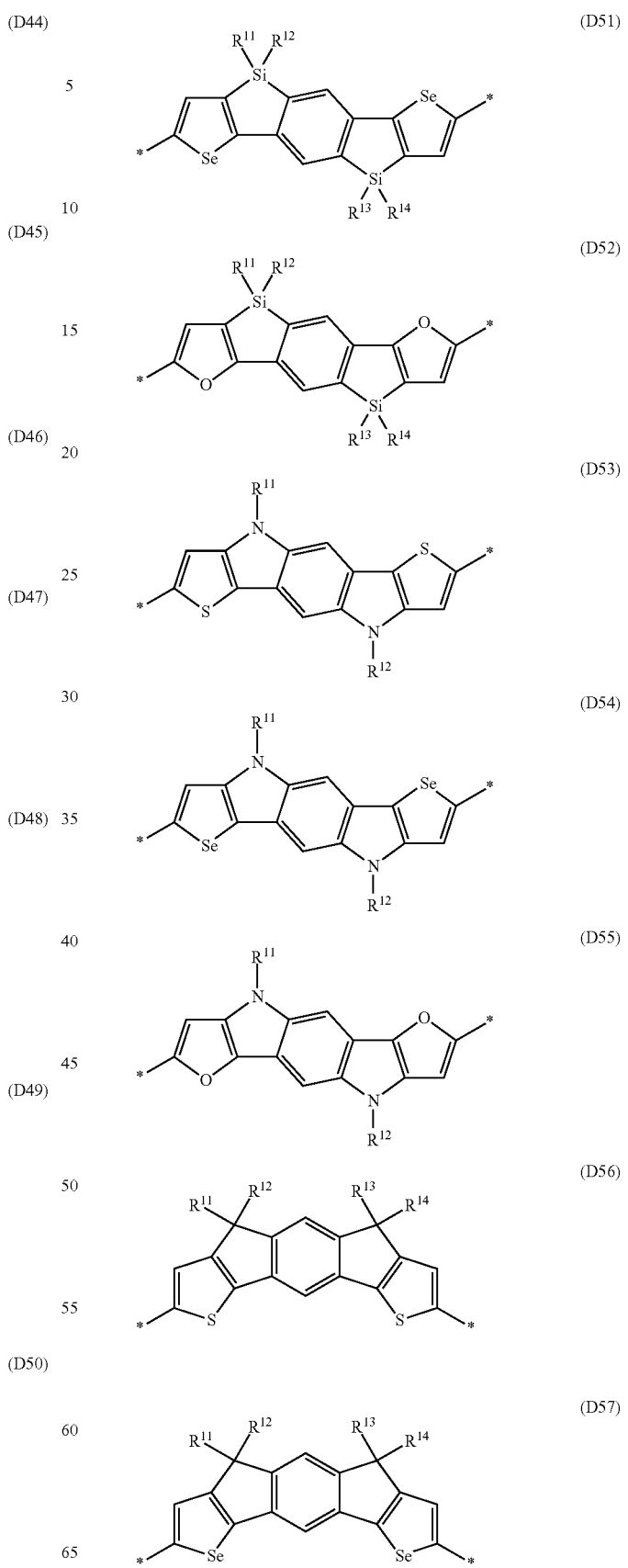

333
-continued
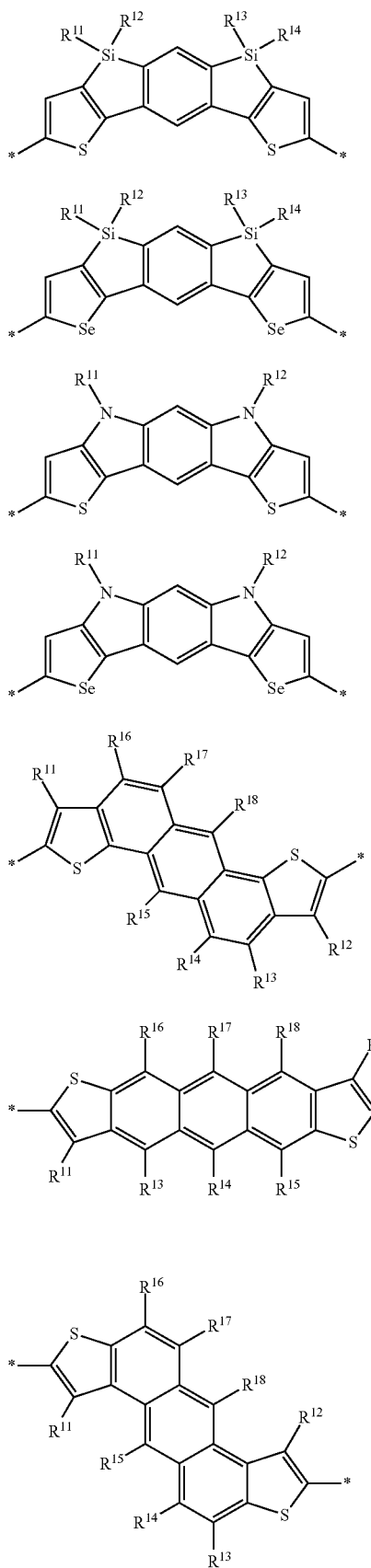
(D58)
(D59)
(D60)
(D61)
(D62)
(D63)
(D64)
334
-continued
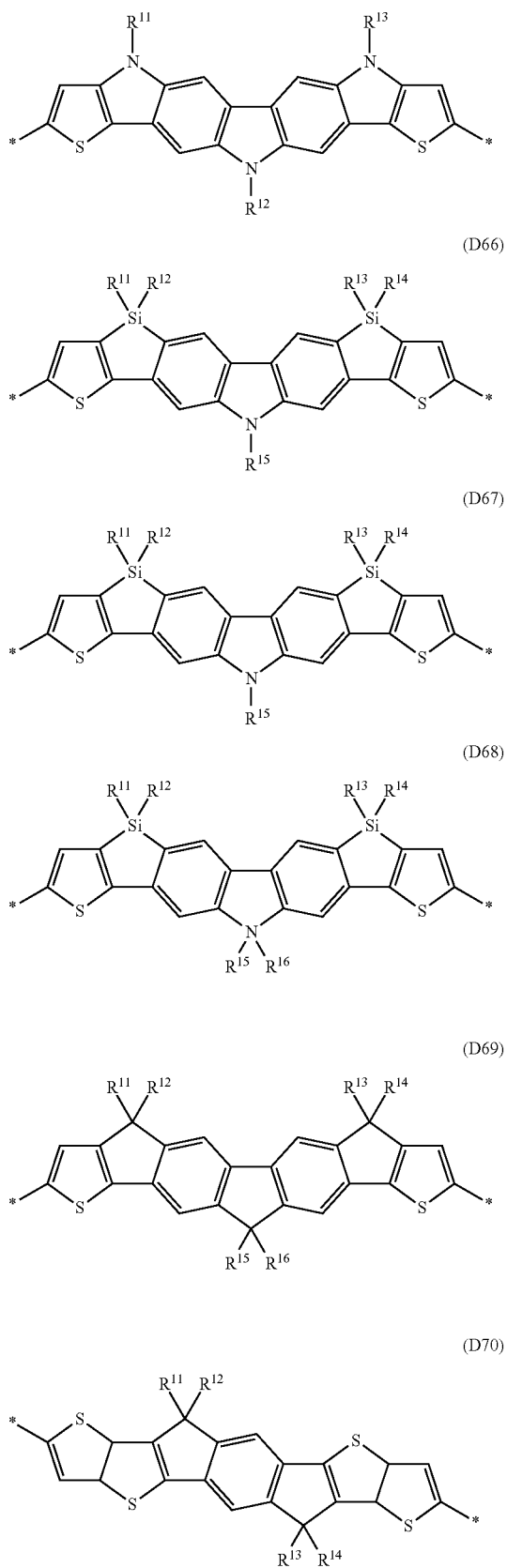
(D65)
(D66)
(D67)
(D68)
(D69)
(D70)

-continued (D71)
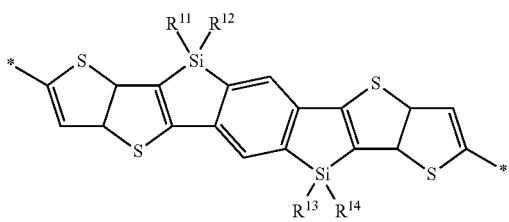

(D72)
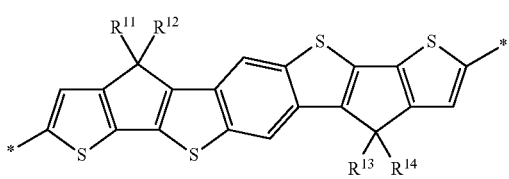

wherein one of $X^{11}$ and $X^{12}$ is S and the other is Se, and $R^{11}$, $R^{12}$, $R^{13}$, $R^{14}$, $R^{15}$, $R^{16}$, $R^{16}$, $R^{17}$ and $R^{18}$ independently of each other denote H, halogen, or an optionally substituted carbyl or hydrocarbyl group wherein one or more C atoms are optionally replaced by a hetero atom, or is selected from the group consisting of the following formulae:

Sp1
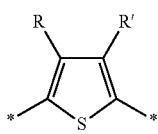

Sp2
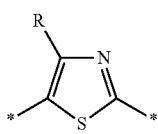

Sp3
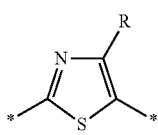

Sp4
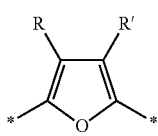

Sp5
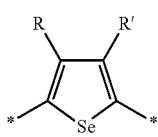

Sp6
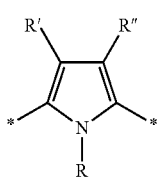

Sp7
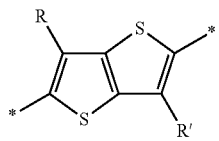

Sp8
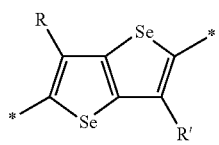

Sp9
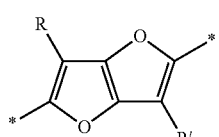

Sp10
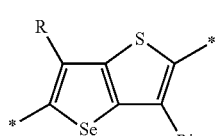

Sp11
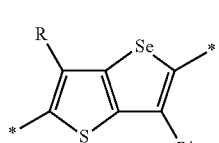

Sp12
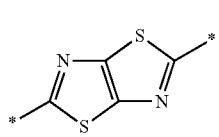

Sp13
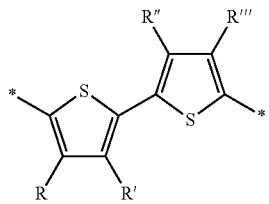

Sp14
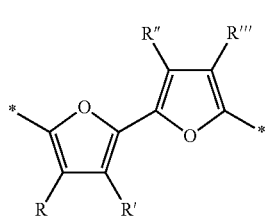

Sp15
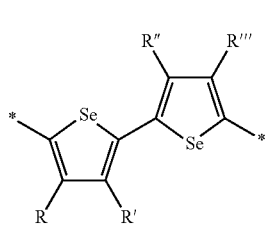

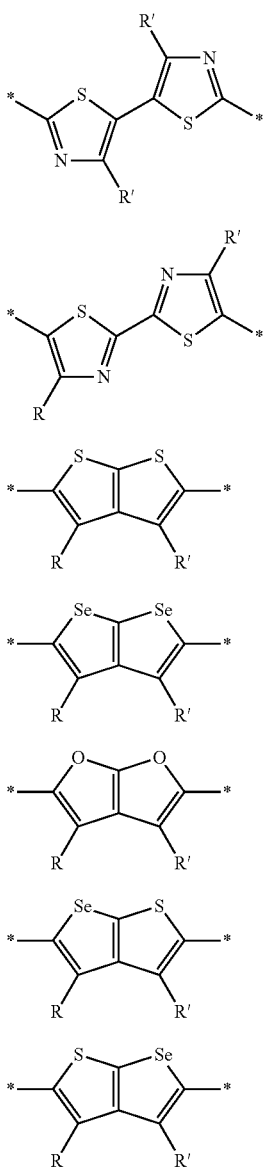

wherein R, R', R'' and R''' independently of each other denote H, halogen, straight-chain, branched or cyclic alkyl with 1 to 30 C atoms, in which one or more non-adjacent CH$_2$ groups are optionally replaced by —O—, —S—, —C(O)—, —C(O)—O—, —O—C(O)—, —O—C(O)—O—, —SO$_2$—, —SO$_3$—, —NR$^o$—, —SiR$^o$R$^{oo}$—, —CF$_2$—, —CHR$^o$=CR$^{oo}$—, —CY$^1$=CY$^2$— or —C≡C— in such a manner that O and/or S atoms are not linked directly to one another, and in which one or more H atoms are optionally replaced by F, Cl, Br, I or CN, or denote aryl or heteroaryl that is optionally substituted and has 4 to 30 ring atoms, wherein R$^o$ and R$^{oo}$ are independently of each other H or optionally substituted C$_{1-40}$ carbyl or hydrocarbyl, and Y$^1$ and Y$^2$ denote H, F or CN, or denote —CY$^1$=CY$^2$— or —C≡C—, wherein Y$^1$ and Y$^2$ independently of each other denote H, F, Cl or CN, a, b independently of each other denote 1, 2, 3 or 4, c, d independently of each other denote 0, 1, 2, 3 or 4, A is a unit of formula III1, III2, III3 or III4 or its mirror image, B and C are independently of each other a unit of formula III5 or III6 or its mirror image, x is >0 and <1, y is >0 and <1, z is ≥0 and >1, y≥x, x+y+z is 1, and wherein a unit D$^1$ is not linked to a unit Sp$^1$ -D$^1$-(A$^1$)$_a$-   III1

(A$^1$)$_a$-D$^1$-(A$_2$)$_b$-   III2

-(A$^1$)$_a$-D$^1$-(A$^2$)$_b$-(Sp$^1$)$_c$-   III3

-(A$^1$)$_a$-D$^1$-(A$^2$)$_b$-(Sp$^1$)$_c$-(A$^1$)$_a$-(Sp$^2$)$_d$-   III4

-(Sp$^1$)$_c$-(A$^1$)$_a$-(Sp$^2$)$_d$-   III5

-(Sp$^1$)$_c$-(A$^1$)$_a$-   III6

R$^5$ and R$^6$ independently of each other denote H, halogen, or an optionally substituted carbyl or hydrocarbyl group wherein one or more C atoms are optionally replaced by a hetero atom, or denote, independently of each other, H, F, Br, Cl, I, —CH$_2$Cl, —CHO, —CR$^a$=CR$^b{}_2$, —SiR$^a$R$^b$R$^c$, —SiR$^a$X$^a$X$^b$, —SiR$^a$R$^b$X$^a$, —SnR$^a$R$^b$R$^c$, —BR$^a$R$^b$, —B(OR$^a$)(OR$^c$), —B(OH)$_2$, —O—SO$_2$R$^a$, —C≡CH, —C≡C—SiR$^a{}_3$, —MgX$^a$, —ZnX$^a$, or an endcap group, wherein X$^a$ and X$^b$ denote halogen, R$^a$, R$^b$ and R$^c$ independently of each other denote H or alkyl with 1 to 20 C atoms, and two of R$^a$, R$^b$ and R$^c$ optionally form an aliphatic ring together with the hetero atom to which they are attached.

25. A mixture or polymer blend comprising one or more polymers according to claim 1 and one or more compounds or polymers having semiconducting, charge transport, hole/electron transport, hole/electron blocking, electrically conducting, photoconducting or light emitting properties.

26. The mixture or polymer blend according to claim 25, which comprises one or more n-type organic semiconductor compounds.

27. The mixture or polymer blend according to claim 26, wherein the n-type organic semiconductor compound is selected from the group consisting of fullerenes, substituted fullerenes, graphene and metal oxides.

28. The mixture or polymer blend according to claim 27, wherein the n-type organic semiconductor compound is selected from the group consisting of PCBM-C$_{60}$, PCBM-C$_{70}$, bis-PCBM-C$_{60}$, bis-PCBM-C$_{70}$, ICMA-C$_{60}$, ICMA-C$_{70}$, ICBA-C$_{60}$, ICBA-C$_{70}$, oQDM-C$_{60}$, oQDM-C$_{70}$, bis-oQDM-C$_{60}$, bis-oQDM-C$_{70}$, graphene, ZnO$_x$, TiO$_x$, ZTO, MoO$_x$, NiO$_x$, CdSe, and CdS.

29. A formulation comprising one or more polymers according to claim 1, or mixtures or polymer blends that comprise said one or more polymers, and one or more solvents.

30. The conjugated polymer according to claim 18, wherein the total number of repeat units n is ≥50 and ≤2,000.

31. A charge transport, semiconducting, electrically conducting, photoconducting or light emitting material comprising a polymer according to claim 1, mixture that comprises said polymer, polymer blend that comprises said polymer or formulation that comprises said polymer.

32. An optical, electrooptical, electronic, electroluminescent or photoluminescent device, or a component thereof, or an assembly comprising it, which comprises a polymer according to claim 1, mixture that comprises said polymer, polymer blend that comprises said polymer or formulation that comprises said polymer, or comprises a charge transport, semiconducting, electrically conducting, photoconducting or light emitting material that comprises said polymer, mixture, polymer blend or formulation.

33. The optical, electrooptical, electronic, electroluminescent or photoluminescent device according to claim 32, which is selected from the group consisting of organic field effect transistors (OFET), organic thin film transistors (OTFT), organic light emitting diodes (OLED), organic light emitting transistors (OLET), organic photovoltaic devices (OPV), organic solar cells, laser diodes, organic plasmon-emitting diodes (OPEDs), Schottky diodes, organic photoconductors (OPCs) and organic photodetectors (OPDs).

34. The device according to claim 32, which is an OFET, bulk heterojunction (BHJ) OPV device or inverted BHJ OPV device.

35. The component according to claim 32, which is selected from the group consisting of charge injection layers, charge transport layers, interlayers, planarising layers, antistatic films, polymer electrolyte membranes (PEM), conducting substrates and conducting patterns.

36. The assembly according to claim 32, which is selected from the group consisting of integrated circuits (IC), radio frequency identification (RFID) tags, security markings containing an RFID tag, security devices containing an RFID tag, flat panel displays, backlights of flap panel displays, electrophotographic devices, electrophotographic recording devices, organic memory devices, sensor devices, biosensors and biochips.

37. Electrode materials in batteries, or in components or devices for detecting and discriminating DNA sequences, comprising a polymer according to claim 1, mixture that comprises said polymer, polymer blend that comprises said polymer or formulation that comprises said polymer.

38. The conjugated polymer according to claim 20, wherein the total number of repeat units n is ≥50 and ≤2,000.

39. A process of preparing a conjugated polymer according to claim 1, that comprises in its backbone one or more electron donor units $D^i$ and one or more electron acceptor units $A^i$, and optionally one or two terminal or endcap units T, wherein each donor unit $D^i$ in the polymer backbone is flanked by two acceptor units $A^i$ to form a triad $A^i$-$D^i$-$A^i$, except for $D^i$ units adjacent to a terminal or endcap group T, which polymer fulfils the condition f≤s/2+2, wherein f is the total number of units $D^i$ in the polymer backbone, s is the total number of units $A^i$ in the polymer backbone and s is at least 2, and excluding polymers comprising repeating units [A-D-A] wherein A is optionally substituted pyrazolone and D is optionally substituted benzo[1,2-b:4,5-b']dithiophene, comprising coupling one or more monomers of formula VII

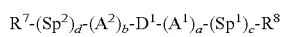   VII wherein $D^1$ is a first unit selected from the group consisting of formula Ia to Ig, Ia1, Ia2 and Ia3

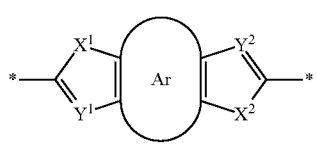   Ia

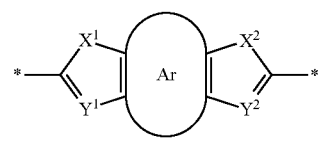   Ib

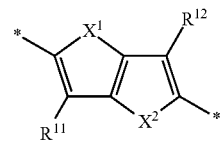   Ic

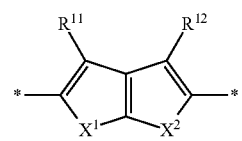   Id

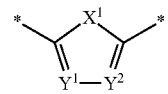   Ie

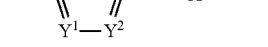   If

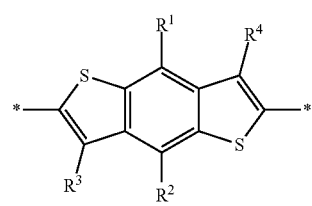   Ig wherein
Ar denotes a carbocyclic, heterocyclic, aromatic or heteroaromatic group, which comprises one or more saturated or unsaturated rings that are covalently linked or fused, which is fused to the terminal five-membered rings in formula Ia or Ib to form a conjugated system, and which is unsubstituted or substituted,
$Ar^1$ denotes a carbocyclic, heterocyclic, aromatic or heteroaromatic group, which comprises one or more saturated or unsaturated rings that are covalently linked or fused, which is fused to the divalent five-membered ring in formula Ig, and which is unsubstituted or substituted,
$X^1$ and $X^2$ denote independently of each other O, S, Se, Si or $NR^1$,
$Y^{1-4}$ denote independently of each other $CR^1$ or N,
$R^1$ denotes H, halogen, or an optionally substituted carbyl or hydrocarbyl group, wherein one or more C atoms are optionally replaced by a hetero atom, and
$R^{11}$ and $R^{12}$ independently of each other have one of the meanings of $R^1$, Ia1

-continued

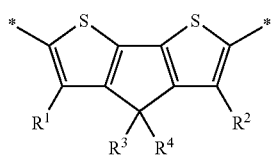
Ia2

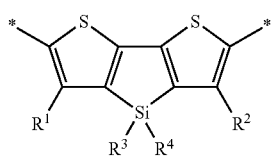
Ia3 wherein $R^{1-4}$ independently of each other denote H, halogen, or an optionally substituted carbyl or hydrocarbyl group wherein one or more C atoms are optionally replaced by a hetero atom, $A^1$ and $A^2$ independently of each other denote an acceptor unit that is different from $D^1$, $Sp^1$ and $Sp^2$, and is arylene or heteroarylene that is mono- or polycyclic and optionally substituted, or is selected from the group consisting of the following formulae and their mirror images:

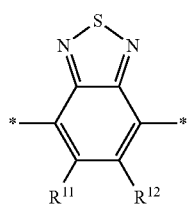
(A1)

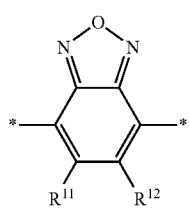
(A2)

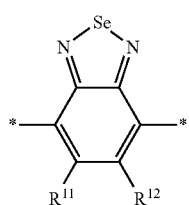
(A3)

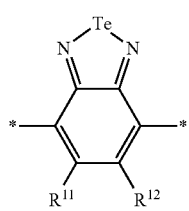
(A4)

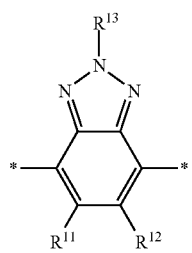
(A5)

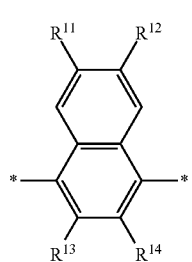
(A6)

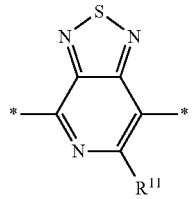
(A7)

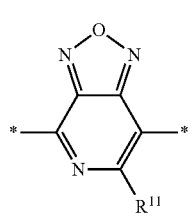
(A8)

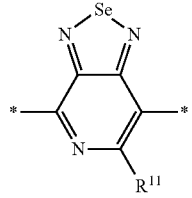
(A9)

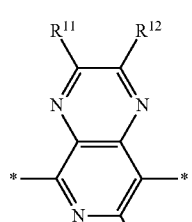
(A10)

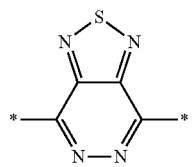
(A11)

-continued
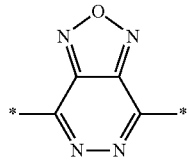 (A12)
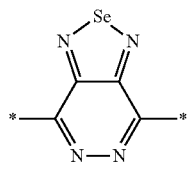 (A13)
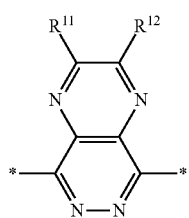 (A14)
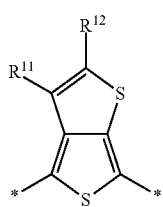 (A15)
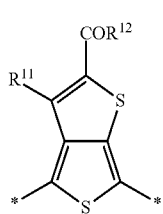 (A16)
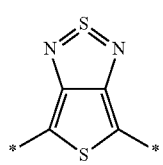 (A17)
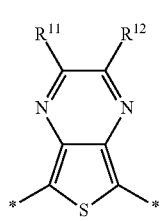 (A18)
-continued
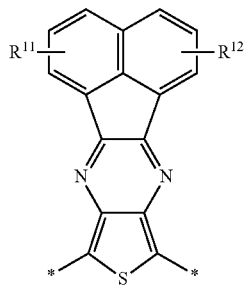 (A19)
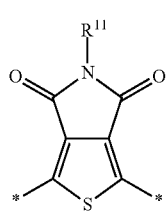 (A20)
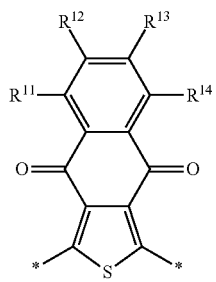 (A21)
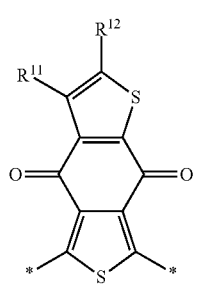 (A22)
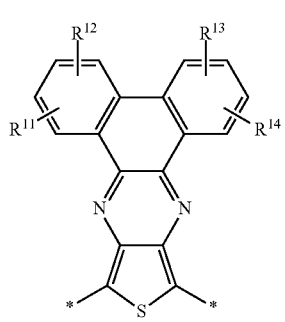 (A23)

-continued
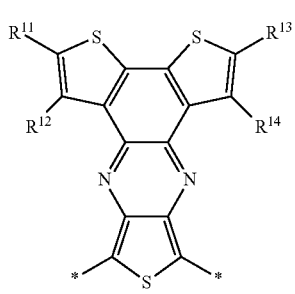 (A24)
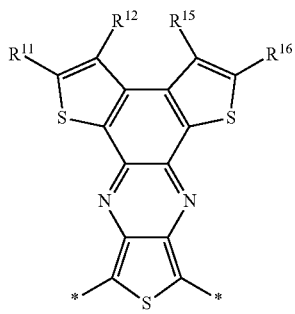 (A25)
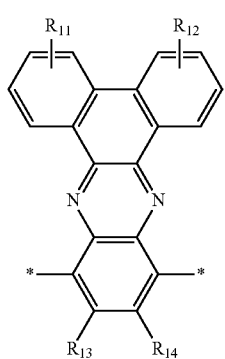 (A26)
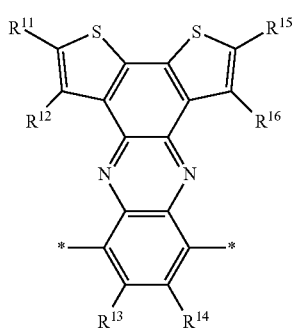 (A27)
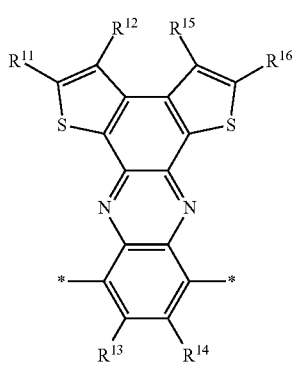 (A28)
-continued
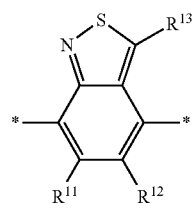 (A29)
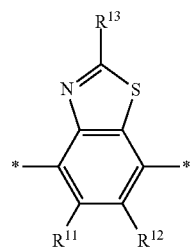 (A30)
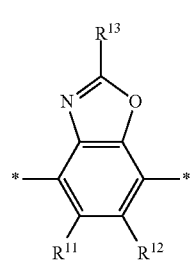 (A31)
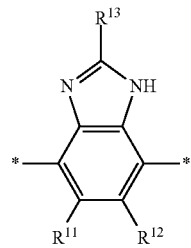 (A32)
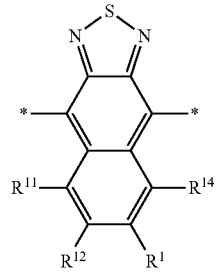 (A33)
(A34)

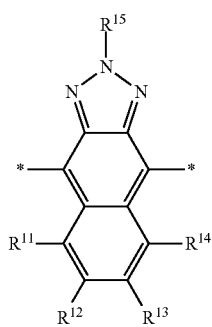 (A35)
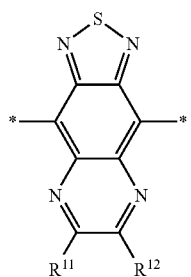 (A36)
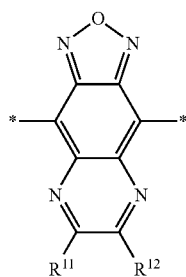 (A37)
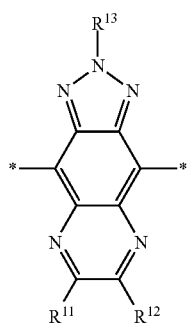 (A38)
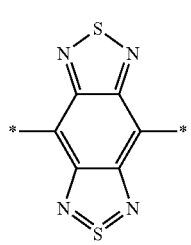 (A39)
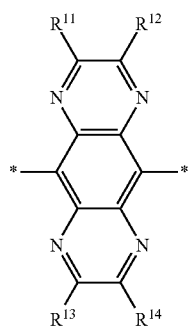 (A40)
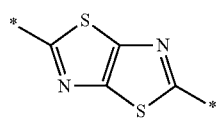 (A41)
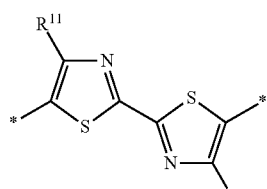 (A42)
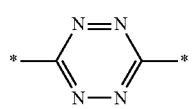 (A43)
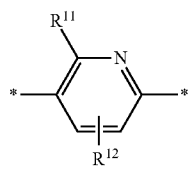 (A44)
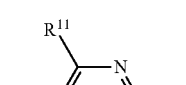 (A45)
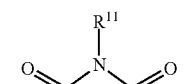 (A46)
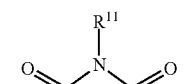 (A47)

-continued
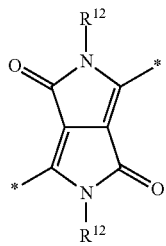
(A48)
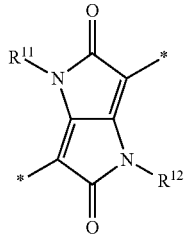
(A49)
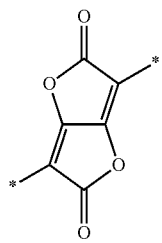
(A50)
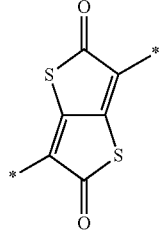
(A51)
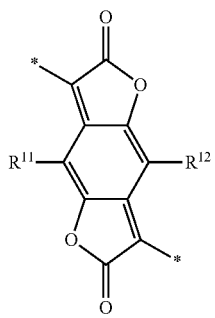
(A52)
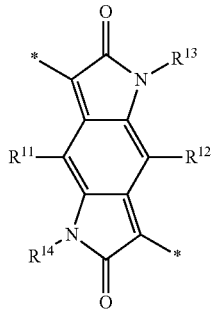
(A53)
-continued
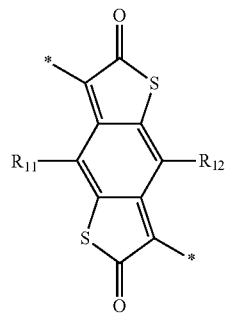
(A54)
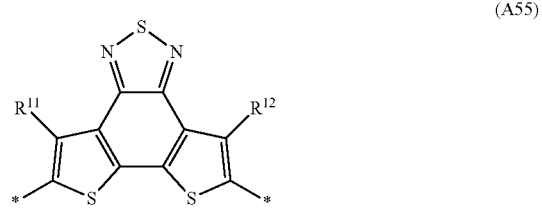
(A55)
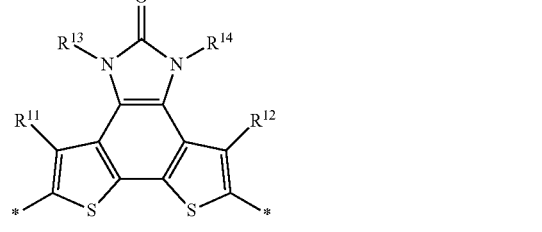
(A56)
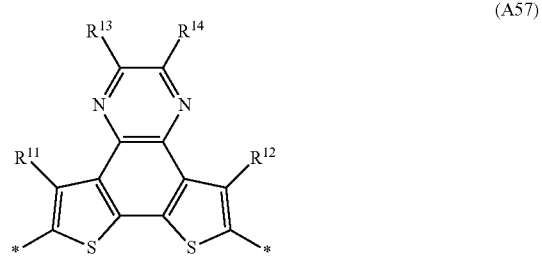
(A57)
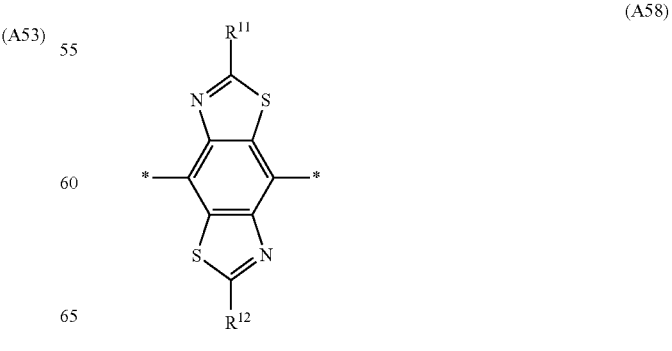
(A58)

351
-continued
(A59) 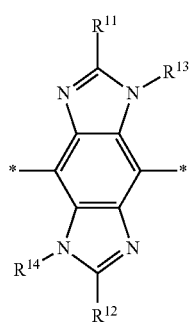
(A60) 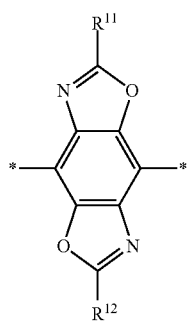
(A61) 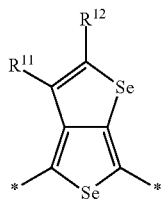
(A62) 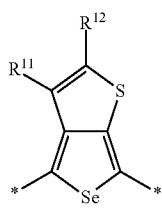
(A63) 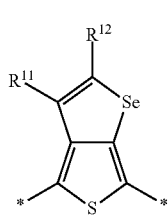
(A64) 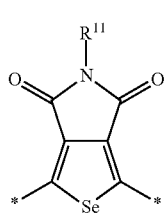
352
-continued
(A65) 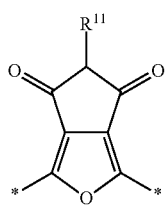
(A66) 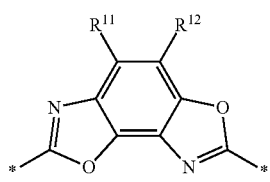
(A67) 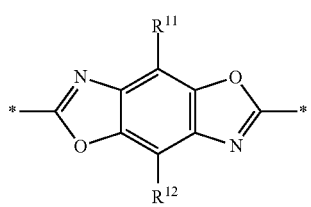
(A68) 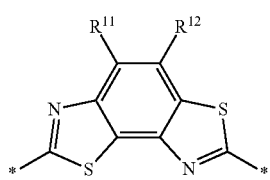
(A69) 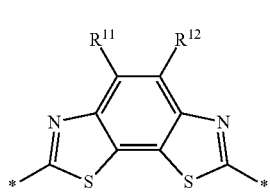
(A70) 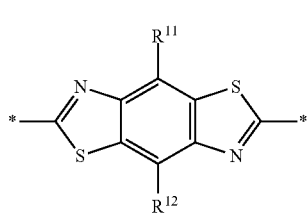
(A71) 
(A72)

-continued
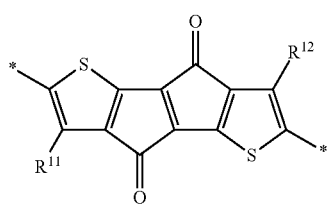 (A73)
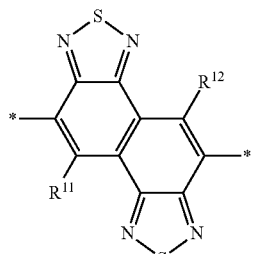 (A74)
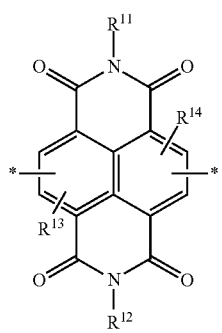 (A75)
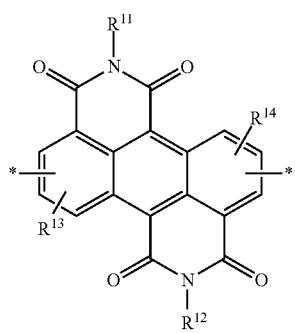 (A76)
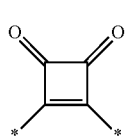 (A77)
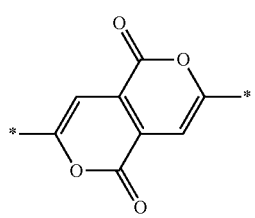 (A78)
-continued
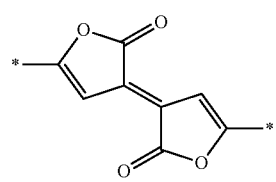 (A79)
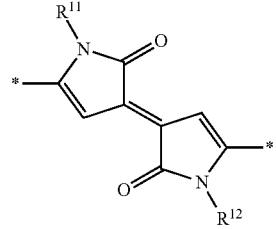 (A80)
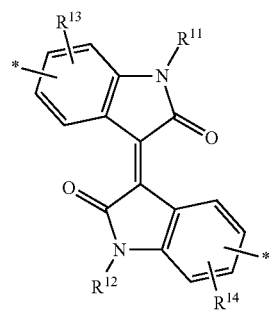 (A81)
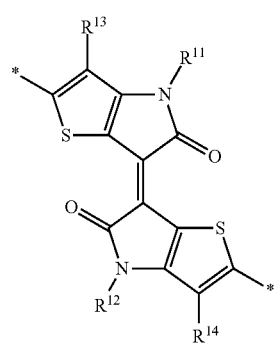 (A82)
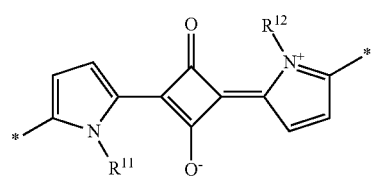 (A83)

-continued
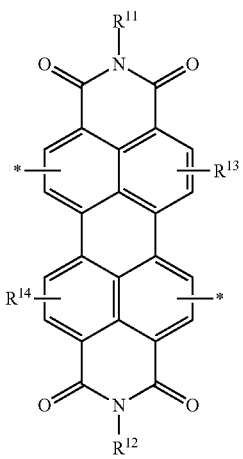 (A84)
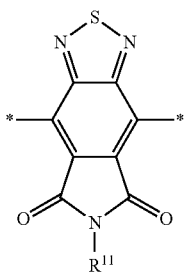 (A85)
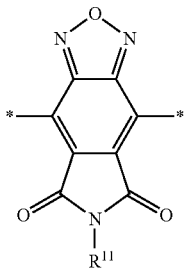 (A86)
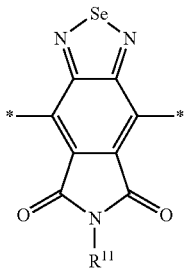 (A87)
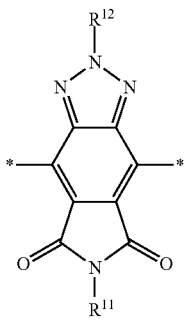 (A88)
-continued
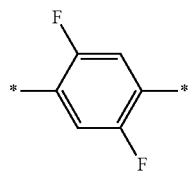 (A89)
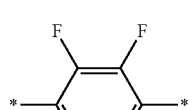 (A90)
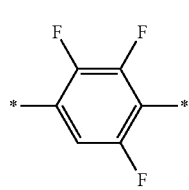 (A91)
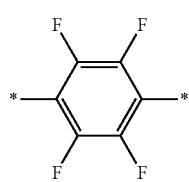 (A92)
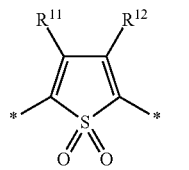 (A93)
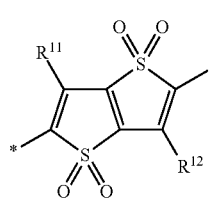 (A94)
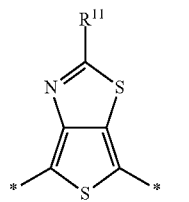 (A95)
 (A96)
wherein
$R^{11}$, $R^{12}$, $R^{13}$ and $R^{14}$ independently of each denote H, halogen, or an optionally substituted carbyl or hydrocarbyl group wherein one or more C atoms are optionally replaced by a hetero atom, Sp¹ and Sp² independently of each other denote a spacer unit, which is different from D¹, A¹ and A², and is arylene or heteroarylene that is mono- or polycyclic and optionally substituted,
or is selected from the group consisting of the following formulae and their mirror images:
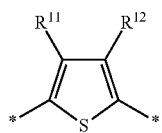
(D1)
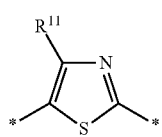
(D2)
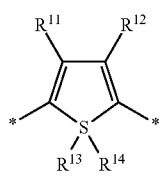
(D3)
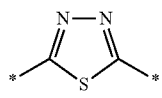
(D4)
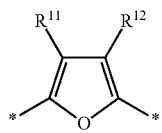
(D5)
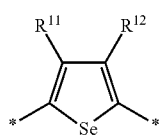
(D6)
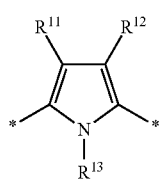
(D7)
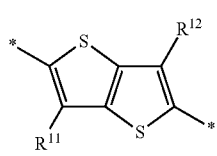
(D8)
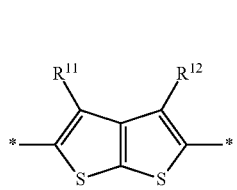
(D9)
-continued
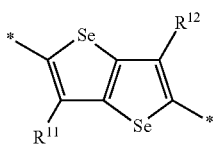
(D10)
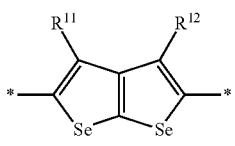
(D11)
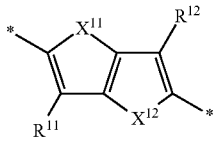
(D12)
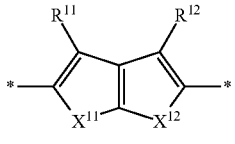
(D13)
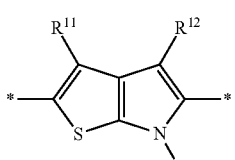
(D14)
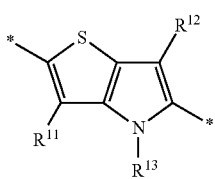
(D15)
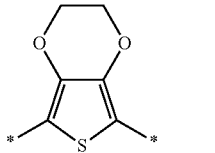
(D16)
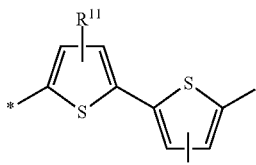
(D17)
(D18)

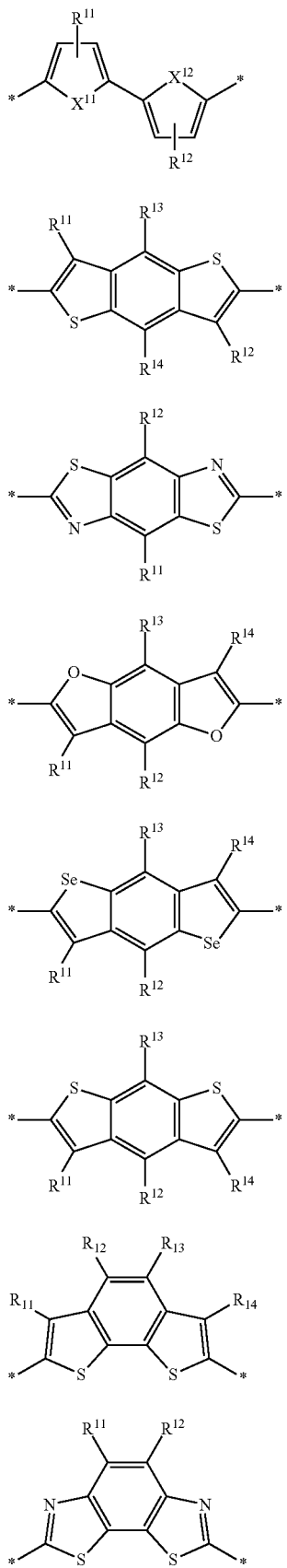
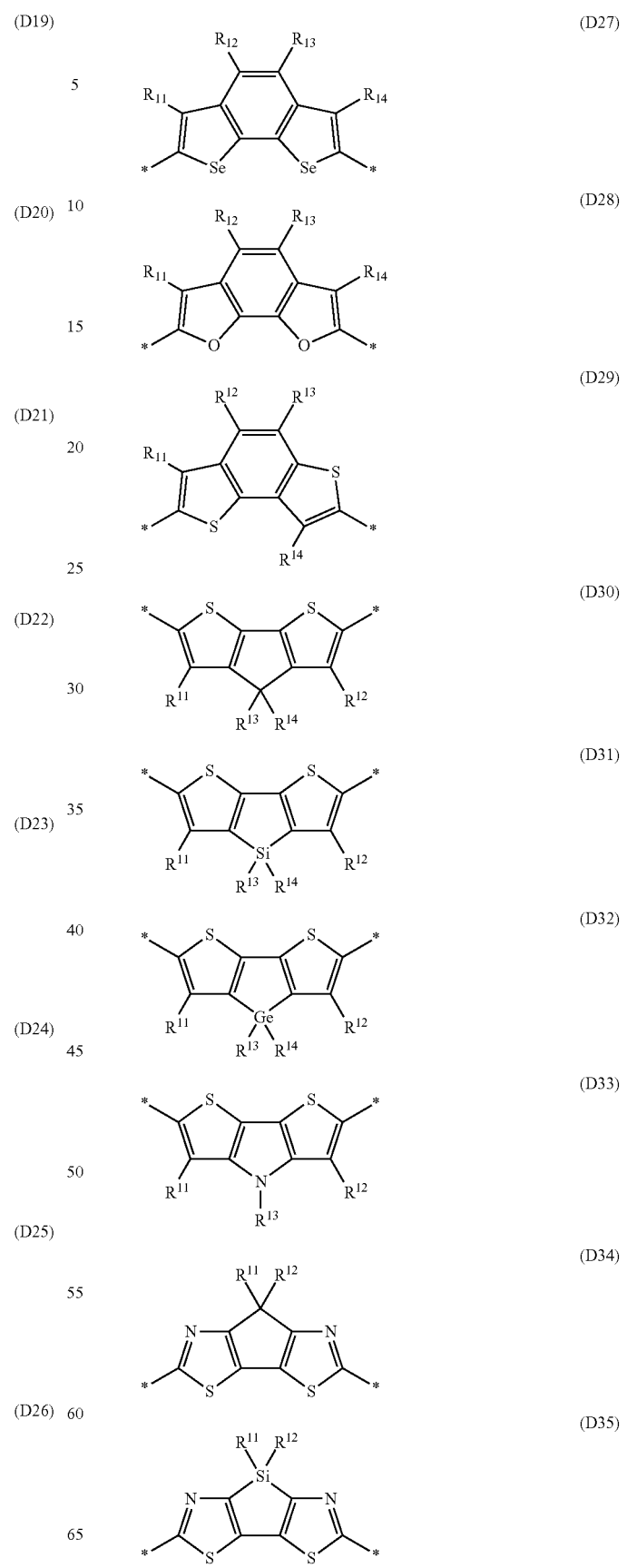

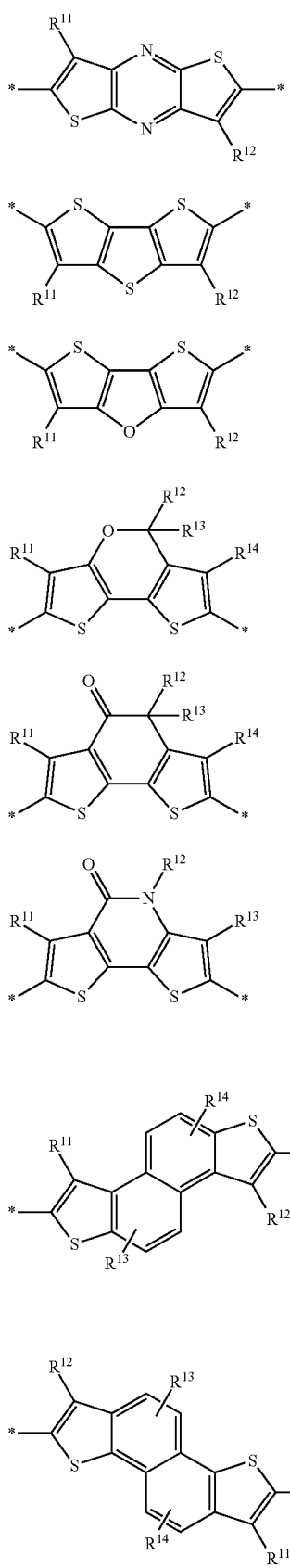
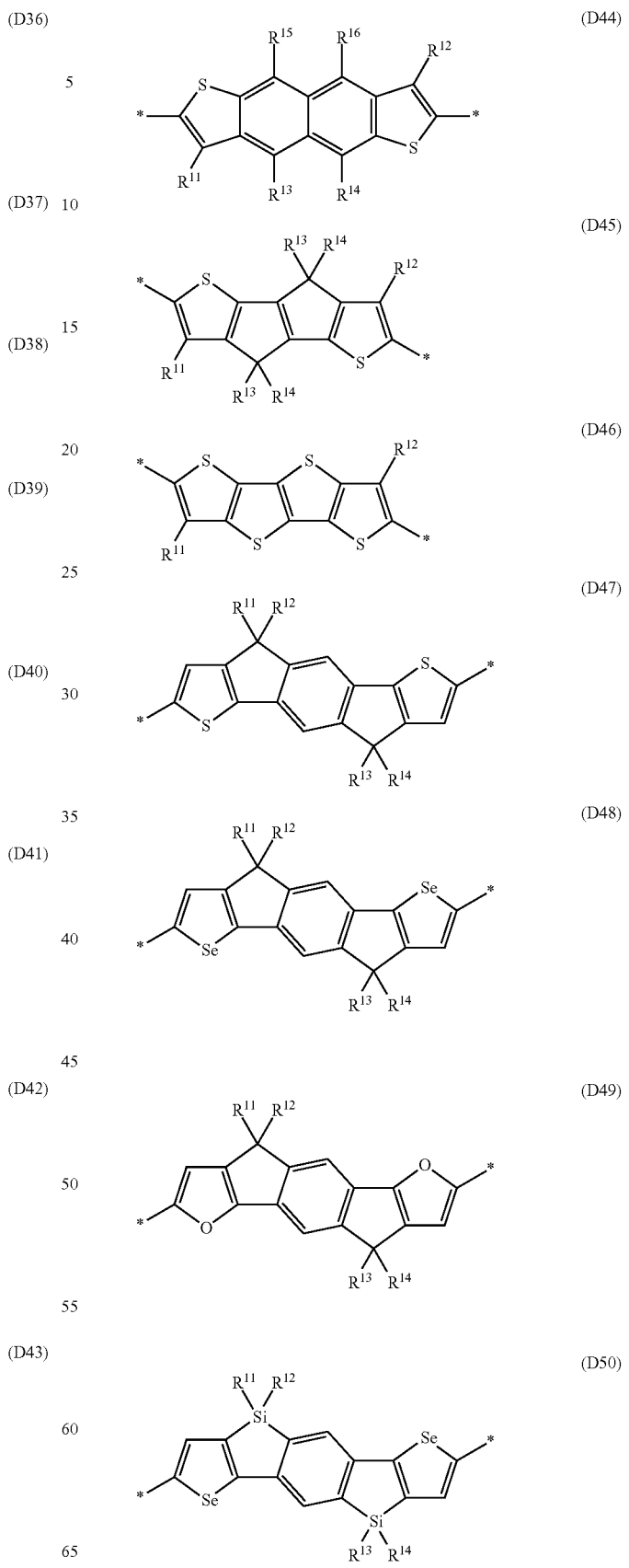

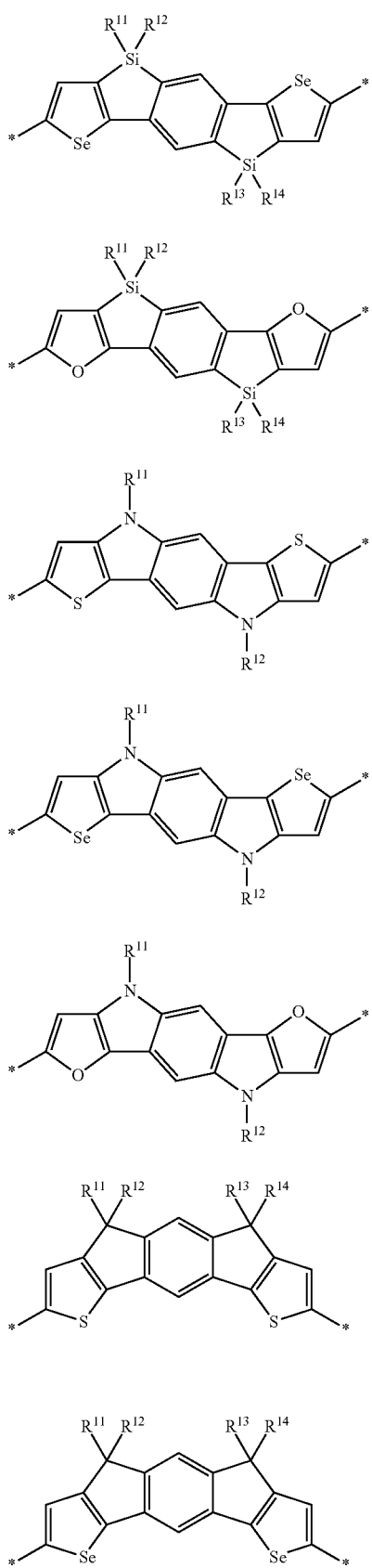
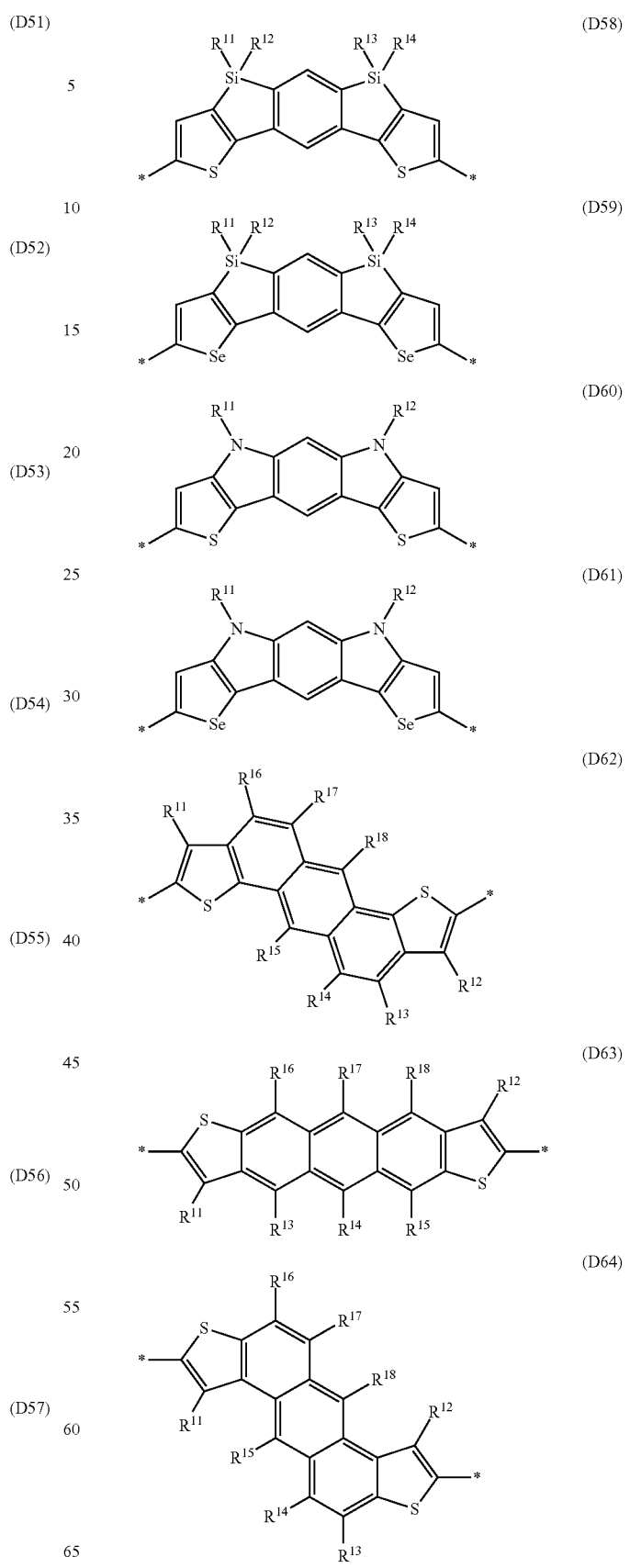

(D65) 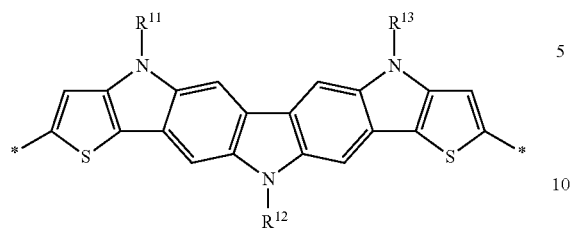

(D66) 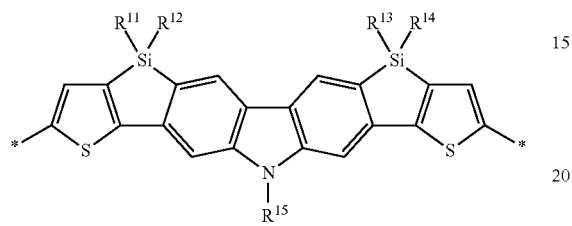

(D67) 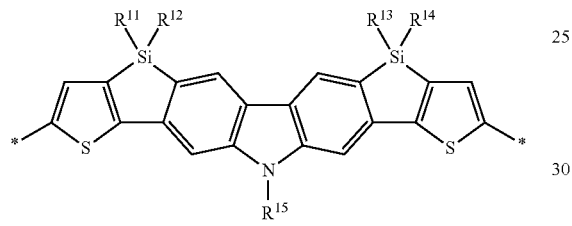

(D68) 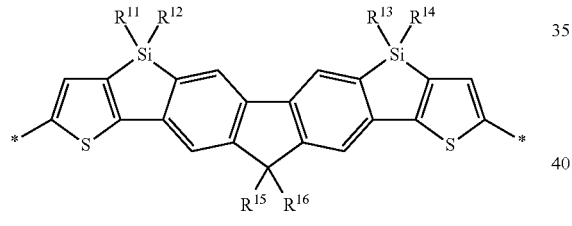

(D69) 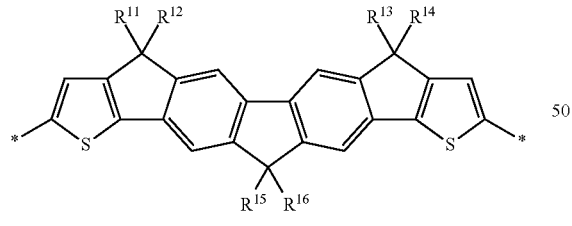

(D70) 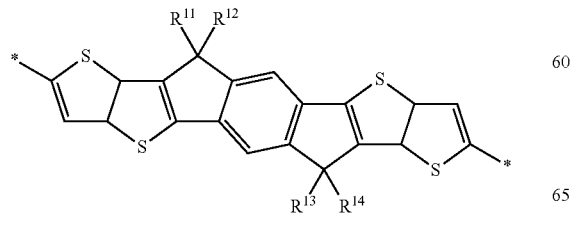

(D71) 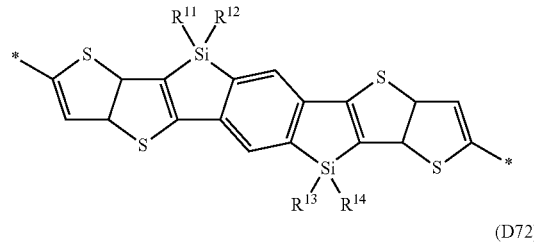

(D72) 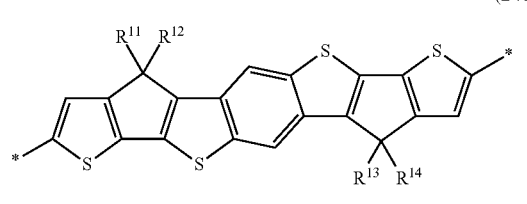

wherein one of $X^1$ and $X^{12}$ is S and the other is Se, and $R^{11}$, $R^{12}$, $R^{13}$, $R^{14}$, $R^{15}$, $R^{16}$, $R^{16}$, $R^{17}$ and $R^{18}$ independently of each other denote H, halogen, or an optionally substituted carbyl or hydrocarbyl group wherein one or more C atoms are optionally replaced by a hetero atom, or is selected from the group consisting of the following formulae:

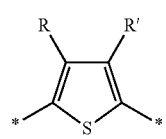   Sp1

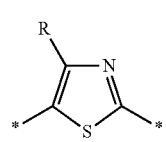   Sp2

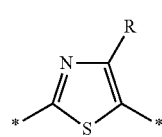   Sp3

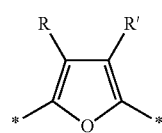   Sp4

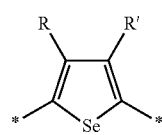   Sp5

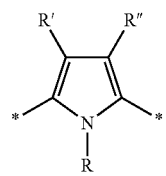   Sp6

-continued

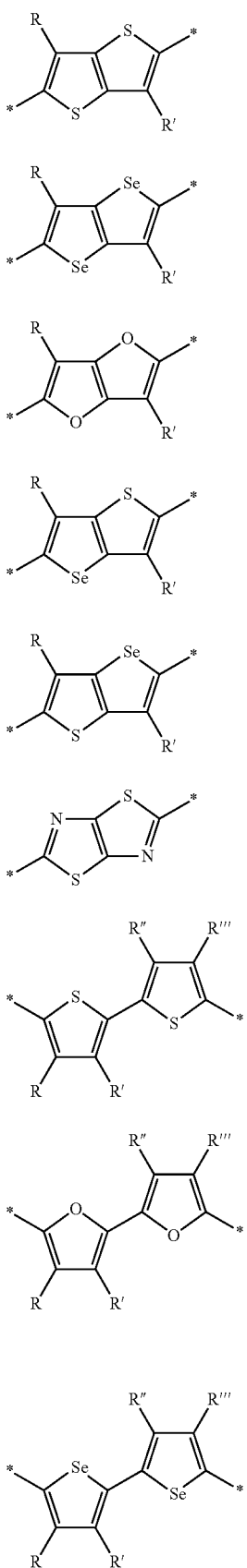

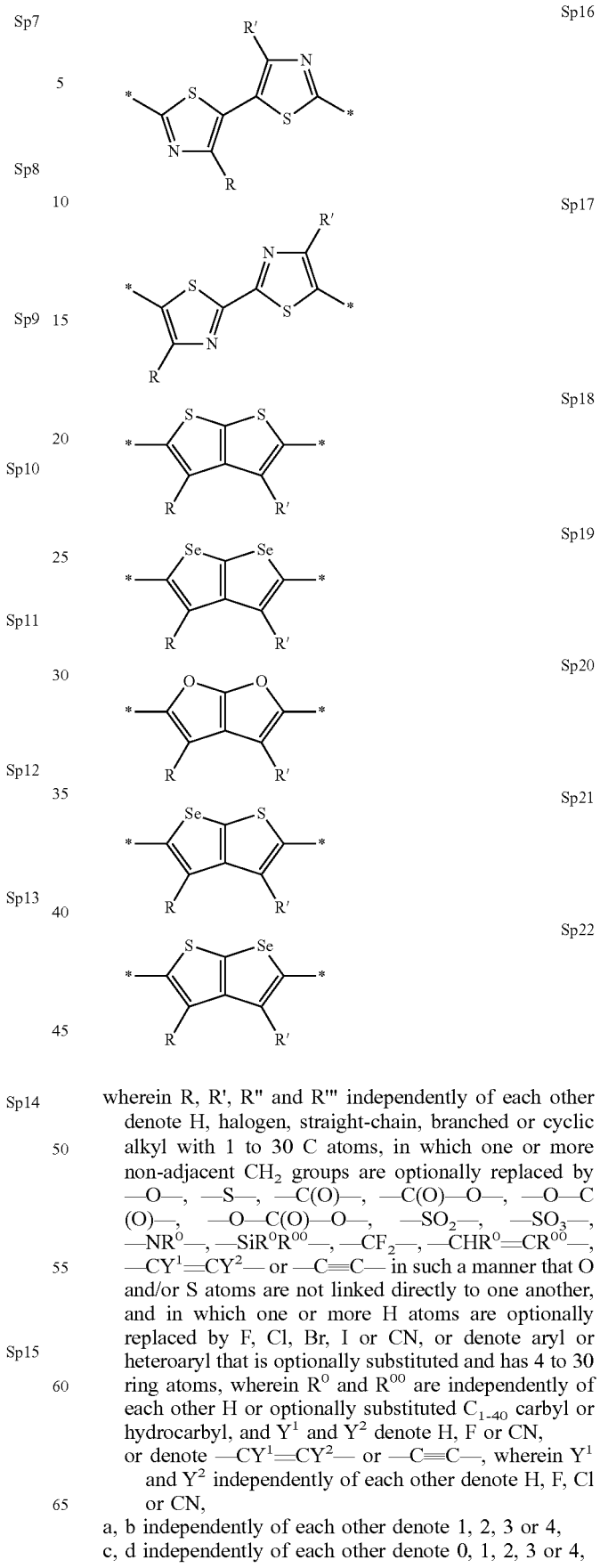

wherein R, R', R" and R'" independently of each other denote H, halogen, straight-chain, branched or cyclic alkyl with 1 to 30 C atoms, in which one or more non-adjacent CH$_2$ groups are optionally replaced by —O—, —S—, —C(O)—, —C(O)—O—, —O—C(O)—, —O—C(O)—O—, —SO$_2$—, —SO$_3$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, or denote aryl or heteroaryl that is optionally substituted and has 4 to 30 ring atoms, wherein R$^0$ and R$^{00}$ are independently of each other H or optionally substituted C$_{1-40}$ carbyl or hydrocarbyl, and Y$^1$ and Y$^2$ denote H, F or CN, or denote —CY$^1$=CY$^2$— or —C≡C—, wherein Y$^1$ and Y$^2$ independently of each other denote H, F, Cl or CN, a, b independently of each other denote 1, 2, 3 or 4, c, d independently of each other denote 0, 1, 2, 3 or 4, and wherein $R^7$ and $R^8$ are selected from the group consisting of Cl, Br, I, $-B(OZ^2)_2$ and $-Sn(Z^4)_3$, $Z^2$ and $Z^4$ are selected from the group consisting of alkyl and aryl, each being optionally substituted, and two groups $Z^2$ optionally together form a cyclic group, with each other or with one or more co-monomers in an aryl-aryl coupling reaction.

40. The process according to claim 1, wherein the monomer is selected from the group consisting of the following formulae

| | |
|---|---|
| $R^7-A^2-D^1-A^1-R^8$ | VII1 |
| $R^7-Sp^2-A^2-D^1-R^8$ | VII2 |
| $R^7-D^1-A^1-Sp^1-R^8$ | VII3 |
| $R^7-Sp^2-A^2-D^1-A^1-R^8$ | VII4 |
| $R^7-A^2-D^1-A^1-Sp^1-R^8$ | VII5 |
| $R^7-Sp^2-A^2-D^1-A^1-Sp^1-R^8$ | VII6 | wherein $D^1$, $A^1$, $A^2$, $Sp^1$, $R^7$, $R^8$, a, b and c are as defined for the monomer of formula VII.

41. The conjugated polymer according to claim 1, wherein the donor units $D^i$ contain one or more of the following units benzo[1,2-b:4,5-b']dithiophene-2,6-diyl that is optionally substituted in one or more of the 3-, 4-, 7- and 8-positions, 7H-3,4-dithia-7-sila-cyclopenta[a]pentalene-di-2,5-diyl, that is optionally substituted in one or more of the 1-, 6-, 7-, 7'-positions, or 4H-cyclopenta[2,1-b;3,4-b']dithiophene-2,6-diyl, that is optionally substituted in one or more of the 3-, 4-, 4'-, 5-positions.

42. The conjugated polymer according to claim 1, wherein the donor units $D^i$ are selected from the group consisting of benzo[1,2-b:4,5-b']dithiophene-2,6-diyl that is optionally substituted in one or more of the 3-, 4-, 7- and 8-positions, 7H-3,4-dithia-7-sila-cyclopenta[a]pentalene-di-2,5-diyl, that is optionally substituted in one or more of the 1-, 6-, 7-, 7'-positions, and 4H-cyclopenta[2,1-b;3,4-b']dithiophene-2,6-diyl, that is optionally substituted in one or more of the 3-, 4-, 4'-, 5-positions.

43. The conjugated polymer according to claim 22, wherein the total number of repeat units n is ≥50 and ≤2,000.

44. The conjugated polymer according to claim 24, wherein the total number of repeat units n is ≥50 and ≤2,000.

* * * * *